(12) United States Patent
Hannam et al.

(10) Patent No.: US 7,638,629 B2
(45) Date of Patent: Dec. 29, 2009

(54) PIPERIDINES AND RELATED COMPOUNDS FOR TREATMENT OF ALZHEIMER'S DISEASE

(75) Inventors: Joanne Clare Hannam, Stansted (GB); Janusz Jozef Kulagowski, Sawbridgeworth (GB); Andrew Madin, Sawbridgeworth (GB); Mark Peter Ridgill, Watton-at-Stone (GB); Eileen Mary Seward, Bishops Stortford (GB)

(73) Assignee: Merck Sharp & Dohme Ltd,, Hoddesdon, Hertfordshire (GB)

( * ) Notice: Subject to any disclaimer, the term of this patent is extended or adjusted under 35 U.S.C. 154(b) by 62 days.

(21) Appl. No.: 11/664,678

(22) PCT Filed: Oct. 20, 2005

(86) PCT No.: PCT/GB2005/004040

§ 371 (c)(1),
(2), (4) Date: Apr. 4, 2007

(87) PCT Pub. No.: WO2006/043064

PCT Pub. Date: Apr. 27, 2006

(65) Prior Publication Data

US 2008/0021043 A1 Jan. 24, 2008

(30) Foreign Application Priority Data

Oct. 21, 2004 (GB) .................. 0423356.5

(51) Int. Cl.
C07D 451/02 (2006.01)
C07D 211/08 (2006.01)
A01N 43/42 (2006.01)
A61K 31/445 (2006.01)

(52) U.S. Cl. ............... 546/124; 546/192; 514/304; 514/317

(58) Field of Classification Search ............. 546/124, 546/192; 514/317, 304

See application file for complete search history.

(56) References Cited

U.S. PATENT DOCUMENTS 3,250,771 A * 5/1966 Leonard et al. ............ 544/141

2003/0114496 A1 6/2003 Churcher et al.
2004/0142974 A1 7/2004 Hoemann

FOREIGN PATENT DOCUMENTS

EP 0 436 334 12/1990

OTHER PUBLICATIONS

Int. Rev. Psy., Dec. 2007, 19, 693-706.*
J. M. Aurrecoechea et al., "Diastereoselective Synthesis of Pyrrolidines by 5-Exo-trig Cyclizations . . . ", Synlett, vol. 1996, No. 1, pp. 39-42 (1996).
F. Bustos et al., "Synthesis of 2,4-, 3,4-, 2,3,4-substituted pyrrolidines by cyclization of neutral C-centered alpha-aminoalkyl redicals", Tetrahedron, vol. 58, pp. 6837-6842 (2002).
K. Achiwa et al., "1,3-Dipolar Cycloaddition Leading To N-Alkylpyrrolidines", Chemical and Pharmaceutical Bulletin, vol. 32, pp. 2878-2881 (1984).
International Preliminary Report on Patentability for PCT/GB2005/004040 (Apr. 24, 2007).

* cited by examiner

Primary Examiner—Rita J Desai
Assistant Examiner—John Mabry
(74) Attorney, Agent, or Firm—William Kronatin; Raynard Yuro

(57) ABSTRACT

Compounds of formula I:

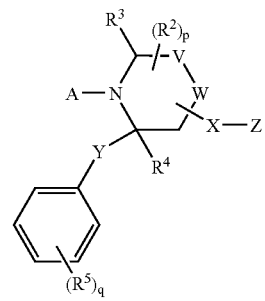

selectively inhibit production of Aβ(1-42) and hence are useful in treatment or prevention of disease associated with deposition of β-amyloid in the brain.

8 Claims, No Drawings

PIPERIDINES AND RELATED COMPOUNDS FOR TREATMENT OF ALZHEIMER'S DISEASE

This invention relates to compounds for use in therapeutic treatment of the human body. In particular, it provides carboxy-functional 1,2-disubstituted piperidines and related compounds useful for treating diseases associated with the deposition of β-amyloid peptide in the brain, such as Alzheimer's disease, or of preventing or delaying the onset of dementia associated with such diseases.

Alzheimer's disease (AD) is the most prevalent form of dementia. Its diagnosis is described in the Diagnostic and Statistical Manual of Mental Disorders, 4th ed., published by the American Psychiatric Association (DSM-IV). It is a neurodegenerative disorder, clinically characterized by progressive loss of memory and general cognitive function, and pathologically characterized by the deposition of extracellular proteinaceous plaques in the cortical and associative brain regions of sufferers. These plaques mainly comprise fibrillar aggregates of β-amyloid peptide (Aβ). Aβ is formed from amyloid precursor protein (APP) via separate intracellular proteolytic events involving the enzymes β-secretase and γ-secretase. Variability in the site of the proteolysis mediated by γ-secretase results in Aβ of varying chain length, e.g. Aβ(1-38), Aβ(1-40) and Aβ(1-42). N-terminal truncations such as Aβ(4-42) are also found in the brain, possibly as a result of variability in the site of proteolysis mediated by β-secretase. For the sake of convenience, expressions such as "Aβ(1-40)" and "Aβ(1-42)" as used herein are inclusive of such N-terminal truncated variants. After secretion into the extracellular medium, Aβ forms initially-soluble aggregates which are widely believed to be the key neurotoxic agents in AD (see Gong et al, *PNAS*, 100 (2003), 10417-22), and which ultimately result in the insoluble deposits and dense neuritic plaques which are the pathological characteristics of AD.

Other dementing conditions associated with deposition of Aβ in the brain include cerebral amyloid angiopathy, hereditary cerebral haemorrhage with amyloidosis, Dutch-type (HCHWA-D), multi-infarct dementia, dementia pugilistica and Down syndrome.

Various interventions in the plaque-forming process have been proposed as therapeutic treatments for AD (see, for example, Hardy and Selkoe, *Science*, 297 (2002), 353-6). One such method of treatment that has been proposed is that of blocking or attenuating the production of Aβ for example by inhibition of β- or γ-secretase. It has also been reported that inhibition of glycogen synthase kinase-3 (GSK-3), in particular inhibition of GSK-3α, can block the production of Aβ (see Phiel et al, *Nature*, 423 (2003), 435-9).

Other proposed methods of treatment include administering a compound which blocks the aggregation of Aβ, and administering an antibody which selectively binds to Aβ.

Another proposed treatment is that of modulation of the action of γ-secretase so as to selectively attenuate the production of Aβ(1-42). This results in preferential secretion of the shorter chain isoforms of Aβ, which are believed to have a reduced propensity for self-aggregation and plaque formation, and hence are more easily cleared from the brain, and/or are less neurotoxic. Compounds showing this effect include certain non-steroidal antiinflammatory drugs (NSAIDs) and their analogues (see WO 01/78721 and US 2002/0128319 and Weggen et al *Nature*, 414 (2001) 212-16; Morihara et al, *J. Neurochem.*, 83 (2002), 1009-12; and Takahashi et al, *J. Biol. Chem.*, 278 (2003), 18644-70). Compounds which modulate the activity of PPARα and/or PPARδ are also reported to have the effect of lowering Aβ(1-42) (WO 02/100836). NSAID derivatives capable of releasing nitric oxide have been reported to show improved anti-neuroinflammatory effects and/or to reduce intracerebral Aβ deposition in animal models (WO 02/092072; Jantzen et al, *J. Neuroscience*, 22 (2002), 226-54). US 2002/0015941 teaches that agents which potentiate capacitative calcium entry activity can lower Aβ(1-42).

It has now been found that certain carboxy-functional 1,2-disubstituted piperidines and related compounds have the desirable property of selectively inhibiting production of Aβ(1-42).

According to the present invention there is provided a compound of formula I:

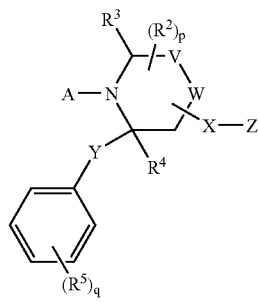

or a pharmaceutically acceptable salt thereof; wherein:

p is 0 or 1;

q is 0, 1, 2 or 3;

V represents a bond or a carbon atom whose remaining valencies are satisfied via bonding to H, $R^2$ or X—Z or to any combination thereof;

W represents a nitrogen atom or a carbon atom whose remaining valencies are satisfied via bonding to H, $R^2$ or X—Z or to any combination thereof, provided that when W represents a nitrogen atom, V represents a carbon atom and the moiety X—Z is attached to W;

X represents a bond or $C(R^1)_2$ or $CH_2C(R^1)_2$, provided that when W represents N, X does not represent a bond;

Y represents a bond or $CH_2$ or $CH_2CH_2$;

Z represents $CO_2H$ or a tetrazole ring;

A represents hydrocarbon group of from 5 to 25 carbon atoms optionally bearing up to 5 substituents selected from halogen, CN, $N_3$, $NO_2$, $C_{1-4}$perfluoroalkyl, $OR^6$, $SR^6$, OH, $CO_2R^6$, $OCOR^6$ and $COR^6$;

each $R^1$ independently represents H or a non-aromatic hydrocarbon group of up to 6 carbon atoms; or the two $R^1$ groups complete a $C_{3-6}$alicyclic group;

$R^2$ represents a non-aromatic hydrocarbon group of up to 6 carbon atoms;

$R^3$ and $R^4$ each represents H, or when V and W each represents a carbon atom, $R^3$ and $R^4$ may together represent a $CH_2CH_2$ bridge;

each $R^5$ independently represents halogen, CN, $NO_2$, $R^6$, $OR^6$, $CO_2R^6$, $OCOR^6$ or $COR^6$; and $R^6$ represents a hydrocarbon group of up to 7 carbon atoms which is optionally substituted with up to 3 halogen atoms.

In a particular embodiment, the compound is in accordance with formula IA:

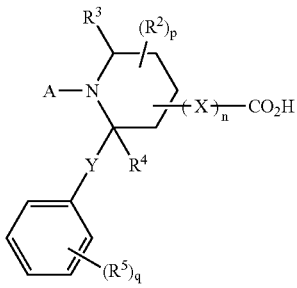

IA or a pharmaceutically acceptable salt thereof; wherein:

the moiety —(X)$_n$—CO$_2$H is attached to the 3-, 4- or 5-position of the piperidine ring;

n is 0 or 1;

p is 0 or 1;

q is 0, 1, 2 or 3;

A represents hydrocarbon group of from 5 to 20 carbon atoms optionally bearing up to 3 substituents selected from halogen, CN, NO$_2$, R$^6$, OR$^6$, CO$_2$R$^6$, OCOR$^6$ or COR$^6$;

X represents C(R$^1$)$_2$ or CH$_2$C(R$^1$)$_2$;

Y represents a bond or CH$_2$ or CH$_2$CH$_2$;

each R$^1$ independently represents H or a non-aromatic hydrocarbon group of up to 6 carbon atoms; or the two R$^1$ groups complete a C$_{3-6}$alicyclic group;

R$^2$ represents a non-aromatic hydrocarbon group of up to 6 carbon atoms;

R$^3$ and R$^4$ each represents H or together represent a CH$_2$CH$_2$ bridge;

each R$^5$ independently represents halogen, CN, NO$_2$, R$^6$, OR$^6$, CO$_2$R$^6$, OCOR$^6$ or COR$^6$; and R$^6$ represents a hydrocarbon group of up to 7 carbon atoms which is optionally substituted with up to 3 halogen atoms.

Where a variable occurs more than once in formula I, the identity taken by said variable at any particular occurrence is independent of the identity taken at any other occurrence.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits unless otherwise indicated.

As used herein, the expression "C$_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "C$_{2-6}$alkenyl", "hydroxyC$_{1-6}$alkyl", "heteroarylC$_{1-6}$alkyl", "C$_{2-6}$alkynyl" and "C$_{1-6}$alkoxy" are to be construed in an analogous manner.

The expression "perfluoroC$_{1-4}$alkyl" refers to linear or branched alkyl groups of up to 4 carbon atoms in which all the hydrogen atoms are replaced by fluorine atoms.

The expression "C$_{3-6}$alicyclic" refers to cyclic non-aromatic hydrocarbon groups containing from 3 to 6 ring carbon atoms. Examples include cyclopropyl, cyclobutyl, cyclopentenyl, cyclopentyl and cyclohexyl.

The term "halogen" as used herein includes fluorine, chlorine, bromine and iodine, of which fluorine and chlorine are preferred unless otherwise indicated.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, a pharmaceutically acceptable salt may be formed by neutralisation of the carboxylic acid group with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

It is to be understood that all the isomeric forms encompassed by formula I, both optical and geometrical, fall within the scope of the invention, singly or as mixtures in any proportion. Thus the moieties:

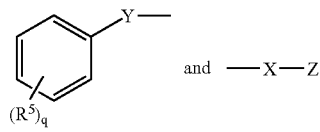

may be in a cis- or trans-configuration with respect to the ring completed by V-W. Furthermore, a given compound in the cis- or trans-configuration has two enantiomeric forms, both of which are within the scope of the invention, whether as single homochiral compounds or as racemic mixtures in any proportion. For the avoidance of any doubt, structural formulae such as (A) and (B):

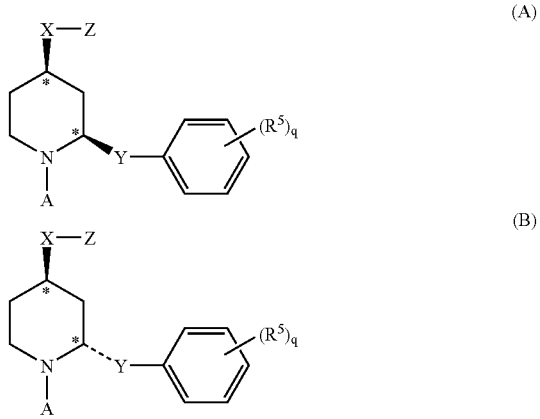

as used herein shall be taken to be definitive of the relative configurations of the carbon atoms marked with asterisks, but not their absolute configurations, unless expressly stated otherwise.

In formula I, V represents a bond or a carbon atom and W represents a nitrogen atom or a carbon atom, with the proviso that when W represents a nitrogen atom, V cannot be a bond and the moiety X—Z must be attached to W. Formula I therefore encompasses pyrrolidine, piperidine and piperazine derivatives, depending on the identities of V and W. In preferred embodiments, V represents a carbon atom, and hence completes a piperidine or piperazine ring. Most preferably, V and W both represent carbon atoms, and hence complete a piperidine ring. When one or both of V and W represents a carbon atom, the remaining valencies of said carbon atom(s) are satisfied via bonding to H, $R^2$ or X—Z, or to any combination thereof.

The moiety X—Z may be attached at any available ring position, including ring positions represented by V and W, but when W represents a nitrogen atom, X—Z must be attached to W. Preferably, X—Z is not attached at either of the positions adjacent to the nitrogen atom which is bonded to A. Thus, in the case of the preferred piperidine rings, X—Z is typically attached at the 3-, 4- or 5-position, most preferably at the 4-position. For the avoidance of doubt, the nitrogen atom of the piperidine ring shall be taken as the 1-position, and the carbon atom bonded to Y and $R^4$ as the 2-position.

Z represents $CO_2H$ or a tetrazole ring, in particular, Z represents $CO_2H$ or 1,2,3,4-tetrazol-5-yl, but preferably represents $CO_2H$.

The group X represents a bond, $C(R^1)_2$ or $CH_2C(R^1)_2$, where each $R^1$ independently represents H or a non-aromatic hydrocarbon group of up to 6 carbon atoms; or the two $R^1$ groups complete a $C_{3-6}$alicyclic group (such as cyclopropyl, cyclobutyl, cyclopentenyl or cyclopentyl). Preferably, one $R^1$ group is H and the other is H or $C_{1-6}$alkyl such as methyl, ethyl, propyl or butyl. Particular identities for X include a bond, $CH_2$, $CH(CH_3)$, $CH_2CH_2$, cyclopent-3-en-1,1-diyl and cyclopent-3-en-1,1-diyl, with the proviso that when W represents a nitrogen atom, X cannot be a bond. Preferably, X represents a bond or $CH_2$, and most preferably X represents $CH_2$.

Y represents a bond, $CH_2$ or $CH_2CH_2$, preferably a bond or $CH_2$, and most preferably a bond.

The group $R^2$ (when present) may be attached at any available position on the ring, including a carbon atom represented by V or W and including a carbon atom to which the moiety X—Z is attached. In one particular embodiment, p is 0 and $R^2$ is absent. In another particular embodiment, p is 1, V and W complete a piperidine ring and $R^2$ and the moiety X—Z are both attached at the 4-position thereof. In another particular embodiment, p is 1, V and W complete a piperidine ring, $R^2$ is attached at the 3-position and the moiety X—Z is attached at the 4-position. In another particular embodiment, p is 1, $R^3$ is H, V and W complete a piperidine ring, $R^2$ is attached at the 6-position and the moiety X—Z is attached at the 4-position. Typical identities for $R^2$ include $C_{1-6}$alkyl, such as methyl, ethyl or n-propyl, and $C_{2-6}$alkenyl, such as allyl.

$R^3$ and $R^4$ each represent H, or when V and W each represents a carbon atom, $R^3$ and $R^4$ may together represent —$CH_2CH_2$—, thereby completing a bridged bicyclic structure. When $R^3$ and $R^4$ together represent —$CH_2CH_2$—, p is preferably 0, and Y is preferably a bond.

In formula I, q is preferably 1 or 2, most preferably 1. Each $R^5$ independently represents halogen, CN, $NO_2$, $R^6$, $OR^6$, $CO_2R^6$, $OCOR^6$ or $COR^6$, where $R^6$ represents a hydrocarbon group of up to 7 carbon atoms which is optionally substituted with up to 3 halogen atoms. Most suitably, $R^5$ represents halogen (especially F), $R^6$ or $OR^6$ and $R^6$ represents $C_{1-6}$alkyl bearing 0-3 fluorine substituents or $C_{2-6}$alkenyl. When one $R^5$ is present, it is very suitably (but not necessarily) attached in the 4-position. Typical identities for $(R^5)_q$ include 2-$CF_3$, 3-$CF_3$, 4-$CF_3$, 2,4-di($CF_3$), 2-F-4-$CF_3$, 4-$OCF_3$, 4-allyl, 4-n-propyl, 4-isopropyl and 4-tert-butyl. In a preferred embodiment, $(R^5)_q$ represents 4-$CF_3$.

The group A is a hydrocarbon group of from 5 to 25 carbon atoms, preferably from 5 to 20 carbon atoms, optionally bearing up to 5 (preferably up to 3) substituents selected from halogen, CN, $N_3$, $NO_2$, $C_{1-4}$perfluoroalkyl, $OR^6$, $SR^6$, OH, $CO_2R^6$, $OCOR^6$ and $COR^6$; where $R^6$ is as defined previously. Examples of suitable substituents include halogen, CN, $N_3$, $C_{1-4}$ perfluoroalkyl (e.g. $CF_3$ or $C_2F_5$), $OCF_3$, $SCF_3$, OH, $OC_{1-4}$alkyl, $COC_{1-4}$alkyl and $COC_6H_5$. Typically, not more than one $N_3$, $OC_{1-4}$alkyl, $COC_{1-4}$alkyl or $COC_6H_5$ substituent is present. In one embodiment, A comprises an acetylenic triple bond and is unsubstituted, an example being 4,4-dimethylpent-2-ynyl. In a preferred embodiment, A comprises at least one carbocyclic ring. Said ring or rings may have one or more acyclic hydrocarbon groups attached thereto, consistent with the total number of carbon atoms being in the range of from 5 to 25. In an example of this embodiment, said carbocyclic ring or rings are 5- or 6-membered ring and the optional substituents borne by A are attached thereto. Very suitably, such a ring is attached to the 1-position of the piperidine ring by a direct bond or via a one-carbon or two-carbon spacing group, most preferably by a bond or a one-carbon spacing group.

Therefore, in a preferred embodiment, A may be represented as:

where m is 0 or 1;

$R^7$ is H or a hydrocarbon group of up to 10 carbon atoms, and A' represents a 3- to 12-membered carbocyclic ring system optionally having one or more acyclic hydrocarbon groups attached thereto, such that the total number of carbon atoms is in the range of 5 to 25;

A' and $R^7$ optionally and independently bearing one or more additional substituents, up to a maximum of 5 in combined total, selected from halogen, CN, $N_3$, $NO_2$, $C_{1-4}$ perfluoroalkyl, $OR^6$, $SR^6$, OH, $CO_2R^6$, $OCOR^6$ and $COR^6$; where $R^6$ is as defined previously.

Typically, when the total number of substituents is greater than 3, at least one of the substituents is halogen. Most preferably, the total number of substituents is not greater than 3. When one or more substituents are present on $R^7$, said one or more substituents are preferably selected from $C_{1-4}$alkoxy, halogen and $C_{1-4}$perfluoroalkyl.

In a particular embodiment, $R^7$ is H or a non-aromatic hydrocarbon group of up to 6 carbon atoms; and A' represents a 5-10 membered carbocyclic ring system optionally bearing up to 3 substituents selected from halogen, CN, $NO_2$, $R^6$, $OR^6$, $CO_2R^6$, $OCOR^6$ and $COR^6$ where $R^6$ represents a hydrocarbon group of up to 7 carbon atoms which is optionally substituted with up to 3 halogen atoms.

Typical identities for $R^7$ include H; $C_{1-10}$alkyl such as methyl, ethyl, n-propyl, n-butyl, isobutyl, n-pentyl, isopentyl, isoamyl and 3,3-dimethylbutyl; substituted $C_{1-6}$alkyl such as 3,3,3-trifluoropropyl, 1-ethoxyethyl, t-butoxymethyl and 3-methoxypropyl; $C_{2-10}$alkenyl such as allyl, 3-methylbuten-1-yl and but-3-en-1-yl; $C_{2-10}$alkynyl such as propynyl and 3-methylbut-3-en-1-ynyl; $C_{3-6}$cycloalkyl such as cyclopropyl, cyclopentyl and cyclohexyl; $C_{3-6}$cycloalkyl$C_{1-4}$alkyl such as cyclopropylmethyl; optionally-substituted phenyl$C_{1-4}$ alkyl such as benzyl, 2-phenylethyl, 2-(4-trifluoromethylphenyl)ethyl and 2-(3,4-difluorophenyl)ethyl; optionally-substituted phenylC$_{2-6}$alkynyl such as phenylethynyl; and optionally-substituted phenyl such as 4-trifluoromethylphenyl.

In a particular embodiment R$^7$ is H. In a further embodiment, R$^7$ is C$_{1-6}$alkyl.

Ring systems represented by A' may be fully saturated (such as cyclopropane, cyclopentane or cyclohexane), partially unsaturated (such as cyclohexene or tetrahydronaphthalene) or aromatic (such as benzene, biphenyl or naphthalene). In a particular embodiment, A' represents an aromatic ring system, and in a most preferred embodiment A' represents phenyl optionally having attached thereto up to 2 acyclic hydrocarbon groups selected from C$_{1-6}$alkyl (such as methyl, ethyl, n-propyl, isopropyl, n-butyl or tert-butyl) and C$_{2-6}$alkenyl (such as allyl or vinyl), and optionally bearing up to 3 further substituents as defined previously, but preferably not more than two such substituents. Preferred substituents include halogen, CN, N$_3$, C$_{1-4}$perfluoroalkyl, OR$^6$, SR$^6$ and COR$^6$. In this context R$^6$ is very suitably C$_{1-4}$alkyl (such as methyl, ethyl, n-propyl, isopropyl, n-butyl or tert-butyl), fluorinated C$_{1-4}$alkyl (such as CHF$_2$ or CF$_3$), or phenyl. Examples of optionally-substituted phenyl groups represented by A' include phenyl, vinylphenyl, fluorophenyl, chlorophenyl, bromophenyl, iodophenyl, isopropylphenyl, tert-butylphenyl, trifluoromethylphenyl, pentafluoroethylphenyl, cyanophenyl, methoxyphenyl, trifluoromethoxyphenyl, difluoromethoxyphenyl, trifluoromethylthiophenyl, benzoylphenyl, biphenyl, 4'-trifluoromethylbiphenyl, bis(trifluoromethyl)phenyl, dichlorophenyl, dimethylphenyl, 2-azido-4-iodophenyl, 5-fluoro-2-(trifluoromethyl)phenyl, 5-chloro-2-(trifluoromethyl)phenyl, 2-chloro-5-(trifluoromethyl)phenyl, 5-propyl-2-(trifluoromethyl)phenyl and 2-propyl-5-(trifluoromethyl)phenyl. (Unless otherwise indicated, all the possible positional isomers are included in the above list).

A first subset of the compounds according to the invention consists of the compounds of formula II:

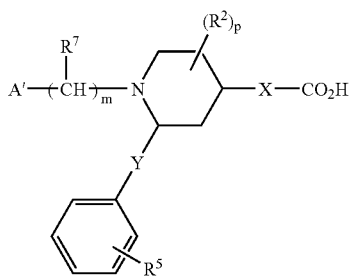

and the pharmaceutically acceptable salts thereof;

wherein m, p, A', X, Y, R$^5$, R$^6$ and R$^7$ have the same definitions and preferred identities as before.

In a particular embodiment of this subset, R$^7$ is H or a non-aromatic hydrocarbon group of up to 6 carbon atoms; and A' represents a 5-10 membered carbocyclic ring system optionally bearing up to 3 substituents selected from halogen, CN, NO$_2$, R$^6$, OR$^6$, CO$_2$R$^6$, OCOR$^6$ or COR$^6$.

A second subset of the compounds according to the invention consists of the compounds of formula III:

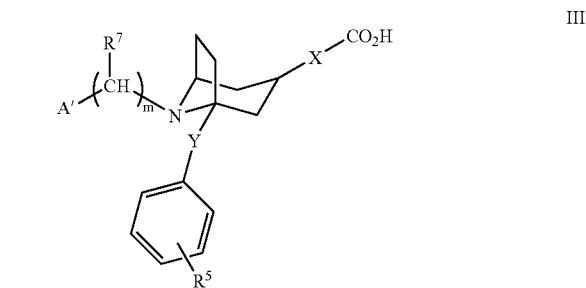

and the pharmaceutically acceptable salts thereof;

wherein m, A', X, Y, R$^5$, R$^6$ and R$^7$ have the same definitions and preferred identities as before.

In a particular embodiment of this subset, R$^7$ is H or a non-aromatic hydrocarbon group of up to 6 carbon atoms; and A' represents a 5-10 membered carbocyclic ring system optionally bearing up to 3 substituents selected from halogen, CN, NO$_2$, R$^6$, OR$^6$, CO$_2$R$^6$, OCOR$^6$ or COR$^6$.

Within this subset, Y is preferably a bond.

A third subset of the compounds according to the invention consists of the compounds of formula IV:

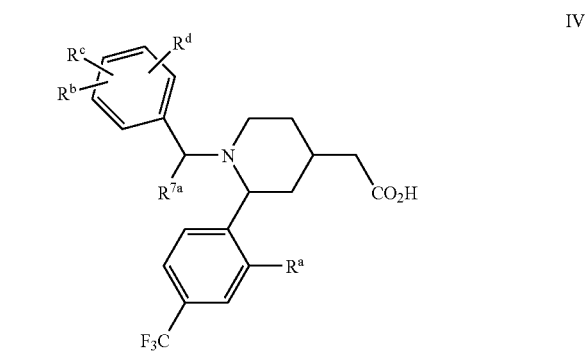

and the pharmaceutically acceptable salts thereof; wherein:

R$^a$ represents H, halogen or CF$_3$;

R$^b$, R$^c$ and R$^d$ are independently selected from H, halogen, CN, N$_3$, C$_{1-4}$ perfluoroalkyl, C$_{1-4}$alkoxy, OCF$_3$, SCF$_3$, C$_{1-4}$alkyl, C$_{2-4}$alkenyl, and phenyl which is optionally substituted with halogen or C$_{1-4}$perfluoroalkyl, provided that R$^b$, R$^c$ and R$^d$ together contain not more than 8 carbon atoms; and R$^{7a}$ represents a hydrocarbon group of up to 10 carbon atoms optionally bearing a C$_{1-4}$ perfluoroalkyl substituent or up to 2 halogen substituents.

The substituted phenyl group attached to the 2-position of the piperidine ring and the CH$_2$CO$_2$H group attached in the 4-position are advantageously (but not necessarily) in the cis-configuration with respect to the piperidine ring.

In a particular embodiment, R$^a$ represents H.

Preferably, at least one of R$^b$, R$^c$ and R$^d$ is H, and in a particular embodiment two of R$^b$, R$^c$ and R$^d$ represent H. In that embodiment, the remaining one of R$^b$, R$^c$ and R$^d$ is suitably (but not necessarily) attached to the 4-position. Typically, not more than one of R$^b$, R$^c$ and R$^d$ represents N$_3$, and not more than one of R$^b$, R$^c$ and R$^d$ may represent optionally-substituted phenyl.

Examples of optionally-substituted phenyl groups completed by $R^b$, $R^c$ and $R^d$ include phenyl, vinylphenyl, fluorophenyl, chlorophenyl, bromophenyl, iodophenyl, isopropylphenyl, tert-butylphenyl, trifluoromethylphenyl, pentafluoroethylphenyl, cyanophenyl, methoxyphenyl, trifluoromethoxyphenyl, difluoromethoxyphenyl, trifluoromethylthiophenyl, biphenyl, 4'-trifluoromethylbiphenyl, bis(trifluoromethyl)phenyl, dichlorophenyl, dimethylphenyl, 5-fluoro-2-(trifluoromethyl)phenyl, 5-chloro-2-(trifluoromethyl)phenyl, 2-chloro-5-(trifluoromethyl)phenyl, 5-propyl-2-(trifluoromethyl)phenyl and 2-propyl-5-(trifluoromethyl)phenyl. (Unless otherwise indicated, all the possible positional isomers are included in the above list). In a particularly preferred embodiment, $R^b$, $R^c$ and $R^d$ complete a 4-trifluoromethylphenyl group.

$R^{7a}$ is preferably unsubstituted or bears a $C_{1-4}$perfluoroalkyl substituent such as $CF_3$. Typical identities for $R^7$, include $C_{1-10}$alkyl such as methyl, ethyl, n-propyl, n-butyl, isobutyl, n-pentyl, isopentyl, isoamyl, or 3,3-dimethylbutyl; substituted $C_{1-6}$alkyl such as 3,3,3-trifluoropropyl; $C_{2-10}$alkenyl such as allyl, 3-methylbuten-1-yl or but-3-en-1-yl; $C_{2-10}$alkynyl such as propynyl or 3-methylbut-3-en-1-ynyl; $C_{3-6}$cycloalkyl such as cyclopropyl, cyclopentyl or cyclohexyl; $C_{3-6}$cycloalkyl$C_{1-4}$alkyl such as cyclopropylmethyl; optionally-substituted phenyl$C_{1-4}$alkyl such as benzyl, 2-phenylethyl, 2-(4-trifluoromethylphenyl)ethyl or 2-(3,4-difluorophenyl)ethyl; optionally-substituted phenyl$C_{2-6}$alkynyl such as phenylethynyl; and optionally-substituted phenyl such as 4-trifluoromethylphenyl. In a preferred embodiment, $R^{7a}$ represents a branched alkyl group of up to 6 carbon atoms such as isopentyl (i.e. 3-methylbutyl), a branched alkenyl group of up to 6 carbon atoms such as 3-methylbuten-1-yl, or a branched alkynyl group of up to 6 carbon atoms such as 3-methylbut-3-en-1-ynyl.

Specific examples of compounds in accordance with formula IV include those in which the variables are as follows:

| $R^a$ | $R^b/R^c/R^d$ | $R^{7a}$ |
|---|---|---|
| H | H,H,H | methyl |
| H | 4-$CF_3$ | n-propyl |
| H | 2,5-bis($CF_3$) | n-propyl |
| H | 4-$CF_3$ | 3-methylbut-3-en-1-ynyl |
| H | 4-$CF_3$ | 3-methylbutyl |
| F | 4-$CF_3$ | 3-methylbut-3-en-1-ynyl |
| H | 4-t-butyl | n-propyl |
| H | 2,5-bis($CF_3$) | methyl |
| H | 2,5-bis($CF_3$) | 3-methylbutyl |
| H | 4-$CF_3$ | ethynyl |
| H | 4-$CF_3$ | ethyl |
| H | 2-$CF_3$ | 3-methylbut-3-en-1-ynyl |
| H | 4-$OCF_3$ | 3-methylbut-3-en-1-ynyl |
| H | 3-$CF_3$ | 3-methylbut-3-en-1-ynyl |
| H | 4-$OCH_3$ | 3-methylbut-3-en-1-ynyl |
| H | H,H,H | 3-methylbut-3-en-1-ynyl |
| H | 4-F | 3-methylbut-3-en-1-ynyl |
| H | 3,4-dichloro | 3-methylbut-3-en-1-ynyl |
| H | 4-methyl | 3-methylbut-3-en-1-ynyl |
| H | 4-$OCHF_2$ | 3-methylbut-3-en-1-ynyl |
| H | 4-F-2-$CF_3$ | 3-methylbut-3-en-1-ynyl |
| H | 4-chloro | 3-methylbut-3-en-1-ynyl |
| H | 2-chloro | 3-methylbut-3-en-1-ynyl |
| H | 3-chloro | 3-methylbut-3-en-1-ynyl |
| H | 2,4-dichloro | 3-methylbut-3-en-1-ynyl |
| H | 3,5-dichloro | 3-methylbut-3-en-1-ynyl |
| H | 4-bromo | 3-methylbut-3-en-1-ynyl |
| H | 2-F-5-$CF_3$ | 3-methylbut-3-en-1-ynyl |
| H | 2-$CF_3$-5-F | 3-methylbut-3-en-1-ynyl |
| H | 2-F-3-Cl-6-$CF_3$ | 3-methylbut-3-en-1-ynyl |
| H | 4-$SCF_3$ | 3-methylbut-3-en-1-ynyl |
| H | 2-F-4-$CF_3$ | 3-methylbut-3-en-1-ynyl |

-continued

| $R^a$ | $R^b/R^c/R^d$ | $R^{7a}$ |
|---|---|---|
| H | 4-$CF_3$ | phenylethynyl |
| H | 4-iodo | 3-methylbut-3-en-1-ynyl |
| H | 4-$C_2F_5$ | 3-methylbut-3-en-1-ynyl |
| H | 4-CN | 3-methylbut-3-en-1-ynyl |
| H | 4-phenyl | 3-methylbut-3-en-1-ynyl |
| H | 4-(4'-$CF_3$-phenyl) | 3-methylbut-3-en-1-ynyl |
| H | H,H,H | 3-methylbutyl |
| H | 4-F-2-$CF_3$ | 3-methylbutyl |
| H | 4-$OCF_3$ | 3-methylbutyl |
| H | 4-$C_2F_5$ | 3-methylbutyl |
| H | 4-t-butyl | 3-methylbutyl |
| H | 4-$CF_3$ | cyclohexyl |
| H | 4-$CF_3$ | n-pentyl |
| H | 4-$CF_3$ | cyclopropyl |
| H | 4-$CF_3$ | 2-phenylethyl |
| H | 4-$CF_3$ | allyl |
| H | 4-$CF_3$ | 4-methylpentyl |
| H | 4-$CF_3$ | but-3-en-1-yl |
| H | 4-$CF_3$ | 3,3-dimethylbutyl |
| H | 4-$CF_3$ | 2-methylpropyl |
| H | 4-$CF_3$ | n-butyl |
| H | 4-$CF_3$ | 3,3,3-trifluoropropyl |
| H | 4-iodo | 3-methylbutyl |
| H | 4-vinyl | 3-methylbutyl |
| H | 2,5-bis($CF_3$) | 3-methylbuten-1-yl |
| H | 4-$CF_3$ | 3-methylbuten-1-yl |
| H | 4-Cl | 3-methylbutyl |
| H | 4-allyl | 3-methylbutyl |
| H | 4-n-propyl | 3-methylbutyl |
| H | 4-$CF_3$ | 4-$CF_3$Ph |

Syntheses of these and other compounds in accordance with the invention are described in the Examples section appended hereto.

The compounds of formula I in which Z is $CO_2H$ are typically obtained by hydrolysis of the corresponding esters (1):

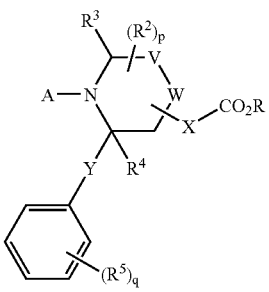

(1)

where R represents $C_{1-6}$alkyl such as methyl or ethyl and p, q, V, W, X, Y, A, $R^2$, $R^3$, $R^4$ and $R^5$ have the same meanings as before, e.g. by refluxing with LiOH in aqueous THF.

Corresponding compounds in which Z represents 1H-tetrazol-5-yl are obtainable by conversion of the esters (1) to the corresponding nitriles, followed by treatment with azidotrimethylsilane in refluxing toluene in the presence of tributyltin oxide. The conversion to the nitrile may be carried out by adding trimethylaluminium to a suspension of ammonium chloride in toluene, then adding the ester (1), refluxing the mixture, and treating with solid potassium sodium tartrate.

Compounds (1) may be obtained by reaction of compounds (2) with A—L:

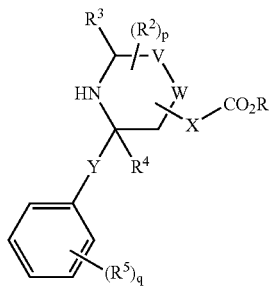
(2)

where L is a leaving group such as halide (especially bromide or iodide), tosylate, mesylate or triflate, and R, p, q, V, W, X, Y, A, $R^2$, $R^3$, $R^4$ and $R^5$ have the same meanings as before. When the attachment point of the group A forms part of an aromatic ring, L is preferably Br or I and the reaction is suitably carried out in the presence of strong base such as potassium t-butoxide, a Pd(0) catalyst such as tris(dibenzylideneacetone)dipalladium(0) and an additional ligand such as 2-dicyclohexylphosphino-2',4',6'-tripropyl-1,1'-biphenyl in THF with microwave heating. When the attachment point of the group A is an sp3 carbon atom, normal alkylating conditions may be employed, e.g. heating in DMF solution in the presence of base such as potassium carbonate.

Alternatively, compounds (2) may undergo reductive alkylation with precursors of the group A which contain an aldehyde or ketone functionality. This route is particularly useful when A takes the form A'—CH($R^7$)—, where A' and $R^7$ have the same meanings as before. In such cases, the compound (2) may be refluxed with A'-CO—$R^7$ in toluene in the presence of an acid catalyst, with azeotropic removal of water, and the resulting adduct reduced using sodium triacetoxyborohydride. In a variant of this route, useful when $R^7$ is an alkyn-1-yl group, a compound (2) is reacted with A'—CHO and $R^7$—H in the presence of gold(III) bromide, e.g. via microwave heating at 70° C. in water.

In another variant, the compound (2), A'—CHO and benzotriazole are refluxed in toluene with azeotropic removal of water, and the resulting adduct reacted with $R^7$—Zn—Hal where Hal represents halide (preferably chloride) and A' and $R^7$ have the same meanings as before. The reaction is suitably carried out in an anhydrous aprotic solvent such as dichloromethane at reduced temperature, e.g. below 10° C.

Piperidines (2) in which V and W are both carbon atoms and $R^3$ and $R^4$ are H may be obtained by hydrogenation of the corresponding pyridines (3):

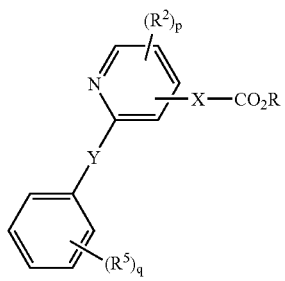
(3)

where R, p, q, X, Y, $R^2$ and $R^5$ have the same meanings as before, e.g. in methanolic HCl over a $PtO_2$ catalyst.

Pyridines (3) in which X is a bond and Y is a bond are obtainable by coupling of chloropyridines (4a) with arylboronic acids (5a):

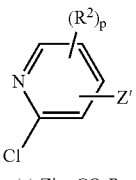
(4)

(a) Z' = $CO_2R$
(b) Z' = $CH_3$

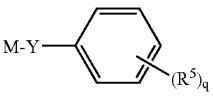
(5)

(a) M-Y = $B(OH)_2$
(b) M-Y = $BrZnCH_2$
(c) M-Y = HC≡C where R, p, q, $R^2$ and $R^5$ have the same meanings as before. The reaction takes place under standard Suzuki coupling conditions, e.g. in aqueous dimethoxyethane in the presence of sodium carbonate and $Pd(PPh_3)_4$.

Pyridines (3) in which X is a bond and Y is $CH_2$ are obtainable by coupling of chloropyridines (4a) with benzylzinc derivatives (5b). The reaction may be carried out at 0° C. to ambient temperature in THF in the presence of a nickel catalyst such as $(Ph_3P)_2NiCl_2$.

Pyridines (3) in which X is a bond and Y is $CH_2CH_2$ are obtainable by coupling of chloropyridines (4a) with alkynes (5c) followed by hydrogenation. The coupling may be carried out in the presence of CuI and a Pd(0) catalyst such as Pd$(Ph_3)_4$, e.g. in a mixture of dioxan and triethylamine with microwave heating. The hydrogenation takes place under similar conditions to the conversion of pyridines (3) to piperidines (2), and indeed is preferably combined with that process.

Pyridines (3) in which X is $CH_2$ may be obtained by elaboration of chloropyridines (4b) with (5a), (5b) or (5c) as described above, then treating the product with $CO(OR)_2$ in the presence of strong base such as lithium diisopropylamide, where R has the same meaning as before. Alternatively, the chloropyridines (4b) may be treated with $CO(OR)_2$ prior to the reaction with (5a), (5b) or (5c).

Piperidines of formula (2) in which V and W are both carbon atoms and $R^3$ and $R^4$ are H, X is a bond, p is 1 and $R^2$ is attached to the same ring position as the $CO_2R$ group are obtained by alkylation of the corresponding compounds in which p is 0 with $R^2$—L, where L has the same meaning as before. The reaction may be carried out in THF solution in the presence of strong base such as lithium hexamethyldisilazide (HMDS). During this procedure, it is preferable to protect the 1-position of the piperidine ring, e.g. as the BOC derivative.

An alternative route to esters (1) in which V and W are both carbon atoms and $R^3$ and $R^4$ are H, p is 0, X is $CH_2$ and the $CH_2CO_2R$ group is attached to the 4-position involves condensation of piperidones (6) with $(RO)_2P(O)CH_2CO_2R$, followed by hydrogenation of the resulting olefin (7):

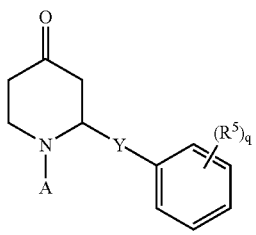

(6)

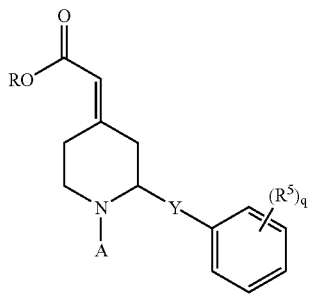

(7)

where R, A, Y, q and $R^5$ have the same meanings as before. The condensation takes place in THF in the presence of NaH, while the hydrogenation may be carried out over a Pd/C catalyst in ethanol. Corresponding esters of formula (1) in which n is 0 may be obtained by treatment of ketones (6) with KHMDS and $Tf_2NPh$, then with CO and ROH in the presence of a Pd(II) catalyst, followed by hydrogenation of the resulting tetrahydropyridine derivative.

Ketones (6) are available by reduction of dihydropyridones (8):

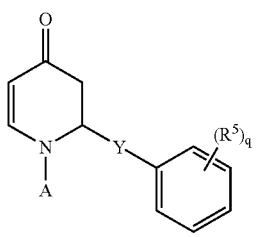

(8)

where A, Y, L, q and $R^5$ have the same meanings as before. The reduction may be carried out using a borohydride reductant such as L-Selectride in THF at −78° C.

Compounds (8) are available by the Diels-Alder reaction between trans-1-methoxy-3-(trimethylsilyloxy)-1,3-butadiene and the imine formed from condensation of A—$NH_2$ an aldeyde (9):

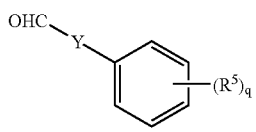

(9)

where A, Y, q and $R^5$ have the same meanings as before. The cycloaddition may be carried out in acetonitrile at ambient temperature in the presence of In(III) triflate, followed by quenching with aqueous bicarbonate.

Alternatively, piperidones (6) may be obtained in a one-pot process by reacting the aforesaid imines with trimethyl[(1-methyleneprop-2-en-1-yl)oxy]silane (e.g. in dichloromethane at ambient temperature under an inert atmosphere), then adding tetrabutylammonium fluoride.

An alternative route to piperidines (2) in which V and W are both carbon atoms and $R^3$ and $R^4$ are H, p is 0, X is $CH_2$ and the $CH_2CO_2R$ group is attached to the 4-position involves elaboration of the dihydropyridones (10):

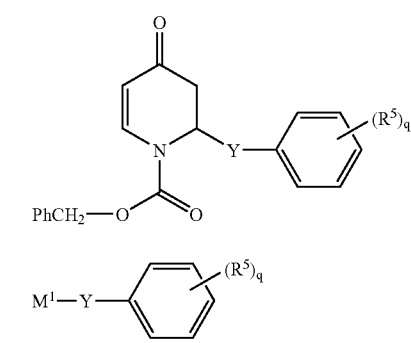

where Y, q and $R^5$ have the same meanings as before, in the manner described above for dihydropyridines (8), followed by removal of the benzyloxycarbonyl protecting group (e.g. by treatment with acid). Compounds (10) are available by a one-pot reaction of 4-methoxypyridine with benzyl chloroformate and organometallic derivatives (11), where $M^1$ is Li or Mg-halide, and Y, q and $R^5$ have the same meanings as before. The reaction takes place at reduced temperature (e.g. −25° C.) in a solvent such as THF.

In the above-described routes involving dihydropyridines (8) or (10), Y is preferably a bond.

The above-described routes involving dihydropyridines (8) or (10) may be adapted to provide products having an $R^2$ in the 3-position of the piperidine ring via alkylation of the compounds (8) or (10) with $R^2$—L, where $R^2$ and L have the same meanings as before. Said alkylation takes place under conventional conditions (e.g. in THF in the presence of lithium diisopropylamide).

Alternatively, the aforesaid routes may be adapted to provide products having an $R^2$ group in the 6-position of the piperidine ring via treatment of compounds (8) or (10) with $R^2$—Mg-halide in the presence of CuI, where $R^2$ has the same meaning as before. The reaction may be carried out in THF at reduced temperature (e.g. −78° C. to −10° C.).

In a further alternative, the aforesaid routes may be adapted to provide products in which the —$CH_2CO_2R$ group is attached at the 3-position of the piperidine ring via alkylation of compounds (8) or (10) with L—$CH_2CO_2R$, where L and R have the same meanings as before, followed by reduction of the keto group to $CH_2$. The alkylation takes place under conventional conditions, and reduction of the keto group is readily effected via treatment with 1,2-ethanedithiol to form the dithioketal, followed by treatment with Raney nickel.

An alternative route to piperidines of formula (1) in which V and W are both carbon atoms and $R^3$ and $R^4$ are both H, X is a bond, p is 0 and $CO_2R$ is attached to the 5-position involves cyclisation of dienes (12) followed by reduction of the resulting 1,2,3,6-tetrahydropyridine derivative:

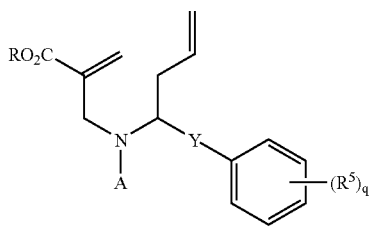

(12)

where R, A, Y, q and $R^5$ have the same meanings as before. The cyclisation takes place in the presence of a Ru catalyst and the reduction may be effected by treatment with Mg in methanol. Dienes (12) are obtainable by alkylation of secondary amines (13) with the appropriate bromomethacrylate ester, and amines (13) are available by condensation of aldehydes (9) with A-NH$_2$ and treatment of the product with allyltributylstannane:

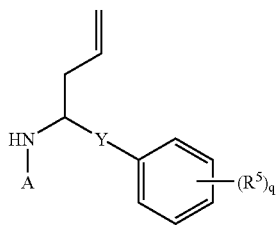

(13)

where A, Y, q and $R^5$ have the same meanings as before.

Another route to piperidines of formula (1) in which V and W are both carbon atoms, p is 0, $R^3$ and $R^4$ are both H, X is a bond and $CO_2R$ is attached in the 4-position involves monodecarboxylation of bis-esters (14):

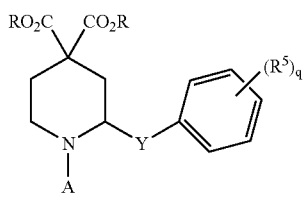

(14)

where R, A, Y, q and $R^5$ have the same meanings as before. The reaction may be carried out by heating at about 160° C. with sodium chloride in DMSO. Subsequent reflux of the product with sodium methoxide in methanol causes epimerisation at the 4-position and enrichment with the cis-isomer at the expense of the trans-isomer. Bis-esters (14) are available from the reaction of amines A-NH$_2$ with diketones (15):

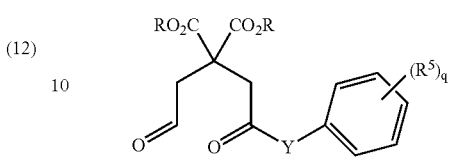

(15)

followed by reduction with sodium cyanoborohydride in a one-pot procedure, where R, A, Y, q and $R^5$ have the same meanings as before. The first step may be carried out in dimethoxyethane in the presence of a tertiary amine and TiCl$_4$ at −78° C. with warming to ambient. The second step may be carried out by adding a methanolic solution of sodium cyanoborohydride to the reaction mixture at room temperature. Diketones (15) may be obtained by alkylation of the appropriate allylmalonate dialkyl ester with a compound of formula (16):

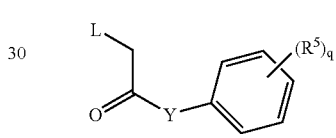

(16)

followed by ozonolysis of the allyl group, where L, R, Y, q and $R^5$ have the same meanings as before. The alkylation may be carried out in DMF in the presence of NaH (e.g. at ambient temperature). The ozonolysis may be effected by passing ozone-enriched oxygen through a dichloromethane solution of the substrate at −78° C., adding dimethyl sulfide, then stirring overnight at ambient temperature.

Piperidines of formula (2) in which $R^3$ and $R^4$ complete a —CH$_2$CH$_2$— bridge and Y is a bond may be obtained by elaboration of bicyclic ketones (14):

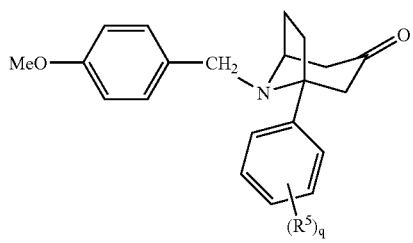

(17)

wherein q and $R^5$ have the same meanings as before, by the methods described above for the conversion of ketones (6) to esters (1), followed by removal of the protecting group 4-methoxybenzyl by hydrogenation.

The bicyclic ketones (17) are available by reaction of 4-methoxybenzylamine with acetonedicarboxylic acid, then treatment of the product in situ with a ketoaldehyde (18):

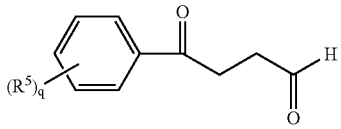

(18)

where R⁵ and q have the same meanings as before.

A preferred route to piperazines of formula (1) in which V is a carbon atom and W is a nitrogen atom involves alkylation of compounds (19) with L—X'—CO₂R:

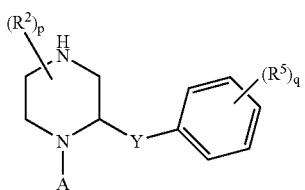

(19)

where X' is X that is other than a bond and all other variables are as defined previously. Compounds (19) are available from compounds (20):

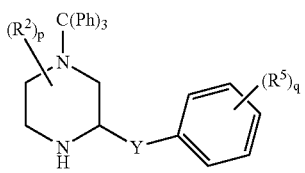

(20)

using the methods described previously for conversion of compounds (2) to compounds (1), followed by removal of the trityl group (e.g. by treatment with methanolic HCl). Compounds (20) are available via coupling of compounds (5a), (5b) or (5c) with the appropriate pyrazine derivatives in the manner described above for the synthesis of pyridines (3), followed by hydrogenation (as in the conversion of compounds (3) to compounds (2)) and tritylation by standard methods.

A preferred route to pyrrolidines of formula (1) in which V is a bond, p is 0 and X represents CH₂ involves the steps of (a) condensing an aldehyde (9) with t-butylsulphinamide and reacting the resulting imine with allylMgBr to provide the adduct (21a):

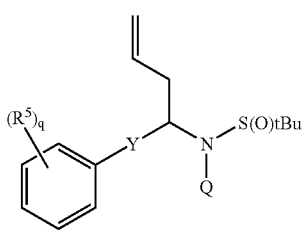

(21)

(a) Q = H
(b) Q = A (b) N-alkylation or arylation to provide compounds (21b) (e.g. by any of the methods described previously for converting (2) to (1));

(c) reaction with CH₂=CH—CO₂R in the presence of a ruthenium catalyst (e.g. Zhan I), followed by treatment with methanolic HCl, to provide compounds (22a):

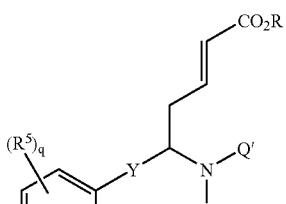

(22)

(a) Q' = H
(b) Q' = 1-benzotriazolylmethyl (d) reaction with 1-hydroxymethylbenzotriazole (e.g. in refluxing benzene with molecular sieves) to provide compounds (22b); and (e) cyclisation by treatment with SmI₂ and t-butanol in THF at −78° C.

It will be readily apparent that several of the above-described routes are suitable for the synthesis of compounds of formula IV. Thus, in one preferred route to compounds of formula IV, a piperidine of formula (2a), an aldehyde of formula (23) and benzotriazole are refluxed in toluene with azeotropic removal of water, and the resulting adduct reacted with $R^{7a}$—Zn—Hal

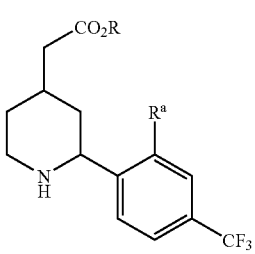

(2a)

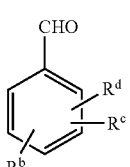

(23)

where Hal represents halide (preferably chloride) and $R^a$, $R^b$, $R^c$, $R^d$ and $R^{7a}$ have the same meanings as before. The reaction is suitably carried out in an anhydrous aprotic solvent such as dichloromethane at reduced temperature, e.g. below 10° C. Piperidines (2a) are available via coupling of pyridines (4b) with the appropriate boronic acid (5a) and further elaboration of the product as described previously.

In another preferred route to compounds of formula IV, a piperidine of formula (2a), an aldehyde of formula (23) and a 1-alkyne are subjected to microwave heating in the presence of gold(III) bromide (e.g. at about 70° C.), providing compounds of formula IV in which $R^{7a}$ is 1-alkynyl. If desired, the corresponding compounds in which $R^{7a}$ is alkyl or alkenyl may be obtained by hydrogenation of the alkynyl derivatives (e.g. in ethyl acetate over a Pd/C catalyst).

In a third route to compounds of formula IV, the appropriate diketone of formula (15) (Y=a bond) is reacted with an amine of formula (24):

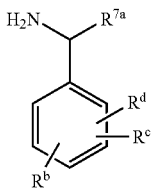

followed by treatment with sodium cyanoborohydride as described previously for the preparation of compounds (14). Thereafter, mono-decarboxylation (as described previously) and homologation (as described below) provide the compounds of formula IV.

Carboxylic acids of formula I in which X is a bond may be converted to the corresponding compounds in which X is $CH_2$ by standard methods of homologation, for example sequential treatment with oxalyl chloride; trimethylsilyldiazomethane and acetonitrile; ROH and silver benzoate; then hydrolysis of the resulting ester. Similar treatment of the corresponding compounds in which X is $CH_2$ provides the compounds in which X is $CH_2CH_2$. Esters of formula (1) in which X is $C(R^1)_2$ or $CH_2C(R^1)_2$ and at least one $R^1$ is other than H may be prepared by alkylation of the corresponding compounds in which each $R^1$ is H by standard methods.

Similarly, a given compound in accordance with formula I may be converted to a different compound in accordance with formula I by means of the standard techniques of bond formation or cleavage known to those skilled in the art of organic synthesis.

Where they are not themselves commercially available, the starting materials for the synthetic schemes described above are available by straightforward chemical modifications of commercially available materials.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallisation and regeneration of the free base. The novel compounds may also be resolved by formation of diastereomeric esters or amides, followed by chromatographic separation and removal of the chiral auxiliary. Alternatively, racemic intermediates in the preparation of compounds of formula I may be resolved by the aforementioned techniques, and the desired enantiomer used in subsequent steps. For example, racemic piperidine derivatives (2a) may be resolved via salt formation with L-mandelic acid.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, $3^{rd}$ ed., 1999. The protecting groups may be removed at a convenient subsequent stage using methods known from the art.

The compounds of the invention have the useful property of modifying the action of γ-secretase on amyloid precursor protein so as to selectively reduce the formation of the 1-42 isoform of Aβ, and hence find use in the development of treatments for diseases mediated by Aβ(1-42), in particular diseases involving deposition of β-amyloid in the brain.

According to a further aspect of the invention there is provided the use of a compound according to formula I as defined above, or a pharmaceutically acceptable salt thereof, for the manufacture of a medicament for treatment or prevention of a disease associated with the deposition of β-amyloid in the brain.

The disease associated with deposition of Aβ in the brain is typically Alzheimer's disease (AD), cerebral amyloid angiopathy, HCHWA-D, multi-infarct dementia, dementia pugilistica or Down syndrome, preferably AD.

In a further aspect, the invention provides the use of a compound of Formula I as defined above, or a pharmaceutically acceptable salt thereof, in the manufacture of a medicament for treating, preventing or delaying the onset of dementia associated with Alzheimer's disease, cerebral amyloid angiopathy, HCHWA-D, multi-infarct dementia, dementia pugilistica or Down syndrome.

The invention also provides a method of treating or preventing a disease associated with deposition of Aβ in the brain comprising administering to a patient in need thereof a therapeutically effective amount of a compound of Formula I as defined above or a pharmaceutically acceptable salt thereof.

In a further aspect, the invention provides a method of treating, preventing or delaying the onset of dementia associated with Alzheimer's disease, cerebral amyloid angiopathy, HCHWA-D, multi-infarct dementia, dementia pugilistica or Down syndrome comprising administering to a patient in need thereof a therapeutically effective amount of a compound of Formula I as defined above or a pharmaceutically acceptable salt thereof.

The compounds of Formula I modulate the action of γ-secretase so as to selectively attenuate production of the (1-42) isoform of Aβ without significantly lowering production of the shorter chain isoforms such as Aβ(1-40). This results in secretion of Aβ which has less tendency to self-aggregate and form insoluble deposits, is more easily cleared from the brain, and/or is less neurotoxic. Therefore, a further aspect of the invention provides a method for retarding, arresting or preventing the accumulation of Aβ in the brain comprising administering to a subject in need thereof a therapeutically effective amount of a compound of Formula I as defined above or a pharmaceutically acceptable salt thereof.

Because the compounds of formula I modulate the activity of γ-secretase, as opposed to suppressing said activity, it is believed that the therapeutic benefits described above will be obtained with a reduced risk of side effects, e.g. those that might arise from a disruption of other signalling pathways (e.g. Notch) which are controlled by γ-secretase.

In one embodiment of the invention, the compound of Formula I is administered to a patient suffering from AD, cerebral amyloid angiopathy, HCHWA-D, multi-infarct dementia, dementia pugilistica or Down syndrome, preferably AD.

In an alternative embodiment of the invention, the compound of Formula I is administered to a patient suffering from mild cognitive impairment or age-related cognitive decline. A favourable outcome of such treatment is prevention or delay of the onset of AD. Age-related cognitive decline and mild cognitive impairment (MCI) are conditions in which a memory deficit is present, but other diagnostic criteria for dementia are absent (Santacruz and Swagerty, *American Family Physician*, 63 (2001), 703-13). (See also "The ICD-10 Classification of Mental and Behavioural Disorders", Geneva: World Health Organisation, 1992, 64-5). As used herein, "age-related cognitive decline" implies a decline of at least six months' duration in at least one of: memory and learning; attention and concentration; thinking; language; and visuospatial functioning and a score of more than one standard deviation below the norm on standardized neuropsychologic testing such as the MMSE. In particular, there may be a progressive decline in memory. In the more severe condition MCI, the degree of memory impairment is outside the range considered normal for the age of the patient but AD is not present. The differential diagnosis of MCI and mild AD is described by Petersen et al., *Arch. Neurol.*, 56 (1999), 303-8. Further information on the differential diagnosis of MCI is provided by Knopman et al, *Mayo Clinic Proceedings*, 78 (2003), 1290-1308. In a study of elderly subjects, Tuokko et al (*Arch, Neurol.*, 60 (2003) 577-82) found that those exhibiting MCI at the outset had a three-fold increased risk of developing dementia within 5 years.

Grundman et al (*J. Mol. Neurosci.*, 19 (2002), 23-28) report that lower baseline hippocampal volume in MCI patients is a prognostic indicator for subsequent AD. Similarly, Andreasen et al (*Acta Neurol. Scand*, 107 (2003) 47-51) report that high CSF levels of total tau, high CSF levels of phospho-tau and lowered CSF levels of Aβ42 are all associated with increased risk of progression from MCI to AD.

Within this embodiment, the compound of Formula I is advantageously administered to patients who suffer impaired memory function but do not exhibit symptoms of dementia. Such impairment of memory function typically is not attributable to systemic or cerebral disease, such as stroke or metabolic disorders caused by pituitary dysfunction. Such patients may be in particular people aged 55 or over, especially people aged 60 or over, and preferably people aged 65 or over. Such patients may have normal patterns and levels of growth hormone secretion for their age. However, such patients may possess one or more additional risk factors for developing Alzheimer's disease. Such factors include a family history of the disease; a genetic predisposition to the disease; elevated serum cholesterol; and adult-onset diabetes mellitus.

In a particular embodiment of the invention, the compound of Formula I is administered to a patient suffering from age-related cognitive decline or MCI who additionally possesses one or more risk factors for developing AD selected from: a family history of the disease; a genetic predisposition to the disease; elevated serum cholesterol; adult-onset diabetes mellitus; elevated baseline hippocampal volume; elevated CSF levels of total tau; elevated CSF levels of phospho-tau; and lowered CSF levels of Aβ(1-42), A genetic predisposition (especially towards early onset AD) can arise from point mutations in one or more of a number of genes, including the APP, presenilin-1 and presenilin-2 genes. Also, subjects who are homozygous for the 64 isoform of the apolipoprotein E gene are at greater risk of developing AD.

The patient's degree of cognitive decline or impairment is advantageously assessed at regular intervals before, during and/or after a course of treatment in accordance with the invention, so that changes therein may be detected, e.g. the slowing or halting of cognitive decline. A variety of neuropyschological tests are known in the art for this purpose, such as the Mini-Mental State Examination (MMSE) with norms adjusted for age and education (Folstein et al., *J. Psych. Res.*, 12 (1975), 196-198, Anthony et al., *Psychological Med.*, 12 (1982), 397-408; Cockrell et al., *Psychopharmacology*, 24 (1988), 689-692; Crum et al., *J. Am. Med. Assoc'n.* 18 (1993), 2386-2391). The MMSE is a brief, quantitative measure of cognitive status in adults. It can be used to screen for cognitive decline or impairment, to estimate the severity of cognitive decline or impairment at a given point in time, to follow the course of cognitive changes in an individual over time, and to document an individual's response to treatment. Another suitable test is the Alzheimer Disease Assessment Scale (ADAS), in particular the cognitive element thereof (ADAS-cog) (See Rosen et al., *Am. J. Psychiatry*, 141 (1984), 1356-64).

The compounds of Formula I are typically used in the form of pharmaceutical compositions comprising one or more compounds of Formula I and a pharmaceutically acceptable carrier. Accordingly, in a further aspect the invention provides a pharmaceutical composition comprising a compound of formula I as defined above, or a pharmaceutically acceptable salt thereof, and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions useful in the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

For treating or preventing Alzheimer's disease, a suitable dosage level is about 0.01 to 250 mg/kg per day, preferably about 0.01 to 100 mg/kg per day, and more preferably about 0.05 to 50 mg/kg of body weight per day, of the active compound. The compounds may be administered on a regimen of 1 to 4 times per day. In some cases, however, a dosage outside these limits may be used.

The compounds of Formula I optionally may be administered in combination with one or more additional compounds known to be useful in the treatment or prevention of AD or the symptoms thereof. Such additional compounds thus include cognition-enhancing drugs such as acetylcholinesterase inhibitors (e.g. donepezil and galanthamine), NMDA antagonists (e.g. memantine) or PDE4 inhibitors (e.g. Ariflo™ and the classes of compounds disclosed in WO 03/018579, WO 01/46151, WO 02/074726 and WO 02/098878). Such additional compounds also include cholesterol-lowering drugs such as the statins, e.g. simvastatin. Such additional compounds similarly include compounds known to modify the production or processing of Aβ in the brain ("amyloid modifiers"), such as compounds which inhibit the secretion of Aβ (including γ-secretase inhibitors, β-secretase inhibitors, and GSK-3α inhibitors), compounds which inhibit the aggregation of Aβ, and antibodies which selectively bind to Aβ. Such additional compounds also include growth hormone secretagogues, as disclosed in WO 2004/110443.

In this embodiment of the invention, the amyloid modifier may be a compound which inhibits the secretion of Aβ, for example an inhibitor of γ-secretase (such as those disclosed in WO 01/53255, WO 01/66564, WO 01/70677, WO 01/90084, WO 01/77144, WO 02/30912, WO 02/36555, WO 02/081435, WO 02/081433, WO 03/018543, WO 03/093252, WO 03/093264, WO 03/093251, WO 03/093253, WO 03/013506, WO 03/013527 and WO 03/014075), or a O-secretase inhibitor (such as those disclosed in WO 03/037325, WO 03/030886, WO 03/006013, WO 03/006021, WO 03/006423, WO 03/006453, WO 02/002122, WO 01/70672, WO 02/02505, WO 02/02506, WO 02/02512, WO 02/02520, WO 02/098849 and WO 02/100820), or any other compound which inhibits the formation or release of Aβ including those disclosed in WO 98/28268, WO 02/47671, WO 99/67221, WO 01/34639, WO 01/34571, WO 00/07995, WO 00/38618, WO 01/92235, WO 01/77086, WO 01/74784, WO 01/74796, WO 01/74783, WO 01/60826, WO 01/19797, WO 01/27108, WO 01/27091, WO 00/50391, WO 02/057252, US 2002/0025955 and US2002/0022621, and also including GSK-3 inhibitors, particularly GSK-3α inhibitors, such as lithium, as disclosed in Phiel et al, *Nature*, 423 (2003), 435-9.

Within this embodiment, the amyloid modifier is advantageously a γ-secretase inhibitor, preferred examples of which include a compound of formula XI:

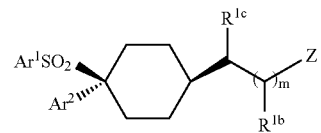

XI wherein m, Z, $R^{1b}$, $R^{1c}$, $Ar^1$ and $Ar^2$ are as defined in WO 03/018543;

or a pharmaceutically acceptable salt thereof.

Such compounds may be prepared as described in WO 03/018543. Preferred examples include those defined by formula XIa:

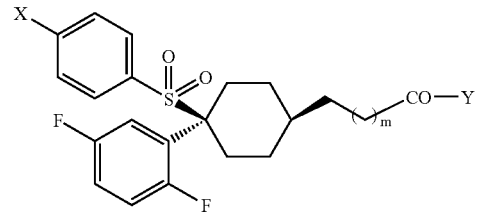

XI(a)

and the pharmaceutically acceptable salts thereof, wherein m is 0 or 1, X is $C_1$ or $CF_3$, and Y is OH, $OC_{1-6}$alkyl, $NH_2$ or $NHC_{1-6}$alkyl. Particular examples include those in which m is 1 and Y is OH (or the sodium salts thereof), and those in which m is 0 and Y is $NH_2$ or $NHC_{1-6}$alkyl.

Another preferred class of γ-secretase inhibitors for use in this embodiment of the invention is that defined by formula XII:

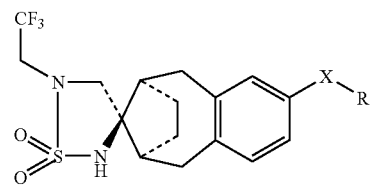

XII wherein X and R are as defined in WO 03/093252;

or a pharmaceutically acceptable salt thereof.

X is very aptly 5-substituted-thiazol-2-yl, 5-substituted-4-methylthiazol-2-yl, 5-substituted-1-methylpyrazol-3-yl, 1-substituted-imidazol-4-yl or 1-substituted-1,2,4-triazol-3-yl. Preferably, R represents optionally-substituted phenyl or heteroaryl such as phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Particularly preferred identities of R—X— include 5-(4-fluorophenyl)-1-methylpyrazol-3-yl, 5-(4-chlorophenyl)-1-methylpyrazol-3-yl and 1-(4-fluorophenyl)imidazol-4-yl. Such compounds may be prepared by methods disclosed in WO 03/093252.

Further preferred classes of γ-secretase inhibitors include those disclosed in WO 03/093264, WO 03/093251, WO 03/093253, WO 2004/039370, WO 2004/39800 and WO 2004/031139.

Alternatively, the amyloid modifier may be a compound which inhibits the aggregation of Aβ. Suitable examples include chelating agents such as clioquinol (Gouras and Beal, *Neuron*, 30 (2001), 641-2) and the compounds disclosed in WO 99/16741, in particular that known as DP-109 (Kalendarev et al, *J. Pharm. Biomed. Anal.*, 24 (2001), 967-75). Other inhibitors of Aβ aggregation suitable for use in the invention include the compounds disclosed in WO 96/28471, WO 98/08868 and WO 00/052048, including the compound known as Apan™ (Praecis); WO 00/064420, WO 03/017994, WO 99/59571 and the compound known as Alzhemed™ (Neurochem); WO 00/149281 and the compositions known as PTI-777 and PTI-00703 (ProteoTech); WO 96/39834, WO 01/83425, WO 01/55093, WO 00/76988, WO 00/76987, WO 00/76969, WO 00/76489, WO 97/26919, WO 97/16194, and WO 97/16191.

Alternatively, the amyloid modifier may be an antibody which binds selectively to Aβ. Said antibody may be polyclonal or monoclonal, but is preferably monoclonal, and is preferably human or humanized. Preferably, the antibody is capable of sequestering soluble Aβ from biological fluids, as described in WO 03/016466, WO 03/016467, WO 03/015691 and WO 01/62801. Suitable antibodies include humanized antibody 266 (described in WO 01/62801) and the modified version thereof described in WO 03/016466.

As used herein, the expression "in combination with" requires that therapeutically effective amounts of both the compound of Formula I and the additional compound are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible. When the additional compound is an antibody, it will typically be administered parenterally and separately from the compound of Formula I.

In a further aspect, the invention provides the combination of a compound of formula I or a pharmaceutically acceptable salt thereof and a compound of formula XI(a) or a pharmaceutically acceptable salt thereof for use in treatment or prevention of a disease associated with deposition of β-amyloid in the brain. Said use may involve the simultaneous or separate administration of the respective compounds to a patient in need of such treatment or prevention.

In a further aspect, the invention provides a pharmaceutical composition comprising, in a pharmaceutically acceptable carrier, a compound of formula I or a pharmaceutically acceptable salt thereof and a compound of formula XI(a) or a pharmaceutically acceptable salt thereof. Preferably, the pharmaceutical composition is in a unit dose form suitable for oral administration, such as a tablet or a capsule.

EXAMPLES

The ability of the compounds of Formula I to selectively inhibit production of Aβ(1-42) was determined using the following assay:

Cell-Based γ-Secretase Assay

Human SH-SY5Y neuroblastoma cells overexpressing the direct γ-secretase substrate SPA4CT were induced with sodium butyrate (10 mM) for 4 hours prior to plating. Cells were plated at 35,000 cells/well/100 μl in 96-well plates in phenol red-free MEM/10% FBS, 50 mM HEPES, 1% Glutamine and incubated for 2 hrs at 37° C., 5% $CO_2$.

Compounds for testing were diluted into $Me_2SO$ to give a ten point dose-response curve. Typically 10 μl of these diluted compounds in $Me_2SO$ were further diluted into 182 μl dilution buffer (phenol red-free MEM/10% FBS, 50 mM HEPES, 1% Glutamine) and 10 μl of each dilution was added to the cells in 96-well plates (yielding a final $Me_2SO$ concentration of 0.5%). Appropriate vehicle and inhibitor controls were used to determine the window of the assay.

After incubation overnight at 37° C., 5% $CO_2$, 10 μl and 50 μl media were transferred into a fresh Costar round-bottom 96-well plate for detection of Aβ(40) and Aβ(42) peptides, respectively. 40 μl Origen buffer (PBS, 2% BSA, 0.2% Tween-20) was added to the Aβ(40) wells followed by the addition of 25 μl the respective antibody premixes to the wells:

Aβ(40) premix: 1 μg/ml ruthenylated G2-10 antibody, 4 μg/ml biotinylated 4G8 antibody diluted in Origen buffer Aβ(42) premix: 0.5 μg/ml ruthenylated G2-11 antibody, 4 μg/ml biotinylated 4G8 antibody diluted in Origen buffer (Biotinylated 4G8 antibody supplied by Signet Pathology Ltd; G2-10 and G2-11 antibodies supplied by Chemicon)

After overnight incubation of the assay plates on a shaker at 4° C., the Origen M8 Analyser (Igen Inc.) was calibrated according to the manufacturer's instructions. 25 μl of streptavidin magnetic bead (Dynal) premix (400 μg/ml streptavidin beads/ml in Origen buffer) was added to the assay plates and incubated on a shaker for 15 minutes. 150 μl Origen buffer was added to each well and the plates were read on the Origen M8 Analyser according to the manufacturer's instructions.

Cell viability was measured in the corresponding cells after removal of the media for the Aβ assays by a colorimetric cell proliferation assay (CellTiter 96™ AQ assay, Promega) utilizing the bioreduction of MTS (Owen's reagent) to formazan according to the manufacturer's instructions. Briefly, 5 μl of 10×MTS/PES was added to the remaining 50 μl of media before returning to the incubator. The optical density was read at 495 nm after ~4 hours.

$LD_{50}$ and $IC_{50}$ values for inhibition of Aβ(40) and Aβ(42) were calculated by nonlinear regression fit analysis using the appropriate software (eg. Excel fit). The total signal and the background were defined by the corresponding $Me_2SO$ and inhibitor controls.

The compounds listed in the following examples all gave $IC_{50}$ values for Aβ(1-42) inhibition that were at least 2-fold lower than the corresponding $IC_{50}$ values for Aβ(1-40) inhibition, typically at least 5-fold lower, and in the preferred cases at least 50-fold lower.

Example 1 and 1a (±)-cis-{-(4-Isopropylphenyl)-2-[4-(trifluoromethyl)phenyl]piperidin-4-yl}acetic acid and (±)-trans-{1-(4-Isopropylphenyl)-2-[4-(trifluoromethyl)phenyl]piperidin-4-yl}acetic acid

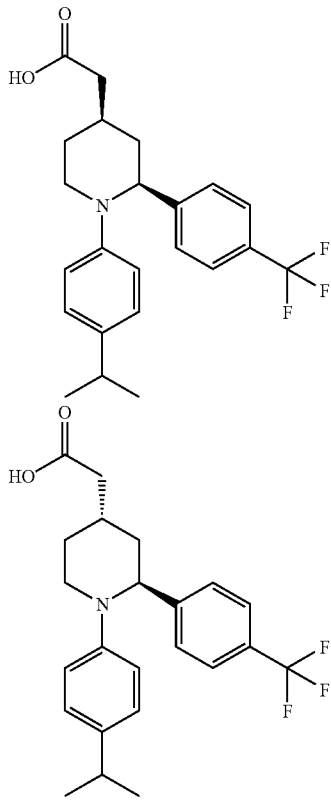

Step 1: (4-Isopropylphenyl){(1E)-[4-(trifluoromethyl)phenyl]methylene}amine

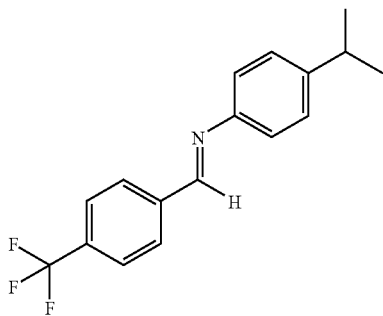

4-Isopropylaniline (5.5 ml, 40.2 mmol) was added to a vigorously stirred mixture of 4-(trifluoromethyl)benzaldehyde (5.5 ml, 40.2 mmol) in H₂O (60 ml) at room temperature. After 2 hours, DCM (100 ml) was added and the mixture was stirred for 20 minutes. The phases were separated and the organic phase was dried (Na₂SO₄), filtered and evaporated to give the imine (11.6 g, 99%) as a beige solid. ¹H NMR (360 MHz, CDCl₃) δ: 1.28 (6H, d, J 6.9), 2.95 (1H, septet, J 6.9), 7.18-7.21 (2H, m), 7.25-7.29 (2H, m), 7.71-7.73 (2H, m), 8.00-8.02 (2H, m), 8.52 (1H, s).

Step 2: (±)-1-(4-Isopropylphenyl)-2-[4-(trifluoromethyl)phenyl]-2,3-dihydropyridin-4(1H)-one

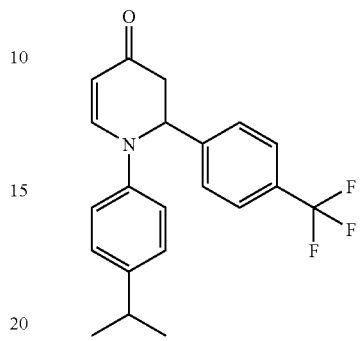

{[(2E)-3-Methoxy-1-methyleneprop-2-en-1-yl]oxy}(trimethyl)silane (5 g, 29 mmol) was added to a stirred solution of the imine (Step 1, 4.8 g, 16.5 mmol) and indium (III) trifluoromethanesulfonate (550 mg, 1.0 mmol) in dry acetonitrile (70 ml) at room temperature under N₂. After 3 hours the reaction was quenched with saturated aqueous NaHCO₃ solution (50 ml) and then diluted with EtOAc (100 ml). The layers were separated and the aqueous layer was further extracted with EtOAc (1×100 ml). The combined extracts were dried (Na₂SO₄), filtered and evaporated. The residue was purified by chromatography on silica, eluting with 20-40-60% EtOAc/isohexane to give the enone (3.98 g, 67%) as a yellow solid. ¹H NMR (400 MHz, CDCl₃) δ: 1.21 (6H, d, J 6.9), 2.75 (1H, ddd, f 16.4, 2.8, 1.1), 2.87 (1H, septet, J 6.9), 3.33 (1H, dd, J 16.4, 7.0), 5.26-5.32 (2H, m), 6.90-6.94 (2H, m), 7.15-7.18 (2H, m), 7.40 (2H, d, J 8.4), 7.59 (2H, d, J 8.2), 7.67 (1H, dd, J 7.8, 1.1); M/Z (ES⁺) 360 (MH⁺).

Step 3: (±)-(1-(4-Isopropylphenyl)-2-[4-(trifluoromethyl)phenyl]piperidin-4-one

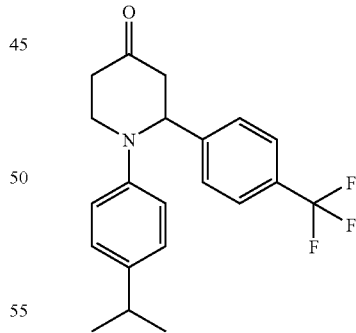

L-Selectride® (1.0 M in THF, 2.70 ml, 2.70 mmol) was added slowly to a stirred solution of the enone (Step 2, 950mg, 2.64 mmol) in dry THF (27 ml) under N₂, such that the internal temperature was kept below −70° C. The reaction was maintained at −78° C. for 90 minutes, then quenched with saturated aqueous NH₄Cl solution. After warming to room temperature the mixture was partitioned between EtOAc and H₂O. The layers were separated and the aqueous layer was further extracted with EtOAc (×2). The combined extracts were washed with brine (×1), dried (Na₂SO₄), filtered and evaporated. The residue was purified by chromatography on silica, eluting with 10-20% EtOAc/isohexane to give the ketone (820 mg, 85%) as an oil. $^1$H NMR (400 MHz, CDCl$_3$) δ: 1.21 (6H, d, J 6.9), 2.54-2.59 (1H, m), 2.61-2.67 (1H, m), 2.83 (1H, septet, J 6.9), 2.92 (1H, dd, J 15.5, 4.7), 3.00 (1H, dd, J 15.4, 6.1), 3.57-3.62 (1H, m), 3.72-3.77 (1H, m), 5.12 (1H, t, J 5.3), 6.80 (2H, d, J 8.6), 7.11 (2H, d, J 8.6), 7.43 (2H, d, J 8.2), 7.56 (2H, d, J 8.2); M/Z (ES$^+$) 362 (MH$^+$).

Step 4: (±)-Ethyl{1-(4-isopropylphenyl)-2-[4-(trifluoromethyl)phenyl]piperidin-4-ylidene}acetate

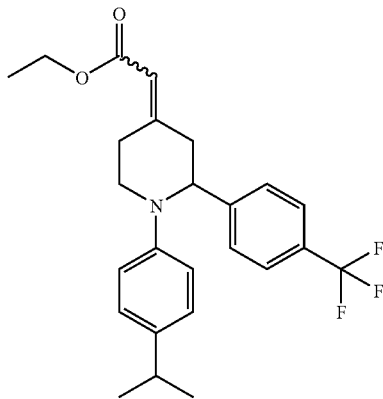

NaH (60% dispersion in oil, 352 mg, 8.8 mmol) was added portionwise to a stirred solution of triethylphosphonoacetate (1.75 ml, 8.8 mmol) in dry DMF (8 ml) at room temperature under N$_2$. After 45 minutes a solution of the ketone (Step 3, 800 mg, 2.2 mmol) in dry DMF (8 ml) was added. After 3 hours at room temperature the reaction was quenched with saturated aqueous NH$_4$Cl solution, then partitioned between EtOAc and H$_2$O. The layers were separated and the aqueous layer was further extracted with EtOAc (×2). The combined extracts were washed with brine (×1), dried (Na$_2$SO$_4$), filtered and evaporated. The residue was purified by chromatography on silica, eluting with 10-20% EtOAc/isohexane to give the unsaturated ester (886 mg, 90%, mixture of isomers) as an oil. M/Z (ES$^+$) 432 (M).

Step 5: (±)-Ethyl{1-(4-isopropylphenyl)-2-[4-(trifluoromethyl)phenyl]piperidin-4-yl}acetate

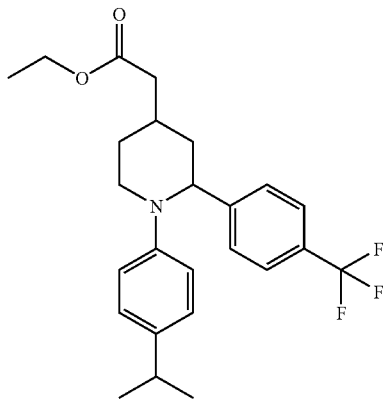

The unsaturated ester (Step 4, 149 mg, 0.35 mmol) was taken up in ethanol (25 ml) and hydrogenated at 25 psi over 10% Pd/C (20 mg) for 1 hour. The catalyst was removed by filtration. The filtrate was evaporated, and the residue was purified by chromatography on silica, eluting with 10-20% EtOAc/isohexane to give the saturated ester (122 mg, 80%, mixture of isomers) as an oil. M/Z (ES$^+$) 434

Step 6: (±)-cis-{1-(4-Isopropylphenyl)-2-[4-(trifluoromethyl)phenyl]piperidin-4-yl}acetic acid and (±)-trans-{1-(4-Isopropylphenyl)-2-[4-(trifluoromethyl)phenyl]piperidin-4-yl}acetic acid

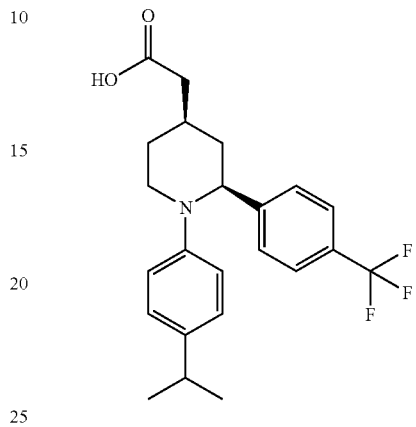

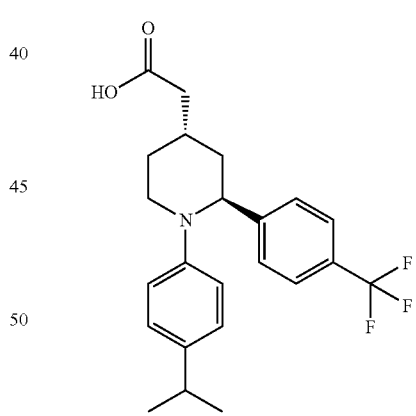

A solution of LiOH (48 mg, 2 mmol) in H$_2$O (0.5 ml) was added to a stirred solution of the ester (Step 4, 113 mg, 0.26 mmol) in THF (2 ml) at room temperature. After 16 hours an extra portion of LiOH (10 mg) was added and the mixture was heated at 75° C. for 90 minutes. After cooling to room temperature 2N HCl (1.5 ml) was added. The mixture was partitioned between EtOAc and H$_2$O. The layers were separated and the aqueous layer was further extracted with EtOAc (×2). The combined extracts were washed with brine (×1), dried (Na$_2$SO$_4$), filtered and evaporated. The residue was purified by reverse phase HPLC to give:

(±)-cis-{1-(4-Isopropylphenyl)-2-[4-(trifluoromethyl) phenyl]piperidin-4-yl}acetic acid (64 mg) as a colourless solid. $^1$H NMR (360 MHz, CD$_3$OD) δ: 1.11 (6H, d, J 6.9), 1.44 (1H, q, J 11.5), 1.64 (1H, qd, J 12.3, 3.8), 1.90-2.20 (3H, m), 2.29-2.31 (2H, m), 2.73 (1H, septet, J 6.9), 2.88-2.98 (1H, m), 3.48-3.53 (1H, m), 4.23 (1H, brd), 6.93-7.00 (4H, m), 7.40-7.46 (4H, m); M/Z (ES$^+$) 406 (MF$^+$).

(±)-trans-{1-(4-Isopropylphenyl)-2-[4-(trifluoromethyl) phenyl]piperidin-4-yl}acetic acid (21 mg) as a colourless solid. $^1$H NMR (360 MHz, CDCl$_3$) δ: 1.20 (6H, d, J 6.9), 1.47 (1H, qd, J 11.4, 4.1), 1.74-1.84 (2H, m), 1.95-2.08 (1H, m), 2.30-2.40 (3H, m), 2.81 (1H, septet, J 6.9), 3.16-3.24 (1H, m), 3.72 (1H, dt, J 13.3, 3.7), 5.10 (1H, brs), 6.80 (2H, d, J 8.7), 7.08 (2H, d, J 8.7), 7.45 (2H, d, J 8.3), 7.56 (2H, d, J 8.3); M/Z (ES$^+$) 406 (MH$^+$).

Example 2

[2R/S,(2R*,4S*)]-2-{1-(4-Isopropylphenyl)-2-[4-(trifluoromethyl)phenyl]piperidin-4-yl}propanoic acid

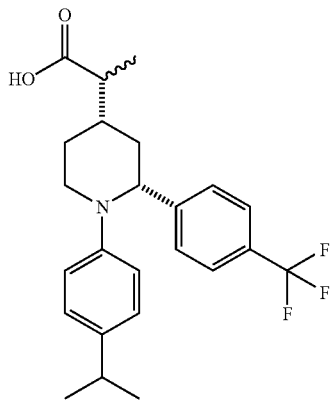

Step 1: [2R/S,(2R*,4S*)]-Ethyl 2-{1-(4-isopropylphenyl)-2-[4-(trifluoromethyl)phenyl]piperidin-4-yl}propanoate

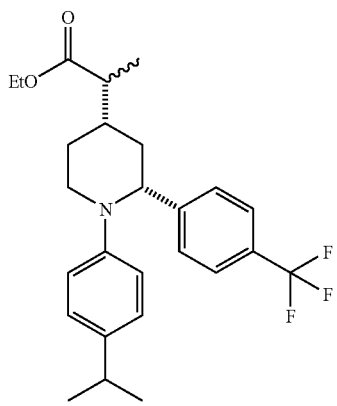

Lithium bis(trimethylsilyl)amide (1.0M in THF, 0.4 ml, 0.4 mmol) was added slowly to a stirred solution of the ester from Example 1, Step 5 (cis isomer, 155 mg, 0.36 mmol) in dry THF under N$_2$ at −78° C. After 30 minutes methyl iodide (45 μl, 0.72 mmol) was added. The reaction was maintained at this temperature for 30 minutes, then transferred to an ice bath. After 1 hour the reaction was quenched with saturated aqueous NaHCO$_3$, and then partitioned between EtOAc/ H$_2$O. The aqueous layer was extracted with EtOAc (×2). The combined extracts were washed with brine (×1), dried (Na$_2$SO$_4$), filtered and evaporated. The residue was purified by chromatography on silica, eluting with 5% EtOAc/isohexane to give the ester as a mixture of diastereomers (110 mg, 68%) as an oil. M/Z (ES$^+$) 448 (MH$^+$).

Step 2: [2R/S,(2R*,4S*)]-2-{1-(4-Isopropylphenyl)-2-[4-(trifluoromethyl)phenyl]piperidin-4-yl}propanoic acid

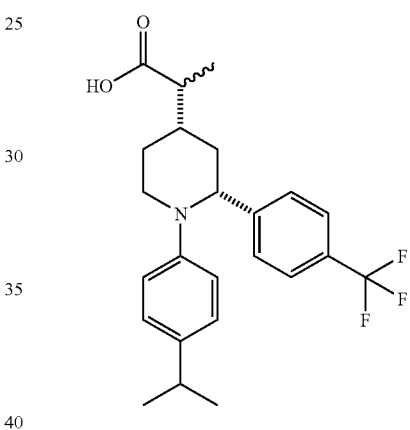

A solution of LiOH (27 mg, 1.1 mmol) in H$_2$O (0.5 ml) was added to a stirred solution of the ester (Step 1, 100 mg, 0.22 mmol) in THF (1 ml) at room temperature. After 60 hours an extra portion of LiOH (30 mg) and dioxane (1 ml) were added. The mixture was heated at 110° C. for 16 hours. After cooling to room temperature the mixture was acidified with 5N HCl. The mixture was partitioned between EtOAc/H$_2$O. The layers were separated and the aqueous layer was further extracted with EtOAc (×2). The combined extracts were washed with brine (×1), dried (Na$_2$SO$_4$), filtered and evaporated. The residue was purified by reverse phase HPLC to give the acid as a 3:2 mixture of diastereomers (90 mg, 94%) as colourless solid. $^1$H NMR (500 MHz, CDCl$_3$) δ: 1.12-1.14 (6H, m), 1.21-1.26 (3H, m), 2.01-2.25 (3H, m), 2.26-2.40 (1H, m), 2.50-2.59 (2H, m), 2.78-2.83 (1H, m), 3.48-3.51 (1H, m), 3.91-3.95 (1H, m), 4.35-4.40 (1H, m), 7.12-7.14 (2H, m), 7.24-7.26 (2H, m), 7.42-7.53 (4H, m); M/Z (ES$^+$) 420 (MH$^+$).

Example 3

(±)-cis-{1-(4-Chlorophenyl)-2-[4-(trifluoromethyl)phenyl]piperidin-4-yl}acetic acid

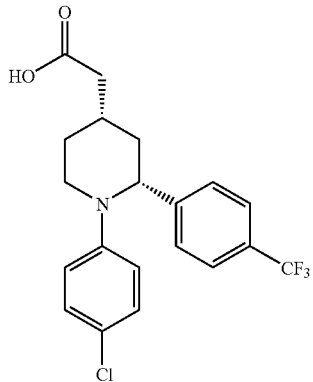

Step 1:
4-Methyl-2-[4-(trifluoromethyl)phenyl]pyridine

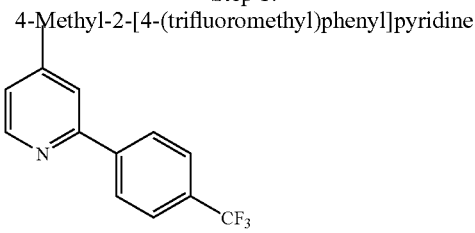

A mixture of 2-chloro-4-methylpyridine (1.9 ml, 21.6 mmol) and 4-(trifluoromethyl)benzeneboronic acid (5.0 g, 26 mmol) in DME (40 ml) and aqueous $Na_2CO_3$ (2M, 40 ml) was degassed (Firestone® valve×3). Tetrakis(triphenylphosphine) palladium (0) (1.15 g, 1.0 mmol, 5 mol %) was added and following a further degassing (Firestone® valve×3) the mixture was heated at reflux for 16 hours. The reaction was cooled to room temperature diluted with $H_2O$ (100 ml) and EtOAc (150 ml). The mixture was filtered through a Celite® pad, washing through with EtOAc. The phases were separated and the aqueous layer was extracted with EtOAc (200 ml). The combined extracts were washed with $H_2O$ (100 ml) and brine (×1), then dried ($MgSO_4$), filtered and evaporated. The residue was purified by chromatography on silica, eluting with 10% EtOAc/isohexane to give the ester (3.5 g, 68%) as a white solid. $^1$H NMR (360 MHz, $CDCl_3$) δ: 2.44 (3H, s), 7.13 (2H, d, J 5.0), 7.58 (1H, s), 7.72 (2H, d, J 8.2), 8.09 (2H, d, J 8.2), 8.57 (1H, d, J 5.0).

Step 2: Methyl{2-[4-(trifluoromethyl)phenyl]pyridin-4-yl}acetate

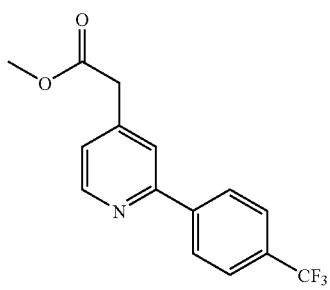

A solution of LDA (2M in THF/heptane/ethyl benzene, 44 ml, 88 mmol) was added dropwise to a stirred solution of 4-methyl-2-[4-(trifluoromethyl)phenyl]pyridine (10.5 g, 44 mmol) in dry THF (300 ml) under $N_2$, such that the internal temperature remained <−70° C. After 1 hour at this temperature, dimethyl carbonate (8.9 ml, 106 mmol) was added. After 30 minutes the cooling bath was removed. When the internal temperature had reached −20° C. the reaction was transferred to a cold bath at −10° C., and then allowed to warm slowly to 0° C. After 1 hour at 0° C. the reaction was quenched with aqueous $NH_4Cl$ (half saturated, 100 ml). The reaction mixture was concentrated in vacuo. The residue was diluted with $H_2O$ (200 ml) and extracted with EtOAc (2×200 ml). The combined extracts were washed with brine (×1), then dried ($MgSO_4$), filtered and evaporated. The residue was purified by chromatography on silica, eluting with 10-30% EtOAc/isohexane to give the ester (9.2 g, 71%) as a pale yellow liquid. $^1$H NMR (400 MHz, $CDCl_3$) δ: 3.72 (2H, s), 3.75 (3H, s), 7.24 (1H, dd, J 1.4, 5.0), 7.72 (3H, t, J 8.4), 8.11 (2H, d, J 8.2), 8.68 (1H, d, J 5.0).

Step 3: (±)-Methyl{2-[4-(trifluoromethyl)phenyl]piperidin-4-yl}acetate hydrochloride

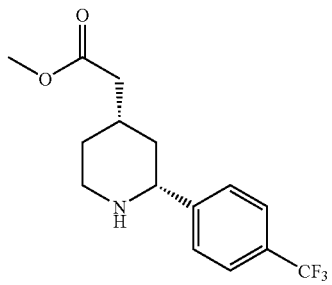

A mixture of methyl{2-[4-(trifluoromethyl)phenyl]pyridin-4-yl}acetate (6.2 g, 21 mmol), $PtO_2$ (200 mg, 0.9 mmol) and HCl solution (4N in dioxane, 5.8 ml, 23 mmol) in MeOH (100 ml) was hydrogenated at 20 psi on a Parr® apparatus for 5 hours. The catalyst was removed by filtration and the filtrate evaporated in vacuo to give the desired piperidine as white solid (7.1 g, quant). $^1$H NMR (400 MHz, $CD_3OD$) δ: 1.58-1.72 (1H, m), 1.75-1.85 (1H, m), 2.08 (1H, d, J 14.2), 2.19 (1H, t, J 14.2), 2.28-2.38 (1H, m), 2.45 (2H, d, J 6.9), 3.24-3.32 (1H, m), 3.51-3.57 (1H, m), 3.67 (3H, s), 4.46 (1H, d, J 10.2), 7.72 (2H, d, J 8.3), 7.79 (2H, d, J 8.4).

The free base was obtained by treatment with NaHCO$_3$ (aq) and extraction in to DCM. The organic extracts were dried, filtered and evaporated.

Step 4: (±)-Methyl{1-(4-chlorophenyl)-2-[4-(trifluoromethyl)phenyl]piperidin-4-yl}acetate

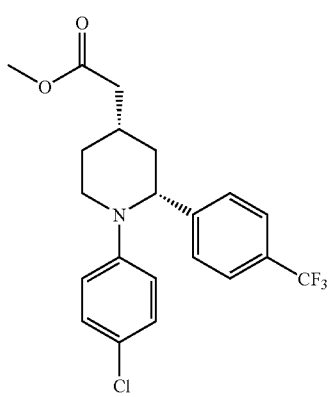

Potassium tert-butoxide (1M in THF, 1.1 ml, 1.1 mmol) was added to a mixture of tris (dibenzylideneacetone) dipalladium (0) (45 mg, 0.05 mmol) and 2-dicyclohexyl phosphino-2', 4', 6'-tripropyl-1,1'-biphenyl (95 mg, 0.2 mmol), under a N$_2$ atmosphere and the mixture was deoxygenated (evacuated and N$_2$ filled ×3). Methyl{2-[4-(trifluoromethyl) phenyl]piperidin-4-yl}acetate (free base, 301 mg, 11.0 mmol) and 4-bromo chlorobenzene (156 mg, 0.81 mmol) were added and the dark mixture was heated at reflux for 20 hours. The cooled mixture was diluted with H$_2$O (20 ml) and EtOAc (20 ml) and filtered through a Celite® pad. The phases were separated and the aqueous extracted with EtOAc (30 ml). The combined extracts were washed with brine (×1), then dried (MgSO$_4$), filtered and evaporated. The residue was purified by chromatography on silica, eluting with 7.5% EtOAc/isohexane to give the methyl ester (36 mg, 11%). $^1$H NMR (400 MHz, CDCl$_3$) δ: 1.29 (1H, m), 1.50-1.58 (1H, m), 1.81 (1H, d, J 12.5), 1.91 (1H, d, J 12.5), 1.99-2.08 (1H, m), 2.18-2.26 (2H, m), 2.71-2.79 (1H, m), 3.43 (1H, dt, J 12.5, 3.1), 3.60 (3H, s), 3.98 (1H, dd, J 2.8, 10.9), 6.77 (2H, d, 18.7), 6.98 (2H, d, J 8.7), 7.27 (2H, d, J 8.2), 7.35 (2H, d, J 8.3). Also obtained was the tert-butyl ester (26 mg, 7%). M/Z (ES$^+$) 454 (mW).

Step 5: (±)-{1-(4-Chlorophenyl)-2-[4-(trifluoromethyl)phenyl]piperidin-4-yl}acetic acid

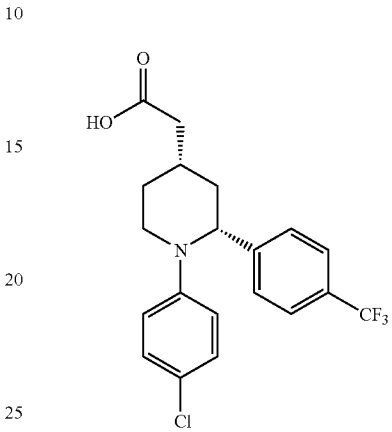

A solution of methyl{1-(4-chlorophenyl)-2-[4(trifluoromethyl)phenyl]piperidine-4-yl}acetate (34 mg, 0.08 mmol) in THF (2 ml) and H$_2$O (2 ml) was treated with LiOH (19 mg, 0.8 mmol) and the mixture was stirred at room temperature for 20 hours. The reaction was diluted with hydrochloric acid (1N, 20 ml) and extracted with EtOAc (2×20 ml). The combined extracts were washed with brine (×1), then dried (MgSO$_4$), filtered and evaporated. The residue was purified by chromatography on silica, eluting with 7.5% MeOH/DCM give the acid as a clear gum (15 mg, 45%). $^1$H NMR (400 MHz, CD$_3$OD) δ: 1.34-1.40 (1H, m), 1.54-1.67 (1H, m), 1.84-2.12 (3H, m), 2.24-2.30 (2H, m), 2.86 (1H, dt, J 12.1, 2.4), 3.47-3.54 (1H, m), 4.15 (1H, dd, J 11.5, 2.7), 6.95 (2H, d, J 8.8), 7.06 (2H, d, J 8.8), 7.44 (4H, s).

Examples 4-8

The examples in the following table were prepared in an analogous manner to Example 3:

| Example | Structure | Name | M/Z ES$^+$ [MH]$^+$ |
|---|---|---|---|
| 4 | 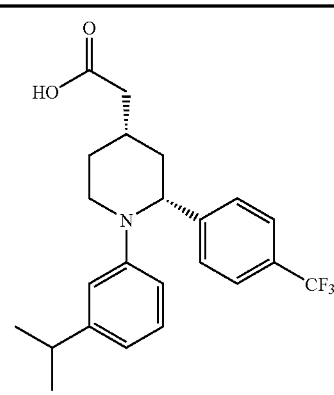 | (±)-cis-{1-(3-Isopropylphenyl)-2-[4-(trifluoromethyl)phenyl]piperidin-4-yl}acetic acid | 406 |

-continued

| Example | Structure | Name | M/Z ES+ [MH]+ |
|---|---|---|---|
| 5 | 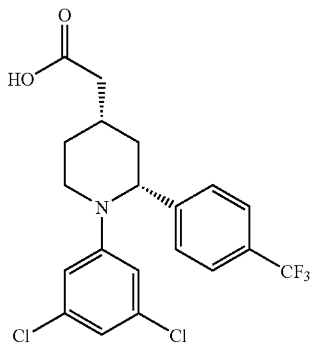 | (±)-cis-{1-(3,5-Dichlorophenyl)-2-[4-(trifluoromethyl)phenyl]piperidin-4-yl}acetic acid | 432/434 |
| 6† | 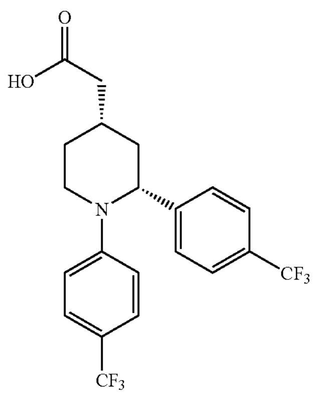 | (±)-cis-{1,2-Bis[4-(trifluoromethyl)phenyl]piperidin-4-yl}acetic acid | 432 |
| 7* | 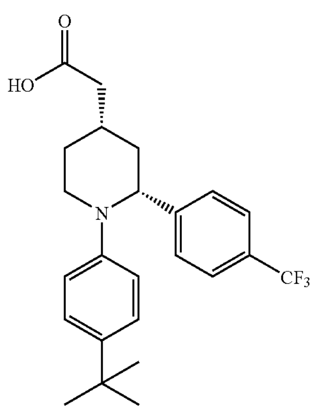 | (±)-cis-{1-(4-tert-Butylphenyl)-2-[4-(trifluoromethyl)phenyl]piperidin-4-yl}acetic acid | 420 |
| 8* | 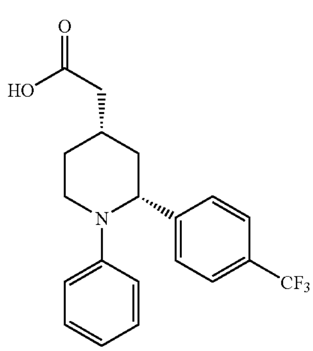 | (±)-cis-{1-Phenyl-2-[4-(trifluoromethyl)phenyl]piperidin-4-yl}acetic acid | 364 |

*Reaction carried out with 2 equivalents of butoxide and heated at 150° C. under microwave irradiation for 1 hour.
†Reaction carried out with 1 equivalent of butoxide and heated at 150° C. under microwave irradiation for 1 hour.

Example 9

(±)-cis-{2-(4-Isopropylphenyl)-1-[4-(trifluoromethyl)phenyl]piperidin-4-yl}acetic acid

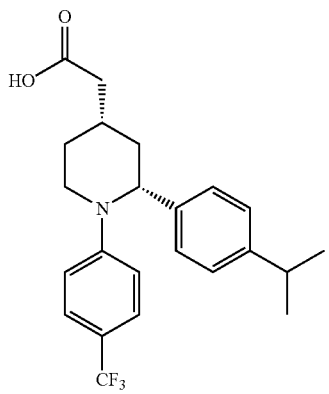

The title compound was prepared in the same manner as Example 3 substituting 4-(isopropyl)phenylboronic acid for 4-(trifluoromethyl)benzeneboronic acid in Step 2 and using the coupling procedure used to prepare Example 7. M/Z (ES$^+$) 406 (MH$^+$).

Example 10

(±)-cis-[1,2-Bis(4-isopropylphenyl)piperidin-4-yl] acetic acid

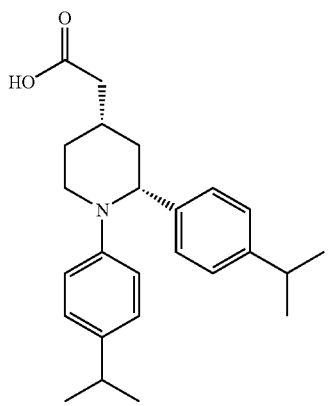

The title compound was prepared in the same manner as Example 3 substituting 4-(isopropyl)phenylboronic acid for 4-(trifluoromethyl)benzeneboronic acid and using the coupling procedure used to prepare Example 7. M/Z (ES$^+$) 380 (M+).

Example 11

(±)-cis-{1-(4-Isopropylphenyl)-2-[4-(trifluoromethoxy)phenyl]piperidin-4-yl}acetic acid

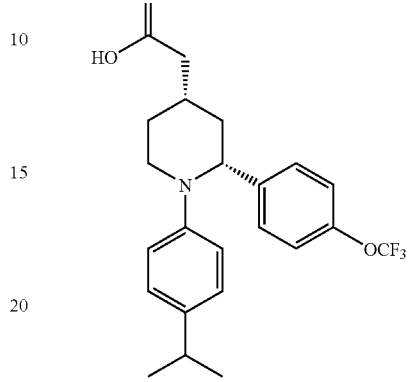

Step 1: Methyl(2-chloropyridin-4-yl)acetate

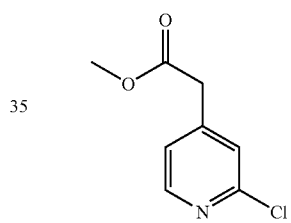

A solution of LDA (1.8M in THF/heptane/ethyl benzene, 223 ml, 401 mmol) was added slowly to a stirred solution of 2-chloro-4-methylpyridine (17.5 ml, 200 mmol) in dry THF (1 L) under N$_2$, such that the internal temperature <−70° C. After 1 hour at this temperature, dimethyl carbonate (40 ml, 475 mmol) was added. After 30 minutes the reaction was transferred to a cold bath at −40° C., and then allowed to warm slowly to 0° C. After 1 hour at 0° C. the reaction was quenched with saturated aqueous NH$_4$Cl (250 ml). The mixture was partitioned between EtOAc/H$_2$O. The aqueous layer was extracted with EtOAc (×2). The combined extracts were washed with brine (×1), then dried (Na$_2$SO$_4$), filtered and evaporated. The residue was purified by chromatography on silica, eluting with 10-25% EtOAc/isohexane to give the ester (27.8 g, 75%) as a pale yellow liquid. $^1$H NMR (400 MHz, CDCl$_3$) δ: 3.63 (2H, s), 3.73 (3H, s), 7.17 (1H, dd, J 5.1, 1.4), 7.28 (1H, s), 8.34 (1H, d, J 5.1).

Step 2: Methyl{2-[4-(trifluoromethoxy)phenyl]pyridin-4-yl}acetate

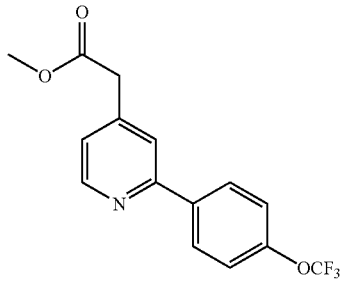

A mixture of methyl(2-chloropyridin-4-yl)acetate (1.0 g, 5.4 mmol), 4-(trifluoromethoxy)phenylboronic acid (1.67 g, 8.0 mmol) and potassium phosphate (1.7 g, 8.0 mmol) in toluene (15 ml) was degassed, evacuated and $N_2$ filled (×3). [1,1'-bis(diphenylphosphino)ferrocene]dichloro palladium (H), complex with DCM (1:1) (330 mg, 0.4 mmol, 5 mol %) was added and following a further degassing, evacuation and $N_2$ fill (×3), the mixture was heated at reflux for 16 hours. The reaction was cooled to room temperature and diluted with EtOAc (100 ml). The mixture was filtered through a Celite® pad, washing through with EtOAc and the filtrate was evaporated. The residue was purified by chromatography on silica, eluting with 15-20% EtOAc/isohexane to give the ester (1.25 g, 75%) as a pale gum. $^1$H NMR (400 MHz, $CDCl_3$) δ: 3.70 (2H, s), 3.74 (3H, s), 7.20 (1H, dd, J 1.5, 5.0), 7.31 (2H, d, J 8.8), 7.64 (1H, s), 8.00-8.04 (2H, m), 8.64 (1H, d, J 5.0).

Step 3: (±)-Methyl-2-[4-(trifluoromethoxy)phenyl]piperidin-4-yl}acetate Hydrochloride

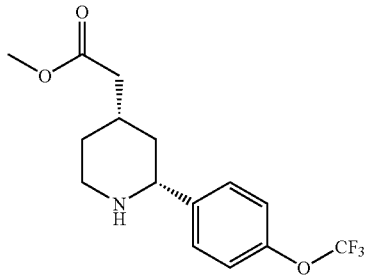

A mixture of methyl {2-[4-(trifluoromethoxy)phenyl]pyridin-4-yl}acetate (1.15 g, 3.7 mmol), $PtO_2$ (50 mg, 0.22 mmol) and HCl solution (4N in dioxane, 1.0 ml, 4.0 mmol) in MeOH (50 ml) was hydrogenated at 20 psi on a Parr® apparatus for 5 hours. The catalyst was removed by filtration and the filtrate evaporated in vacuo. The residue was triturated with $Et_2O$/EtOAC to give the desired piperidine hydrochloride as a white solid (0.69 g, 53%). $^1$H NMR (500 MHz, $CDCl_3$): δ: 7.65 (2H, d, J 8.6), 7.20 (2H, d, J 8.2), 3.97 (1H, d, J 11.9), 3.67 (3H, s), 3.04 (1H, d, J 12.3), 2.81 (1H, s), 2.39-2.29 (2H, m), 2.15 (1H, s), 2.05 (1H, d, J 14.0), 1.89-1.75 (3H, m).

Step 4: (±)-{(2R*,4S*)-1-(4-Isopropylphenyl)-2-[4-(trifluoromethoxy)phenyl]piperidin-4-yl}acetic acid

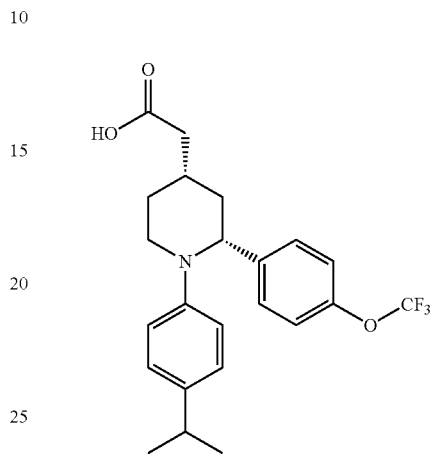

The title compound was prepared from methyl 2-[4-(trifluoromethoxy)phenyl]piperidin-4-yl}acetate (Step 3) coupling in the same manner as Example 7, substituting the appropriate aryl bromide, and hydrolysing as example 3 step 5. M/Z (ES$^+$) 422 (MH$^+$).

Example 12

(±)-cis-{1-(4-Isopropylphenyl)-2-[3-(trifluoromethyl)phenyl]piperidin-4-yl}acetic acid

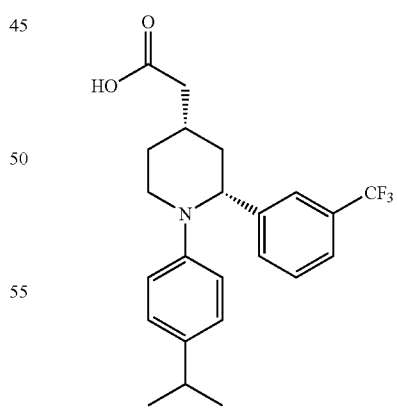

The title compound was prepared in the same manner as Example 3 substituting 3-(trifluoromethyl)phenylboronic acid for 4-(trifluoromethyl)benzeneboronic acid and using the coupling procedure used to prepare Example 7. M/Z (ES$^+$) 406 (MH$^+$).

Example 13

(±)-(3R*,6R*)-1-(4-Isopropylphenyl)-6-[4-(trifluoromethyl)phenyl]piperidine-3-carboxylic acid

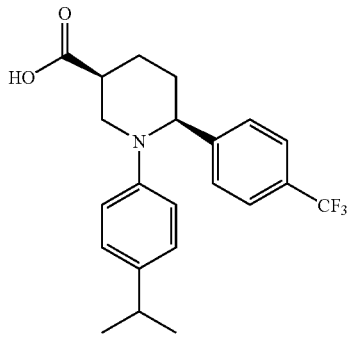

a) (±)-(4-Isopropylphenyl){1-[4-(trifluoromethyl)phenyl]but-3-en-1-yl}amine

Lanthanum triflate (0.141 g, 0.24 mmol, 2 mol %) and benzoic acid (1.49 g, 12.2 mmol) were dissolved in CH$_3$CN (20 ml) and the suspension was stirred under nitrogen until dissolved. 4-(Trifluoromethyl)benzaldehyde (2.12 g, 12.2 mmol) was added followed by 4-isopropylaniline (1.65 g). Allyl(tributyl)stannane (4.54 ml, 14.6 mmol) was then added and the mixture was stirred at room temperature overnight. The mixture was then quenched with NaOH (2M, 20 ml) and extracted into DCM (3×100 ml). The combined extracts were dried (MgSO$_4$) and the solvent was removed in vacuo to yield the crude homoallylic amine product. This was purified by chromatography on silica using 10-30% ether in hexane as eluant to yield the product as a colourless oil (3.65 g, 90%). $^1$H NMR (500 MHz, CDCl$_3$) δ: 1.16 (6H, dd, J 1.3, 6.9), 2.42-2.48 (1H, m), 2.56-2.62 (1H, m), 2.71-2.79 (1H, qn, J 6.7), 4.07 (1H, s), 4.38 (1H, dd, J 4.9, 8.1), 5.18 (2H, m), 5.69-5.77 (1H, m), 6.40 (2H, d, J 8.4), 6.95 (2H, d, J 8.5), 7.49 (2H, d, J 8.1), 7.57 (2H, d, J 8.1); M/Z (ES$^+$) 334 (MH$^+$).

b) (±)-Methyl 2-[((4-isopropylphenyl){1-[4-(trifluoromethyl)phenyl]but-3-en-1-yl}amino)methyl]acrylate The homoallylic amine described in a) above (3.33 g, 0.01 mol) was dissolved in DCM (30 ml) and Et$_3$N (2 nm, 0.015 mol) was added and the solution was cooled to 0° C. Methyl 2-(bromomethyl)acrylate (1.8 ml, 0.015 mol) was added dropwise and the mixture was stirred overnight at room temperature. The solution was washed with water, dried (MgSO$_4$) and the solvent was removed in vacuo to yield the crude amine product. This was purified by chromatography on silica using 5-20% ether in hexane as eluant to yield the product as a pale orange oil (3.85 g, 90%). $^1$H NMR (500 MHz, CDCl$_3$) δ: 1.21 (6H, d, J 6.9), 2.72-2.84 (3H, m), 3.74 (3H, s), 3.96 (1H, d, J 18.7), 4.05 (1H, d, J 18.7), 5.03-5.11 (3H, m), 5.60 (1H, d, J 1.4), 5.75-5.83 (1H, m), 6.16 (1H, d, J 1.3), 6.69 (2H, d, J 8.7), 7.06 (2H, d, J 8.6), 7.39 (2H, d, J 8.1), 7.54 (2H, d, J 8.1); M/Z (ES$^+$) 432 (MH$^+$).

c) (±)-Methyl 1-(4-isopropylphenyl)-6-[4-(trifluoromethyl)phenyl]-1,2,5,6-tetrahydropyridine-3-carboxylate The diene described in b) above (4.3 g, 0.01 mol) was dissolved in DCM (30 ml) under nitrogen. Grubbs II catalyst [1,3-bis-(2,4,6-(trimethylphenyl)-2-imidazolidinylidene)dichloro(phenylmethylene)-tricyclohexylphosphine]ruthenium (0.169 g, 2 mol %) was added and the mixture was stirred for 4 h. The mixture was stirred with charcoal overnight. The charcoal was removed by filtration through Celite and the solvent was removed in vacuo. The crude product was purified by chromatography on silica using 5-20% ether in hexane as eluant to yield the product as a colourless oil (3.6 g, 90%). $^1$H NMR (500 MHz, CDCl$_3$) δ: 1.21 (6H, d, J 6.9), 2.76 (1H, dd, J 5.8, 19.8), 2.82 (1H, qn, J 6.9), 2.92-2.98 (1H, m), 3.76 (3H, s), 3.76 (1H, m), 4.08 (1H, d, J 17.6), 5.11 (1H, d, J 5.1), 6.84 (2H, d, J 8.6), 7.11 (2H, d, J 8.6), 7.15 (1H, dd, J 2.4, 5.5), 7.23 (4H, s), 7.48 (2H, d, J 8.2); M/Z (ES$^+$) 404 (MH$^+$).

d) (±)-Methyl(3R*,6R*)-1-(4-isopropylphenyl)-6-[4-(trifluoromethyl)phenyl]piperidine-3-carboxylate The tetrahydropyridine described in c) above (1.01 g, 2.5 mmol) was dissolved in MeOH (anhydrous, 50 ml) and Mg (0.6 g, excess) was added. The mixture was stirred for 1 h whereupon an exothermic reaction developed. This was stirred overnight under nitrogen. The solution was neutralized by pouring onto cold HCl (1N) and was then extracted with EtOAc. The combined extracts were washed with water, brine, dried (MgSO$_4$) and concentrated in vacuo. Analysis of the mixture by $^1$H NMR showed the major product to be the cis isomer. The crude product was dissolved in MeOH (anhydrous, 50 ml) and sodium (0.6 g, excess) was added. This solution was heated under reflux overnight and then cooled in ice. The solution was neutralized by pouring onto cold HCl (1N) and was then extracted with EtOAc. The combined extracts were washed with water, brine, dried (MgSO$_4$) and concentrated in vacuo to give a mixture of 2 epimers which were separated by chromatography on silica using DCM as eluant.

Analyses for epimer a, cis ester: $^1$H NMR (500 MHz, CDCl$_3$) δ: 1.19 (6H, d, J 6.9), 1.85-1.91 (2H, m), 1.97-2.04 (1H, m), 2.15-2.21 (1H, m), 2.74-2.82 (2H, m), 3.42 (1H, dd, J 9.0, 13.5), 3.67 (1H, t, J 6.8), 3.73 (3H, s), 4.76 (1H, t, J 4.8), 6.83 (2H, d, J 8.6), 7.06 (2H, d, J 8.5), 7.41 (2H, d, J 8.1), 7.52 (2H, d, J 8.2); M/Z (ES$^+$) 406 (MH$^+$).

e) (±)-(3R*,6R*)-1-(4-Isopropylphenyl)-6-[4-(trifluoromethyl)phenyl]piperidine-3-carboxylic acid The cis ester described in d) (200 mg, 0.5 mmol) above was dissolved in MeOH (2 ml) and NaOH (0.6 ml, 4N) was added. The solution was heated at 60° C. overnight. The cooled solution was evaporated and neutralized with HCl (2 ml, 2N) and extracted with EtOAc. The combined extracts were washed with water, brine, dried (MgSO$_4$) and concentrated in vacuo to give a colourless oil. This was purified by chromatography on silica using 50-75% EtOAc in hexane as eluant. It was further purified by recrystallisation from hexane to give colourless crystals. $^1$H NMR (500 MHz, CDCl$_3$) δ: 1.14 (6H, d, J 6.9), 1.91-2.13 (3H, m), 2.18-2.20 (1H, m), 2.73-2.81 (1H, m), 2.90 (1H, s), 3.29 (1H, dd, J 2.3, 12.7), 3.53 (1H, dd, J 3.9, 12.6), 4.30 (1H, dd, J 3.2, 9.3), 6.92 (2H, d, J 8.4), 7.03 (2H, d, J 8.4), 7.31 (2H, d, J 8.0), 7.45 (2H, d, J 8.1); M/Z (ES$^+$) 392 (MH$^+$).

Example 13a (±)-(3R*,6S*)-1-(4-Isopropylphenyl)-6-[4-(trifluoromethyl)phenyl]piperidin-3-yl}acetic acid

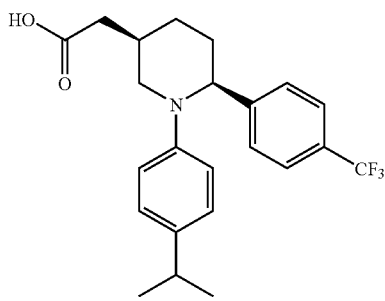

a) (±)-Benzyl{(3R*,6S*)-1-(4-isopropylphenyl)-6-[4-(trifluoromethyl)phenyl]piperidin-3-yl}acetate The compound of Example 13 (100 mg, 0.25 mmol) was dissolved in DCM (2 ml) and oxalyl chloride (0.12 ml) was added followed by 1 drop DMF. Effervescence was observed and slowly a white precipitate appeared over 30 min. The reaction was monitored by quenching an aliquot of reaction mixture in MeOH and this was analysed by mass spectrometry. The mixture was evaporated and dried in vacuo. It was re-dissolved in $CH_3CN$ (1.5 ml) and THF (1.5 ml) and cooled to 0° C. Trimethylsilyldiazomethane (0.5 ml, 2M in hexane) was added and the mixture was stirred overnight. The solution was evaporated and benzyl alcohol (55 µl) and 2,4,6-trimethylpyridine (2 ml) were added and the mixture was heated in an oil bath pre-heated to 180° C. for 7 min. The solution was cooled and the dark mixture was diluted with EtOAc and washed with citric acid (10%), $H_2O$, brine and the organic extract was dried ($MgSO_4$) and evaporated. The crude material was purified by chromatography on silica using 5-10% ether in hexane as eluant to give the product as a white solid (40 mg, 40%). $^1$H NMR (400 MHz, $CDCl_3$) δ: 1.17-1.23 (6H, d, J 6.9), 1.27-1.35 (1H, m), 1.69-1.81 (1H, m), 1.97-2.05 (1H, m), 2.12-2.19 (1H, m), 2.28-2.46 (3H, m), 2.79 (1H, qn, J 6.9), 2.90 (1H, dd, J 9.0, 13.3), 3.59 (1H, dd, J 3.7, 13.8), 4.80 (1H, s), 5.15 (2H, s), 6.77 (2H, d, J 8.6), 7.01 (2H, d, J 8.6), 7.33-7.37 (5H, m), 7.40 (2H, d, J 8.2), 7.51 (2H, d, J 8.2); M/Z (ES$^+$) 496 (MH$^+$).

b) (±)-(3R*,6S*)-1-(4-Isopropylphenyl)-6-[4-(trifluoromethyl)phenyl]piperidin-3-yl}acetic acid The benzyl ester described in a) above (40 mg) was dissolved in EtOAc and palladium on carbon (10%, 10 mg) was added. The mixture was hydrogenated at 1 atm $H_2$ for 2 h. The mixture was filtered to remove palladium and the solvent was evaporated. The crude product was crystallized from isohexane to give the product as white crystals. $^1$H NMR (500 MHz, $CDCl_3$) δ: 1.19 (6H, d, J 6.9), 1.34-1.41 (1H, m), 1.78-1.82 (1H, m), 1.98-2.05 (1H, m), 2.12-2.18 (1H, m), 2.30-2.32 (1H, m), 2.39 (1H, dd, J 6.2, 15.8), 2.48 (1H, dd, J 7.7, 15.8), 2.75-2.82 (1H, qn, J 6.9), 2.96 (1H, dd, J 8.7, 13.2), 3.60 (1H, dd, J 3.5, 13.2), 4.77 (1H, t, J 4.5), 6.83 (2H, d, J 8.6), 7.05 (2H, d, J 8.5), 7.42 (2H, d, J 8.2), 7.53 (2H, d, J 8.2); M/Z (ES$^+$) 406 (MH$^+$).

Example 14

(±)-(3R*,6S*)-1-(4-Isopropylphenyl)-6-[4-(trifluoromethyl)phenyl]piperidine-3-carboxylic acid a) (±)-Methyl(3R*,6S*)-1-(4-isopropylphenyl)-6-[4-(trifluoromethyl)phenyl]piperidine-3-carboxylate The crude mixture of epimers described in Example 13(d) was separated by chromatography on silica using DCM as eluant to afford isomer b, the trans isomer (60%) as a colourless oil.

Analyses for epimer b, trans ester: $^1$H NMR (500 MHz, $CDCl_3$) δ: 1.14 (6H, dd, J 2.1, 6.9), 1.67-1.77 (2H, m), 2.00-2.12 (2H, m), 2.70-2.78 (1H, m), 2.84-2.90 (1H, m), 3.01 (1H, t, J 11.3), 3.68 (4H, s), 4.11 (1H, t, J 4.6), 6.85 (2H, d, J 8.5), 6.97 (2H, d, J 8.4), 7.36 (2H, d, J 8.2), 7.42 (2H, d, J 8.2); M/Z (ES$^+$) 406 (MH$^+$).

b) (±)-(3R*,6S*)-1-(4-Isopropylphenyl)-6-[4-(trifluoromethyl)phenyl]piperidine-3-carboxylic acid The trans ester described in a) above (200 mg, 0.5 mmol) above was dissolved in MeOH (2 ml) and NaOH (0.6 ml, 4N) was added. The solution was heated at 60° C. overnight. The cooled solution was evaporated and neutralized with HCl (2 ml, 2N) and extracted with EtOAc. The combined extracts were washed with water, brine, dried ($MgSO_4$) and concentrated in vacuo to give a colourless oil. This was purified by chromatography on silica using 50-75% EtOAc in hexane as eluant. It was further purified by recrystallisation from hexane to give colourless crystals. $^1$H NMR (500 MHz, $CDCl_3$) δ: 1.11 (6H, dd, J 1.6, 6.9), 1.67-1.75 (2H, m), 1.98-2.02 (1H, m), 2.15 (1H, s), 2.69-2.75 (1H, m), 2.86-2.90 (2H, m), 3.63 (1H, d, J 9.4), 4.13 (1H, d, J 10.0, 3.1), 6.95 (4H, q, J 8.8), 7.43 (4H, q, J 6.9); M/Z (ES$^+$) 392 (MH$^+$).

Example 14a (±)-{(3R*,6R*)-1-(4-Isopropylphenyl)-6-[4-(trifluoromethyl)phenyl]piperidin-3-yl}acetic acid

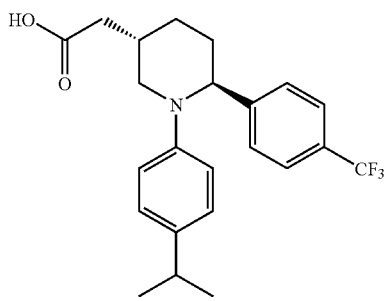

(a) (±)-Benzyl{(3R*,6R*)-1-(4-isopropylphenyl)-6-[4-(trifluoromethyl)phenyl]piperidin-3-yl}acetate The compound of Example 14 was reacted according to the procedure described in Example 13a (section a) to afford the homologated benzyl ester: $^1$H NMR (400 MHz, CDCl$_3$) δ: 1.14 (6H, dd, J 1.8, 7.0), 1.19-1.29 (1H, m), 1.67-1.73 (1H, m), 1.88-1.98 (2H, m), 2.27-2.33 (2H, m), 2.37-2.43 (1H, m), 2.56 (1H, dd, J 10.0, 11.7), 2.69-2.77 (1H, qn, J 6.7), 3.50 (1H, dd, J 2.0, 11.7), 4.04 (1H, dd, J 2.4, 9.8), 5.14 (2H, d, J 1.0), 6.79 (2H, d, J 8.6), 6.94 (2H, d, J 8.6), 7.34-7.42 (9H, m); M/Z (ES$^+$) 496 (MH$^+$).

b) (±)-(3R*,6R*)-1-(4-Isopropylphenyl)-6-[4-(trifluoromethyl)phenyl]piperidin-3-yl}acetic acid The benzyl ester described above was hydrogenated according to the procedure described in Example 13a (section b) to give the product:
$^1$H NMR (500 MHz, CDCl$_3$) δ: 1.13 (6H, dd, J 2.1, 6.9), 1.23-1.21 (1H, m), 1.66-1.75 (1H, m), 1.95-1.99 (2H, m), 2.28-2.43 (3H, m), 2.59 (1H, t, J 11.0), 2.73 (1H, qn, J 6.7), 3.53 (1H, dd, J 11.6, 2.5), 4.06 (1H, dd, J 10.6, 2.3), 6.84 (2H, d, J 8.5), 6.96 (2H, d, J 8.4), 7.36 (2H, d, J 8.2), 7.41 (2H, d, J 8.2); M/Z (ES$^+$) 406 (MH$^+$).

Example 15

(±)-{(2R*,3R*)-1-(4-Isopropylphenyl)-2-[4-(trifluoromethyl)phenyl]piperidin-3-yl}acetic acid

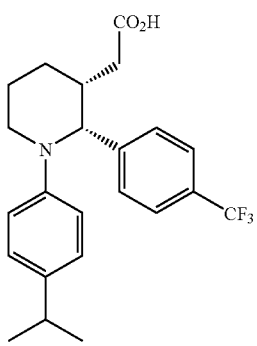

Step 1: 3-Methyl-2-[4-(trifluoromethyl)phenyl]pyridine

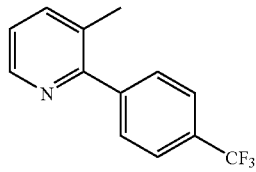

A mixture of 2-chloro-3-methylpyridine (6.38 g, 50 mmol) and 4-(trifluoromethyl)benzeneboronic acid (9.59 g, 50 mmol) in DME (75 ml) and Na$_2$CO$_3$ solution (2M, 75 ml) was deoxygenated by bubbling nitrogen through the mixture for 15 mins. Tetrakis (triphenylphosphine) palladium (0) (1.155 g, 1.0 mmol) was added and the reaction was degassed for a further 10 mins. The reaction was heated at reflux for 16 hrs then cooled to rt. The mixture was extracted with EtOAc (×3), the combined extracts were washed with brine, dried (MgSO$_4$), filtered and evaporated. The residue was purified by chromatography (silica, 10-30% EtOAc/isohexane) to give the pyridine (10.75 g, 91%). $^1$H NMR (360 MHz, CDCl$_3$) δ: 2.36 (3H, s), 7.21-7.26 (1H, m), 7.60-7.72 (5H, m), 8.54-8.55 (1H, m).

Step 2: Methyl{2-[4-(trifluoromethyl)phenyl]pyridin-3-yl}acetate

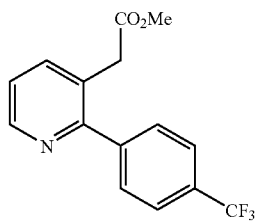

A solution of diisopropylamine (4.8 ml, 34 mmol) in dry THF (20 ml) was cooled to 0° C. and n-butyllithium (1.6M in hexanes, 21.3 ml, 34 mmol) was added dropwise. After stirring at 0° C. for 30 mins, 1,3-dimethyl-3,4,5,6-tetrahydro-2(1H)-pyrimidinone (4.1 ml, 34 mmol) was added. After 15 mins a solution of the pyridine (Step 1, 4.033 g, 17 mmol) in dry THF (10 ml) was added. The reaction was stirred for 15 mins at 0° C. then cooled to −78° C. and dimethyl carbonate (3.4 ml, 40 mmol) in dry THF (10 ml) was added. The reaction was allowed to warm to −5° C. and stirred for 1 hr then quenched with saturated NH$_4$Cl solution. The mixture was extracted with EtOAc (×3), the combined extracts were washed with brine, dried (MgSO$_4$), filtered and evaporated. The residue was purified by chromatography (silica, 10-30% EtOAc/hexanes) to give the ester (0.621 g, 12%). $^1$H NMR (500 MHz, CDCl$_3$) δ: 3.65 (2H, s), 3.67 (3H, s), 7.31-7.34 (1H, m), 7.61-7.62 (2H, m), 7.71-7.75 (3H, m), 8.63-8.64 (1H, m).

Step 3: (±)-{(2R*,3R*)-1-(4-Isopropylphenyl)-2-[4-(trifluoromethyl)phenyl]piperidin-3-yl}acetic acid

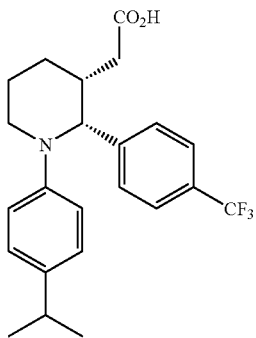

The title compound was prepared from the pyridine in Step 2 using the method in Example 3 Step 3 followed by the method in Example 65 Step 4. 1H NMR (360 MHz, CD$_3$OD) δ: 1.15 (6H, dd, J 2.0, 6.9), 1.74-1.86 (3H, m), 2.09-2.18 (2H, m), 2.36 (1H, dd, J 8.8, 15.9), 2.58-2.63 (1H, m), 2.75 (1H, septet, J 6.9), 3.02-3.08 (1H, m), 3.47-3.53 (1H, m), 4.81 (1H, d, J 4.2), 6.88 (2H, d, J 8.5), 7.00 (2H, d, J 8.5), 7.41-7.49 (4H, m); M/Z (ES$^+$) 406 (MH$^+$).

Example 16

(±)-{(2R*,3R*,4R*)-1-(4-Isopropylphenyl)-3-propyl-2-[4-(trifluoromethyl)phenyl]piperidin-4-yl}acetic acid

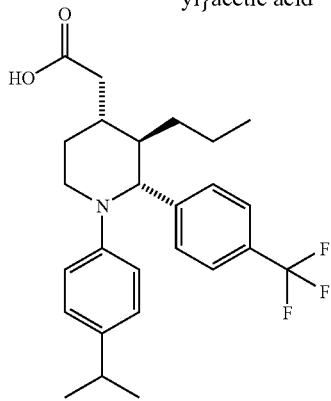

Step 1: (±)-(2R*,3S*)-3-Allyl-1-(4-isopropylphenyl)-2-[4-(trifluoromethyl)phenyl]-2,3-dihydropyridin-4(1H)-one

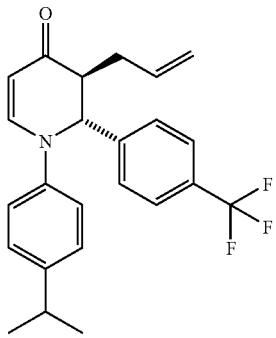

A solution of LDA (1.8M in THF/heptane/ethyl benzene, 1.2 ml, 2.16 mmol) was added slowly to a stirred solution of the enone from Example 1, step 2 (750 mg, 2.1 mmol) in dry THF (10 ml) under N$_2$, such that the internal temperature <−70° C. After 30 minutes at this temperature allyl bromide (360 μl, 4.2 mmol) was added. After an additional 30 minutes the reaction was transferred to an ice bath and kept at this temperature for 30 minutes. The reaction was quenched with saturated aqueous NH$_4$Cl, and then partitioned between EtOAc/H$_2$O. The aqueous layer was extracted with EtOAc (×2). The combined extracts were washed with brine (×1), dried (Na$_2$SO$_4$), filtered and evaporated. The residue was purified by chromatography on silica, eluting with 20-30% EtOAc/isohexane to give the ketone (716 mg, 85%) as an oil. 1H NMR (500 MHz, CDCl$_3$) δ: 1.22 (6H, d, J 6.9), 2.38-2.45 (1H, m), 2.58-2.62 (2H, m), 2.84-2.92 (1H, m), 5.02 (1H, d, J 17.0), 5.12-5.16 (2H, m), 5.22 (1H, d, J 7.7), 5.83-5.91 (1H, m), 6.94 (2H, d, J 8.6), 7.18 (2H, d, J 8.5), 7.37 (2H, d, J 8.2), 7.57 (2H, d, J 8.2), 7.66 (1H, dd, J 7.7, 1.1).

Step 2: (±)-(2R*,3S*)-3-Allyl-1-(4-isopropylphenyl)-2-[4-(trifluoromethyl)phenyl]piperidin-4-one

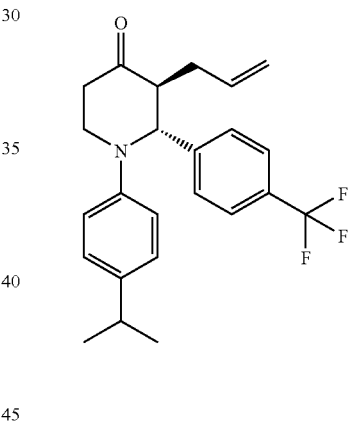

L-Selectride® (1.0 M in THF, 1.4 ml, 1.4 mmol) was added slowly to a stirred solution of the enone (Step 1, 538 mg, 1.35 mmol) in dry THF (10 ml) under N$_2$, such that the internal temperature was kept below −70° C. The reaction was maintained at −78° C. for 1 hour, then quenched with saturated aqueous NH$_4$Cl solution. After warming to room temperature the mixture was partitioned between EtOAc/H$_2$O. The layers were separated and the aqueous layer was further extracted with EtOAc (×2). The combined extracts were washed with brine (×1), dried (Na$_2$SO$_4$), filtered and evaporated. The residue was purified by chromatography on silica, eluting with 5-10% EtOAc/isohexane to give the ketone (458 mg, 85%) as an oil. 1H NMR (500 MHz, CDCl$_3$) δ: 1.21 (6H, d, J 6.9), 2.48 (2H, t, J 7.0), 2.56-2.62 (1H, m), 2.67-2.73 (1H, m), 2.78-2.85 (1H, m), 2.98-3.00 (1H, m), 3.47-3.53 (1H, m), 3.65-3.71 (1H, m), 4.95 (1H, d, J 3.3), 5.03 (1H, dd, J 17.0, 1.3), 5.10 (1H, d, J 9.2), 5.75-5.83 (1H, m), 6.76 (2H, d, J 8.6), 7.09 (2H, d, J 8.5), 7.29 (2H, d, J 8.1), 7.51 (2H, d, J 8.2).

Step 3: (±)-Ethyl(2E/Z)-{(2R*,3R*)-3-Allyl-1-(4-isopropylphenyl)-2-[4-(trifluoromethyl)phenyl]piperidin-4-ylidene}acetate

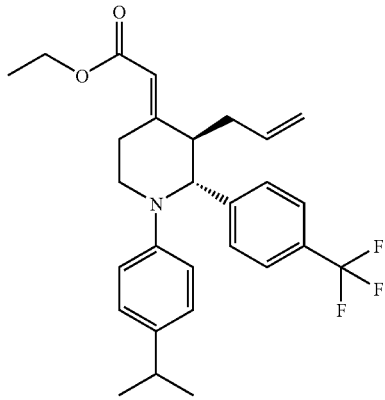

NaH (60% dispersion in oil, 110 mg, 2.75 mmol) was added portionwise to a stirred solution of triethylphosphonoacetate (0.55 ml, 2.7 mmol) in dry THF (3 ml) at 0° C. under N$_2$. After 1 hour a solution of the ketone (Step 2, 223 mg, 0.56 mmol) in dry THF (2 ml) was added. After 30 minutes at 0° C. the reaction was removed from the ice bath and stirred at room temperature for 20 hours. The reaction was quenched with saturated aqueous NH$_4$Cl solution, and then partitioned between EtOAc/H$_2$O. The layers were separated and the aqueous layer was further extracted with EtOAc (×2). The combined extracts were washed with brine (×1), dried (Na$_2$SO$_4$), filtered and evaporated. The residue was purified by chromatography on silica, eluting with 10-20% EtOAc/isohexane to give the unsaturated ester (251 mg, 95%, mixture of isomers) as an oil. M/Z (ES$^+$) 472 (MH$^+$).

Step 4: (±)-Ethyl{(2R*,3R*,4R*)-1-(4-isopropylphenyl)-3-propyl-2-[4-(trifluoromethylphenyl]piperidin-4-yl}acetate

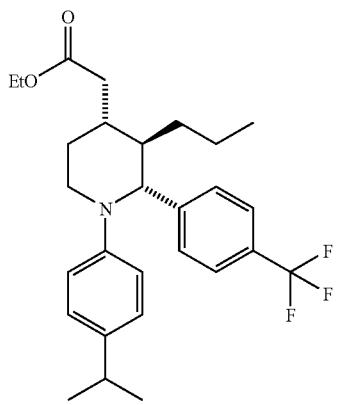

The unsaturated ester (Step 3, 237 mg, 0.50 mmol) was taken up in ethanol (25 ml) and hydrogenated at 25 psi over 10% Pd/C (40 mg) for 1 hour. The catalyst was removed by filtration. The filtrate was evaporated, and the residue was purified by chromatography on silica, eluting with 2-10% diethyl ether/isohexane to give the saturated ester (124 mg, 52%, mixture of isomers) as an oil. M/Z (ES$^+$) 476 (MH$^+$).

Step 5: (±)-{(2R*,3R*,4R*)-1-(4-Isopropylphenyl)-3-propyl-2-[4-(trifluoromethyl)phenyl]piperidin-4-yl}acetic acid

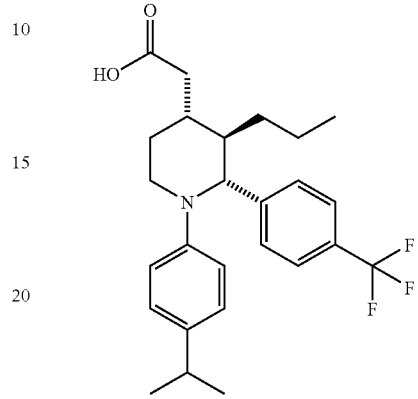

A mixture of LiOH (30 mg, 1.25 mmol) and the ester (Step 4, 112 mg, 0.24 mmol) in THF/H$_2$O (3:1, 2 ml) was stirred and heated at 75° C. for 16 hours. After cooling to room temperature the mixture was acidified with 2N HCl, and then partitioned between EtOAc/H$_2$O. The layers were separated and the aqueous layer was further extracted with EtOAc (×2). The combined extracts were washed with brine (×1), dried (Na$_2$SO$_4$), filtered and evaporated. The residue was purified by chromatography on silica, eluting with 2-4% MeOH/DCM to give the acid (40 mg, 37%) as a colourless foam. $^1$H NMR (500 MHz, CDCl$_3$) δ: 0.78 (3H, t, J 7.0), 1.09-1.20 (8H, m, [inc d, J 6.9]), 1.25-1.41 (2H, m), 1.65-1.71 (1H, m), 1.82-1.86 (1H, m), 1.98 (2H, brd, J 9.4), 2.12 (1H, dd, J 15.0, 8.7), 2.47 (1H, dd, J 15.1, 4.1), 2.70-2.77 (1H, m), 3.10 (1H, t, J 10.5), 3.39-3.42 (1H, m), 4.16 (1H, d, J 7.0), 6.74 (2H, d, J 8.3), 6.96 (2H, d, J 8.5), 7.34 (2H, d, J 8.0), 7.43 (2H, d, J 8.1); M/Z (ES$^+$) 448 (MH$^+$).

Example 17

(±)-(3R*,6S*)-1-(4-Isopropylbenzyl)-6-[4-(trifluoromethyl)phenyl]piperidine-3-carboxylic acid

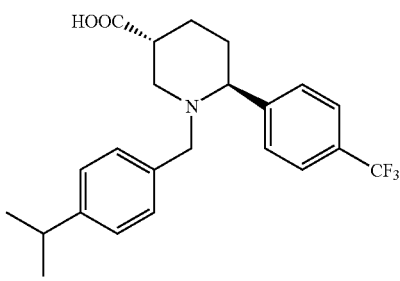

a) 6-[4-(Trifluoromethyl)phenyl]nicotinic acid

6-Chloronicotinic acid (1.57 g, 0.01 mmol), [4-(trifluoromethyl)phenyl]boronic acid (1.9 g, 0.01 mol), tetrakis (triphenylphosphine) palladium (0) (230 mg, 2 mol %), Na$_2$CO$_3$ (2M, 5 ml) in THF (15 ml) were placed in a microwave tube and the contents were heated in the microwave oven for 20 min at 150° C. The cooled mixture was filtered through Hyflo® to remove inorganic material, the Hyflo® was washed with EtOAc and the combined organic extracts were dispersed between aq. NaOH and EtOAc. The aqueous extracts were acidified (aq. HCl) and extracted with EtOAc; the organic extracts were washed with brine, dried (MgSO$_4$) and evaporated to give the product (0.8 g, 30%). $^1$H NMR (400 MHz, CD$_3$OD) δ: 7.85 (2H, d, J 8.2), 8.10 (1H, dd, J 0.8, 8.4), 8.31 (2H, d, J 8.2), 8.49 (1H, dd, J 2.2, 8.2), 9.26 (1H, dd, J 0.8, 2.1).

b) (±)-Methyl(3R*,6S*)-6-[4-(trifluoromethyl)phenyl]piperidine-3-carboxylate The acid described in a) above (0.8 g) was dissolved in MeOH. Ethereal HCl (5 ml, 1M) was added followed by PtO$_2$ (60 mg) and the mixture was hydrogenated at 30 psi for 2 h. The mixture was filtered through Hyflo® to remove platinum and the solvent was removed in vacuo to afford the product as an oil. The oil was dissolved in EtOAc and basified with NaHCO$_3$; the organic extract was washed with brine, dried (MgSO$_4$) and concentrated to give an oil. $^1$H NMR (400 MHz, CDCl$_3$) δ: 1.67-1.81 (4H, m), 2.31-2.35 (1H, m), 2.59 (1H, br s), 2.98 (1H, dd, J 3.5, 12.5), 3.61 (1H, d, J 12.5), 3.70 (1H, dd, J 10.5, 2.8), 3.76 (3H, s), 7.47 (2H, d, J 8.1), 7.56 (2H, d, J 8.1); M/Z (ES$^+$) 288 (MH$^+$).

c) (±)-Methyl(3R*,6S*)-1-(4-isopropylbenzyl)-6-[4-(trifluoromethyl)phenyl]piperidine-3-carboxylate The amine described in b) above (100 mg, 0.35 mmol), 4-isopropylbenzyl bromide (0.14 g, 0.7 mmol) and K$_2$CO$_3$ (0.1 g, 0.7 mmol) were dissolved in DMF (1 ml) and the mixture was heated at 60° C. overnight. The cooled mixture was diluted with H$_2$O (20 ml) and was extracted with EtOAc (3×5 ml). The organic extracts were washed with H$_2$O, brine, dried (MgSO$_4$) and evaporated. The crude product was purified on silica using 3-7% EtOAc in iso-hexane as eluant. $^1$H NMR (400 MHz, CDCl$_3$) δ: 1.24 (6H, d, J 6.9), 1.57 (1H, tt, J 13.7, 4.5), 1.69 (1H, dd, J 3.1, 13.8), 1.93-2.03 (1H, m), 2.19-2.27 (2H, m), 2.63 (1H, s), 2.82 (1H, d, J 11.0), 2.87 (1H, qn, J 6.9), 3.24 (1H, dd, J 11.1, 3.2), 3.42 (1H, dt, J 11.7, 2.4), 3.63 (1H, d, J 11.0), 3.70 (3H, s), 7.13 (4H, q, J 6.3), 7.52 (4H, q, J 8.2). M/Z (ES$^+$) 420 (MH$^+$).

d) (±)-(3R*,6S*)-1-(4-Isopropylbenzyl)-6-[4-(trifluoromethyl)phenyl]piperidine-3-carboxylic acid The ester described in c) above was hydrolysed according to the procedure described in Example 13 (section e) to give the product as a white solid.

$^1$H NMR (500 MHz, CD$_3$OD) δ: 1.23 (6H, d, J 6.9), 1.79-1.87 (1H, m), 2.18 (2H, s), 2.33 (1H, d, J 12.7), 2.89-2.99 (2H, m), 3.16 (1H, t, J 12.4), 3.68 (1H, d, J 10.0), 3.94 (1H, d, J 13.3), 4.11 (1H, d, J 13.2), 4.32-4.41 (1H, m), 7.21 (2H, d, J 8.0), 7.29 (2H, d, J 8.0), 7.81 (2H, t, J 8.4), 7.87 (2H, d, J 8.2); M/Z (ES$^+$) 406 (MH$^+$).

Example 18

(±)-(cis)-1-(4-Isopropylbenzyl)-2-[4-(trifluoromethyl)phenyl]piperidine-4-carboxylic acid

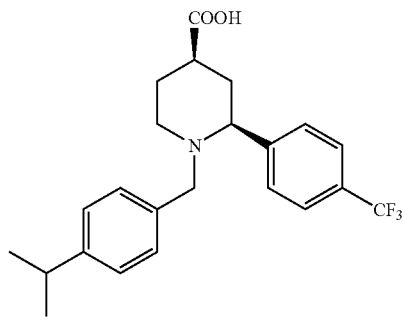

a) Methyl 2-[4-(trifluoromethyl)phenyl]isonicotinate

Methyl 2-chloroisonicotinate (427 mg), 4-(trifluoromethyl)phenylboronic acid (474 mg), potassium phosphate (800 mg), 1,1-[bis(diphenylphosphino)ferrocene]dichloropalladium(II) (102 mg), in PhMe (5 ml) were placed in a microwave tube and the contents were heated in the microwave oven for 20 min at 150° C. The cooled mixture was filtered through Hyflo® to remove inorganic material, the Hyflo® was washed with EtOAc and the combined organic extracts were dispersed between H$_2$O and EtOAc. The organic extracts were washed with brine, dried (MgSO$_4$) and evaporated. The crude oil was purified by chromatography on silica using 10-25% EtOAc in hexane to yield the product as a crystalline solid (560 mg, 85%). $^1$H NMR (400 MHz, CDCl$_3$) δ: 4.01 (3H, s), 7.76 (2H, d, J 8.3), 7.84 (1H, dd, J 1.4, 4.9), 8.18 (2H, d, J 8.2), 8.33 (1H, t, J 1.1), 8.87 (1H, dd, J 0.6, 4.8).

b) (±)-Methyl(cis)-2-[4-(trifluoromethyl)phenyl]piperidine-4-carboxylate hydrochloride Methyl 2-[4-(trifluoromethyl)phenyl]isonicotinate (5 g) was dissolved in MeOH (180 ml) and HCl in dioxane (4.5 ml, 4N). To this solution was added platinum oxide (500 mg) and the mixture was hydrogenated at 30 psi for 2 h. The mixture was filtered through Hyflo® to remove the catalyst and the solution was evaporated and azeotroped with toluene to yield the product as a white crystalline solid (5 g). $^1$H NMR (400 MHz, CDCl$_3$) δ: 1.95-2.03 (1H, m), 2.09-2.17 (1H, m), 2.33 (1H, d, J 14.5), 2.44 (1H, d, J 14.2), 2.95-3.02 (1H, m), 3.35-3.39 (1H, m), 3.60-3.64 (1H, m), 3.75 (3H, s), 4.51 (1H, dd, J 2.7, 12.6), 7.74 (2H, d, J 8.2), 7.83 (2H, d, J 8.2); M/Z (ES$^+$) 288 (MH$^+$).

c) (±)-Methyl(cis)-1-(4-isopropylbenzyl)-2-[4-(trifluoromethyl)phenyl]piperidine-4-carboxylate Methyl(cis)-2-[4-(trifluoromethyl)phenyl]piperidine-4-carboxylate (0.22 g), 4-isopropylbenzyl bromide (240 mg), NaI (15 mg), $K_2CO_3$ (287 mg) in DMF (2 ml) were placed in a microwave tube and the contents were heated in the microwave oven for 20 min at 150° C. The cooled mixture was dispersed between $H_2O$ and EtOAc and the organic extracts were washed with brine, dried ($MgSO_4$) and evaporated. The crude oil was purified by chromatography on silica using 5-8% EtOAc in hexane to yield a colourless oil (260 mg, 81%) which crystallized on standing. $^1$H NMR (400 MHz, $CDCl_3$) δ: 1.23 (6H, d, J 6.9), 1.71-1.81 (2H, m), 1.92 (1H, d, J 12.9), 1.97-2.04 (2H, m), 2.44-2.50 (1H, m), 2.82-2.90 (2H, m), 3.08-3.10 (1H, m), 3.25 (1H, dd, J 2.8, 11.3), 3.66 (4H, t, J 9.1), 7.14 (4H, q, J 6.3), 7.58 (4H, s); M/Z (ES$^+$) 420 (MH$^+$).

d) (±)-(cis)-1-(4-Isopropylbenzyl)-2-[4-(trifluoromethyl)phenyl]piperidine-4-carboxylic acid The ester described in c) above (67 mg) was dissolved in THF (2 ml) and LiOH (20 mg) in $H_2O$ (2 ml) was added. The colourless solution was stirred overnight. The solution was evaporated and acidified with HCl (3 ml, 2M) and extracted with EtOAc. The organic extracts were washed with brine, dried ($MgSO_4$) and evaporated to give a white solid. $^1$H NMR (500 MHz, $CD_3OD$) δ: 1.23 (6H, d, J 6.9), 1.98 (1H, d, J 10.7), 2.21 (1H, t, J 12.8), 2.28 (1H, d, J 14.8), 2.36 (1H, d, J 14.5), 2.82-2.96 (2H, m), 3.16 (1H, t, J 13.0), 3.57 (1H, d, J 12.9), 3.88-3.94 (1H, m), 4.06-4.12 (1H, m), 4.48 (1H, d, J 11.2), 7.20 (2H, d, J 8.1), 7.30 (2H, d, J 8.1), 7.81 (2H, d, J 7.9), 7.88 (2H, d, J 8.2); M/Z (ES$^+$) 406 (MH$^+$).

Example 19

(±)-(cis)-1-[2,5-Bis(trifluoromethyl)benzyl]-2-[4-(trifluoromethyl)phenyl]piperidine-4-carboxylic acid

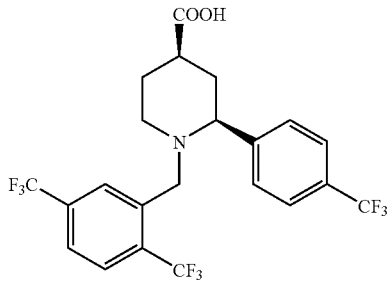

a) (±)-Methyl(cis)-1-[2,5-bis(trifluoromethyl)benzyl]-2-[4-(trifluoromethyl)phenyl]piperidine-4-carboxylate (±)-Methyl(cis)-2-[4-(trifluoromethyl)phenyl]piperidine-4-carboxylate (Example (18b) (88 mg), 2,5-bis(trifluoromethyl)benzyl bromide (110 mg), NaI (25 mg) and $K_2CO_3$ (100 mg) in DMF (3 ml) were placed in a microwave tube and the contents were heated in the microwave oven for 20 min at 150° C. The cooled mixture was dispersed between water and EtOAc and the organic extracts were washed with sodium thiosulfate, brine, dried ($MgSO_4$) and evaporated. The crude oil was purified by chromatography on silica using 5-8% EtOAc in hexane to yield a colourless oil (98 mg, 62%) which crystallized on standing. $^1$H NMR (400 MHz, $CDCl_3$) δ: 1.81-1.89 (2H, m), 1.97 (1H, d, J 13.2), 2.09-2.17 (2H, m), 2.49-2.56 (1H, m), 2.94-2.96 (1H, m), 3.34 (1H, d, J 15.6), 3.40 (1H, dd, J 2.6, 11.3), 3.66 (4H, d, J 15.6), 7.53-7.59 (5H, m), 7.68 (1H, d, J 8.2), 8.19 (1H, s); M/Z (ES$^+$) 514 (MH$^+$).

b) (±)-(cis)-1-[2,5-Bis(trifluoromethyl)benzyl]-2-[4-(trifluoromethyl)phenyl]piperidine-4-carboxylic acid The ester described in a) above (90 mg) was dissolved in dioxane (2 ml) and NaOH (0.3 ml, 4N) was added. The colourless solution was stirred overnight at room temperature and heated under reflux for 3 h. The cooled solution was evaporated and acidified with HCl (3 ml, 2M) and extracted with EtOAc. The organic extracts were washed with brine, dried ($MgSO_4$) and evaporated to give a white solid which was crystallized from hexane. $^1$H NMR (500 MHz, $CD_3OD$) δ: 1.75-1.87 (2H, m), 1.99 (1H, d, J 12.6), 2.07 (1H, d, J 10.6), 2.24 (1H, t, J 11.2), 2.53-2.59 (1H, m), 2.94 (1H, dd, J 3.3, 8.6), 3.39 (1H, d, J 14.7), 3.51 (1H, dd, J 2.7, 11.3), 3.67 (1H, d, J 15.7), 7.62 (4H, q, J 7.1), 7.69 (1H, d, J 8.3), 7.79 (1H, d, J 8.2), 8.25 (1H, s); M/Z (ES$^+$) 500 (MH$^+$).

Example 20

(±)-cis-{1-Benzyl-2-[4-(trifluoromethyl)phenyl]piperidin-4-yl}acetic acid

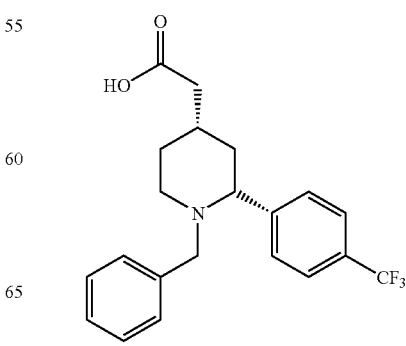

Step 1: (±)-cis-Methyl{1-benzyl-2-[4-(trifluoromethyl)phenyl]piperidin-4-yl}acetate

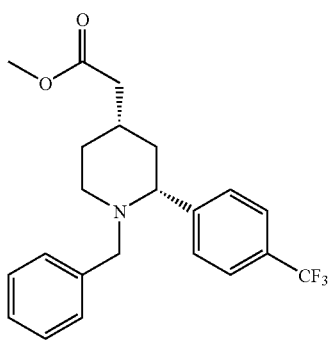

A clear solution of methyl(±)-(2R*,4S*)-2-[4-(trifluoromethyl)phenyl]piperidin-4-yl}acetate hydrochloride (Example 3, Step 3, 150 mg, 0.45 mmol), K$_2$CO$_3$ (604 mg, 2.25 mmol), NaI (13 mg, 0.09 mmol) and benzyl bromide (100 µl, 0.84 mmol) in DMF (2 ml) was stirred in the microwave at 150° C. for 15 min. The dark orange reaction mixture was diluted with NaHCO$_3$ (sat, 10 ml) and extracted with EtOAc (2×20 ml). Extracts were washed with H$_2$O (4×10 ml), brine (10 ml) and dried (MgSO$_4$) to give an orange gum (180 mg). The crude product was purified using chromatography on silica using 8% EtOAc/isohexane to give a pale gum (120 mg, 0.31 mmol, 68%). $^1$H NMR (400 MHz, CDCl$_3$) δ: 1.37-1.29 (2H, m), 1.69 (1H, d, J 12.7), 1.84 (1H, dd, J 2.8, 12.9), 2.06-1.98 (2H, m), 2.29-2.17 (2H, m), 2.84 (1H, d, J 13.6), 3.02-2.98 (1H, m), 3.27 (1H, dd, J 2.8, 11.2), 3.64 (3H, s), 3.70 (1H, d, J 13.7), 7.23 (3H, t, J 6.9), 7.29 (2H, t, J 4.1), 7.58 (4H, s). M/Z (ES$^+$) 392 (MH$^+$).

Step 2: (±)-cis-{1-Benzyl-2-[4-(trifluoromethyl)phenyl]piperidin-4-yl}acetic acid

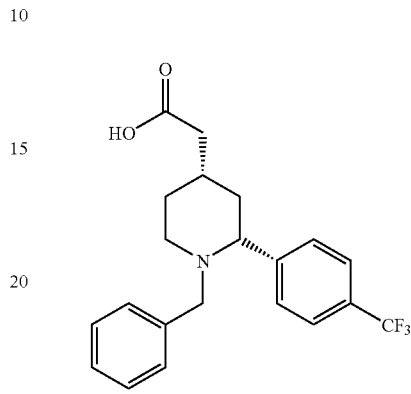

The title compound was prepared in the same manner as Example 3, Step 5. $^1$H NMR (400 MHz, CD$_3$OD) δ: 1.43-1.33 (2H, m), 1.77 (1H, d, J 12.9), 1.88 (1H, dd, J 2.8, 13.2), 1.99-1.95 (1H, m), 2.24-2.14 (3H, m), 2.96 (1H, d, J 13.3), 3.03 (1H, dd, J 3.1, 8.5), 3.43 (1H, dd, J 2.6, 11.3), 3.69 (1H, d, J 13.2), 7.29-7.21 (5H, m), 7.67 (4H, s); M/Z 378 (MH$^+$).

Examples 21-49

The examples in the following table were prepared in an analogous manner to Example 20, using the appropriate benzyl or alkyl bromide.

| Example | Structure | Name | M/Z ES$^+$ [MH]$^+$ |
|---|---|---|---|
| 21 | ![structure] | (±)-cis-{1-(2-Naphthylmethyl)-2-[4-(trifluoromethyl)phenyl]piperidin-4-yl}acetic acid | 428 |

-continued

| Example | Structure | Name | M/Z ES+ [MH]+ |
|---|---|---|---|
| 22 | 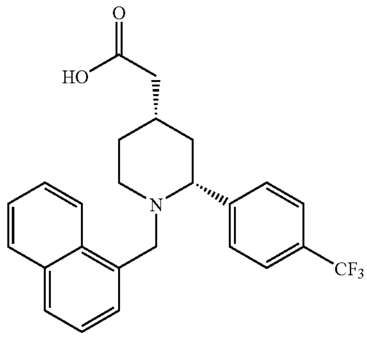 | (±)-cis-{1-(1-Naphthylmethyl)-2-[4-(trifluoromethyl)phenyl]piperidin-4-yl}acetic acid | 428 |
| 23 | 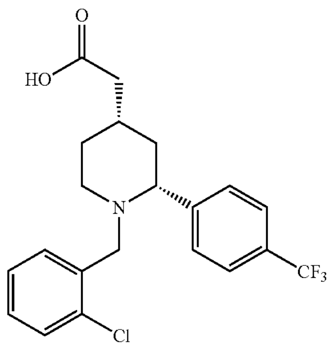 | (±)-cis-{1-(2-Chlorobenzyl)-2-[4-(trifluoromethyl)phenyl]piperidin-4-yl}acetic acid | 412 |
| 24 | 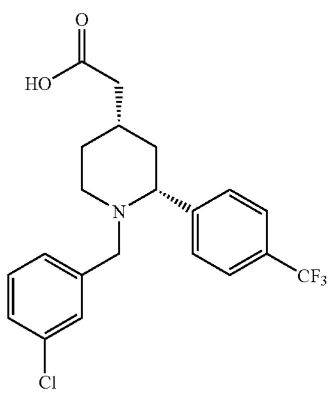 | (±)-cis-{1-(3-Chlorobenzyl)-2-[4-(trifluoromethyl)phenyl]piperidin-4-yl}acetic acid | 412 |
| 25 | 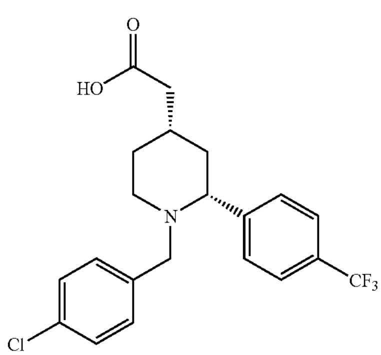 | (±)-cis-{1-(4-Chlorobenzyl)-2-[4-(trifluoromethyl)phenyl]piperidin-4-yl}acetic acid | 412 |

-continued

| Example | Structure | Name | M/Z ES+ [MH]+ |
|---|---|---|---|
| 26 | 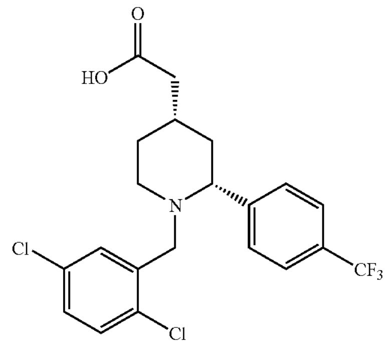 | (±)-cis-{1-(2,5-Dichlorobenzyl)-2-[4-(trifluoromethyl)phenyl]piperidin-4-yl}acetic acid | 446/448 |
| 27 | 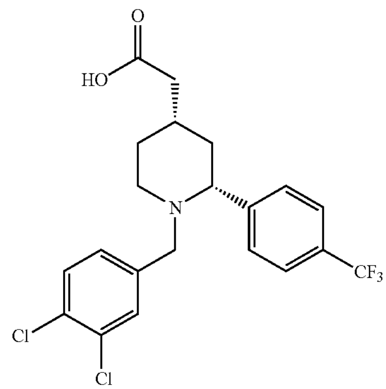 | (±)-cis-{1-(3,4-Dichlorobenzyl)-2-[4-(trifluoromethyl)phenyl]piperidin-4-yl}acetic acid | 446/448 |
| 28 | 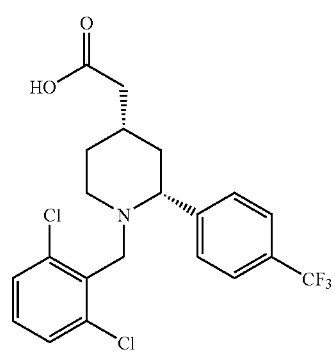 | (±)-cis-{1-(2,6-Dichlorobenzyl)-2-[4-(trifluoromethyl)phenyl]piperidin-4-yl}acetic acid | 446/448 |
| 29 | 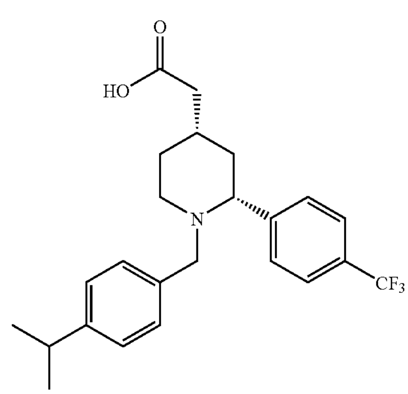 | (±)-cis-{1-(4-Isopropylbenzyl)-2-[4-(trifluoromethyl)phenyl]piperidin-4-yl}acetic acid | 420 |

-continued

| Example | Structure | Name | M/Z ES+ [MH]+ |
|---|---|---|---|
| 30 | 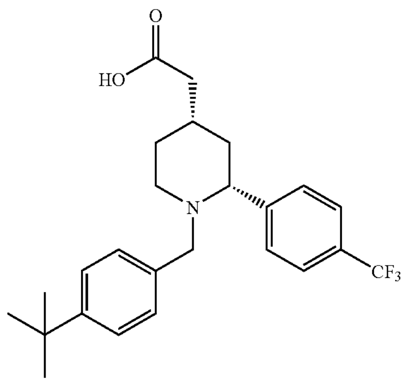 | (±)-cis-{1-(4-tert-Butylbenzyl)-2-[4-(trifluoromethyl)phenyl]piperidin-4-yl}acetic acid | 434 |
| 31 | 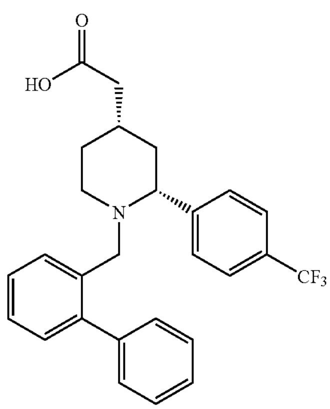 | (±)-cis-{1-(Biphenyl-2-ylmethyl)-2-[4-(trifluoromethyl)phenyl]piperidin-4-yl}acetic acid | 454 |
| 32 | 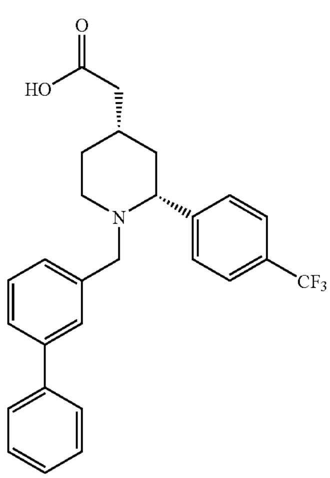 | (±)-cis-{1-(Biphenyl-3-ylmethyl)-2-[4-(trifluoromethyl)phenyl]piperidin-4-yl}acetic acid | 454 |

| Example | Structure | Name | M/Z ES+ [MH]+ |
|---|---|---|---|
| 33 | 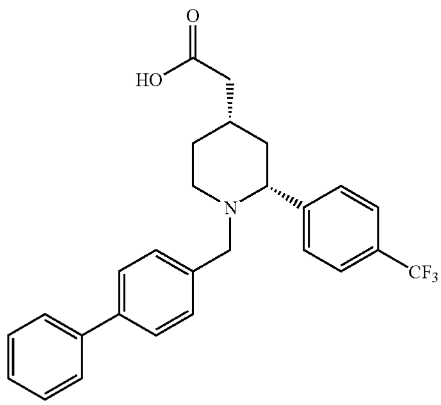 | (±)-cis-{1-(Biphenyl-4-ylmethyl)-2-[4-(trifluoromethyl)phenyl]piperidin-4-yl}acetic acid | 454 |
| 34 | 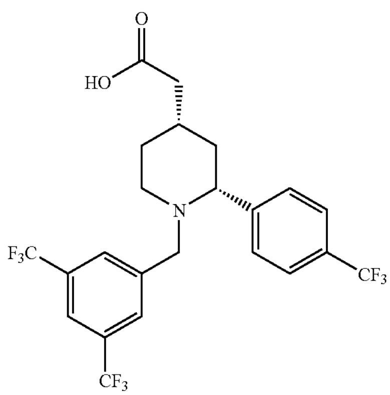 | (±)-cis-{1-[3,5-Bis(trifluoromethyl)benzyl]-2-[4-(trifluoromethyl)phenyl]piperidin-4-yl}acetic acid | 514 |
| 35 | 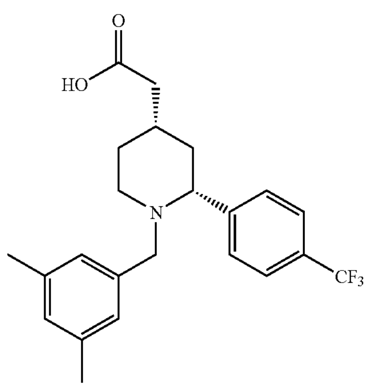 | (±)-cis-{1-[3,5-Dimethylbenzyl]-2-[4-(trifluoromethyl)phenyl]piperidin-4-yl}acetic acid | 406 |
| 36 | 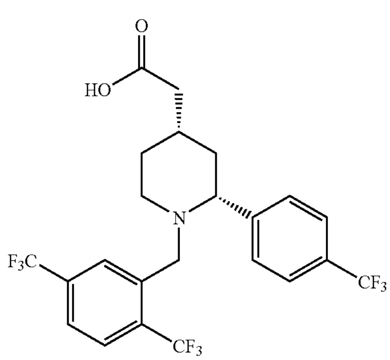 | (±)-cis-{1-[2,5-Bis(trifluoromethyl)benzyl]-2-[4-(trifluoromethyl)phenyl]piperidin-4-yl}acetic acid | 514 |

-continued

| Example | Structure | Name | M/Z ES+ [MH]+ |
|---|---|---|---|
| 37 | 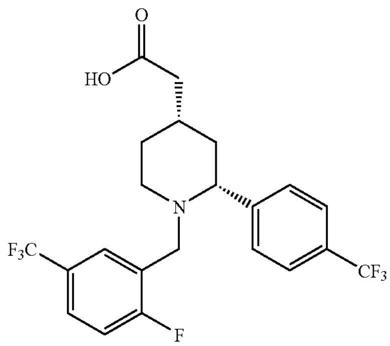 | (±)-cis-{1-[2-Fluoro-5-(trifluoromethyl)benzyl]-2-[4-(trifluoromethyl)phenyl]piperidin-4-yl}acetic acid | 464 |
| 38 | 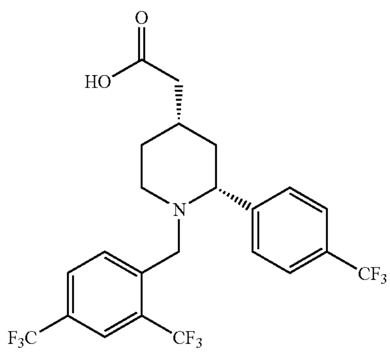 | (±)-cis-{1-[2,4-Bis(trifluoromethyl)benzyl]-2-[4-(trifluoromethyl)phenyl]piperidin-4-yl}acetic acid | 514 |
| 39 | 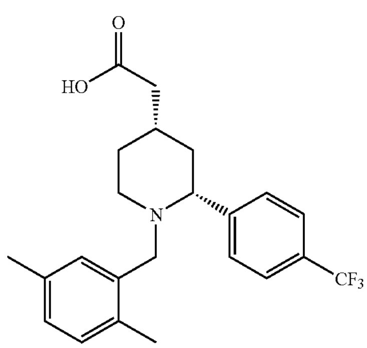 | (±)-cis-{1-(2,5-Dimethylbenzyl)-2-[4-(trifluoromethyl)phenyl]piperidin-4-yl}acetic acid | 406 |
| 40 | 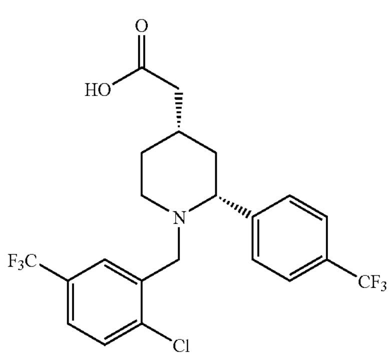 | (±)-cis-{1-[2-Chloro-5-(trifluoromethyl)benzyl]-2-[4-(trifluoromethyl)phenyl]piperidin-4-yl}acetic acid | 480 |

-continued

| Example | Structure | Name | M/Z ES+ [MH]+ |
|---|---|---|---|
| 41 | 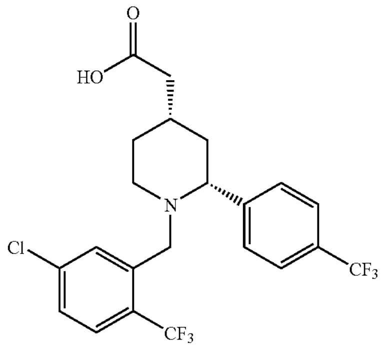 | (±)-cis-{1-[5-Chloro-2-(trifluoromethyl)benzyl]-2-[4-(trifluoromethyl)phenyl]piperidin-4-yl}acetic acid | 480 |
| 42 | 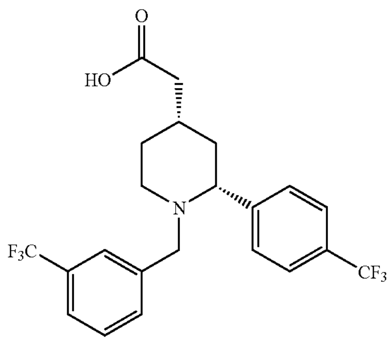 | (±)-cis-{1-[3-(Trifluoromethyl)benzyl]-2-[4-(trifluoromethyl)phenyl]piperidin-4-yl}acetic acid | 446 |
| 43 | 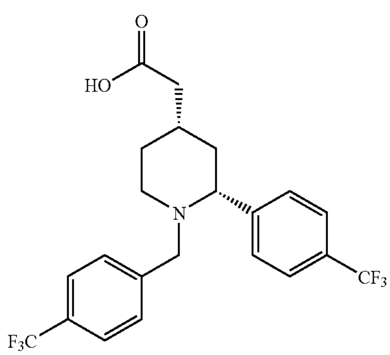 | (±)-cis-{1-[4-(Trifluoromethyl)benzyl]-2-[4-(trifluoromethyl)phenyl]piperidin-4-yl}acetic acid | 446 |
| 44 | 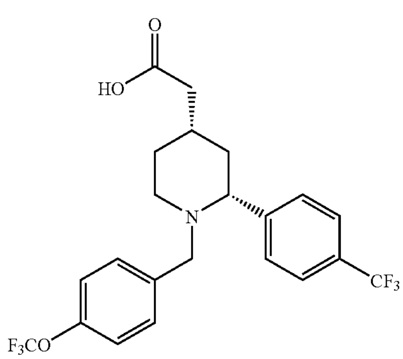 | (±)-cis-{1-[4-(Trifluoromethoxy)benzyl]-2-[4-(trifluoromethyl)phenyl]piperidin-4-yl}acetic acid | 462 |

| Example | Structure | Name | M/Z ES+ [MH]+ |
|---|---|---|---|
| 45 | 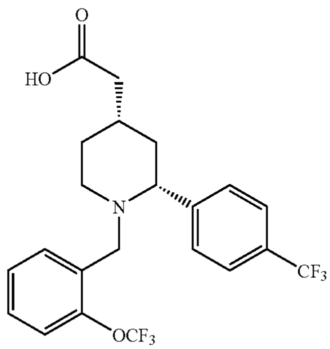 | (±)-cis-{1-[2-(Trifluoromethoxy)benzyl]-2-[4-(trifluoromethyl)phenyl]piperidin-4-yl}acetic acid | 462 |
| 46 | 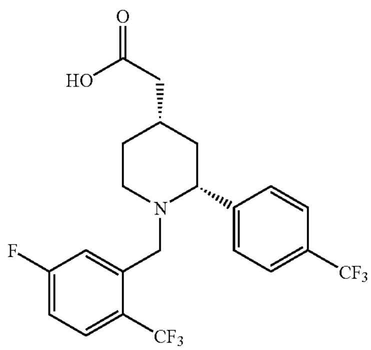 | (±)-cis-{1-[5-Fluoro-2-(trifluoromethyl)benzyl]-2-[4-(trifluoromethyl)phenyl]piperidin-4-yl}acetic acid | 478 |
| 47 | 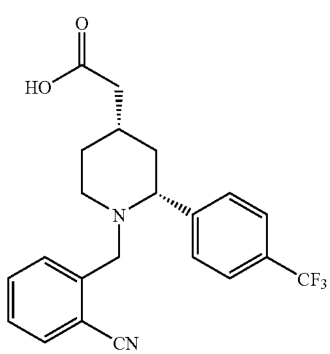 | (±)-cis-{1-(2-Cyanobenzyl)-2-[4-(trifluoromethyl)phenyl]piperidin-4-yl}acetic acid | 417 |
| 48 | 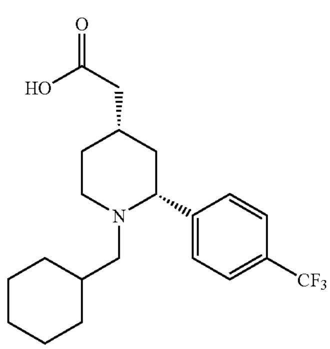 | (±)-cis-{1-(Cyclohexylmethyl)-2-[4-(trifluoromethyl)phenyl]piperidin-4-yl}acetic acid | 384 |

| Example | Structure | Name | M/Z ES+ [MH]+ |
|---|---|---|---|
| 49 | 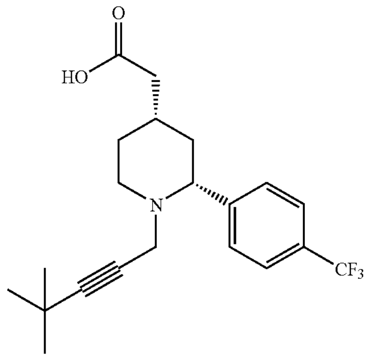 | (±)-cis-{1-(4,4-Dimethylpent-2-ynyl)-2-[4-(trifluoromethyl)phenyl]piperidin-4-yl}acetic acid | 396 |

Example 50

(±)-cis-{1-[5-Propyl-2-(trifluoromethyl)benzyl]-2-[4-(trifluoromethyl)phenyl]piperidin-4-yl}acetic acid

Step 1: (±)-cis-Methyl{1-[5-chloro-2-(trifluoromethyl)benzyl]-2-[4-(trifluoromethyl)phenyl]piperidin-4-yl}acetate

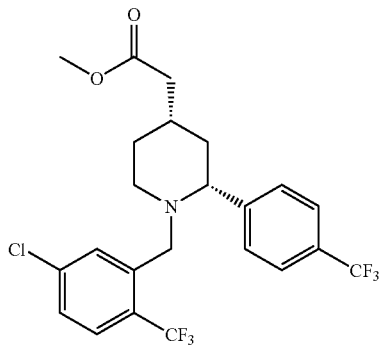

A solution of (±)-methyl{2-[4-(trifluoromethyl)phenyl]pyridin-4-yl}acetate (Example 3, Step 3) (1 g, 2.96 mmol), K₂CO₃ (2.05 mg, 14.8 mmol), NaI (89 mg, 0.59 mmol) and 5-chloro-2-(trifluoromethyl)benzyl bromide (960 µl, 5.92 mmol) in DMF (14 ml) was stirred at 80° C. under N₂ for 16 h. The dark orange reaction mixture was diluted with NaHCO₃ (sat, 150 ml) and extracted with EtOAc (2×100 ml). Extracts were washed with H₂O (4×25 ml), brine (25 ml) and dried (MgSO₄) to give a yellow oil (2.12 g). The crude product was purified using column chromatography on silica using 5% EtOAc/isohexane to give a clear gum (1.34 g, 2.72 mmol, 92%). ¹H NMR (400 MHz, CDCl₃) δ: 1.43-1.35 (2H, m), 1.76-1.72 (1H, m), 1.90-1.86 (1H, m), 2.17-1.99 (2H, m), 2.33-2.21 (2H, m), 2.92-2.88 (1H, m), 3.24 (1H, dd, J 1.9, 15.5), 3.38 (1H, dd, J 2.8, 11.2), 3.57 (1H, d, J 15.5), 3.65 (3H, s), 7.27 (1H, d, J 8.4), 7.48 (1H, d, J 8.4), 7.52 (2H, d, J 8.2), 7.57 (2H, d, J 8.4), 7.89 (1H, s); M/Z (ES⁺) 494 ([MH]⁺).

Step 2: (±)-cis-Methyl{1-[5-propyl-2-(trifluoromethyl)benzyl]-2-[4-(trifluoromethyl)phenyl]piperidin-4-yl}acetate and (±)-cis-methyl {1-[2-(trifluoromethyl)benzyl]-2-[4-(trifluoromethyl)phenyl]piperidin-4-yl}acetate

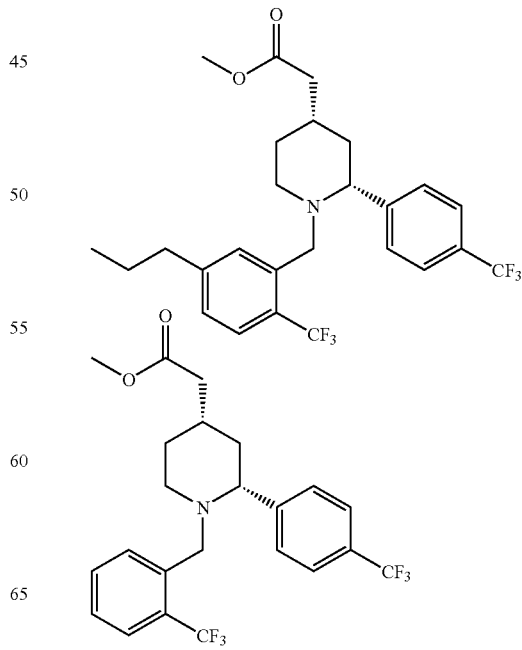

Dihydrogen di-μ-chlorotetrakis(di-tert-butylphosphinito-κP)dipalladate(2−) (POPd1, 38 mg, 0.04 mmol) was added to a clear solution of methyl{1-[5-chloro-2-(trifluoromethyl)benzyl]-2-[4-(trifluoromethyl)phenyl]piperidin-4-yl}acetate (200 mg, 0.41 mmol), ⁿpropylboronic acid (54 mg, 0.62 mmol) and cesium carbonate (401 mg, 1.23 mmol) in THF (3 ml) in air. The yellow solution was then stirred at 130° C. in the microwave for 2 h. The dark yellow solution was diluted with H₂O (20 ml) and extracted with EtOAc (2×20 ml). Extracts were washed with H₂O (20 ml), brine (10 ml) and dried (MgSO₄). Solvent was removed in vacuo to yield a yellow gum (221 mg). The mixture was purified by chromatography eluting with 5% EtOAc/isohexane to yield the title compound as a clear gum, (98 mg, 48%). $^1$H NMR (400 MHz, CDCl₃) δ: 0.98 (3H, t, J 7.3), 1.42-1.24 (2H, m), 1.72-1.68 (3H, m), 1.89-1.85 (1H, m), 2.11-1.97 (2H, m), 2.31-2.21 (2H, m), 2.66 (2H, t, J 7.6), 2.93-2.89 (1H, m), 3.21 (1H, dd, J 1.9, 15.0), 3.36 (1H, dd, J 2.8, 11.2), 3.58 (1H, s), 3.65 (4H, s), 7.08 (1H, d, J 8.0), 7.45 (1H, d, J 8.0), 7.55 (4H, s), 7.68 (1H, s); M/Z (ES⁺) 502 (MH⁺).

Also obtained from the chromatography was methyl{1-[2-(trifluoromethyl)benzyl]-2-[4-(trifluoromethyl)phenyl]piperidin-4-yl}acetate as a clear gum, (46 mg, 24%). $^1$H NMR (400 MHz, CDCl₃) δ: 1.42-1.32 (2H, m), 1.71 (1H, dd, J 2.8, 9.9), 1.89-1.85 (1H, m), 2.13-1.97 (2H, m), 2.31-2.19 (2H, m), 2.92-2.88 (1H, m), 3.25 (1H, dd, J 1.9, 15.1), 3.38 (1H, dd, J 2.9, 11.2), 3.62 (4H, t, J 9.8), 7.29 (1H, t, J 7.7), 7.54 (6H, t, J 6.2), 7.91 (1H, d, J 7.7); M/Z (ES⁺) 460 (MH⁺).

Step 3: (±)-cis-{1-[5-Propyl-2-(trifluoromethyl)benzyl]-2-[4-(trifluoromethyl)phenyl]piperidin-4-yl}acetic acid

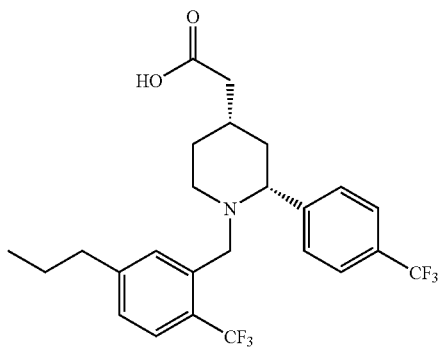

The title compound was prepared as described for Example 3, Step 5. M/Z (ES⁺) 488 ([MH]⁺).

Example 51

(±)-cis-{1-[2-(Trifluoromethyl)benzyl]-2-[4-(trifluoromethyl)phenyl]piperidin-4-yl}acetic acid

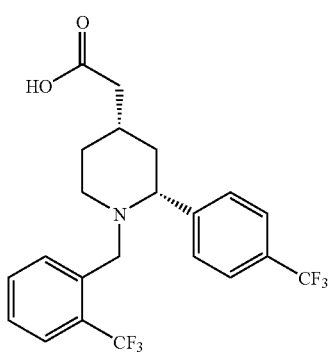

The title compound was prepared from the byproduct of Example 50 Step 2 as described for Example 3, Step 5. M/Z (ES⁺) 446 ([MH]⁺).

Example 52

(±)-cis-{1-[2-Propyl-5-(trifluoromethyl)benzyl]-2-[4-(trifluoromethyl)phenyl]piperidin-4-yl}acetic acid

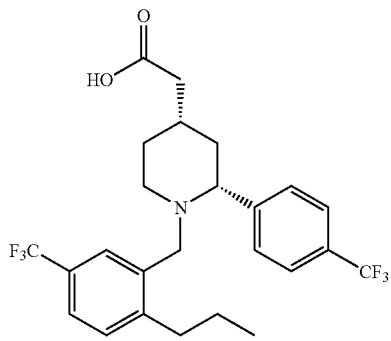

Step 1: (±)-cis-Methyl{1-[2-chloro-5-(trifluoromethyl)benzyl]-2-[4-(trifluoromethyl)phenyl]piperidin-4-yl}acetate

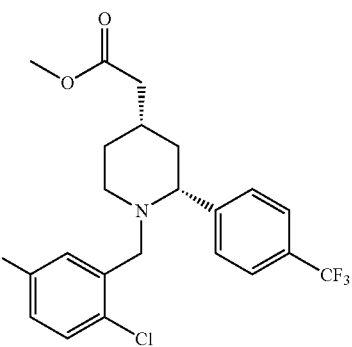

The compound was prepared analogously to Example 50, Step 1 using 2-chloro-5-(trifluoromethyl)benzyl bromide to furnish a pale yellow oil. M/Z (ES⁺) 494 (MH⁺).

Step 2: (±)-cis-Methyl{1-[2-propyl-5-(trifluoromethyl)benzyl]-2-[4-(trifluoromethyl)phenyl]piperidin-4-yl}acetate

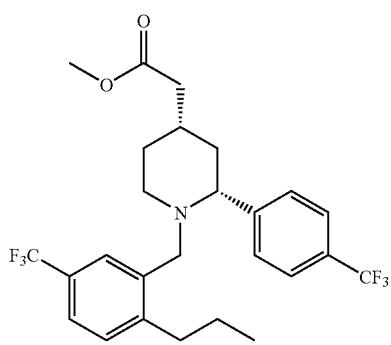

Methyl{1-[2-chloro-5-(trifluoromethyl)benzyl]-2-[4-(trifluoromethyl)phenyl]piperidin-4-yl}acetate (100 mg, 0.20 mmol), n-propylboronic acid (21 mg, 0.24 mmol), CTC Q-Phos (1,2,3,4,5-Pentaphenyl-1'-(di-t-butylphosphino)ferrocene) (3 mg, 0.004 mmol), Pd(dba)₂ (1 mg, 0.002 mmol) and K₃PO₄ (85 mg, 0.40 mmole) were combined in a sealed tube accommodating a septum. Toluene (1 ml) was added and the resulting red solution was degassed with bubbling N₂ for 10 min. The reaction mixture was then stirred at 100° C. for 3 h. The red reaction mixture was then directly chromatographed (silica, 5% EtOAc/isohexane) to give a pale red gum (70 mg). The crude product was further purified using preparatory HPLC to yield a colourless gum (41 mg, 0.07 mmol, 35%). ¹H NMR (400 MHz, CD₃OD) δ: 0.65 (3H, t, J 7.3), 1.22-1.14 (2H, m), 1.30-1.24 (1H, m), 1.54 (1H, d, J 11.2), 1.89 (1H, d, J 12.7), 2.01 (1H, d, J 14.6), 2.11 (1H, dd, J 2.7, 14.4), 2.33-2.15 (4H, m), 2.49 (1H, s), 3.25 (1H, d, J 3.3), 3.47 (1H, d, J 12.1), 3.56 (3H, s), 4.01 (1H, d, J 13.7), 4.11 (1H, d, J 13.8), 7.37 (1H, d, J 8.0), 7.56 (2H, t, J 7.6), 7.72 (2H, d, J 8.0), 7.80 (2H, d, J 8.2); M/Z (ES⁺) 502 (MH⁺).

Step 3: (±)-cis-{1-[2-Propyl-5-(trifluoromethyl)benzyl]-2-[4(trifluoromethyl)phenyl]piperidin-4-yl}acetic acid The title compound was prepared as described for Example 3, Step 5. M/Z (ES⁺) 488 (MH⁺).

Example 53

(±)-cis-{1-[2,5-Bis(trifluoromethyl)benzyl]-2-[3-(trifluoromethyl)phenyl]piperidin-4-yl}acetic acid

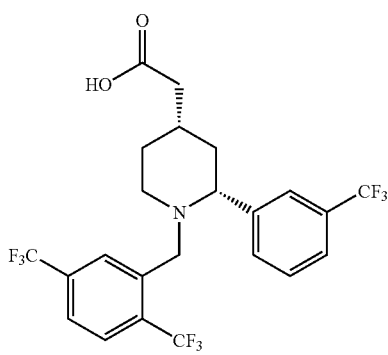

Step 1: (±)-cis-Methyl{2-[3-(trifluoromethyl)phenyl]piperidin-4-yl}acetate hydrochloride

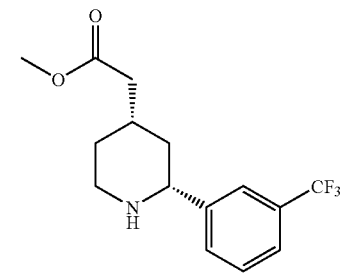

The compound was prepared in the manner of Example 3 substituting 3-(trifluoromethyl)benzeneboronic acid in the sequence. M/Z (ES⁺) 302 (MH⁺).

Step 2: (±)-cis-{1-[2,5-Bis(trifluoromethyl)benzyl]-2-[3-(trifluoromethyl)phenyl]piperidin-4-yl}acetic acid

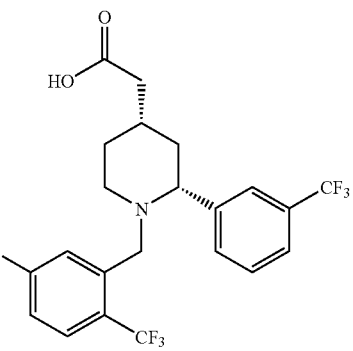

The compound was prepared in the manner of Example 20 to give a pale white solid. M/Z (ES⁺) 514 (MH⁺).

Examples 54 to 57

The following examples were prepared by reaction of 2,4-bis(trifluoromethyl)benzyl bromide and a piperidine as described in Example 20. The piperidines were prepared by either the route described in Example 3 or Example 11.

| Example | Structure | Name | M/Z ES+ [MH]+ |
|---|---|---|---|
| 54 | 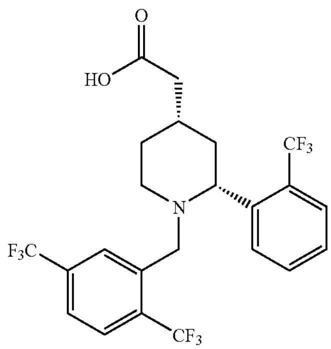 | (±)-cis-{1-(2,5-Bis(trifluoromethyl)benzyl]-2-[2-(trifluoromethyl)phenyl]piperidin-4-yl}acetic acid | 514 |
| 55 | 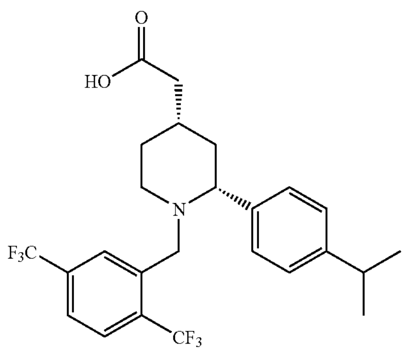 | (±)-cis-[1-[2,5-Bis(trifluoromethyl)benzyl]-2-(4-isopropylphenyl)piperidin-4-yl]acetic acid | 488 |
| 56 | 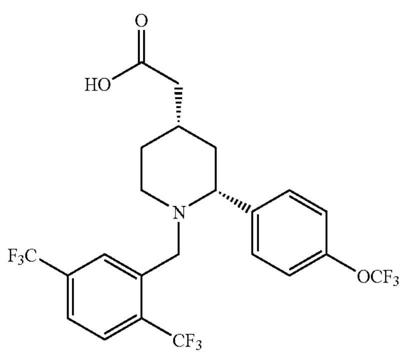 | (±)-cis-{1-[2,5-Bis(trifluoromethyl)benzyl]-2-[4-(trifluoromethoxy)phenyl]piperidin-4-yl}acetic acid | 530 |
| 57 | 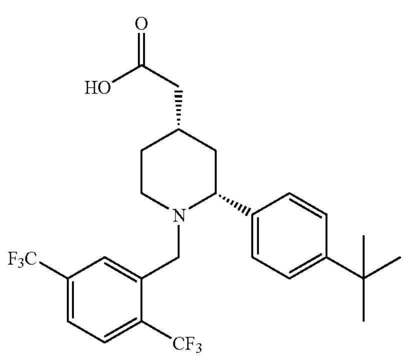 | (±)-cis-[1-[2,5-Bis(trifluoromethyl)benzyl]-2-(4-tert-butylphenyl)piperidin-4-yl]acetic acid | 502 |

Example 58

(±)-cis-3-{-1-[2,5-Bis(trifluoromethyl)benzyl]-2-[4-(trifluoromethyl)phenyl]piperidin-4-yl}propanoic acid

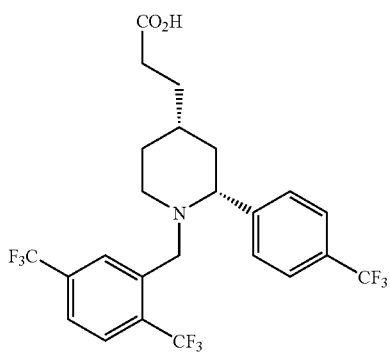

Step 1: (±)-cis-1-{-1-[2,5-Bis(trifluoromethyl)benzyl]-2-[4-(trifluoromethyl)phenyl]piperidin-4-yl}-3-diazoacetone

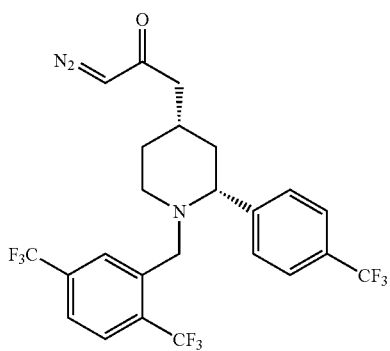

Oxalyl chloride (65 µl, 0.77 mmol) was added to a suspension of (±)-cis-{1-[2,5-bis(trifluoromethyl)benzyl]-2-[4-(trifluoromethyl)phenyl]piperidin-4-yl}acetic acid (Example 56) (157 mg, 0.30 mmol) in DCM (10 ml). DMF (5 µl) was added and the pale yellow solution obtained was stirred at RT under $N_2$, for 2 h. The yellow solution was concentrated in vacuo and oxalyl chloride removed by azeotroping with toluene to yield a yellow solid. This was dissolved in THF/MeCN (5 ml/5 ml) cooled to 0° C. and TMS diazomethane (0.3 ml, 2M in hexane, 0.60 mmol) was added under $N_2$. The mixture was stirred for 5 h at 0° C. and then at RT for 16 h. The yellow solution was evaporated in vacuo to give a pale brown gum (164 mg). The crude product was purified by chromatography (silica, 10% EtOAc/isohexane) to give a clear gum (91 mg, 56%). M/Z (ES$^+$) 488 (MH$^+$).

Step 2: (±)-cis-Methyl 3-{-1-[2,5-bis(trifluoromethyl)benzyl]-2-[4-(trifluoromethyl)phenyl]piperidin-4-yl}propanoate To a solution of 1-{-1-[2,5-bis(trifluoromethyl)benzyl]-2-[4-(trifluoromethyl)phenyl]piperidin-4-yl}-3-diazoacetone (91 mg, 0.17 mmol) in MeOH (2 ml) at RT, under $N_2$, was added 160 µl of a filtered solution of silver benzoate in triethylamine (0.5 g/5 ml), equivalent to 0.07 mmol of silver benzoate. The resulting deep purple solution was stirred at RT, under $N_2$, for 1 h, then quenched with $NaHCO_3$ (20 ml) and extracted into EtOAc (2×20 ml). Organic extracts were washed with $H_2O$ (20 ml), brine (20 ml) and dried ($MgSO_4$). Solvent was removed in vacuo to yield a clear gum (58 mg). The crude product was purified by chromatography (silica, 3% EtOAc/isohexane) to give a clear gum (38 mg, 0.07 mmol, 41%). $^1$H NMR (500 MHz, CDCl$_3$) δ: 1.40-1.26 (3H, m), 1.61 (2H, q, J 6.9), 1.71 (1H, d, J 12.5), 1.84 (1H, d, J 10.3), 2.10 (1H, t, J 11.0), 2.33 (2H, t, J 7.6), 2.88 (1H, d, J 11.8), 3.31 (1H, d, J 15.2), 3.36 (1H, t, J 5.6), 3.63 (1H, d, J 15.7), 3.66 (3H, s), 7.57-7.51 (5H, m), 7.67 (1H, d, J 8.0), 8.20 (1H, s); M/Z (ES$^+$) 542 (MH$^+$).

Step 3: (±)-cis-3-{-1-[2,5-Bis(trifluoromethyl)benzyl]-2-[4-(trifluoromethyl)phenyl]piperidin-4-yl}propanoic acid

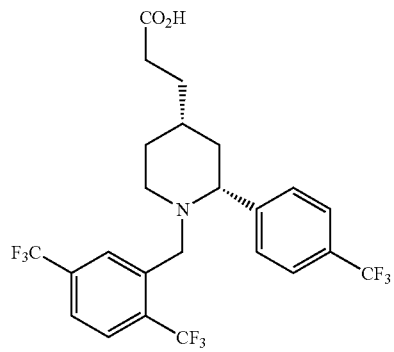

Example 59

(±)-{(2R*,3R*)-1-[2,5-Bis(trifluoromethyl)benzyl]-2-[4-(trifluoromethyl)phenyl]piperidin-3-yl}acetic acid

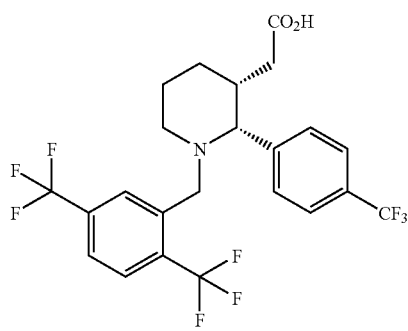

The title compound was prepared from the pyridine in Example 15 Step 2 using the method in Example 3 Step 3 followed by the method in Example 64 Steps 5 and 6.¹H NMR (500 MHz, CD₃OD) δ: 1.59-1.63 (1H, m), 1.80-1.96 (3H, m), 2.22-2.31 (2H, m), 2.45-2.58 (2H, m), 2.97-2.99 (1H, m), 3.38 (1H, d, J 16.3), 3.85 (1H, d, J 16.3), 3.91 (1H, d, J 3.4), 7.52 (2H, d, J 8.2), 7.64 (2H, d, J 8.2), 7.77 (1H, d, J 8.2), 7.87 (1H, d, J 8.2), 8.40 (1H, s); M/Z (ES⁺) 514 (MH⁺).

Example 60

(±)-(2S*,4R*)-4-Allyl-1-[2,5-bis(trifluoromethyl)benzyl]-2-[4-(trifluoromethyl)phenyl]piperidine-4-carboxylate

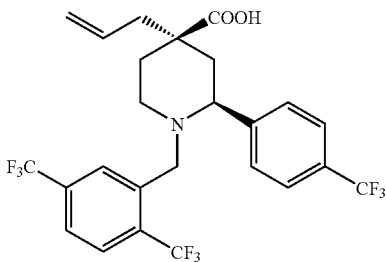

a) (±)-1-tert-Butyl 4-methyl 2-[4-(trifluoromethyl)phenyl]piperidine-1,4-dicarboxylate The compound of Example 18b (3.23 g) was dissolved in DCM (75 ml) and Na₂CO₃ solution (100 ml, 2N) was added. Tert-butyl dicarbonate (2.4 g) was added and the two-phase mixture was stirred overnight. The organic layer was separated, dried (brine, MgSO₄) and evaporated to yield a colourless oil (3.8 g). ¹H NMR (400 MHz, CDCl₃) δ: 1.33 (9H, s), 1.86-2.00 (2H, m), 2.20-2.34 (2H, m), 2.66-2.76 (1H, m), 3.34-3.42 (1H, m), 3.44 (3H, s), 4.04-4.10 (1H, m), 5.06 (1H, t, J 7.0), 7.30 (2H, d, J 8.4), 7.56 (2H, d, J 8.2).

b) (±)-1-tert-Butyl (2S*,3R*)4-methyl 4-allyl-2-[4-(trifluoromethyl)phenyl]piperidine-1,4-dicarboxylate The ester described in a) (0.9 g) was dissolved in anhydrous THF (30 ml) and the solution cooled to −78° C. Lithium hexamethyldisilazide (3.5 ml, IM) was added dropwise and the solution stirred for 30 min at −30° C. The mixture was re-cooled to −78° C. and allyl bromide (0.4 ml) added. This mixture was stirred overnight slowly warming to room temperature. The solution was quenched with citric acid (10 ml, 2N) and extracted with EtOAc. The organic extracts were washed with brine, dried (MgSO₄) and evaporated. The crude oil was purified by chromatography on silica using 5-10% EtOAc in hexane to yield the desired product as the major epimer (390 mg, 40%). ¹H NMR (500 MHz, CDCl₃) δ: 1.38 (10H, d, J 11.9), 1.98 (1H, dd, J 6.4, 14.2), 2.12 (1H, dd, J 7.4, 13.5), 2.18 (1H, d, J 13.6), 2.40 (1H, dd, J 7.4, 13.5), 2.67 (1H, d, J 14.2), 3.03 (3H, s), 3.31-3.37 (1H, m), 4.12 (1H, t, J 12.7), 5.04 (2H, t, J 12.7), 5.39 (1H, s), 5.56-5.64 (1H, m), 7.55 (2H, d, J 8.2).

c) (±)-Methyl{(2S*,3R*)-4-allyl-2-[4-(trifluoromethyl)phenyl]piperidin-4-yl}carboxylate The Boc-protected piperidine described in b) above (390 mg) was dissolved in DCM (3 ml), trifluoroacetic acid (0.6 ml) added and the solution stirred for 1 h. The solution was neutralized with NaHCO₃ (aq, satd.), and stirred until all effervescence had ceased. The organic layer was separated, dried (MgSO₄) and was evaporated to give a pale yellow oil (262 mg, 88%). ¹H NMR (500 MHz, CDCl₃) δ: 1.73 (1H, dd, J 11.9, 13.4), 1.81-1.96 (3H, m), 2.60-2.68 (2H, m), 3.01-3.07 (1H, m), 3.09-3.13 (H, m), 3.66 (3H, s), 3.91 (1H, dd, J 2.2, 11.7), 5.13 (2H, dd, J 11.3, 17.0), 5.64-5.72 (1H, m), 7.47 (2H, d, J 8.1), 7.57 (2H, d, J 8.1).

d) (±)-Methyl{(2S*,3R*)-4-allyl-1-[2,5-bis(trifluoromethyl)benzyl]-2-[4-(trifluoromethyl)phenyl]piperidine-4-carboxylate The amine described in c) above (260 mg), 2,5-bis(trifluoromethyl)benzyl bromide (488 mg), sodium iodide (25 mg), potassium carbonate (327 mg) in dimethylformamide (2 ml) were heated at 60° C. overnight. The cooled mixture was dispersed between water and EtOAc and the organic extracts washed with sodium thiosulfate, brine, then dried (MgSO₄) and evaporated. The crude oil was purified by chromatography on silica using 5-10% ether in hexane to yield the product as a colourless oil (430 mg).

¹H NMR (500 MHz, CDCl₃) δ: 0.82-0.89 (1H, m), 1.83 (1H, dd, J 2.3, 13.8), 1.94-2.08 (3H, m), 2.29 (1H, s), 2.32-2.38 (1H, m), 2.63 (2H, d, J 7.2), 2.74-2.78 (1H, m), 3.38 (1H, d, J 15.6), 3.61 (1H, dd, J 4.1, 10.6), 3.68 (4H, d, J 11.6), 5.14 (2H, dd, J 17.0, 20.7), 5.61-5.69 (1H, m), 7.52-7.60 (5H, m), 7.69 (1H, d, J 8.2), 8.19 (1H, s).

e) (±)-{(2S*,3R*)-4-Allyl-1-[2,5-bis(trifluoromethyl)benzyl]-2-[4-(trifluoromethyl)phenyl]piperidine-4-carboxylic acid The ester described in d) above was dissolved in a dioxane solution of HCl (20 ml, 4N) and the solution was heated under reflux for 1 h. The mixture was evaporated and neutralised with aqueous Na₂CO₃ to pH=4. This mixture was extracted with EtOAc; the organic extracts were washed with brine, dried (MgSO₄) and evaporated. The crude oil was purified by chromatography on silica using 10-50% EtOAc in hexane as eluant to give the product as a white solid (210 mg, 50%). $^1$H NMR (500 MHz, CD$_3$OD) δ: 1.87-1.95 (2H, m), 2.01-2.09 (2H, m), 2.50 (1H, t, J 11.7), 2.66-2.80 (3H, m), 3.49 (1H, d, J 15.4), 3.71 (1H, d, J 15.8), 3.77 (1H, dd, J 2.8, 11.6), 5.14 (1H, d, J 10.1), 5.24 (1H, d, J 15.7), 5.73-5.81 (1H, m), 7.63 (4H, s), 7.72 (1H, d, J 8.1), 7.82 (1H, d, J 8.2), 8.27 (1H, s).

Example 61

(±)-(2S*,3R*)-4-Allyl-1-[2,5-bis(trifluoromethyl) benzyl]-2-[4-(trifluoromethyl)phenyl]piperidin-4-yl}acetic acid

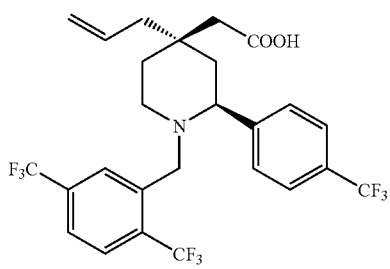

a) (±)-tert-Butyl 4-allyl-1-[2,5-bis(trifluoromethyl) benzyl]-2-[4-(trifluoromethyl)phenyl]piperidin-4-yl}acetate The compound of Example 60 (160 mg) was dissolved in DCM (2 ml) and oxalyl chloride (0.12 ml) was added followed by 1 drop DMF. Effervescence was accompanied by slow appearance of a white precipitate over 30 min. The reaction was monitored by quenching an aliquot of reaction mixture in MeOH and this was analysed by mass spectrometry. The mixture was evaporated and dried in vacuo. The residue was re-dissolved in acetonitrile (1.5 ml) and THF (1.5 ml) and cooled to 0° C. Trimethylsilyldiazomethane (0.5 ml, 2M in hexane) was added and the mixture stirred overnight. The solution was evaporated and re-dissolved in t-butanol (3 ml) containing 10 mg silver benzoate and heated under reflux for 30 min. The solution was cooled and evaporated and the crude material purified by chromatography on silica using 5-10% EtOAc in hexane as eluant to give the product as a white solid (40 mg, 22%). $^1$H NMR (500 MHz, CDCl$_3$) δ: 1.44 (9H, s), 1.64-1.76 (3H, m), 1.81 (1H, d, J 13.8), 2.15 (2H, q, J 11.5), 2.35-2.51 (3H, m), 2.69 (1H, dd, J 3.9, 9.1), 3.38 (1H, d, J 15.4), 3.61-3.67 (2H, m), 5.15-5.19 (2H, m), 5.79-5.87 (1H, m), 7.50 (2H, d, J 7.9), 7.56 (3H, d, J 8.4), 7.68 (1H, d, J 8.1), 8.21 (1H, s); M/Z (ES$^+$) 610 (MH$^+$).

b) (±)-(2S*,3R*)-4-Allyl-1-[2,5-bis(trifluoromethyl) benzyl]-2-[4-(trifluoromethyl)phenyl]piperidin-4-yl}acetic acid The ester described in a) above was dissolved in DCM (1 ml) and trifluoroacetic acid (0.3 ml) and the solution was stirred overnight. The solution was evaporated and the crude material was dissolved in DCM, the organic extract was washed with water, dried (MgSO$_4$) and evaporated. The crude material was purified by chromatography on silica using 10-50% EtOAc in hexane as eluant to give the product as a white solid (23 mg) which was crystallized from ether-hexane to give white crystals. $^1$H NMR (500 MHz, CD$_3$OD) δ: 1.63-1.73 (4H, m), 2.15 (2H, s), 2.36-2.44 (3H, m), 2.60 (1H, dd, J 3.5, 8.9), 3.35 (1H, d, J 15.7), 3.59 (1H, d, J 15.8), 3.66 (1H, dd, J 2.7, 11.3), 5.09 (2H, dd, J 17.0, 26.6), 5.77-5.85 (1H, m), 7.50 (4H, t, J 9.3), 7.59 (1H, d, J 8.2), 7.70 (1H, d, J 8.2), 8.16 (1H, s); M/Z (ES$^+$) 554 (MH$^+$).

Example 62

(±)-{(2R*,4S*)-1-[(1R* or S*)-1-Phenylethyl]-2-[4-(trifluoromethyl)phenyl]piperidin-4-yl}acetic acid

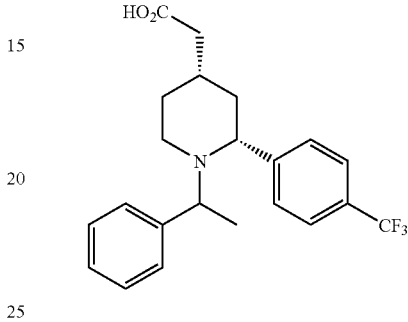

Step 1: (±)-Methyl{(2R*,4S*)-1-[(1R* or S*)-1-phenylethyl]-2-[4-(trifluoromethyl)phenyl]piperidin-4-yl}acetate

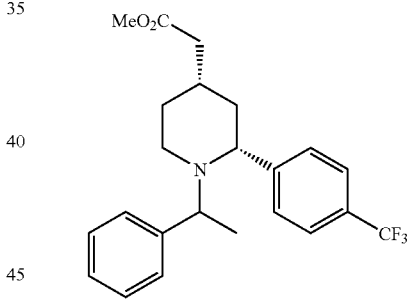

A solution of methyl{2-[4-(trifluoromethyl)phenyl]piperidin-4-yl}acetate, Example 3, Step 3, (220 mg, 0.73 mmol) acetophenone (116 µl, 1 mmol) and p-toluene sulphonic acid (27 mg, 0.15 mmol) in PhMe (10 ml) was heated at reflux under Dean-Stark conditions for 60 hours. The cooled reaction was evaporated in vacuo. The residue was dissolved in DCE (10 ml) treated with sodium triacetoxyborohydride (773 mg, 3.7 mmol) and the mixture stirred at room temperature for 16 hours. The mixture was concentrated in vacuo and the residue was diluted with NaHCO$_3$ solution (sat) and extracted with EtOAc (×2). The combined extracts were washed with brine (×1), then dried (MgSO$_4$), filtered and evaporated. The residue was purified by SCX ion exchange chromatography followed by chromatography on silica, eluting with 10% EtOAc/isohexane to give the ester (4 mg, 1%) M/Z (ES+) 406 (MH$^+$).

Step 2: (±)-{(2R*,4S*)-1-[(1R* or S*)-1-Phenylethyl]-2-[4-(trifluoromethyl)phenyl]piperidin-4-yl}acetic acid

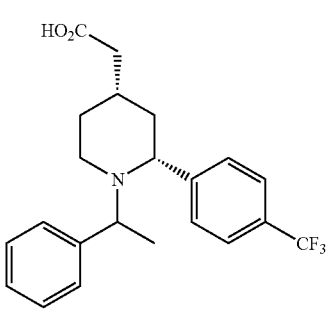

The title compound was prepared by hydrolysis in an analogous fashion to Example 3, Step 5. M/Z (ES+) 392 ([MH]+).

Example 63

(±)-((2R*,4S*)-2-[4-(trifluoromethyl)phenyl]-1-{(1R/S)-1-[4-(trifluoromethyl)phenyl]butyl}piperidin-4-yl)acetic acid

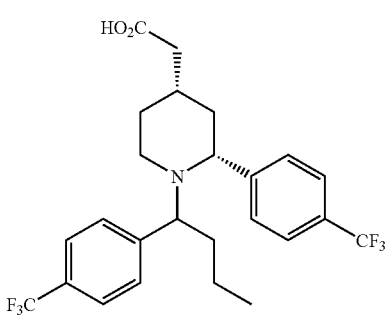

The title compound was prepared analogously to Example 62. M/Z (ES+) 488 (MH+).

Example 64

(±)-{(1S*,3R/S,5R*)-8-(4-Isopropylbenzyl)-1-[4-(trifluoromethyl)phenyl]-8-azabicyclo[3.2.1]oct-3-yl}acetic acid

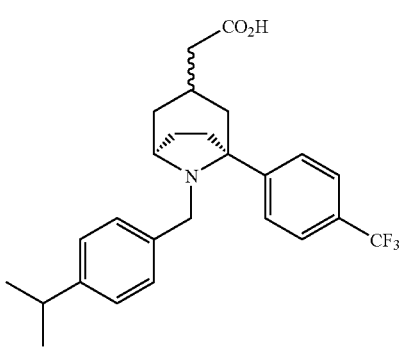

Step 1: 4-Oxo-4-[4-(trifluoromethyl)phenyl]butanal

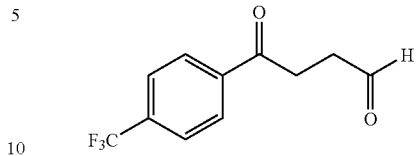

The title compound was prepared by a modification of the literature procedure (J. Org. Chem., 1991, 56, 1822) using 4-trifluoromethylphenyl magnesium bromide prepared from 4-trifluoromethylphenyl bromide (2.52 ml) and magnesium turnings (0.526 g) instead of phenylmagnesium chloride. $^1$H NMR (360 MHz, CDCl$_3$) δ: 2.98 (2H, t, J 6.2), 3.34 (2H, t, J 6.2), 7.75 (2H, d, J 8.1), 8.09 (2H, d, J 8.1), 9.91 (1H, s).

Step 2: (±)-(1S*,5R*)-8-(4-Methoxybenzyl)-1-[4-(trifluoromethyl)phenyl]-8-azabicyclo[3.2.1]octan-3-one

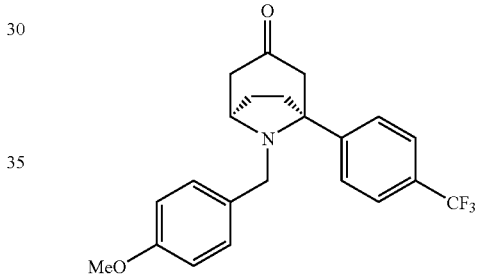

To a mixture of 4-methoxybenzylamine (5.420 g, 39 mmol) and NaOAc.3H$_2$O (29.324 g, 215 mmol) in H$_2$O (25 ml) at 0° C. was added 2N HCl (21.5 ml) followed by acetonedicarboxylic acid (6.559 g, 45 mmol). The reaction was stirred until a clear light brown solution was obtained then the ketoaldehyde (Step 1, 8.267 g, 36 mmol) in THF (25 ml) was added. The reaction was stirred for 30 mins at 0° C. then allowed to warm to rt before heating at 40° C. for 3 hrs. The reaction was allowed to cool and the pH was adjusted to 10 using NaHCO$_3$ and 4N NaOH solution. The mixture was extracted with EtOAc (×3), the combined extracts were washed with brine, dried (MgSO$_4$), filtered and evaporated. The residue was purified by chromatography (silica, 10% EtOAc/isohexane) to give the ketone (3.837 g, 27%). $^1$H NMR (360 MHz, CDCl$_3$) δ: 1.59-1.66 (1H, m), 2.02-2.21 (4H, m), 2.81-2.87 (3H, m), 3.48 (1H, d, J 13.5), 3.55 (1H, d, J 13.5), 3.65 (1H, t, J 4.9), 3.81 (3H, s), 6.86-6.90 (2H, m), 7.26-7.29 (2H, m), 7.63-7.69 (4H, m).

Step 3: (±)-Ethyl(2E/Z)-{(1S*,5R*)-8-(4-methoxybenzyl)-1-[4-(trifluoromethyl)phenyl]-8-azabicyclo[3.2.1]oct-3-ylidene}acetate

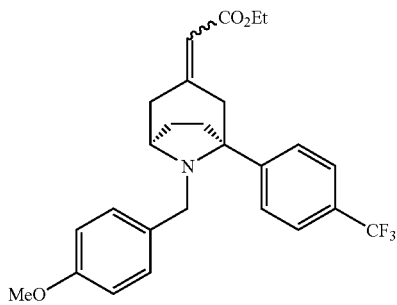

Sodium hydride (60% dispersion in oil, 1.047 g, 26 mmol) was added portionwise to a stirred solution of triethyl phosphonoacetate (5.1 ml, 26 mmol) in dry THF (20 ml) at 0° C. under nitrogen. After 1 hr a solution of the ketone (Step 2, 2.00 g, 5.1 mmol) in dry THF (40 ml) was added. The reaction was heated under reflux for 16 hrs then quenched with $H_2O$. The mixture extracted with EtOAc (×3), the combined extracts were washed with brine, dried ($MgSO_4$), filtered and evaporated. The residue was purified by chromatography (silica, 5-10% EtOAc/isohexane) to give the unsaturated ester (2.10 g, 89%, mixture of isomers). M/Z ($ES^+$) 460 ($MH^+$).

Step 4: (±)-Ethyl{(1S*,3R/S,5R*)-1-[4-(trifluoromethyl)phenyl]-8-azabicyclo[3.2.1]oct-3-yl}acetate

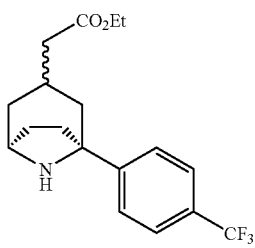

The unsaturated ester (Step 3, 0.800 g, 1.7 mmol) was taken up in ethanol (20 ml) and hydrogenated at 40 psi over 10% Pd/C (100 mg) for 48 hours. The catalyst was removed by filtration. The filtrate was evaporated, and the residue was purified by chromatography (silica, 2-5% 2N ammonia in MeOH/DCM) to give the amine (0.374 g, 63%, mixture of isomers). M/Z ($ES^+$) 342 ($MH^+$).

Step 5: (±)-Ethyl{(1S*,3R/S,5R*)-8-(4-isopropylbenzyl)-1-[4-(trifluoromethyl)phenyl]-8-azabicyclo[3.2.1]oct-3-yl}acetate

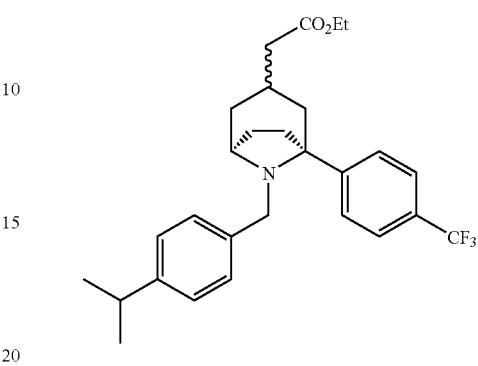

A mixture of the amine from Step 4 (91 mg, 0.27 mmol), 4-isopropyl benzylbromide (0.114 g, 0.53 mmol) and $K_2CO_3$ (0.184 g, 1.33 mmol) in DMF (2 ml) was heated in the microwave at 150° C. for 15 mins. The reaction was diluted with $H_2O$ (10 ml). The mixture extracted with EtOAc (×3), the combined extracts were washed with $H_2O$ (×2) and brine, dried ($MgSO_4$), filtered and evaporated. The residue was purified by chromatography (silica, 10% $Et_2O$/isohexane) to give the ester (0.120 g, 95%, mixture of isomers). M/Z ($ES^+$) 474 ($MH^+$).

Step 6: (±)-{(1S*,3R/S,5R*)-{8-(4-Isopropylbenzyl)-1-[4-(trifluoromethyl)phenyl]-8-azabicyclo[3.2.1]oct-3-yl}acetic acid The ester from Step 5 (120 mg, 0.25 mmol) and LiOH (121 mg, 5.1 mmol) in THF (3 ml) and $H_2O$ (3 ml) was stirred at rt for 16 hours. The reaction was acidified with 2N HCl then extracted with EtOAc (×3). The combined extracts were washed with brine, dried ($MgSO_4$), filtered and evaporated. The residue was purified by chromatography (silica, 5% EtOAc/DCM) to give the acid (0.111 g, 98%, mixture of isomers). $^1$H NMR (500 MHz, $CD_3OD$) δ: 1.23 (6H, d, J 6.9), 1.43 (1H, d, J 14.9), 1.68 (1H, m), 1.86-1.99 (2H, m), 2.24-2.46 (5H, m), 2.56-2.62 (2H, m), 2.89 (1H, septet, J 6.9), 3.35-3.40 (1H, m), 3.55-3.80 (2H, m), 7.20-7.30 (4H, m), 7.70-7.78, (4H, m). M/Z ($ES^+$) 446 ($MH^+$).

Example 65

(±)-{(1S*,3R*,5R*)-8-(4-Isopropylphenyl)-1-[4-(trifluoromethyl)phenyl]-8-azabicyclo[3.2.1]octane-3-carboxylic acid

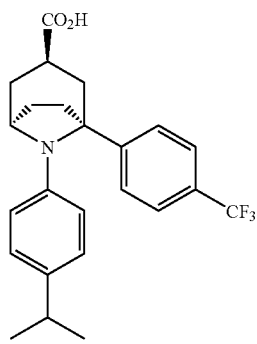

Step 1: (±)-(1R*,5S*)-8-(4-Methoxybenzyl)-1-[4-(trifluoromethyl)phenyl]-8-azabicyclo[3.2.1]oct-2-en-3-yl trifluoromethanesulfonate and (1R*,5S*)-8-(4-methoxybenzyl)-5-[4-(trifluoromethyl)phenyl]-8-azabicyclo[3.2.1]oct-2-en-3-yl trifluoromethanesulfonate

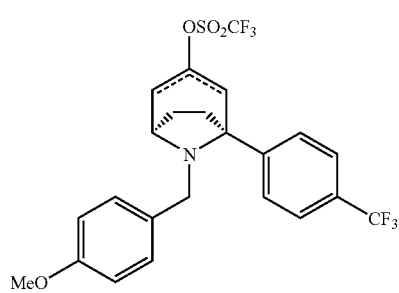

Sodium bis(trimethylsilyl)amide (1.0M in THF, 8.1 ml, 8.1 mmol) was added dropwise to a stirred solution of the ketone (Example 64 Step 2, 2.509 g, 6.4 mmol) in dry THF (20 ml) at −78° C. under nitrogen. After 3 hr a solution of N-phenyltrifluoro methanesulfonimide (2.900 g, 8.1 mmol) in dry THF (10 ml) was added. The reaction was allowed to warm to rt and stirred for 16 hrs. The reaction was concentrated in vacuo and the residue was purified by chromatography (silica, 5% EtOAc/isohexane) to give the vinyl triflate (2.858 g, 85%, mixture of isomers). M/Z (ES$^+$) 522 (MH$^+$).

Step 2: (±)-Methyl(1R*,5S*)-8-(4-methoxybenzyl)-1-[4-(trifluoromethyl)phenyl]-8-azabicyclo[3.2.1]oct-2-ene-3-carboxylate and (±)-methyl(1R*,5S*)-8-(4-methoxybenzyl)-5-[4-(trifluoromethyl)phenyl]-8-azabicyclo[3.2.1]oct-2-ene-3-carboxylate

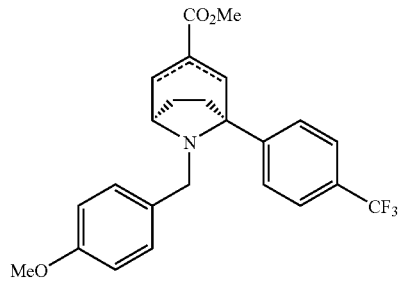

A solution of the vinyl triflate (Step 1, 2.858 g, 5.5 mmol), 1,1'-bis(diphenylphosphino)ferrocene (0.182 g, 0.32 mmol) and triethylamine (1.53 ml, 1 mmol) in MeOH (10 ml) and dry DMF (5 ml) was deoxygenated by bubbling nitrogen through the solution for 10 mins. Palladium (II) acetate (37 mg, 0.16 mmol) was added and carbon monoxide was bubbled through the solution for 5 mins. The reaction was stirred at rt for 16 hrs under a balloon of carbon monoxide. The reaction was concentrated in vacuo. The mixture was partitioned between EtOAc and saturated NaHCO$_3$ solution. The layers were separated and the aqueous layer was further extracted with EtOAc (×2). The combined extracts were washed with H$_2$O then brine, dried (MgSO$_4$), filtered and evaporated. The residue was purified by chromatography (silica, 10% Et$_2$O/isohexane) to give the unsaturated ester (1.579 g, 67%, mixture of isomers). M/Z (ES$^+$) 432 (MH$^+$).

Step 3: (±)-Methyl(1S*,3R/S,5R*)-1-[4-(trifluoromethyl)phenyl]-8-azabicyclo[3.2.1]octane-3-carboxylate

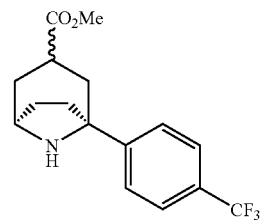

The unsaturated ester (Step 2, 1.475 g, 3.4 mmol) was taken up in MeOH (40 ml) and hydrogenated at 40 psi over 10% Pd/C (150 mg) for 24 hrs. The catalyst was removed by filtration and the filtrate was evaporated to give the amine (0.966 g, 90%, mixture of isomers). M/Z (ES$^+$) 314 (MH$^+$).

Step 4: (±)-{(1S*,3R*,5R*)-8-(4-Isopropylphenyl)-1-[4-(trifluoromethyl)phenyl]-8-azabicyclo[3.2.1]octane-3-carboxylic acid

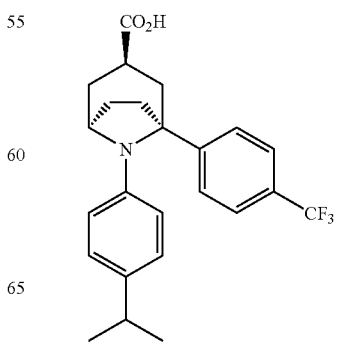

A mixture of the amine from Step 3 (0.200 g, 0.6 mmol), 4-isopropyl bromobenzene (0.127 g, 0.6 mmol), tris(dibenzylideneacetone) dipalladium (0) (29 mg, 0.03 mmol) and 2-dicyclohexylphosphino-2'-(N,N-dimethyl amino)diphenyl (50 mg, 0.13 mmol) in potassium t-butoxide solution (1.0M in THF, 1.28 ml, 1.2 mmol) was heated in the microwave at 150° C. for 1 hr. The reaction was diluted with $H_2O$ and EtOAc and filtered through Hyflo®. The mixture was extracted with EtOAc, the combined extracts washed with $H_2O$ (×2), then brine, dried ($MgSO_4$), filtered and evaporated. The residue was purified by chromatography (silica, 5-10% $Et_2O$/isohexane then 10% MeOH/DCM) to give a mixture of t-butyl and methyl esters and the title compound. M/Z ($ES^+$) 474, 432 and 418 ($MH^+$).

The t-butyl ester was stirred in trifluoroacetic acid (2 ml) for 3 hrs then evaporated to give the crude acid. The methyl ester and LiOH (15 mg, 0.6 mmol) in THF (2 ml) and $H_2O$ (2 ml) was stirred at 60° C. for 16 hrs. The reaction was allowed to cool to rt and then combined with the crude product obtained from the deprotection of the t-butyl ester and the acid obtained in the arylation step above. The mixture was acidified with 2N HCl, then extracted with EtOAc (×3). The combined extracts were washed with brine, dried ($MgSO_4$), filtered and evaporated. The residue was purified by chromatography (silica, 1% MeOH/DCM) to give the acid (0.105 g, 39%). $^1$H NMR (400 MHz, $CD_3OD$) δ: 1.12 (6H, d, J 6.9), 1.62-1.67 (1H, m), 1.84-2.01 (3H, m), 2.25-2.32 (2H, m), 2.41-2.51 (2H, m), 2.68 (1H, septet, J 6.9), 3.09-3.15 (1H, m), 4.67-4.69 (1H, m), 6.46-6.50 (2H, m), 6.83-6.87 (2H, m), 7.58-7.64 (4H, m). M/Z ($ES^+$) 418 ($MH^+$).

Examples 66-71

The following examples were made using either the amine from Example 64 Step 4 or Example 65 Step 3. The amines were N-benzylated and hydrolysed with the appropriate benzyl bromide using the method in Example 64 Steps 5 and 6 or N-arylated and hydrolysed using the method in Example 65 Step 4.

| Example | Structure | Name | M/Z ES+ [MH]+ |
|---|---|---|---|
| 66 | 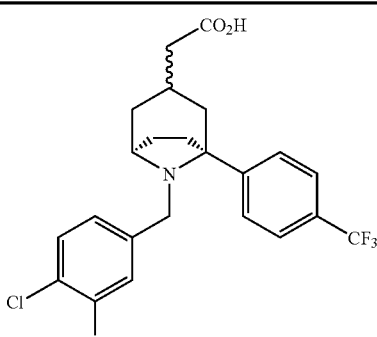 | (±)-{(1S*,3R/S,5R*)-{8-(3,4-Dichlorobenzyl)-1-[4-(trifluoromethyl)phenyl]-8-azabicyclo[3.2.1]oct-3-yl}acetic acid | 472, 474, 476 |
| 67 | 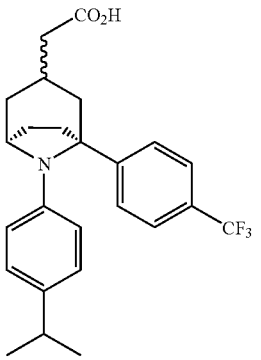 | (±)-{(1S*,3R/S,5R*)-{8-(4-Isopropylphenyl)-1-[4-(trifluoromethyl)phenyl]-8-azabicyclo[3.2.1]oct-3-yl}acetic acid | 432 |
| 68 | 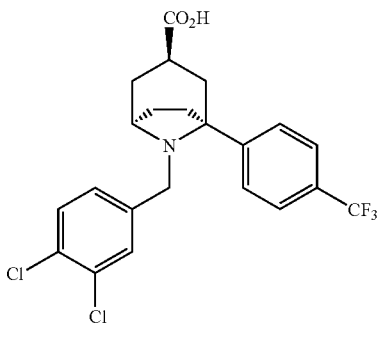 | (±)-{(1S*,3R*,5R*)-8-(3,4-Dichlorobenzyl)-1-[4-(trifluoromethyl)phenyl]-8-azabicyclo[3.2.1]octane-3-carboxylic acid | 458, 460, 462 |

-continued

| Example | Structure | Name | M/Z ES+ [MH]+ |
|---|---|---|---|
| 69 | 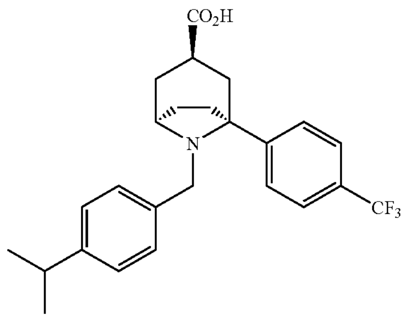 | (±)-{(1S*,3R*,5R*)-8-(4-Isopropylbenzyl)-1-[4-(trifluoromethyl)phenyl]-8-azabicyclo[3.2.1]octane-3-carboxylic acid | 432 |
| 70 | 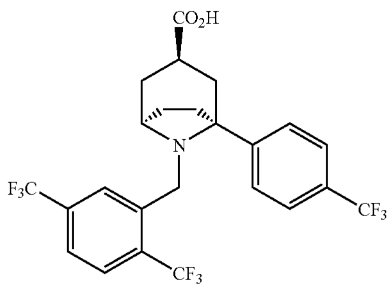 | (±)-{(1S*,3R*,5R*)-8-[2,5-Bis(trifluoromethyl)benzyl]-1-[4-(trifluoromethyl)phenyl]-8-azabicyclo[3.2.1]octane-3-carboxylic acid | 526 |
| 71 | 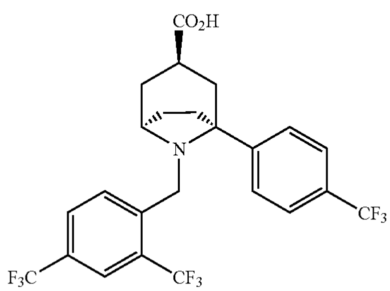 | (±)-{(1S*,3R*,5R*)-8-[2,4-Bis(trifluoromethyl)benzyl]-1-[4-(trifluoromethyl)phenyl]-8-azabicyclo[3.2.1]octane-3-carboxylic acid | 526 |

Example 72

(±)-{(2R*,4S*)-1-{(1R* or S*)-1-[2,5-bis(trifluoromethyl)phenyl]butyl}-2-[4-(trifluoromethyl)phenyl]piperidin-4-yl}acetic acid

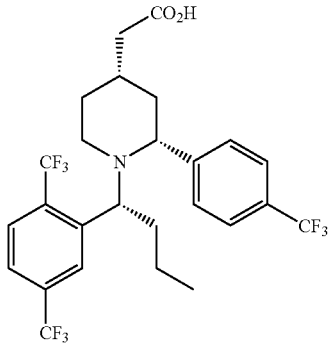

Step 1: (±)-N-{(1E)-[2,5-Bis(trifluoromethyl)phenyl]methylene}-2-methylpropane-2-sulfinamide

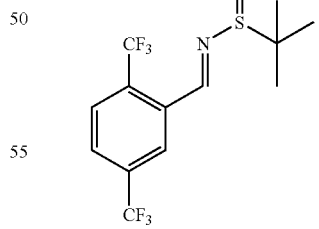

A mixture of 2,5-bis trifluoromethyl benzaldehyde (21.5 g, 51.6 mmol), (±)-tert butyl sulfinamide (16.1 g, 47 mmol) and anhydrous $CuSO_4$ (16.5 g, 103 mmol) in DCM (94 ml) was stirred at room temperature for 16 hours and at reflux for 3 days. The fine suspension was diluted with water and extracted with DCM. The extracts were washed with water, dried ($MgSO_4$) and evaporated in vacuo to an off white solid which was purified by chromatography (silica, 4-10%

EtOAc/isohexane) to give the sulfinamide as a white crystalline solid (14.8 g, 91%). M/Z (ES⁺) 346 (MH⁺).

Step 2: (t)-1-[2,5-Bis(trifluoromethyl)phenyl]butan-1-amine

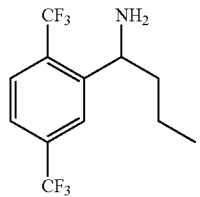

A solution of N-{(1E)-[2,5-bis(trifluoromethyl)phenyl]methylene}-2-methylpropane-2-sulfinamide (6.7 g, 19.4 mmol) in DCM (50 ml) at −78° C. was treated with n-propyl magnesium chloride (2M in DCM, 15 ml, 29 mmol). The resultant mixture was allowed to warm to room temperature over 16 hours. NH₄Cl solution (half saturated, 80 ml) was added and the solution was extracted with DCM. The extracts were washed with brine, dried (MgSO₄) and evaporated in vacuo to a yellow oil (9 g). The oil was dissolved in dry MeOH (200 ml) cooled to 0° C. and treated with HCl (4N in dioxane, 24 ml, 95 mmol). The solution was stirred at 0° C. for 90 minutes before the solvent was evaporated in vacuo. The residue was made basic (NaHCO₃, saturated) and extracted with DCM. The extracts were dried (MgSO₄) and evaporated in vacuo to a yellow oil (6.6 g) which was purified by chromatography (silica, 10-150% EtOAc/isohexane) to give the amine as a pale oil (5.1 g, 94%). M/Z (ES⁺) 286 (MH⁺).

Step 3: (±)-{1-[2,5-Bis(trifluoromethyl)phenyl]butyl}{(1E)-[4-(trifluoromethyl)phenyl]methylene}amine

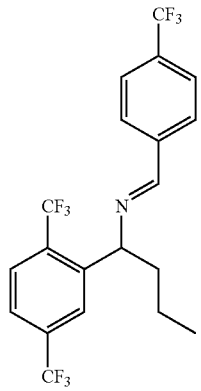

A mixture of 1-[2,5-bis(trifluoromethyl)phenyl]butan-1-amine (2.95 g, 10.3 mmol) and 4-trifluoromethyl benzaldehyde (1.8 g, 10.3 mmol) was swirled together for 30 minutes. M/Z (ES⁺) 442 (ME).

Step 4: (±)-(2R*)-1-{(1R* or S*)-1-[2,5-Bis(trifluoromethyl)phenyl]butyl}-2-[4-(trifluoromethyl)phenyl]piperidin-4-one

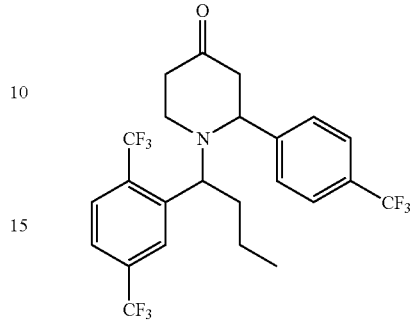

A solution of {1-[2,5-bis(trifluoromethyl)phenyl]butyl}{(1E)-[4-(trifluoromethyl)phenyl]methylene}amine (500 mg, 1.1 mmol) and trimethyl[(1-methyleneprop-2-en-1-yl)oxy]silane (468 mg, 3.3 mmol) in DCM (4 ml) was treated with trimethylsilyl trifluoromethanesulfonate (200 μl, 1.1 mmol) and the mixture was stirred at room temperature for 3 days. Tetrabutylammonioum fluoride (1M in THF, 5 ml, 5 mmol) was added and the mixture was diluted with water and extracted with EtOAc (×2). The extracts were washed with brine, dried (MgSO₄) and evaporated in vacuo to a pale oil (1.1 g) which was purified by chromatography (silica, 10% EtOAc/isohexane) to give the ketone as a pale oil (200 mg, 36%) plus a trace of a lower running diastereomer (4.5 mg, 0.8%). M/Z (ES⁺) 512 (MH⁺).

Step 5: (±)-Ethyl(2E/Z)-{(2R*)-1-{(1R* or S*)-1-[2,5-Bis(trifluoromethyl)phenyl]butyl}-2-[4-(trifluoromethyl)phenyl]piperidin-4-ylidene}acetate

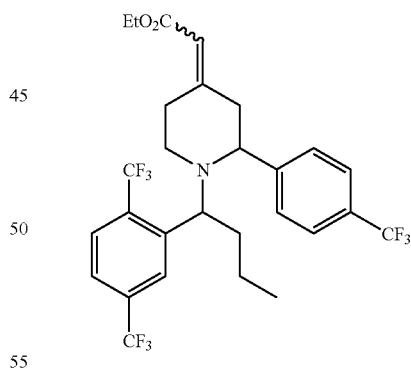

NaH (60%, 80 mg, 2.0 mmol) was added portionwise to a cold (0° C.) solution of triethyl phosphonoacetate (397 μl, 2.0 mmol) in THF (10 ml), under N₂ and the mixture was stirred at 0° C. for 30 minutes before 1-{1-[2,5-bis(trifluoromethyl)phenyl]butyl}-2-[4-(trifluoromethyl)phenyl]piperidin-4-one (200 mg, 0.39 mmol) was added as a solution in THF (5 ml). The mixture was stirred at 0° C. for 30 minutes before NH₄Cl solution (half saturated, 10 ml) was added and the mixture was extracted with EtOAc (2×40 ml). The extracts were washed with brine, dried (MgSO₄) and evaporated in vacuo to a pale mobile oil (543 mg) which was purified by chromatography (silica, 2% EtOAc/isohexane) to give the olefin as clear foamy gum (205 mg, 91%) M/Z (ES⁺) 582 (MH⁺).

Step 6: (±)-Ethyl{(2R*,4S*)-1-{(1R* or S*)-1-[2,5-bis(trifluoromethyl)phenyl]butyl}-2-[4-(trifluoromethyl)phenyl]piperidin-4-yl}acetate

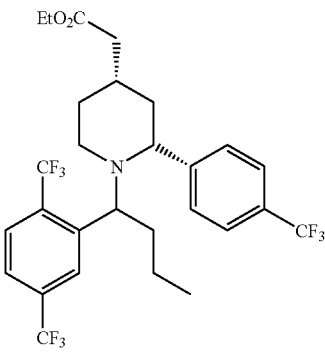

A solution of ethyl(2E)-{1-{1-[2,5-bis(trifluoromethyl)phenyl]butyl}-2-[4-(trifluoromethyl)phenyl]piperidin-4-ylidene}acetate (191 mg, 0.32 mmol) in ethanol (10 ml) was treated with Pd/C (10%, 25 mg) and the mixture was hydrogenated under a balloon of hydrogen for 30 minutes. The hydrogen atmosphere was removed and the catalyst removed by filtration. The filtrate was evaporated in vacuo to a clear oil (164 mg) which was purified by chromatography (silica, 25% DCM/isohexane) to give the cis piperidine as clear gum (81 mg, 42%). ¹H NMR (500 MHz, CDCl₃) δ: 0.75 (3H, t, J 7.3), 0.82-1.10 (2H, m), 1.22 (2H, t, J 7.2), 1.26-1.42 (4H, m), 1.67-2.03 (4H, m), 2.15-2.27 (2H, m), 2.61-2.65 (1H, m), 3.03-3.07 (1H, m), 3.73 (1H, dd, J 2.6, 11.2), 4.06-4.12 (3H, m), 7.36 (2H, d, J 8.1), 7.48 (2H, d, J 8.2), 7.55 (1H, d, J 8.2), 7.67 (1H, d, J 8.3), 7.79 (1H, s); M/Z (ES⁺) 584 (MH⁺).

Step 7: (±)-{(2R*,4S*)-1-{(1R* or S*)-1-[2,5-bis(trifluoromethyl)phenyl]butyl}-2-[4-(trifluoromethyl)phenyl]piperidin-4-yl}acetic acid

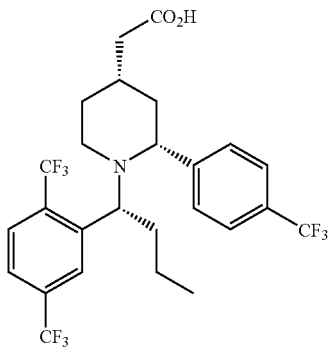

The title compound was prepared by hydrolysis of the ester using the procedure described in Example 3, Step 5 to give a white solid M/Z (ES⁺) 556 (MH⁺).

Example 73

(±)-{(2R*,4S*)-1-{(1S* or R*)-1-[2,5-bis(trifluoromethyl)phenyl]butyl}-2-[4-(trifluoromethyl)phenyl]piperidin-4-yl}acetic acid

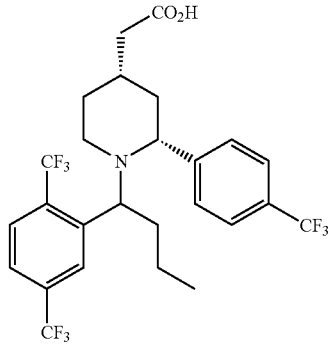

Step 1: (±)-Ethyl{(2R*,4S*)-1-{(1S* or R*)-1-[2,5-bis(trifluoromethyl)phenyl]butyl}-2-[4-(trifluoromethyl)phenyl]piperidin-4-yl}acetate

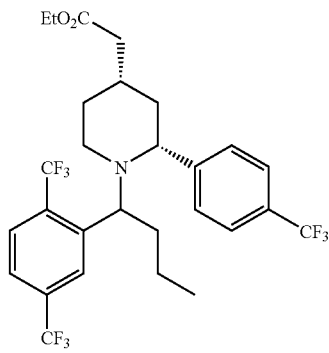

The title compound was prepared in a manner analogous to Example 72. Carrying out Step 4 on a larger scale (4 mmol) for 8 days allowed for the isolation of the lower running diastereomer which was processed through Steps 5 and 6 to give the ester. ¹H NMR (500 MHz, CDCl₃) δ: 0.86 (3H, t, J 7.3), 1.15-1.25 (6H, m), 1.33-1.41 (1H, m), 1.66-1.72 (2H, m), 1.82-1.92 (3H, m), 2.12-2.22 (2H, m), 2.73 (1H, t, J 10.7), 3.34 (1H, d, J 11.2), 3.52 (1H, dd, J 2.7, 10.8), 4.05-4.13 (2H, m), 4.22 (1H, t, J 7.4), 7.16 (2H, t, J 8.1), 7.34 (2H, d, J 8.1), 7.39 (1H, s), 7.48 (1H, d, J 8.2), 7.66 (1H, d, J 8.2).

Step 2: (±)-{(2R*,4S*)-1-{(1S* or R*)-1-[2,5-bis(trifluoromethyl)phenyl]butyl}-2-[4-(trifluoromethyl)phenyl]piperidin-4-yl}acetic acid

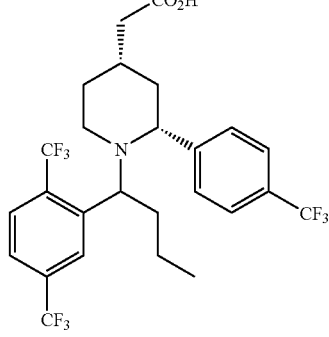

The title compound was prepared by hydrolysis of the ester (Step 1) using the procedure described in Example 3, Step 5 to give a white solid M/Z (ES+) 556 (MH+).

Example 74

(±)-(2S/R)-2-{(2R*,4S*)-1-[2,5-Bis(trifluoromethyl)benzyl]-2-[4-(trifluoromethyl)phenyl]piperidin-4-yl}pentanoic acid

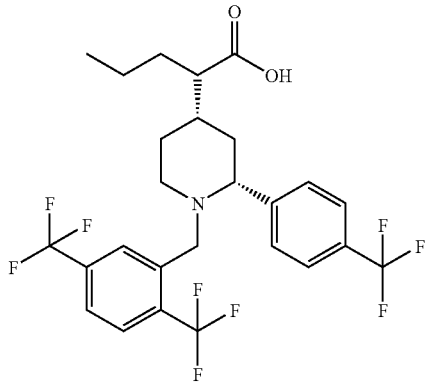

Step 1: (±)-Methyl(2S/R)-2-{(2R*,4S*)-1-[2,5-bis(trifluoromethyl)benzyl]-2-[4-(trifluoromethyl)phenyl]piperidin-4-yl}pent-4-enoate

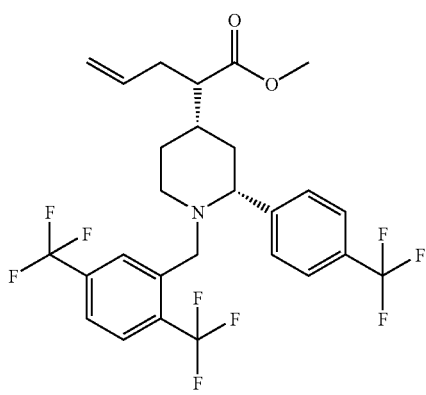

Lithium diisopropylamide (1.8M in hexanes/THF/ethylbenzene, 0.18 ml, 0.32 mmol) was added slowly to a stirred solution of the methyl ester from the prep of Example 36, (cis isomer, 100 mg, 0.21 mmol) in dry THF under $N_2$ at −78° C. This mixture was stirred at 0° C. for 30 min, then recooled to −78° C. and allyl bromide (30 µl, 0.35 mmol) was added. It was then allowed to warm to room temperature. After 30 min additional lithium diisopropylamide (0.12 ml, 0.22 mmol) and allyl bromide (20 µl, 0.22 mmol) were added following the same procedure. The reaction mixture was stirred at room temperature for 30 minutes, then partitioned between 2M HCl (aq) and ether. The aqueous layer was extracted with ether. The combined extracts were washed with brine (×1), dried ($Na_2SO_4$), filtered and evaporated. The residue was purified by chromatography on silica, eluting with 10% ether/isohexane to give the ester as a mixture of epimers (17 mg, 14%) as an oil. $^1$H NMR (400 MHz, CDCl$_3$) δ: 1.96-1.24 (5H, m), 2.13-2.07 (1H, m), 2.33-2.27 (3H, m), 2.92-2.86 (1H, m), 3.37-3.29 (2H, m), 3.66-3.60 (4H, m), 5.07-4.99 (2H, m), 5.74-5.67 (1H, m), 7.58-7.50 (5H, m), 7.72-7.66 (1H, m), 8.17 (1H, s); M/Z (ES+) 568 (MH+).

Step 2: (±)-Methyl(2S/R)-2-{(2R*,4S*)-1-[2,5-bis(trifluoromethyl)benzyl]-2-[4-(trifluoromethyl)phenyl]piperidin-4-yl}pentanoate

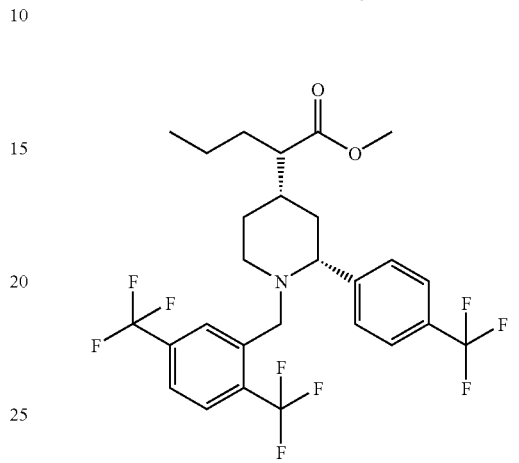

A solution of the alkene from Step 1 (17 mg, 0.03 mmol) in ethanol (1 ml) was stirred with Pd/C (ca. 5 mol % Pd) under an atmosphere of hydrogen (ca. 100 kPa) for ca. 18 h. The reaction mixture was filtered through a pad of Celite® filter aid and the filtrate concentrated to under vacuum to give 15 mg (88%) of the title compound as a colourless oil. $^1$H NMR (400 MHz, CDCl$_3$) δ: 0.91-0.85 (3H, m), 1.94-1.17 (9H, m), 2.10 (1H, t, J 12.4), 2.27-2.19 (1H, m), 2.91-2.85 (1H, m), 3.36-3.28 (2H, m), 3.66-3.60 (4H, m), 7.58-7.50 (5H, m), 7.67 (1H, d, J 8.2), 8.18 (1H, s); M/Z (ES+) 570 (MH+).

Step 3: (±)-(2S/R)-2-{(2R*,4S*)-1-[2,5-Bis(trifluoromethyl)benzyl]-2-[4-(trifluoromethyl)phenyl]piperidin-4-yl}pentanoic acid

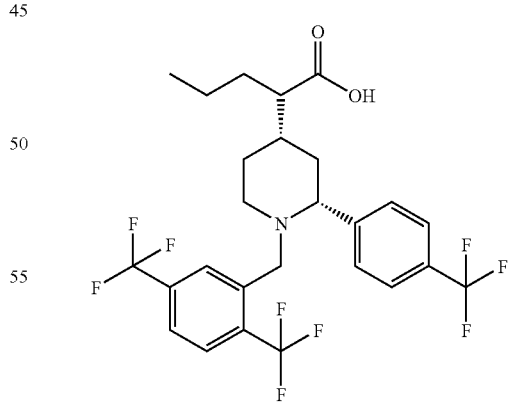

A solution of the ester from Step 2 (15 mg, 0.026 mmol) in 1,4-dioxane containing excess conc. HCl was heated to reflux for 4 h. The dioxane was removed under vacuum and the residual aqueous layer extracted with ether. The combined organic extracts were washed with brine, dried (MgSO$_4$), filtered and evaporated. The oily residue was purified by chromatography on silica eluting with 10-50% EtOAc/isohexane to give 5 mg (33%) of the title compound as a 3:2 mixture of isomers. $^1$H NMR (500 MHz, CDCl$_3$) δ: 0.93-0.86 (3H, m), 1.60-1.20 (4H, m), 1.70-1.66 (1H, m), 1.83-1.80 (2H, m), 2.13-2.10 (1H, m), 2.29-2.22 (1H, m), 2.94-2.88 (1H, m), 3.38-3.31 (2H, m), 3.66-3.62 (1H, m), 4.26-4.18 (2H, m), 7.71-7.48 (6H, m), 8.18 (1H, s); M/Z (ES$^+$) 556 (MH$^+$).

Example 75

(±)-1-{(2R*,4S*)-1-[2,5-Bis(trifluoromethyl)benzyl]-2-[4-(trifluoromethyl)phenyl]piperidin-4-yl}cyclopent-3-ene-1-carboxylic acid

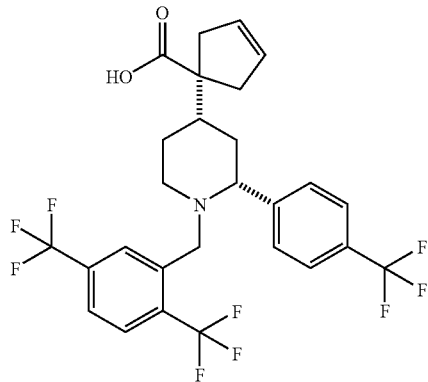

Step 1: (±)-Methyl 1-{(2R*,4S*)-1-[2,5-bis(trifluoromethyl)benzyl]-2-[4-(trifluoromethyl)phenyl]piperidin-4-yl}cyclopent-3-ene-1-carboxylate

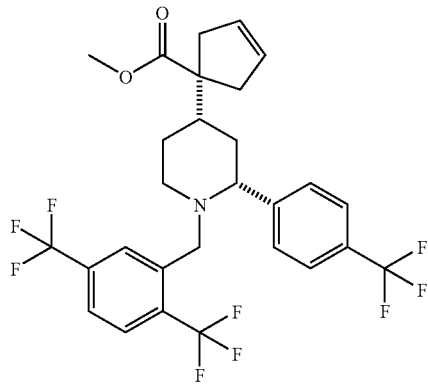

Lithium bis(trimethylsilyl)amide (1.0M in THF, 0.4 ml, 0.4 mmol) was added slowly to a stirred solution of the ester used to prepare Example 36, (100 mg, 0.19 mmol) in dry THF (2 ml) under N$_2$ at −78° C. After 45 minutes cis-1,4-dichloro-2-butene (32 μl, 0.30 mmol) was added. The reaction was maintained at this temperature for 30 minutes, then transferred to an ice bath. After 1 hour the reaction was quenched with saturated aqueous NH$_4$Cl, and then partitioned between EtOAc/H$_2$O. The aqueous layer was extracted with EtOAc (×2). The combined extracts were washed with brine (×1), dried (Na$_2$SO$_4$), filtered and evaporated. The residue was purified by chromatography on silica, eluting with 2-5% EtOAc/isohexane to give the alkylated, but uncyclised product as a mixture of diastereomers (83 mg, 71%) as an oil. M/Z (ES$^+$) 618, 616 (MH$^+$). Potassium tert-butoxide (1.0 M in THF, 0.13 ml, 0.13 mmol) was added to a stirred solution of this product (75 mg, 0.12 mmol) in dry THF (1 ml) under N$_2$ at 0° C. After 30 minutes the reaction was quenched with saturated aqueous NH$_4$Cl, and then partitioned between EtOAc/H$_2$O. The aqueous layer was extracted with EtOAc (×2). The combined extracts were washed with brine (×1), dried (Na$_2$SO$_4$), filtered and evaporated. The residue was purified by chromatography on silica, eluting with 2-5% EtOAc/isohexane to give the title compound (28 mg, 40%) as an oil. $^1$H NMR (400 MHz, CDCl$_3$) δ: 1.39-1.50 (3H, m), 1.62-1.66 (1H, m), 1.92-2.02 (1H, m), 2.07-2.13 (1H, m), 2.39-2.43 (2H, m), 2.86-2.92 (3H, m), 3.29 (1H, dd, J 15.6, 1.8), 3.35 (1H, dd, J 11.0, 2.7), 3.66 (1H, d, J 15.5), 3.69 (3H, s), 5.57 (2H, s), 7.50-7.58 (5H, m), 7.67 (1H, d, J 8.2), 8.16 (1H, s); M/Z (ES$^+$) 580 (MH$^+$).

Step 2: (±)-1-{(2R*,4S*)-1-[2,5-Bis(trifluoromethyl)benzyl]-2-[4-(trifluoromethyl)phenyl]piperidin-4-yl}cyclopent-3-ene-1-carboxylic acid

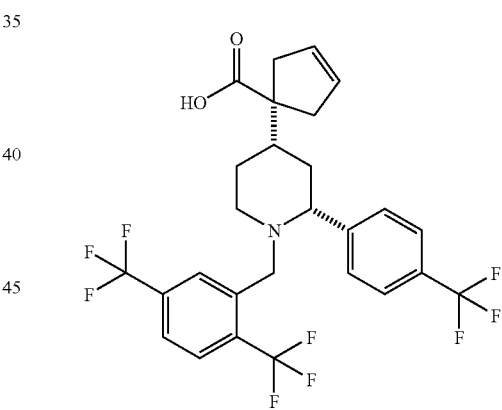

A solution of LiOH (12 mg, 0.5 mmol) in H$_2$O (0.5 ml) was added to a stirred solution of the ester (Step 2, 28 mg, 0.048 mmol) in dioxane (1 ml). The mixture was heated at 110° C. for 20 hours. After cooling to room temperature the mixture was acidified with 2N HCl, and the dioxane was removed in vacuo. The mixture was partitioned between DCM/H$_2$O. The layers were separated and the aqueous layer was further extracted with DCM (×3). The combined extracts were dried (Na$_2$SO$_4$), filtered and evaporated. The residue was purified by chromatography on silica, eluting with 2-4% MeOH/DCM to give the acid (20 mg). This material was further purified by reverse phase HPLC to give the title compound (11 mg, 40%) as colourless solid. M/Z (ES$^+$) 566 (MH$^+$).

Example 76

(±)-1-{(2R*,4S*)-1-[2,5-Bis(trifluoromethyl)benzyl]-2-[4-(trifluoromethyl)phenyl]piperidin-4-yl}cyclopentanecarboxylic acid

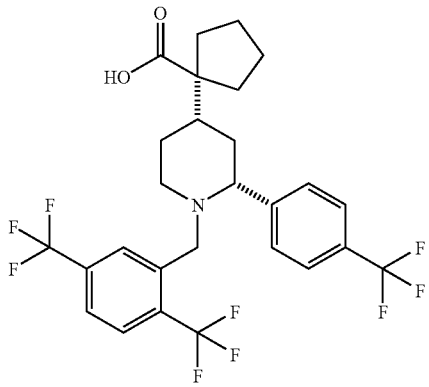

Step 1: (±)-Methyl 1-{2-[4-(trifluoromethyl)phenyl]pyridin-4-yl}cyclopent-3-ene-1-carboxylate

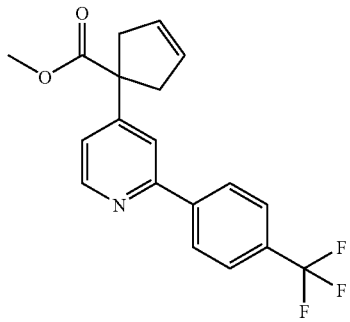

Lithium bis(trimethylsilyl)amide (1.0M in THF, 3.8 ml, 3.8 mmol) was added slowly to a stirred solution of the ester from Example 3, Step 2, (509 mg, 1.7 mmol) in dry THF (8 ml) under $N_2$ such that the internal temperature <−70° C. After 30 minutes cis-1,4-dichloro-2-butene (210 µl, 2.0 mmol) was added. The reaction was maintained at this temperature for 30 minutes, then transferred to an ice bath. After 90 minutes the reaction was removed from the cooling bath and stirred at room temperature for 30 minutes, then quenched with saturated aqueous $NH_4Cl$. The mixture was partitioned between EtOAc/$H_2O$. The aqueous layer was extracted with EtOAc (×2). The combined extracts were washed with brine (×1), dried ($Na_2SO_4$), filtered and evaporated. The residue was purified by chromatography on silica, eluting with 8% EtOAc/isohexane to give the title compound (278 mg, 47%) as an oil, which solidified on standing. $^1$H NMR (400 MHz, CDCl$_3$) δ: 2.81 (2H, d, J 15.2), 3.44 (2H, d, J 15.3), 3.70 (3H, s), 5.79 (2H, s), 7.22 (2H, d, J 4.4), 7.66 (1H, s), 7.73 (2H, d, J 8.1), 8.08 (2H, d, J 8.1), 8.63-8.67 (2H, d, J 5.1); M/Z (ES$^+$) 348 (MH$^+$).

Step 2: (±)-Methyl 1-{(2R*,4S*)-2-[4-(trifluoromethyl)phenyl]piperidin-4-yl}cyclopentanecarboxylate

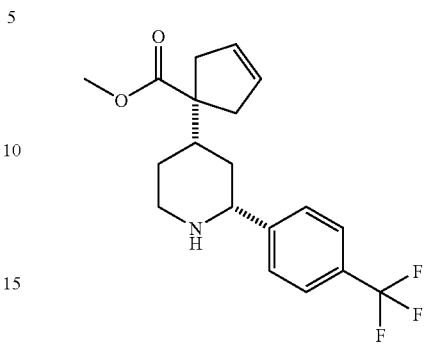

A mixture of the pyridine from Step 1 (270 mg, 0.77 mmol) platinum (IV) oxide (30 mg) and HCl solution (4N in dioxan, 0.2 ml, 0.8 mmol) in MeOH (15 ml) was hydrogenated at 20 psi on a Parr® apparatus for 0.5 hours. The catalyst was removed by filtration and the filtrate evaporated in vacuo. The residue was purified by chromatography on silica, eluting with 1-2% 2M NH$_3$ in MeOH/DCM to give the title compound (168 mg, 61%) as an oil The give the desired piperidine as white solid (7.1 g, quant). M/Z (ES$^+$) 348 (MH$^+$). The product was contaminated with a small amount of over reduced material: M/Z (ES$^+$) 362 (MH$^+$).

Step 3: (±)-Methyl 1-{(2R*,4S*)-1-[2,5-bis(trifluoromethyl)benzyl]-2-[4-(trifluoromethyl)phenyl]piperidin-4-yl}cyclopentanecarboxylate

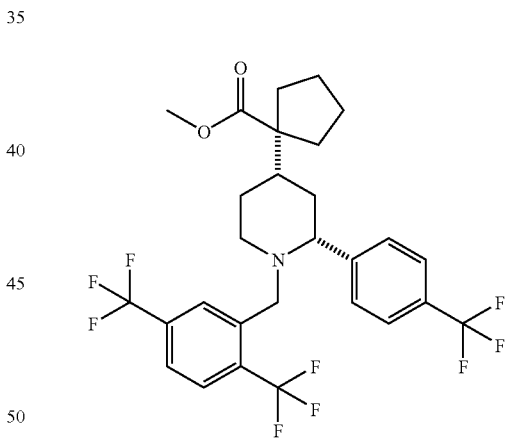

A mixture of the amine from Step 2 (160 mg, 0.45 mmol), 2-(bromomethyl)-1,4-bis(trifluoromethyl)benzene (165 µl, 0.90 mmol) and K$_2$CO$_3$ (0.310 g, 2.2 mmol) in DMF (2 ml) was heated in the microwave at 150° C. for 45 mins. The reaction was partitioned between EtOAc/H$_2$O. The aqueous layer was extracted with EtOAc (×2). The combined extracts were washed with brine (×1), dried (Na$_2$SO$_4$), filtered and evaporated. The residue was purified by chromatography on silica, eluting with 2% EtOAc/isohexane to give the title compound (205 mg). This material was further purified by ion exchange chromatography on a SCX cartridge, eluting with DCM followed by 2M NH$_3$ in MeOH to give the N-benzyl piperidine (175 mg, 67%) as an oil. $^1$H NMR (360 MHz, CDCl$_3$) δ: 1.42-1.67 (9H, m), 1.72-1.76 (1H, m), 1.81-1.85 (1H, m), 2.05-2.19 (3H, m), 2.88-2.93 (1H, m), 3.27-3.36

(2H, m), 3.62 (1H, d, J 15.0), 3.68 (3H, s), 7.50-7.58 (5H, m), 7.67 (1H, d, J 8.2), 8.16 (1H, s); M/Z (ES+) 582 (MH+).

Step 4: (±)-{(2R*,4S*)-1-[2,5-Bis(trifluoromethyl) benzyl]-2-[4-(trifluoromethyl)phenyl]piperidin-4-yl}cyclopentanecarboxylic acid

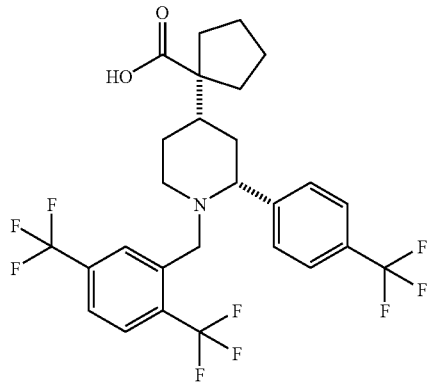

A solution of LiOH (70 mg, 2.9 mmol) in H₂O (1 ml) was added to a stirred solution of the ester from Step 3 (170 mg, 0.29 mmol) in dioxane (2 ml). The mixture was heated at 110° C. for 3.5 days. After cooling to room temperature the mixture was acidified with 2N HCl, and the dioxane was removed in vacuo. The mixture was partitioned between DCM/H₂O. The layers were separated and the aqueous layer was further extracted with DCM (×3). The combined extracts were dried (Na₂SO₄), filtered and evaporated. The residue was purified by chromatography on silica, eluting with DCM to recover unreacted ester, then 1-2-4% MeOH/DCM to give the acid (63 mg). This material was further purified buy reverse phase HPLC to give the title compound (26 mg, 16%) as colourless solid. ¹H NMR (500 MHz, CDCl₃) δ: 1.51-1.64 (8H, m), 1.67-1.70 (1H, m), 1.80-1.82 (1H, m), 1.86-1.93 (1H, m), 2.09-2.17 (3H, m), 2.94 (1H, d, J 11.7), 3.31-3.39 (2H, m), 3.64 (1H, d, J 15.6), 7.52-7.58 (5H, m), 7.68 (1H, d, J 8.3), 8.17 (1H, s) M/Z (ES+) 568 (MH+).

Example 77

(±)-((2S*,4S*)-1-[2,5-Bis(trifluoromethyl)benzyl]-2-{2-[4-(trifluoromethyl)phenyl]ethyl}piperidin-4yl)acetic acid

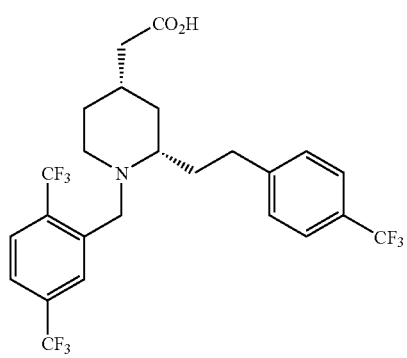

Step 1: Methyl(2-{[4-(trifluoromethyl)phenyl] ethynyl}pyridin-4-yl)acetate

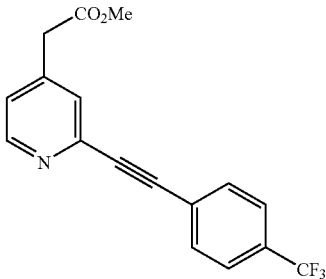

A mixture of methyl(2-chloropyridin-4-yl)acetate (1 g, 5.4 mmol), 1-ethynyl-4-(trifluoromethyl)benzene (3.6 ml, 22 mmol), triphenylphosphine (141 mg, 0.54 mmol), CuI (105 mg, 0.54 mmol), and tetrakis(triphenylphosphine) palladium (0) (312 mg, 0.54 mmol) in Et₃N (5 ml) and dioxane (5 ml) in a sealed microwave vial was heated, under microwave irradiation at 150° C. for 15 minutes. The reaction was treated with NaHCO₃ (half saturated and extracted with EtOAc (×2). The extracts were washed with brine dried (MgSO₄) and evaporated in vacuo to a brown gum which was purified by chromatography (silica, 25% EtOAc/isohexane) to give the acetylene (298 mg, 17%). M/Z (ES+) 320 (MH+).

Step 2: (±)-Methyl((2S*,4R*)-2-{2-[4-(trifluoromethyl)phenyl]ethyl}piperidin-4-yl)acetate

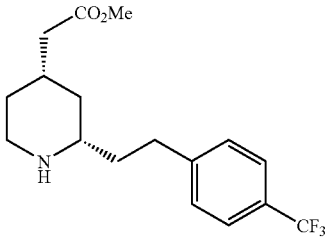

A mixture of methyl(2-{[4-(trifluoromethyl)phenyl] ethynyl}pyridin-4-yl)acetic acid (298 mg, 0.9 mmol) PtO₂ (20 mg, 0.09 mmol) and HCl solution (4N in dioxane. 0.25 ml, 1.0 mmol) in MeOH (30 ml) was hydrogenated at 20 psi on a Parr® apparatus for 5 hours. The catalyst was removed by filtration and the filtrate evaporated in vacuo to give a gum which was purified by chromatography (silica, 5% NH₃ in MeOH (2M)/DCM) to give the piperidine hydrochloride as a pale gum (190 mg, 58%). M/Z (ES+) 330 (MH+).

Step 3: (±)-((2S*,4S*)-1-[2,5-bis(trifluoromethyl) benzyl]-2-{2-[4-(trifluoromethyl) phenyl] ethyl}piperidin-4yl)acetic acid

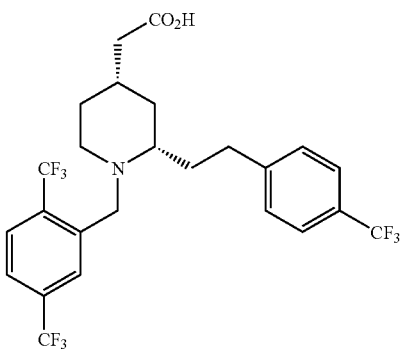

The title compound was prepared using the benzylation described in Example 20, Step 1 and the hydrolysis described in Example 3, Step 5 to give a white solid M/Z (ES+) 542 (MH+).

Example 78

(±)-{(2R,3S*)-1-[2,5-Bis(trifluoromethyl)benzyl]-2-[4-(trifluoromethyl)phenyl]piperidin-3-yl}acetic acid

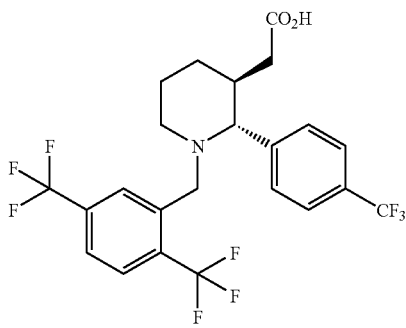

Step 1: (±)-Benzyl 4-oxo-2-[4-(trifluoromethyl)phenyl]-3,4-dihydropyridine-1(2H)-carboxylate

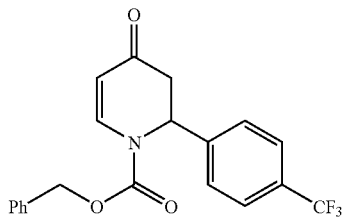

4-Trifluoromethyl bromobenzene (4.2 ml, 30 mmol) was added portionwise to magnesium turnings (0.729 g, 30 mmol) in dry THF (30 ml), a couple of drops of 1,2-dibromoethane was added to initiate the reaction. The resulting brown solution was cooled to −25° C. 4-Methoxypyridine (3.0 ml, 30 mmol) was added followed by benzyl chloroformate (4.3 ml, 30 mmol). The reaction was stirred for 30 mins at −20° C. then quenched with 2N HCl. After stirring for 10 mins the mixture was extracted with EtOAc (×3). The combined extracts were washed with brine, dried (MgSO₄), filtered and evaporated. The residue was purified by chromatography (silica, 10-40% EtOAc/hexanes) to give the dihydropyridine (9.30 g, 83%). ¹H NMR (500 MHz, CDCl₃) δ: 2.77 (1H, d, J 16.6), 3.18 (1H, dd, J 7.7, 16.6), 5.20 (1H, d, J 12.0), 5.27 (1H, d, J 12.0), 5.42 (1H, d, J 8.3), 5.77 (1H, d, J 6.3), 7.24-7.37 (7H, m), 7.54 (2H, d, J 8.2), 8.00 (1H, m).

Step 2: (±)-Benzyl (2R*,3S*)-3-(2-methoxy-2-oxoethyl)-4-oxo-2-[4-(trifluoromethyl)phenyl]-3,4-dihydropyridine-1(2H)-carboxylate

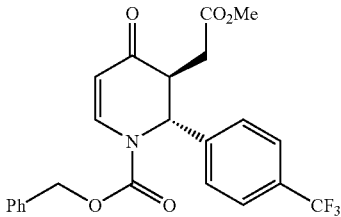

A solution of the dihydropyridine from Step 1 (3.00 g, 8.0 mmol) in dry THF (80 ml) was cooled to −78° C. and lithium bis(trimethylsilyl)amide (1.0M in THF, 9.6 ml, 9.6 mmol) was added dropwise. After stirring at −78° C. for 1 hr, methyl bromoacetate (2.2 ml, 24 mmol) was added. The reaction was stirred at −78° C. for 1 hr then at 0° C. for 1.5 hrs. The reaction was quenched with saturated NH₄Cl solution. The mixture extracted with EtOAc (×3), the combined extracts were washed with brine, dried (MgSO₄), filtered and evaporated. The residue was purified by chromatography (silica, 40% Et₂O/hexanes) to give the ester (2.74 g, 77%). ¹H NMR (360 MHz, CDCl₃) δ: 2.61-2.69 (2H, m), 3.15 (1H, dd, J 5.0, 9.8), 3.74 (3H, s), 5.18-5.28 (2H, m), 5.39 (1H, d, J 8.5), 5.70 (1H, s), 7.18-7.33 (7H, m), 7.54 (2H, d, J 8.3), 8.08 (1H, d, J 8.6).

Step 3: (±)-Benzyl (2R*,3S*)-3-(2-methoxy-2-oxoethyl)-4-oxo-2-[4-(trifluoromethyl)phenyl]piperidine-1-carboxylate

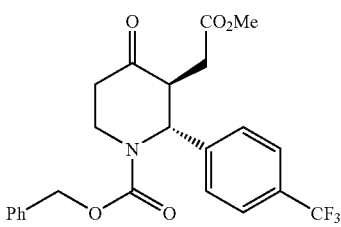

A solution of the enone from Step 2 (1.650 g, 3.7 mmol) in dry THF (40 ml) was cooled to −78° C. and L-Selectride® (1.0M in THF, 4.6 ml, 4.6 mmol) was added. The reaction was stirred for 2 mins then quenched with saturated NH₄Cl solution. The mixture extracted with EtOAc (×3), the combined extracts were washed with brine, dried (MgSO₄), filtered and evaporated. The residue was purified by chromatography (silica, 40-50% Et₂O/hexanes) to give the ketone (1.473 g, 89%). ¹H NMR (360 MHz, CDCl₃) δ: 2.24 (1H, dd, J 4.9, 16.8), 2.57-2.70 (3H, m), 3.46-3.52 (1H, m), 3.58 (3H, s), 3.80-3.89 (1H, m), 4.57 (1H, dd, J 5.2, 14.2), 4.93-4.98 (2H, m), 5.10 (1H, d, J 12.1), 7.07 (2H, s), 7.26-7.41 (5H, m), 7.57 (2H, d, J 8.1).

Step 4: (±)-Methyl{(6S*,7R*)-7-[4-(trifluoromethyl)phenyl]-1,4-dithia-8-azaspiro[4.5]dec-6-yl}acetate

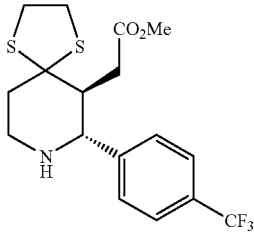

A solution of the ketone from Step 3 (0.772 g, 1.7 mmol) in DCM (20 ml) was cooled to 0° C. and 1,2-ethanedithiol (0.43 ml, 5.1 mmol) and $BF_3.OEt_2$ (1.27 ml, 10 mmol) were added. The reaction was stirred at RT for 48 hrs then diluted with EtOAc. The mixture was washed with 1N NaOH solution then brine, dried ($MgSO_4$), filtered and evaporated. The residue was purified by chromatography (silica, 30% EtOAc/hexanes) to give the dithiane (0.420 g, 63%). $^1$H NMR (360 MHz, $CDCl_3$) δ: 2.03-2.11 (1H, m), 2.20-2.26 (1H, m), 2.35-2.43 (1H, m), 2.73-2.83 (2H, m), 3.06-3.16 (2H, m), 3.24 (3H, s), 3.25-3.32 (4H, m), 3.50 (1H, d, J 9.9), 7.47-7.58 (4H, m).

Step 5: (±)-Methyl{(2R*,3S*)-2-[4-(trifluoromethyl)phenyl]piperidin-3-yl}acetate

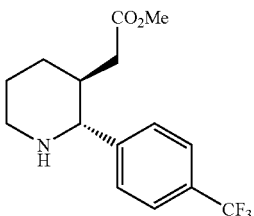

Raney nickel (slurry in water) was added portionwise to a solution of the dithiane from Step 4 (0.418 g, 1.1 mmol) in MeOH (20 ml). The reaction was heated under reflux for 3 hrs then allowed to cool. The reaction was filtered through Hyflo® and the solvent was evaporated. The resulting mixture was extracted with DCM, dried ($MgSO_4$), filtered and evaporated. The residue was purified by chromatography (silica, 2% MeOH/DCM) to give the piperidine (0.168 g, 52%). $^1$H NMR (360 MHz, $CDCl_3$) δ: 1.21-1.26 (1H, m), 1.69-1.75 (2H, m), 1.90-2.10 (4H, m), 2.72-2.80 (1H, m), 3.16 (1H, m), 3.36 (1H, d, J 9.7), 3.50 (3H, s), 7.48 (2H, d, J 8.1), 7.57 (2H, d, J 8.2).

Step 6: (±)-Methyl{(2R*,3S*)-1-[2,5-bis(trifluoromethyl)benzyl]-2-[4-(trifluoromethyl)phenyl]piperidin-3-yl}acetate

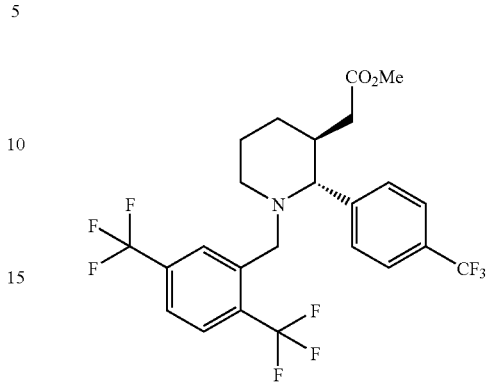

A mixture of the amine from Step 5 (0.113 g, 0.4 mmol), 2,5-bis(trifluoromethyl)benzylbromide (0.230 g, 0.8 mmol) and $K_2CO_3$ (0.156 g, 1.1 mmol) in DMF (6 ml) was heated in the microwave at 100° C. for 20 mins. The reaction was diluted with water (10 ml). The mixture extracted with EtOAc (×3), the combined extracts were washed with water (×2) and brine, dried ($MgSO_4$), filtered and evaporated. The residue was purified by chromatography (silica, 10% $Et_2O$/hexanes) to give the ester (0.170 g, 86%). $^1$H NMR (400 MHz, $CDCl_3$) δ: 1.19-1.26 (1H, m), 1.69-1.74 (2H, m), 1.96-1.99 (3H, m), 2.07-2.17 (1H, m), 2.20-2.30 (1H, m), 2.84 (1H, d, J 11.5), 3.11 (1H, d, J 10.0), 3.32 (1H, dd, J 1.8, 15.5), 3.47-3.52 (1H, m), 3.52 (3H, s), 7.52-7.58 (5H, m), 7.65 (1H, d, J 8.2), 8.15 (1H, s).

Step 7: (±)-{(2R*,3S*)-1-[2,5-Bis(trifluoromethyl)benzyl]-2-[4-(trifluoromethyl)phenyl]piperidin-3-yl}acetic acid

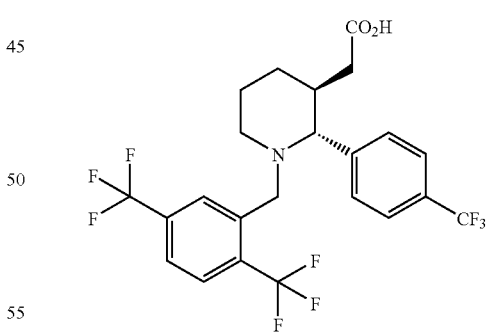

The ester from Step 6 (0.137 g, 0.26 mmol) and LiOH (0.124 g, 5.1 mmol) in THF (3 ml) and water (3 ml) was heated at 60° C. for 16 hours. The reaction was acidified with 2N HCl then extracted with EtOAc (×3). The combined extracts were washed with brine, dried ($MgSO_4$), filtered and evaporated. The residue was purified by chromatography (silica, 5% MeOH/DCM) to give the acid (0.122 g, 92%). $^1$H NMR (400 MHz, $CD_3OD$) δ: 1.26-1.40 (1H, m), 1.72-1.79 (2H, m), 1.88-2.06 (3H, m), 2.16-2.28 (2H, m), 2.85 (1H, d, J 11.4), 3.22 (1H, d, J 10.0), 3.37 (1H, d, J 15.8), 3.55 (1H, d, J 15.8), 7.60-7.66 (5H, m), 7.76 (1H, d, J 8.2), 8.21 (1H, s).

Example 79 and 79a (±)-{(2S*,4S*,6R*)-1-[2,5-Bis(trifluoromethyl)benzyl]-2-propyl-6-[4-(trifluoromethyl)phenyl]piperidin-4-yl}acetic acid and (±)-{(2S*,4R*,6R*)-1-[2,5-Bis(trifluoromethyl)benzyl]-2-propyl-6-[4-(trifluoromethyl)phenyl]piperidin-4-yl}acetic acid

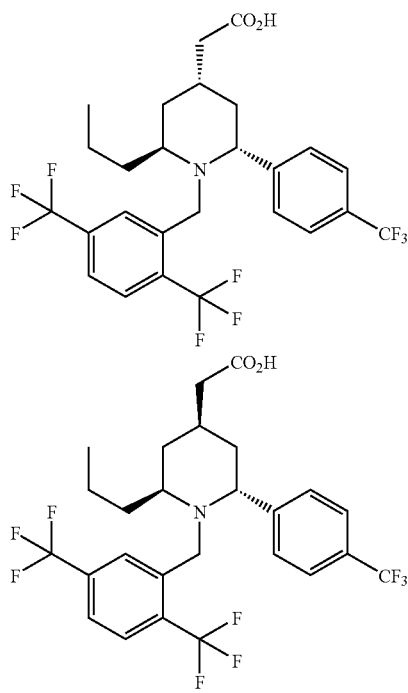

Step 1: (±)-Benzyl(2S*,6R*)-4-oxo-2-propyl-6-[4-(trifluoromethyl)phenyl]piperidine-1-carboxylate and Benzyl(2R*,6R*)-4-oxo-2-propyl-6-[4-(trifluoromethyl)phenyl]piperidine-1-carboxylate

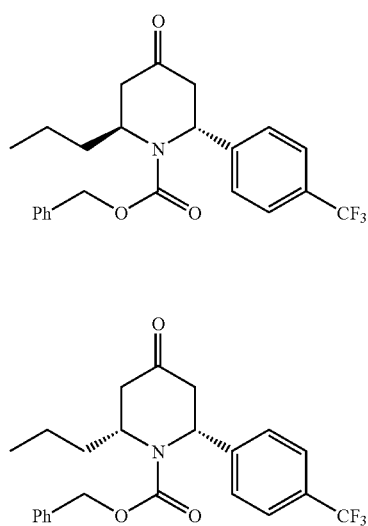

Propylmagnesium chloride (2.0M in ether, 5.0 ml, 10 mmol) was added to copper (I) iodide (1.905 g, 10 mmol) in dry THF (40 ml) at −78° C. The reaction was stirred for 1 hr then a solution of the enone from Example 78 Step 1 (1.877 g, 5 mmol) in dry THF (60 ml) was added. The reaction was allowed to warm to −10° C. and stirred for 1.5 hrs. The reaction was quenched with saturated NH$_4$Cl solution then aqueous ammonia solution was added. After stirring for 10 mins the mixture was extracted with EtOAc (×3). The combined extracts were washed with brine, dried (MgSO$_4$), filtered and evaporated. The residue was purified by chromatography (silica, 15% EtOAc/hexanes) to give the trans propyl compound (1.161 g, 55%). $^1$H NMR (360 MHz, d$_6$-DMSO) δ: 0.86 (3H, t, J 6.9), 1.19-1.35 (2H, m), 1.51-1.57 (1H, m), 1.76-1.80 (1H, m), 2.42-2.51 (1H, m), 2.56 (1H, dt, J 6.1, 18.3), 2.78 (1H, d, J 18.0), 3.29-3.37 (1H, m), 4.44-4.51 (1H, m), 5.03-5.16 (2H, m), 5.55 (1H, d, J 6.2), 7.22-7.32 (5H, m), 7.49 (2H, d, J 8.1), 7.66 (2H, d, J 8.2).

And the cis propyl compound (0.472 g, 22%). $^1$H NMR (360 MHz, d$_6$-DMSO) δ: 0.71 (3H, t, J 6.7), 1.15-1.46 (4H, m), 2.31 (1H, dd, J 2.1, 14.4), 2.80-2.94 (3H, m), 4.57-4.63 (1H, m), 5.00-5.10 (2H, m), 5.58 (1H, s), 7.13 (2H, brs), 7.29 (3H, brs), 7.49 (2H, d, J 8.1), 7.69 (2H, d, J 8.2).

Step 2: (±)-Ethyl{(2S*,4S*,6R*)-2-propyl-6-[4-trifluoromethyl)phenyl]piperidin-4-yl}acetate and (±)-Ethyl{(2S*,4R*,6R*)-2-propyl-6-[4-(trifluoromethyl)phenyl]piperidin-4-yl}

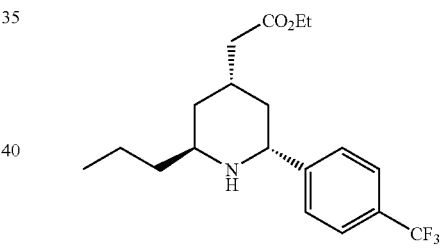

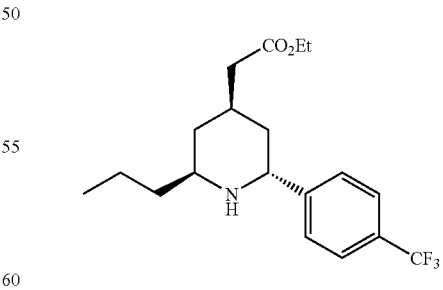

The title compounds were made using the procedures in Example 64 Steps 3 and 4 using the trans compound from Step 1. M/Z (ES$^+$) 358 (MH$^+$).

Step 3: (±)-Ethyl{(2S*,4S*,6R*)-1-[2,5-bis(trifluoromethyl)benzyl]-2-propyl-6-[4-(trifluoromethyl)phenyl]piperidin-4-yl}acetate and (±)-Ethyl{(2S*,4R*,6R*)-1-[2,5-bis(trifluoromethyl)benzyl]-2-propyl-6-[4-(trifluoromethyl)phenyl]piperidin-4-yl}acetate

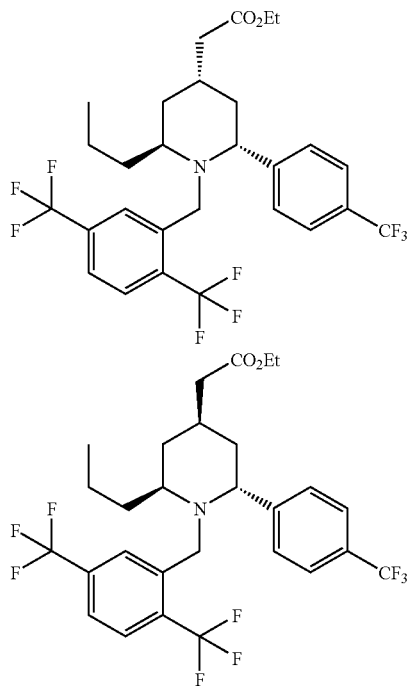

A mixture of the amine from Step 2 (0.270 g, 0.76 mmol), 2,5-bis(trifluoromethyl)benzylbromide (0.928 g, 3.0 mmol) and $K_2CO_3$ (0.626 g, 4.6 mmol) in acetone (6 ml) was heated under reflux for 3 days. The reaction was diluted with water and the solvent evaporated. The mixture was extracted with EtOAc (×3), the combined extracts were washed with brine, dried ($MgSO_4$), filtered and evaporated. The residue was purified by chromatography (silica, 5-60% $Et_2O$/hexanes) to give the title compounds (0.269 g, 61%). M/Z (ES$^+$) 584 (MH$^+$).

Step 4: (±)-{(2S*,4S*,6R*)-1-[2,5-Bis(trifluoromethyl)benzyl]-2-propyl-6-[4-(trifluoromethyl)phenyl]piperidin-4-yl}acetic acid and (±)-{(2S*,4R*,6R*)-1-[2,5-Bis(trifluoromethyl)benzyl]-2-propyl-6-[4-(trifluoromethyl)phenyl]piperidin-4-yl}acetic acid

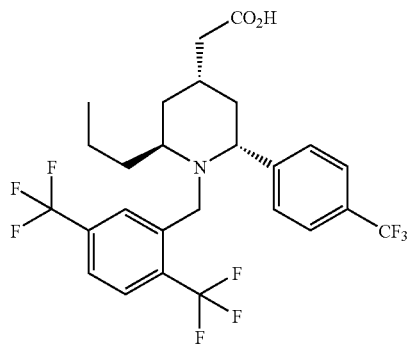

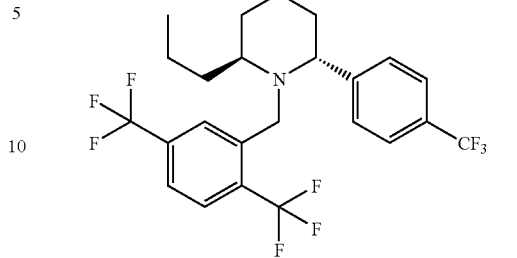

The title compounds were made using the procedure in Example 78 Step 7 then separated using mass directed preparative hplc to give (±)-{(2S*,4S*,6R*)-1-[2,5-Bis(trifluoromethyl)benzyl]-2-propyl-6-[4-(trifluoromethyl)phenyl]piperidin-4-yl}acetic acid. $^1$H NMR (400 MHz, CD$_3$OD) δ: 0.90 (3H, t, J 7.3), 1.15-1.31 (1H, m), 1.31-1.47 (1H, m), 1.50-1.60 (2H, m), 1.67-1.81 (4H, m), 2.26-2.34 (3H, m), 2.80 (1H, m), 3.65 (1H, d, J 16.7), 3.76 (1H, d, J 16.7), 4.13 (1H, dd, J 2.5, 11.6), 7.52 (4H, m), 7.63 (1H, d, J 8.2), 7.73 (1H, d, J 8.2), 8.26 (1H, s).

And (±)-{(2S*,4R*,6R*)—[2,5-Bis(trifluoromethyl)benzyl]-2-propyl-6-[4-(trifluoromethyl)phenyl]piperidin-4-yl}acetic acid. NMR (400 MHz, CD$_3$OD) δ: 0.85 (3H, t, J 7.2), 1.20-1.60 (6H, m), 1.83-1.93 (1H, m), 1.99-2.07 (1H, m), 2.27 (3H, m), 2.87-2.93 (1H, m), 3.88 (1H, m), 4.10 (1H, d, J 16.4), 4.18 (1H, d, J 16.4), 7.64 (2H, d, J 8.3), 7.71 (1H, d, J 8.2), 7.81 (2H, d, J 8.3), 7.87 (1H, d, J 8.2), 8.51 (1H, s).

Example 80

(±)-{(2R*,4S*,6R*)-1-[2,5-Bis(trifluoromethyl)benzyl]-2-propyl-6-[4-(trifluoromethyl)phenyl]piperidin-4-yl}acetic acid

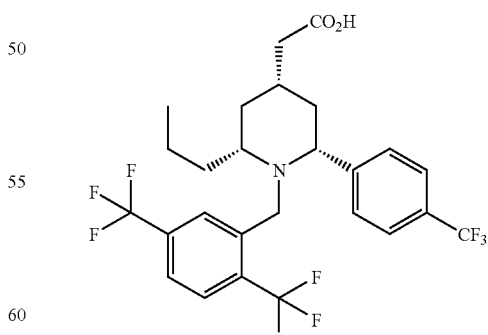

The title compound was made using the procedures in Example 64 Steps 3 and 4 and Example 78 Steps 6 and 7 using the cis compound from Example 79 Step 1. M/Z (ES$^+$) 556 (MH$^+$).

Example 81

(±)-{(2R*,4S*)-1-[2,5-Bis(trifluoromethyl)benzyl]-2-[4-(trifluoromethyl)benzyl]piperidin-4-yl}acetic acid

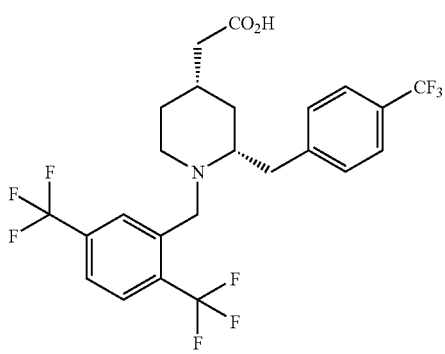

Step 1: Methyl{2-[4-(trifluoromethyl)benzyl]pyridin-4-yl}acetate

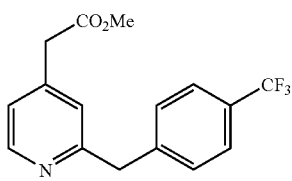

A solution of 4-trifluoromethyl benzylbromide (2.199 g, 9.2 mmol) in dry THF (10 ml) was added to activated zinc (0.732 g, 11.2 mmol) in dry THF (4 ml) at 0° C. The reaction was stirred for 4 hr at 0° C. then the mixture was added to a solution of methyl(2-chloropyridin-4-yl)acetate (1.188 g, 6.4 mmol) and dichlorobis(triphenylphosphine) nickel (II) (0.785 g, 1.2 mmol) in dry THF (80 ml). The reaction was allowed to warm to RT and stirred for 16 hrs. The reaction was quenched with NH$_4$Cl solution then the mixture was extracted with EtOAc (×3). The combined extracts were washed with brine, dried (MgSO$_4$), filtered and evaporated. The residue was purified by chromatography (silica, 30% EtOAc/hexanes) to give the benzyl compound (1.423 g, 72%). $^1$H NMR (500 MHz, CDCl$_3$) δ: 3.58 (2H, s), 3.70 (3H, s), 4.19 (2H, s), 7.06 (1H, s), 7.08 (1H, d, J 5.1), 7.38 (2H, d, J 8.0), 7.55 (2H, d, J 8.1), 8.50 (1H, d, J 5.1).

Step 2: (±)-Methyl{(2R*,4S*)-2-[4-(trifluoromethyl)benzyl]piperidin-4-yl}acetate

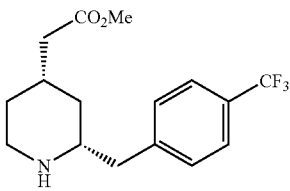

The pyridine from Step 1 was reduced using the procedure in Example 3 Step 3. M/Z (ES$^+$) 316 (MH$^+$).

Step 3: (±)-{(2R*,4S*)-1-[2,5-Bis(trifluoromethyl)benzyl]-2-[4-(trifluoromethyl)benzyl]piperidin-4-yl}acetic acid

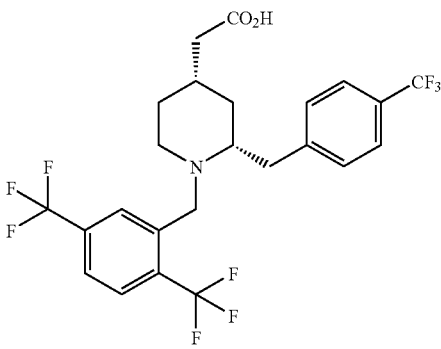

The title compound was made using the procedure in Example 78 Steps 6 and 7. $^1$H NMR (500 MHz, CD$_3$OD) δ: 1.16 (1H, q, J 12.1), 1.29 (1H, dq, J 3.7, 12.5), 1.58-1.68 (2H, m), 1.78-1.86 (1H, m), 2.14-2.22 (2H, m), 2.31-2.35 (1H, m), 2.65 (1H, dd, J 8.2, 13.7), 2.74-2.84 (2H, m), 3.09 (1H, dd, J 4.8, 13.7), 3.62 (1H, d, J 16.1), 4.37 (1H, d, J 16.1), 7.36 (2H, d, J 8.0), 7.52 (2H, d, J 8.0), 7.69 (1H, d, J 8.1), 7.85 (1H, d, J 8.1), 8.11 (1H, s).

Examples 82-84

Examples 82 and 83 were made by the procedure in Example 65 Step 4 using the piperidine from Example 81 Step 2 and the appropriate bromobenzene. Example 84 was made in an analogous way to Example 81 using benzylzinc bromide instead of 4-trifluoromethyl benzylbromide and activated zinc.

| Example | Structure | Name | M/Z ES+ [MH]+ |
|---|---|---|---|
| 82 | 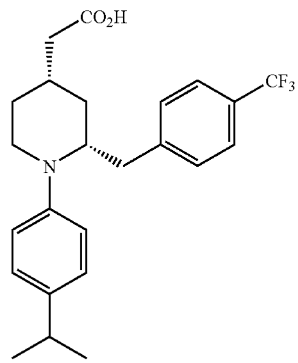 | (±)-(2R*,4S*)-1-(4-Isopropylphenyl)-2-[4-(trifluoromethyl)benzyl]piperidin-4-yl}acetic acid | 420 |
| 83 | 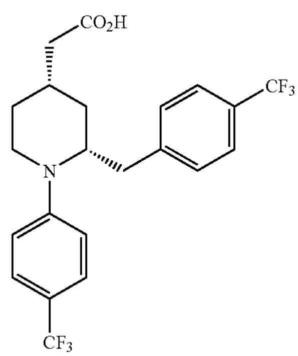 | (±)-{(2R*,4S*)-2-[4-(Trifluoromethyl)benzyl]-1-[4-(trifluoromethyl)phenyl]piperidin-4-yl}acetic acid | 446 |
| 84 | 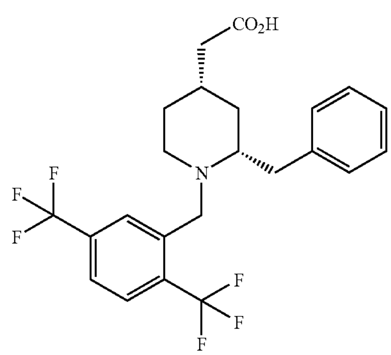 | (±)-{(2R*,4S*)-2-Benzyl-1-[2,5-bis(trifluoromethyl)benzyl]piperidin-4-yl}acetic acid | 460 |

Example 85

(±)-{(2S*,4R*)-1-{(1R*)-4-Methyl-1-[4-(trifluoromethyl)phenyl]pent-4-en-2-yn-1-yl}-2-[4-(trifluoromethyl)phenyl]piperidin-4-yl}acetic acid

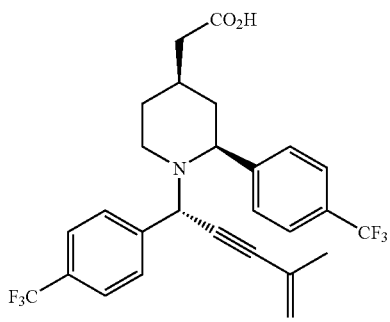

Step 1: (±)-Methyl{(2S*,4R*)-1-(1R*)-{4-methyl-1-[4-(trifluoromethyl)phenyl]pent-4-en-2-yn-1-yl}-2-[4-(trifluoromethyl)phenyl]piperidin-4-yl}acetate

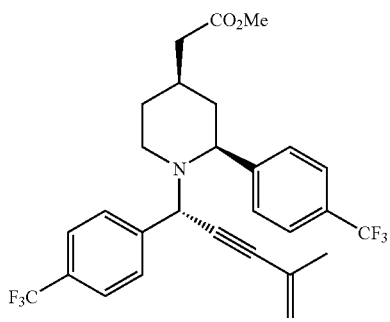

A mixture of the piperidine from Example 3 Step 3 (0.301 g, 1.0 mmol), 4-trifluoromethylbenzaldehyde (0.522 g, 3.0 mmol), 2-methyl-1-buten-3-yne (0.28 ml, 3.0 mmol) and gold (III) bromide (44 mg, 0.1 mmol) in water (1 ml) was heated in the microwave at 70° C. for 1 hr. The crude reaction mixture was filtered through an SCX cartridge (eluting with 2N NH$_3$ in MeOH). The solvent was removed and the mixture was diluted with EtOAc then washed with brine, dried (MgSO$_4$), filtered and evaporated. The residue was purified by chromatography (silica, 5% Et$_2$O/hexanes) to give the ester (0.281 g, 54%). $^1$H NMR (360 MHz, CDCl$_3$) δ: 1.29 (1H, dq, J 4.8, 12.2), 1.41 (1H, q, J 12.2), 1.70 (1H, m), 1.90 (1H, m), 2.02 (4H, m), 2.18-2.32 (2H, m), 2.42-2.52 (2H, m), 3.64 (3H, s), 3.71 (1H, dd, J 2.8, 11.3), 4.60 (1H, s), 5.32 (1H, s), 5.41 (1H, s), 7.55-7.67 (8H, m).

Step 2: (±)-{(2S*,4R*)-1-{(1R*)-4-Methyl-1-[4-(trifluoromethyl)phenyl]pent-4-en-2-yn-1-yl}-2-[4-(trifluoromethyl)phenyl]piperidin-4-yl}acetic acid

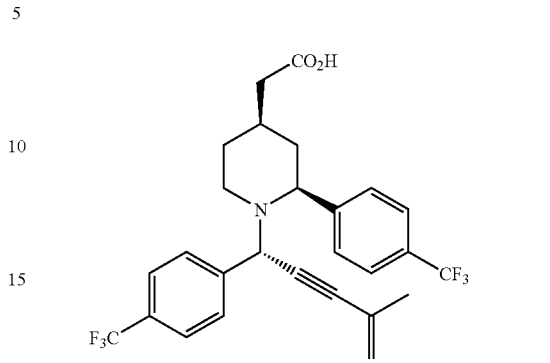

The ester from Step 1 was hydrolysed using the method in Example 78 Step 7. $^1$H NMR (360 MHz, CDCl$_3$) δ: 1.29 (1H, dq, J 4.5, 12.0), 1.44 (1H, q, J 12.0), 1.72 (1H, m), 1.92 (1H, m), 2.02 (4H, m), 2.19-2.33 (2H, m), 2.41-2.52 (2H, m), 3.67 (1H, dd, J 2.5, 11.2), 4.59 (1H, s), 5.32 (1H, s), 5.40 (1H, s), 7.55-7.66 (8H, m).

Example 86

(±)-{(2S*,4R*)-1-{(1R*)-4-methyl-1-[4-(trifluoromethyl)phenyl]pentyl}-2-[4-(trifluoromethyl)phenyl]piperidin-4-yl}acetic acid

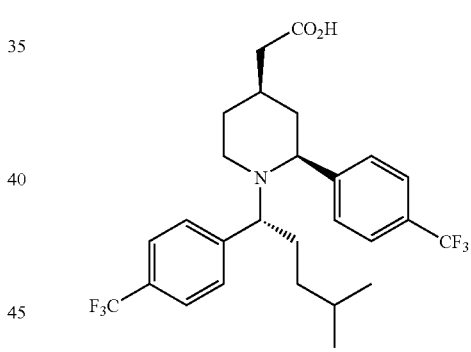

Step 1: (±)-Methyl{(2S*,4R*)-1-{(1R*)-4-methyl-1-[4-(trifluoromethyl)phenyl]pentyl}-2-[4-(trifluoromethyl)phenyl]piperidin-4-yl}acetate

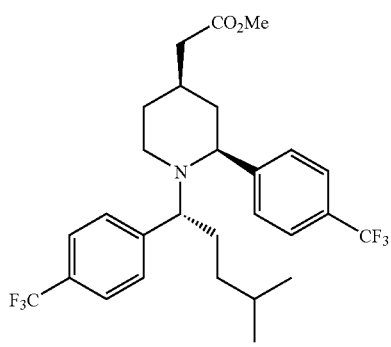

The unsaturated ester from Example 85 Step 1 (0.185 g, 0.3 mmol) was taken up in MeOH (5 ml) and hydrogenated under a balloon of hydrogen over 10% Pd/C (18 mg) for 16 hrs. The catalyst was removed by filtration and the filtrate was evaporated. The residue was purified by chromatography (silica, 5% Et$_2$O/hexanes) to give the ester (0.101 g, 54%). $^1$H NMR (360 MHz, CDCl$_3$) δ: 0.78-0.94 (7H, m), 1.10-1.49 (3H, m), 1.60-1.67 (1H, m), 1.77-1.85 (3H, m), 1.86-1.96 (1H, m), 2.16-2.26 (3H, m), 2.34-2.40 (1H, m), 2.64 (1H, m), 3.45 (1H, m), 3.63 (3H, s), 3.74 (1H, dd, J 2.7, 10.9), 7.36 (2H, d, J 8.2), 7.51-7.64 (6H, m).

Step 2: (±)-{(2S*,4R*)-1-{(1R*)-4-Methyl-1-[4-(trifluoromethyl)phenyl]pentyl}-2-[4-(trifluoromethyl)phenyl]piperidin-4-yl}acetic acid

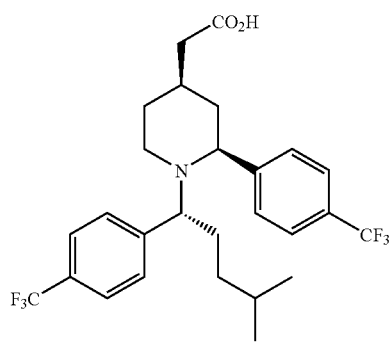

The ester from Step 1 was hydrolysed using the method in Example 78 Step 7. $^1$H NMR (360 MHz, CDCl$_3$) δ: 0.57-0.74 (1H, m), 0.75-1.04 (7H, m), 1.15-1.49 (3H, m), 1.66-1.93 (5H, m), 2.17-2.42 (3H, m), 2.65-2.68 (1H, m), 3.45 (1H, m), 3.73 (1H, d, J 10.6), 7.35 (2H, d, J 7.6), 7.53-7.65 (6H, m).

Example 87

(±)-{(2R*,4S*)-1-{(1R* or 1S*)-4-methyl-1-[4-(trifluoromethyl)phenyl]pent-4-en-2-yn-1-yl}-2-[4-(trifluoromethyl)benzyl]piperidin-4-yl}acetic acid

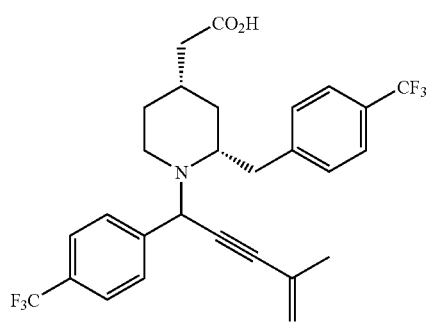

The title compound was prepared in the same way as Example 85 using the piperidine from Example 81 Step 2. $^1$H NMR (400 MHz, CD$_3$OD): δ 1.01-1.19 (2H, m), 1.53-1.73 (3H, m), 2.02 (3H, s), 2.11 (2H, dd, J 2.2, 7.2), 2.25-2.39 (2H, m), 2.70 (1H, dd, J 8.6, 13.3), 2.85-2.89 (1H, m), 3.44 (1H, dd, J 4.0, 13.4), 5.36 (1H, m), 5.41 (1H, s), 5.59 (1H, s), 7.46 (2H, d, J 8.0), 7.60 (2H, d, J 8.0), 7.67 (2H, d, J 8.3), 7.80 (2H, d, J 8.2).

Example 88

(±)-{(2S*,4R*)-2-[2,4-bis(trifluoromethyl)phenyl]-1-[2,5-bis(trifluoromethyl)phenyl]methyl}piperidin-4-yl)acetic acid

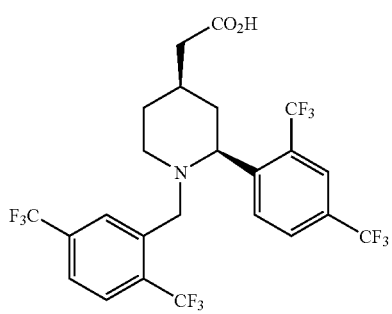

The title compound was prepared via Example 11, Steps 1-3, substituting [[2,4-bis(trifluoromethyl)phenyl]boronic acid for (4-(trifluoromethoxy)phenyl)boronic acid, followed by the procedure of Example 20, substituting 2-(bromomethyl)-1,4-bis(trifluoromethyl)benzene for benzyl bromide. $^1$H NMR (360 MHz, CD$_3$OD): δ 1.50 (2H, d, J 11.5), 1.85 (1H, d, J 13.1), 1.97 (2H, d, J 12.3), 2.22-2.34 (2H, m), 2.97 (1H, s), 3.29-3.35 (1H, m), 3.48-3.52 (2H, m), 3.91 (1H, s), 7.71 (1H, d, J 7.4), 7.81 (1H, d, J 8.0), 7.92 (2H, d, J 12.2), 8.20 (2H, d, J 8.1); M/Z (ES$^+$) 582 (MH$^+$).

Example 89

(±)-{(2S*,4R*)-1-[2,5-bis(trifluoromethyl)benzyl]-2-[2-fluoro-4-(trifluoromethyl)phenyl]piperidin-4-yl}acetic acid

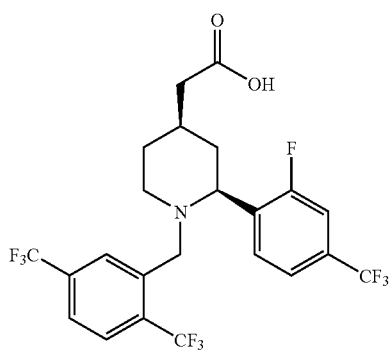

Step 1: (±)-Methyl{(2S*,4R*)-2-[2-fluoro-4-(trifluoromethyl)phenyl]piperidin-4-yl}acetate

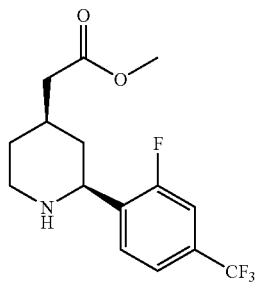

The piperidine was prepared in an analogous manner to Example 11, Steps 2 and 3, substituting [2-fluoro-4-(trifluoromethyl)phenyl]boronic acid for (4-(trifluoromethoxy)phenyl)boronic acid. $^1$H NMR (400 MHz, CDCl$_3$) δ: 1.19 (1H, m), 1.28 (1H, qd, J 12.5, 4.2), 1.76-1.81 (1H, m), 1.89-1.93 (1H, m), 2.04-2.15 (1H, m), 2.25-2.35 (2H, m), 2.87 (1H, td, J 12.0, 2.6), 3.21-3.26 (1H, m), 3.67 (3H, s), 4.05 (1H, dd, J 11.1, 2.0), 7.28 (1H, d, J 9.2), 7.39 (1H, d, J 8.0), 7.65 (1H, t, J 7.5); M/Z (ES$^+$) 320 (MH$^+$).

Step 2: (±)-{(2S*,4R*)-1-[2,5-bis(trifluoromethyl)benzyl]-2-[2-fluoro-4-(trifluoromethyl)phenyl]piperidin-4-yl}acetic acid

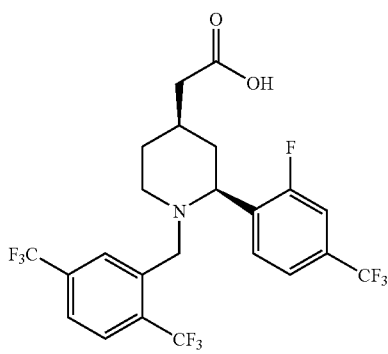

The title compound was prepared in the same manner as described in Example 20, substituting 2-(bromomethyl)-1,4-bis(trifluoromethyl)benzene for benzyl bromide. $^1$H NMR (400 MHz, CDCl$_3$) δ: 1.35 (2H, m), 1.73-1.78 (1H, m), 1.89-1.94 (1H, m), 2.00-2.10 (1H, m), 2.19 (1H, br t, J 12.5), 2.26-2.30 (2H, m), 2.87-2.92 (1H, m), 3.39 (1H, br d, J 15.7), 3.62-3.68 (4H, m), 3.83 (1H, dd, J 11.1, 2.6), 7.29 (1H, d, J 10.0), 7.36 (1H, d, J 8.2), 7.56 (1H, d, J 8.2), 7.68 (2H, t, J 7.0), 8.19 (1H, s); M/Z (ES$^+$) 546 (MH$^+$).

Example 90

(±)-((2S*,4R*)-2-[2-Fluoro-4-(trifluoromethyl)phenyl]-1-{(1S*)-4-methyl-1-[4-(trifluoromethyl)phenyl]pent-4-en-2-yn-1-yl}piperidin-4-yl)acetic acid

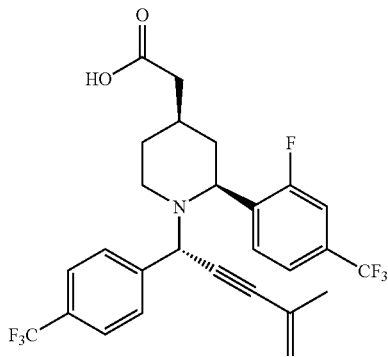

The title compound was prepared as described in Example 85, using the piperidine from Example 89, Step 1 in place of that from Example 3, Step 3 (free base). $^1$H NMR (500 MHz, CD$_3$OD): δ 1.25-1.45 (2H, m), 1.72-1.76 (1H, m), 1.91-2.03 (5H, m), 2.22-2.28 (2H, m), 2.47-2.52 (2H, m), 4.15-4.25 (1H, brm), 4.69 (1H, s), 5.35 (1H, s), 5.41 (1H, s), 7.48 (1H, d, J 10), 7.58 (1H, d, J 7.8), 7.64 (2H, d, J 8.3), 7.75 (2H, d, J 8.2), 7.92-8.02 (1H, brs); M/Z (ES$^+$) 528 (MH$^+$).

Example 91

(±)-{(2S*,4R*)-1-[(4-Iodophenyl)methyl]-2-[4(trifluoromethyl)phenyl]piperidin-4-yl}acetic acid

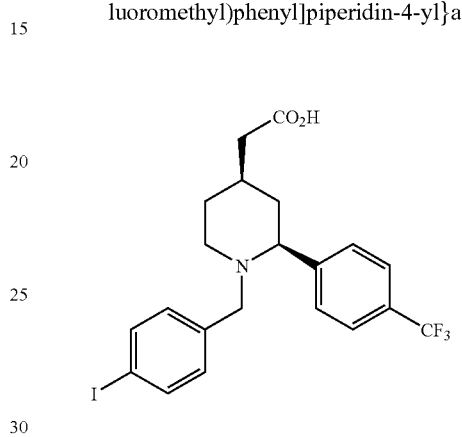

The title compound was prepared in the same manner as described in Example 20, substituting 4-iodo-benzyl bromide for benzyl bromide. $^1$H NMR δ (ppm)(CD$_3$OD): 7.77-7.87 (6H, m), 7.08 (2H, d, J 8.1), 4.52 (1H, d, J 12), 4.05-4.12 (1H, m), 3.94 (1H, d, J 13), 3.45-3.52 (1H, m), 3.19 (1H, t, J 12), 2.25-2.36 (3H, m), 2.07-2.21 (2H, m), 1.89-2.00 (1H, m), 1.66-1.76 (1H, m).

Example 92

(±)-{(2S*,4R*)-1-[(2-Azido-4-iodophenyl)methyl]-2-[4-(trifluoromethyl)phenyl]piperidin-4-yl}acetic acid

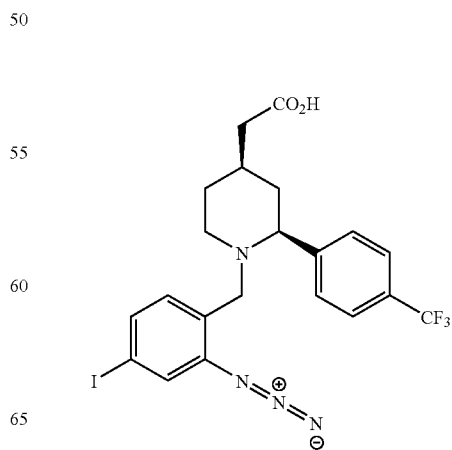

Step 1: 2-Azido-4-iodo-1-methylbenzene

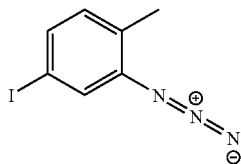

A cold (0° C.) suspension of 5-iodo-2-methylaniline (7.0 g, 0.03M) in HCl (5M, 30 ml) was treated dropwise with a solution of sodium nitrite (2.28 g, 0.033 mmol) in water (3 ml) over 20 minutes. The solution was stirred for 20 minutes before sodium azide was added portionwise over 15 minutes. The mixture was stirred for 30 minutes then poured into water. The mixture was diluted with DCM and the pH adjusted to 7 by the addition of $Na_2CO_3$. The phases were separated and the organic layer was dried ($MgSO_4$) and concentrated under vacuum. The residue was purified by chromatography (silica, 5% $Et_2O$/hexanes followed by 10% EtOAc/Hexanes) to give the azide (5.1 g, 64%). $^1$H NMR (500 MHz, $CDCl_3$): δ 2.14 (3H, s), 6.88 (1H, d, J 7.9), 7.35 (1H, d, J 7.9), 7.39 (1H, d, J 1.3).

Step 2: 2-Azido-1-(bromomethyl)-4-iodobenzene

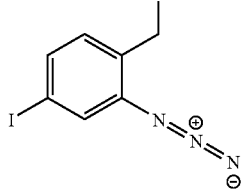

A mixture of the azide from step 1 (9.1 g, 0.035M), N-Bromosuccinimide (6.8 g, 0.039M) and 1,1azobis(cyclohexanecarbonitrile) (0.85 g, 3.5 mmol) in benzene (40 ml) was heated at reflux overnight. The solvent was evaporated under vacuum and the residue was diluted EtOAc (100 ml) and washed with water (50 ml) and brine, dried ($MgSO_4$) and concentrated under vacuum. The residue was purified by chromatography (silica, hexanes) to give the azide as a white solid (8 g, 67%). $^1$H NMR (500 MHz, $CDCl_3$): δ 4.30 (2H, s), 6.98 (1H, d, J 8.0), 7.35 (2H, t, J 7.0).

Step 3: (±)-{(2S*,4R*)-1-[(2-azido-4-iodophenyl)methyl]-2-[4-(trifluoromethyl)phenyl]piperidin-4-yl}acetic acid

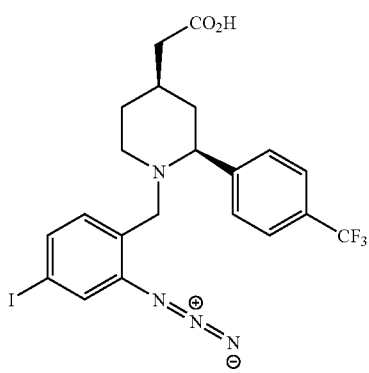

The title compound was prepared in the same manner as described in Example 20, substituting 2-azido-1-(bromomethyl)-4-iodobenzene for benzyl bromide. $^1$H NMR δ (ppm) ($CD_3OD$): 1.22-1.42 (2H, m), 1.77 (1H, m), 1.85 (1H, m), 1.93-2.01 (1H, m), 2.16-2.26 (3H, m), 2.95-2.99 (1H, m), 3.06 (1H, d, J=14.3 Hz), 3.36-3.40 (2H, m), 7.19 (1H, d, J=8.1 Hz), 7.40 (1H, d, J=1.6 Hz), 7.47 (1H, dd, J 1.6, 8.1 Hz), 7.60 (4H, s).

Example 93

(±)-{(2R*,4S*)-{2(R*/S*)-[2,5-Bis(trifluoromethyl)phenyl]pentyl}-2-[4-(trifluoromethyl)phenyl]piperidin-4-yl}acetic acid

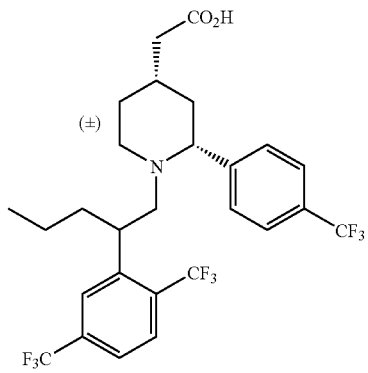

Step 1: (±)-Methyl 2-[2,5-bis(trifluoromethyl)phenyl]pentanoate

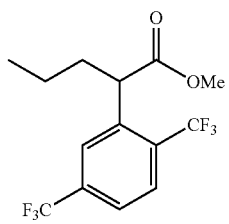

Potassium t-butoxide (7.7 ml, 1M in THF, 7.7 mmol) was added to a solution of methyl 2-[2,5-bis(trifluoromethyl)phenyl]acetate (2 g, 7 mmol) in THF at 0° C. The resulting yellow solution was stirred for 40 min. n-Propyl iodide (1.7 g, 10.5 mmol) was added and the mixture stirred for 1 h. The mixture was poured onto HCl (2M) and extracted into EtOAc. The combined organic phases were washed with $Na_2S_2O_3$ solution, brine, then dried ($MgSO_4$) and concentrated in vacuo to give the product as a yellow oil (2 g, 87%). $^1$H NMR (400 MHz, $CDCl_3$): δ 0.92 (3H, t, J 7.3), 1.23-1.29 (1H, m), 1.35-1.43 (1H, m), 1.67-1.81 (1H, m), 2.05-2.17 (1H, m), 3.69 (3H, s), 4.10 (1H, t, J 7.5), 7.62 (1H, s, J 8.2), 7.78 (1H, d, J 8.2), 7.90 (1H, s).

Step 2: (±)-2-[2,5-Bis(trifluoromethyl)phenyl]pentan-1-ol

DiBAL (7.62 ml, 1M in DCM, 7.62 mmol) was added to a solution of methyl 2-[2,5-bis(trifluoromethyl)phenyl]pentanoate (1 g, 3.05 mmol) in THF at −30° C. The mixture was stirred for 45 min. Sodium potassium tartrate (100 ml, satd. aq. solution) was added and the mixture was stirred at room temperature for 30 min then extracted into EtOAc. The combined organic phases were washed with brine, then dried (MgSO$_4$) and concentrated in vacuo to give the product as a colourless oil. This was purified by chromatography on silica using hexane/EtOAc (9:1) as eluant to afford the product as an oil (710 mg). $^1$H NMR (500 MHz, CDCl$_3$): δ 0.89 (3H, t, J 7.3), 1.10-1.20 (1H, m), 1.28-1.36 (1H, m), 1.60-1.68 (1H, m), 1.80-1.87 (1H, m), 3.33-3.39 (1H, m), 3.79 (2H, t, J 5.5), 7.59 (1H, d, J 8.3), 7.74 (1H, s), 7.79 (1H, d, J 8.2).

Step 3: (±)-Methyl{(2R*,4S*)-1-{2(R*/S*)-[-[2,5-bis(trifluoromethyl)phenyl]pentyl}-2-[4-(trifluoromethyl)phenyl]piperidin-4-yl}acetate Triflic anhydride (147 uL, 0.87 mmol) was added to a solution of the product of Step 2 (200 mg, 0.67 mmol) and triethylamine (121 uL, 0.87 mmol) in DCM (2.6 ml) at −10° C. The mixture was stirred for 30 min then washed with ice-cold HCl (1M), brine, dried (MgSO$_4$) and concentrated in vacuo. This material was dissolved in DCM (2 ml) and the resulting solution was added to a solution of the compound of Example 3, step 3 (240 mg, 0.8 mmol) in DCM (2 ml). This mixture was stirred at room temperature for 18 h and at 40° C. for 6 h. The mixture was cooled and water (2 m) was added. The organic layer was separated and was washed with brine, then dried (MgSO$_4$) and concentrated in vacuo to give the product as an oil. This was purified by chromatography on silica using hexane/EtOAc (9:1) as eluant to afford the product as a mixture of diastereomers (200 mg): $^1$H NMR (500 MHz, CDCl$_3$): δ 0.77-0.83 (6H, m), 0.90-0.94 (2H, m), 0.98-1.12 (3H, m), 1.19-1.42 (8H, m), 1.70-1.80 (3H, m), 1.88-2.12 (7H, m), 2.16-2.30 (4H, m), 2.40 (1H, dd, J 10.2, 12.5), 2.64 (1H, t, J 11.9), 3.03-3.11 (2H, m), 3.20 (1H, d, J 11.7), 3.32 (3H, dd, J 11.9, 20.3), 3.63 (6H, d, J 16.1), 6.94 (2H, d, J 7.4), 7.07 (1H, s), 7.18 (1H, s), 7.34 (2H, d, J 7.9), 7.41 (2H, d, J 7.5), 7.48 (1H, d, J 8.3), 7.53-7.59 (3H, m), 7.70 (1H, d, J 8.2), 7.78 (1H, d, J 8.2). MS (ES$^+$) m/z 584 (100%).

Step 4: (±)-{(2R*,4S*)-1-{2(R*/S*)-[-[2,5-Bis(trifluoromethyl)phenyl]pentyl}-2-[4-(trifluoromethyl)phenyl]piperidin-4-yl}acetic acid The ester described in Step 3 above (203 mg, 0.0348 mmol) was stirred with LiOH (146 mg, 3.48 mmol) in THF (1 ml) and water (1 ml) for 36 h. The mixture was neutralized with HCl (2M aq.) and extracted with EtOAc. The organic layer was separated and was washed with brine, then dried (MgSO$_4$) and concentrated in vacuo to give the product as a white solid (156 mg): MS (ES$^+$) m/z 570 (100%).

Examples 94 and 95

Examples 94 and 95 were made by the procedures in Examples 85 and 86 using the piperidine from Example 78 Step 5 and the appropriate benzaldehyde.

| Example | Structure | Name | M/Z ES$^+$ [MH]$^+$ |
|---|---|---|---|
| 94 | 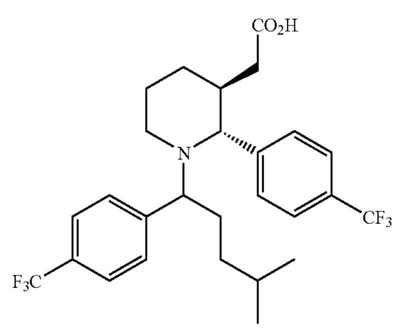 | (±)-{(2R*,3S*)-1-{(1R* or 1S*)-4-methyl-1-[4-(trifluoromethyl)phenyl]pentyl}-2-[4-(trifluoromethyl)phenyl]piperidin-3-yl}acetic acid | 516 |
| 95 | 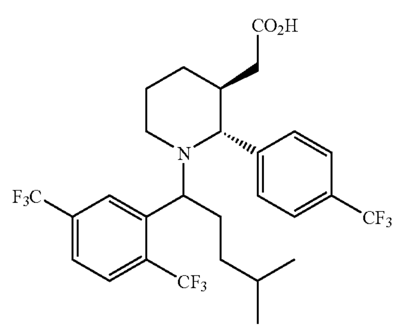 | (±)-{(2R*,3S*)-1-{(1R* or 1S*)-1-[2,5-bis(trifluoromethyl)phenyl]-4-methylpentyl}-2-[4-(trifluoromethyl)phenyl]piperidin-3-yl}acetic acid | 584 |

Example 96

(±)-2-{(2R*,3S*)-1-[2,5-bis(trifluoromethyl)benzyl]-2-[4-(trifluoromethyl)phenyl]piperidin-3-yl}pentanoic acid

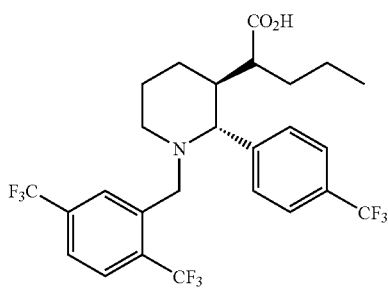

Step 1: (±)-Methyl 2-{(2R*,3S*)-1-[2,5-bis(trifluoromethyl)benzyl]-2-[4-(trifluoromethyl)phenyl]piperidin-3-yl}pentanoate

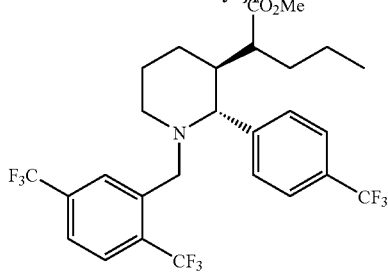

n-BuLi (1.6M in hexanes, 0.22 ml, 0.35 mmol) was added to a solution of diisopropylamine (0.05 ml, 0.35 mmol) in dry THF (2 ml) at 0° C. The reaction was stirred for 30 mins then a solution of the ester from Example 78 Step 6 (0.153 g, 0.29 mmol) in dry THF (4 ml) was added. After 1 hr propyl iodide (0.03 ml, 0.35 mmol) was added. The reaction was stirred for 2 hrs then quenched with water and the mixture was extracted with EtOAc (×3). The combined extracts were washed with sodium thiosulfate solution, then brine, dried (MgSO₄), filtered and evaporated. The residue was purified by chromatography (silica, 5% Et₂O/hexanes) to give the ester (0.101 g, 61%). M/Z (ES⁺) 570 (MH⁺).

Step 2: (±)-2-[(2R*,3S*)-1-{(1R* or 1S*)-1-[2,5-bis(trifluoromethyl)phenyl]-4-methylpentyl]-2-[4-(trifluoromethyl)phenyl]piperidin-3-yl}pentanoic acid

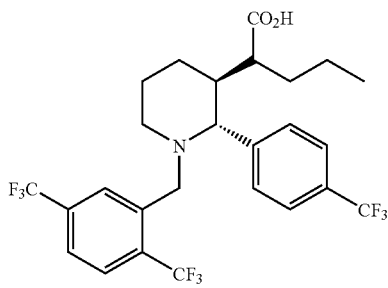

A solution of the ester from Step 1 (0.098 g, 0.17 mmol) and LiOH (0.082 g, 3.4 mmol) in THF (3 ml) and water (3 ml) was heated at 60° C. for 16 hrs. Then dioxane (3 ml) was added and the reaction was heated at 100° C. for 16 hrs. The reaction mixture was acidified to pH6 with 2N HCl and extracted with EtOAc. The combined extracts were washed with brine, dried (MgSO₄), filtered and evaporated. The residue was purified by chromatography (silica, 1-2% MeOH/DCM) to give the acid (0.070 g, 74%). ¹H NMR (400 MHz, CD₃OD): δ 0.84 (3H, t, J 7.2), 0.86-0.97 (1H, m), 1.21-1.47 (3H, m), 1.61-1.83 (5H, m), 2.17 (1H, dt, J 3.0, 11.7), 2.28-2.34 (1H, m), 2.83 (1H, d, J 11.6), 3.37-3.57 (3H, m), 7.65 (5H, m), 7.75 (1H, d, J 8.2), 8.19 (1H, s).

Example 97

(±)-{(2R*,3S*)-1-[2,5-bis(trifluoromethyl)benzyl]-2-[4-(trifluoromethyl)phenyl]piperidin-3-yl}carboxylic acid

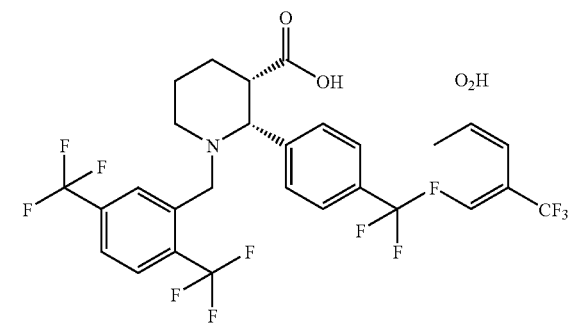

Step 1: Ethyl-2-[4-(trifluoromethyl)phenyl]pyridin-3-yl carboxylate

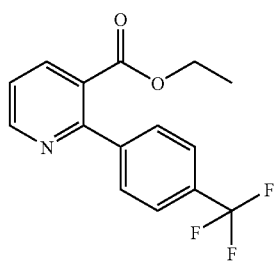

A mixture of ethyl-2-chloronicotinate (9.3 g, 50 mmol), 4-trifluoromethylphenyl boronic acid (12.4 g, 65 mmol), and tripotassium phosphate (14.8 g, 70 mmol) in toluene (200 ml) was degassed with the aid of a Firestone valve. [1,1'-Bis(diphenylphosphino)ferrocene]palladium(II)chloride dichloromethane complex (0.82 g, 1 mmol) was added, the mixture degassed once again then stirred under nitrogen at reflux for 23 h. On cooling, water (100 ml) was added and the resulting emulsion filtered, the organic layer dried (MgSO$_4$), filtered and evaporated to leave the crude product as a brown oil (13.9 g). $^1$H NMR (400 MHz, CDCl$_3$): δ 1.07 (3H, t, J 7.1), 4.17 (2H, q, J 7.1), 7.41 (1H, dd, J 4.9, 7.9), 7.63-7.73 (4H, m), 8.19 (1H, dd, J 1.7, 7.8), 8.80 (1H, dd, J 1.8, 4.8).

Step 2: (±)-{(2R*,3S*)-2-[4-(trifluoromethyl)phenyl]piperidin-3-yl}carboxylate

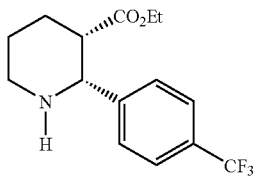

The ester from Step 1 (5.0 g, ca 17 mmol), HCl in dioxan (4M; 5 ml), and palladium hydroxide on carbon (20%; 0.32 g) were shaken for 20 h in ethanol (90 ml) under an atmosphere of hydrogen at 50 psi. The suspension was filtered, platinum oxide (0.29 g) added, and hydrogenation at 50 psi resumed for 5 h, after which the suspension was filtered and the filtrate evaporated. The residue was partitioned between EtOAc (90 ml) and NaHCO$_3$ (satd.; 75 ml), the organic layer washed with water (50 ml), dried (MgSO$_4$), filtered and evaporated to leave a yellow oil (4.69 g) which consisted of an approximately 3:1 mixture of the desired product with fully saturated material. $^1$H NMR (400 MHz, CDCl$_3$): δ 0.97 (3H, t, J 7.2), 1.67-1.87 (3H, m), 2.18-2.22 (1H, m), 2.77-2.83 (1H, m), 2.98-3.00 (1H, m), 3.33-3.37 (1H, m), 3.84-4.00 (3H, m), 7.44 (2H, d, J 8.4), 7.56 (2H, d, J 8.3); M/Z (ES$^+$) 302 (MH$^+$).

Step 3: (±)-Ethyl{(2R*,3S*)-1-[2,5-bis(trifluoromethyl)benzyl]-2-[4-(trifluoromethyl)phenyl]piperidin-3-yl}carboxylate

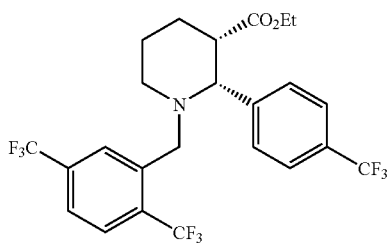

Potassium carbonate (0.55 g, 4 mmol) was added to a solution of the preceding crude ester (1.0 g, ca 3.25 mmol) and 2,5-bis(trifluoromethyl)benzyl bromide (0.6 ml, 3.25 mmol) in dry DMF (15 ml) and the mixture stirred overnight. The resulting suspension was partitioned between water (35 ml) and EtOAc (3×15 ml), the combined organic layers washed with water (20 ml) and brine (20 ml), dried (MgSO$_4$), filtered and evaporated. The residue was purified by chromatography (silica, 10% EtOAc in hexanes) to provide the title compound as a gum (1.01 g). $^1$H NMR (400 MHz, CDCl$_3$): δ 1.01 (3H, t, J 7.2), 1.55-1.64 (1H, m), 1.81-1.89 (1H, m), 2.06-2.30 (3H, m), 2.92-3.02 (2H, m), 3.47 (1H, d, J 16.0), 3.73 (1H, d, J 16.0), 3.82-3.96 (3H, m), 7.48 (2H, d, J 8.2), 7.55 (2H, d, J 8.2), 7.61 (1H, d, J 8.2) 7.72 (1H, d, J 8.2), 8.36 (1H, s).

Step 4: (±)-{(2R*,3S*)-1-[2,5-bis(trifluoromethyl)benzyl]-2-[4-(trifluoromethyl)phenyl]piperidin-3-yl}carboxylic acid

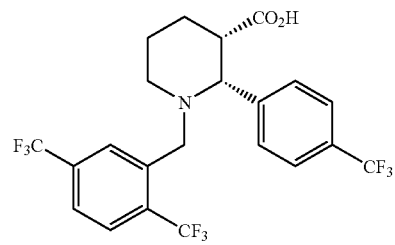

A solution of the ester from the preceding step (215 mg, 0.41 mmol) in MeOH (9 ml) and aqueous NaOH (1M, 1 ml) was stirred for 24 h. More NaOH (4M, 0.25 ml) was added and the mixture stirred overnight at reflux. On cooling, volatiles were removed under reduced pressure and the aqueous residue acidified with citric acid (10%). The resulting suspension was extracted with EtOAc (2×10 ml), the combined extracts dried (MgSO$_4$), filtered and evaporated, and the residue purified by chromatography (silica, 15% EtOAc in hexanes) to afford the crude product as a white foam (167 mg). This was subjected to preparative, reverse phase HPLC.

| Column | Column Dimensions | % Modifier | Solvent | Mobile Phase | Flow | Detection |
|---|---|---|---|---|---|---|
| Supelcosil ABZ + PLUS | (100 × 21.2) mm | 60-40% | MeCN | 0.1% aq. TFA | 15 ml/min | UV 230 nm |

The title compound was obtained as the TFA salt, 40 mg, (20%). $^1$H NMR (500 MHz, CD$_3$OD): δ 1.73-1.75 (1H, m), 1.96-2.03 (2H, m), 2.11-2.19 (2H, m), 2.56-2.65 (1H, m), 3.09 (2H, d, J 4.6), 3.75 (1H, d, J 15.6), 3.93 (1H, d, J 15.4), 4.27 (1H, s), 7.65 (4H, q, J 8.5), 7.80 (1H, d, J 8.3), 7.89 (1H, d, J 8.2), 8.34 (1H, s), M/Z (ES$^-$) 498 (MH$^-$).

Example 98

(±)-{(2R*,3R*)-1-[2,5-bis(trifluoromethyl)benzyl]-2-[4-(trifluoromethyl)phenyl]piperidin-3-yl}carboxylic acid

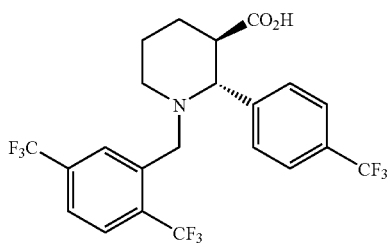

Further elution in the preparative, reverse phase, HPLC purification described in the preceding example provided the alternative diastereoisomer, 58 mg (28%). ¹H NMR (500 MHz, CD₃OD): δ 1.67-1.79 (3H, m), 2.13 (1H, d, J 12.4), 2.25 (1H, t, J 11.0), 2.77-2.83 (1H, m), 2.88 (1H, d, J 11.9), 3.42 (1H, d, J 15.7), 3.61 (1H, d, J 15.7), 3.64 (1H, d, J 10.9), 7.58 (2H, d, J 8.2), 7.64 (2H, d, J 8.2), 7.68 (1H, d, J 8.2), 7.78 (1H, d, 18.2), 8.18 (1H, s), M/Z (ES⁻) 498 (MH⁻).

Example 99

(±)-{(2S*,4R*)-1-{(1R* or S*)-1-[2,5-Bis(trifluoromethyl)phenyl]ethyl}-2-[4-(trifluoromethyl)phenyl]piperidin-4-yl}acetic acid

Step 1: (±)-1-[2,5-Bis(trifluoromethyl)phenyl]ethanamine

Methyl magnesium chloride (1.4M in PhMe/THF [3:1], 5 ml, 21 mmol) was added to a stirred solution of (±)-N-{(1E)-[2,5-Bis(trifluoromethyl)phenyl]methylene}-2-methylpropane-2-sulfinamide (example 72 Step 1, 4.75 g, 13.8 mmol) in dry DCM (32 ml) at 0° C. under N₂. After 90 min the reaction was quenched with saturated aqueous NH₄Cl and then diluted with DCM and H₂O. The aqueous layer was extracted with DCM (×2). The combined extracts were dried (Na₂SO₄), filtered and evaporated to give the sulfinamide (5.4 g) as a waxy solid.

Hydrogen chloride (4N in dioxane, 17 ml, 68 mmol) was added to a stirred solution of the sulphonamide from above (~13.8 mmol) in dry MeOH (140 ml) under N₂ such that the internal temperature <5° C. After 90 min in an ice bath the solvent was removed in vacuo and the residue was partitioned between DCM and saturated aqueous NaHCO₃. The aqueous layer was extracted with DCM (×2). The combined extracts were dried (Na₂SO₄), filtered and evaporated. The residue was purified by chromatography on a SCX cartridge, eluting with DCM then 2M NH₃ in MeOH to give the amine (2.7 g) as a pale yellow liquid. ¹H NMR (360 MHz, CDCl₃): δ 1.40 (3H, d, J 6.5), 4.65 (1H, q, J 6.4), 7.59 (1H, d, J 8.3), 7.73 (1H, d, J 8.2), 8.13 (1H, s).

Step 2: (±)-Ethyl(2E/Z)-{(2S*)-1-{(1R*)-1-[2,5-bis(trifluoromethyl)phenyl]ethyl}-2-[4-(trifluoromethyl)phenyl]piperidin-4-ylidene}acetate and (±)-Ethyl(2E/Z)-{(2S*)-1-{(1S*)-1-[2,5-bis(trifluoromethyl)phenyl]ethyl}-2-[4-(trifluoromethyl)phenyl]piperidin-4-ylidene}acetate Prepared by the procedure of Example 72 Steps 3,4 and 5 using the amine from Step 1, and purified by chromatography (silica, 2-8% EtOAc/isohexane) to give the alkenes (0.93 g, mixture of isomers) as an oil. M/Z (ES⁺) 554 (MH⁺).

Step 3: (±)-Ethyl{(2S*,4R*)-1-[(1R*)-1-[2,5-bis(trifluoromethyl)phenyl]ethyl]-2-[4-(trifluoromethyl)phenyl]piperidin-4-yl}acetate and (±)-Ethyl{(2S*,4R*)-1-{(1S*)-1-[2,5-bis(trifluoromethyl)phenyl]ethyl}-2-[4-(trifluoromethyl)phenyl]piperidin-4-yl}acetate A solution of the alkene (Step 2, 930 mg, 1.68 mmol) in EtOH (10 ml) was hydrogenated over 10% Pd/C (90 mg) under a balloon of H₂ for 2.5 hrs. The catalyst was removed by filtration—washing with EtOAc. The filtrate was evaporated and the residue was purified by chromatography (silica, 2-8% EtOAc/isohexane) to give the ester (642 mg, cis across piperidine—mixture of diastereomers) as an oil. This material was further purified by reverse phase preparative HPLC to give:

Diastereomer A: 1$^{st}$ eluting—442 mg, oil. $^1$H NMR (500 MHz, CDCl$_3$): δ 1.23 (3H, t, J 7.1), 1.28 (3H, d, J 6.7), 1.38 (2H, q, J 12.0), 1.76 (1H, d, J 12.9), 1.83 (1H, d, J 12.3), 1.95-2.05 (1H, m), 2.17-2.27 (2H, m), 2.51 (1H, t, J 11.7), 2.99 (1H, brd, J 11), 3.53 (1H, d, J 10.9), 4.08-4.15 (3H, m), 7.28-7.30 (2H, m), 7.37 (2H, d, J 7.6), 7.49 (1H, d, J 8.1), 7.56 (1H, d, J 8.0), 7.92 (1H, s); M/Z (ES$^+$) 556 (MH$^+$).

Diastereomer B: 2$^{nd}$ eluting—65 mg, oil. $^1$H NMR (500 MHz, CDCl$_3$): δ 1.12 (3H, d, J 5.0), 1.20-1.40 (4H, m), 1.70-1.75 (2H, m), 1.85-1.93 (1H, m), 2.13-2.23 (2H, m), 2.53 (1H, t, J 12.0), 3.05 (1H, d, J 9.2), 3.57 (1H, d, J 11), 4.06-4.13 (2H, m), 4.16-4.21 (1H, m), 7.25-7.35 (4H, m), 7.45 (1H, d, J 7.9), 7.50 (1H, s), 7.66 (1H, d, J 7.7); M/Z (ES$^+$) 556 (MH$^+$).

Step 6: (±)-{(2S*,4R*)-1-{(1R* or S*)-1-[2,5-bis(trifluoromethyl)phenyl]ethyl}-2-[4-(trifluoromethyl)phenyl]piperidin-4-yl}acetic acid

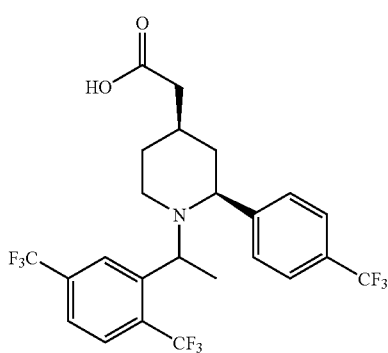

A solution of LiOH (92 mg, 0.77 mmol) in water (1 ml) was added to a stirred solution of the ester (Step 5, Diastereomer A, 428 mg, 0.77 mmol) in THF (2 ml) at RT. The reaction was stirred and heated at 60° C. for 16 hrs. After cooling to RT the reaction was quenched with 2N HCl (1 ml). The mixture was partitioned between EtOAc and H$_2$O. The aqueous layer was extracted with EtOAc (×2). The combined extracts were washed with brine (×1), dried (Na$_2$SO$_4$), filtered and evaporated to give the acid (397 mg) as a pale yellow solid. M/Z (ES$^+$) 528 (MH$^+$).

Example 100

(±)-{(2S*,4R*)-1-{(1S* or R*)-1-[2,5-bis(trifluoromethyl)phenyl]ethyl}-2-[4-(trifluoromethyl)phenyl]piperidin-4-yl}acetic acid

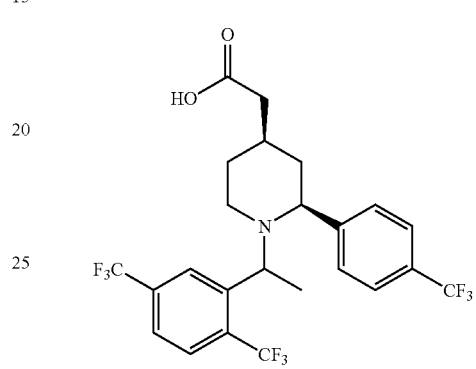

The title compound was prepared as described in Example 99 Step 6, but using Diastereomer B from Example 99 Step 5. The final product was purified by reverse phase HPLC to give the acid (30 mg) as a colourless solid. M/Z (ES$^+$) 528 (MH$^+$).

Examples 101 and 102

These compounds were prepared according to the general procedures described in Examples 99 and 100 but starting with 4-tert-butyl benzaldehyde and replacing MeMgCl with $^n$PrMgCl. The cycloaddition gave ~1:1 mixture of diastereomers, which were separated at the piperidone stage (silica, 4-8% EtOAc/isohexane) and carried through the subsequent steps separately.

| Example | Structure | Name | M/Z ES$^+$ [MH]$^+$ |
|---|---|---|---|
| 101 | ![structure] | (±)-{(2S*,4R*)-1-[(1R* or S*)-1-(4-tert-butylphenyl)butyl]-2-[4-(trifluoromethyl)phenyl]piperidin-4-yl}acetic acid | 476 |

-continued

| Example | Structure | Name | M/Z ES+ [MH]+ |
|---|---|---|---|
| 102 | 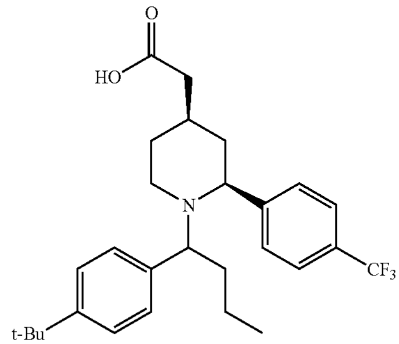 | (±)-{(2S*,4R*)-1-[(1S* or R*)-1-(4-tert-butylphenyl)butyl]-2-[4-(trifluoromethyl)phenyl]piperidin-4-yl}acetic acid | 476 |

Example 103

(±)-{(2S*,4S*)-1-{(1)-1-[2,5-bis(trifluoromethyl)phenyl]butyl}-2-[4-(trifluoromethyl)phenyl]piperidin-4-yl}acetic acid

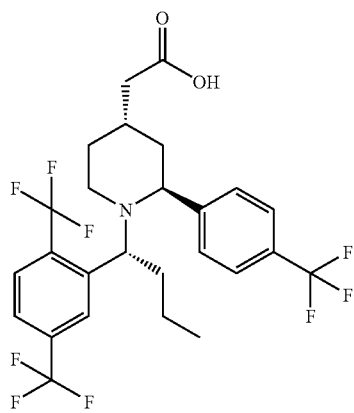

Step 1: (±)-Ethyl{(2S*,4S*)-1-{(1R*)-1-[2,5-bis(trifluoromethyl)phenyl]butyl}-2-[4-(trifluoromethyl)phenyl]piperidin-4-yl}acetate

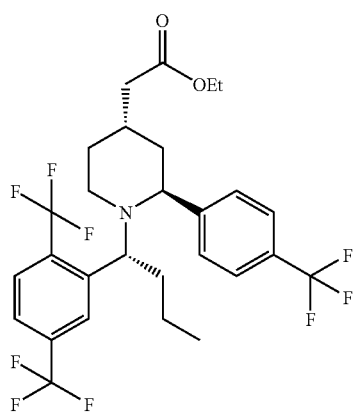

The compound was prepared from the lower running diastereoisomeric piperidone described in Example 72 step 4 and used to prepare Example 73. The ketone was reacted as in Example 72 step 5 and during the hydrogenation, analogous to Example 72 step 6 the trans diastereoisomer of the ester was obtained. $^1$H NMR (400 MHz, CDCl$_3$): δ 0.78-0.86 (3H, m), 0.96-1.12 (1H, m), 1.26 (5H, t, J 7.1), 1.37-1.43 (1H, m), 1.68-1.72 (2H, m), 1.80-1.88 (1H, m), 2.00-2.06 (1H, m), 2.19-2.29 (2H, m), 2.35 (1H, s), 2.45 (1H, d, J 14.2), 2.65-2.73 (1H, m), 4.10-4.18 (2H, m), 4.39 (1H, s), 4.57 (1H, t, J 5.4), 7.14-7.18 (1H, m), 7.23 (1H, s), 7.60-7.68 (4H, m), 7.76 (1H, d, J 8.3), 8.20 (1H, s).

Step 2: (±)-{(2S*,4S*)-1-{(1R*)-1-[2,5-Bis(trifluoromethyl)phenyl]butyl}-2-[4-(trifluoromethyl)phenyl]piperidin-4-yl}acetic acid The title compound was obtained by hydrolysis of the ester in a manner analogous to Example 72 step 7 to give a white solid, after trituration with ether, 30 mg. M/Z (ES+) 556 (MH+).

Example 104

(±)-{(2S*,4R*)-1-[(1R*)-1-[2,5-Bis(trifluoromethyl)phenyl]-4-methylpentyl]-2-[4-(trifluoromethyl)phenyl]piperidin-4-yl}acetic acid

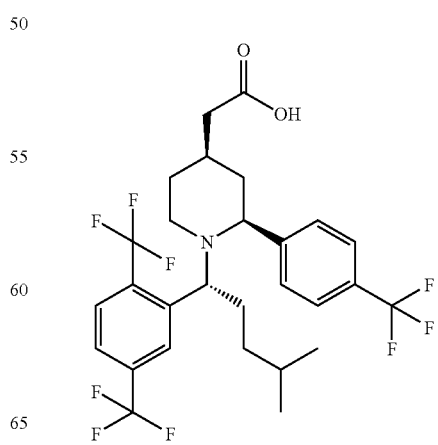

Step 1: (±)-1-[2,5-Bis(trifluoromethyl)phenyl]-4-methylpentan-1-anine

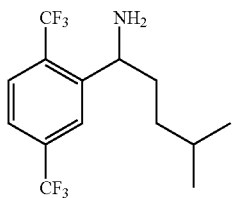

Prepared in analogously to Example 72 step 2 using N-{(1E)-[2,5-bis(trifluoromethyl)phenyl]methylene}-2-methylpropane-2-sulfinamide (Example 72 step 1) and treating with freshly prepared 3-methylbutyl magnesium bromide.

Step 2: (±)-1-[2,5-Bis(trifluoromethyl)phenyl]-4-methyl-N-{(1E)-[4-(trifluoromethyl)phenyl]methylidene}pentan-1-amine

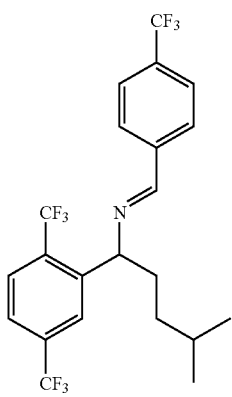

Prepared in a similarly to Example 72 step 3.

Step 3: (±)-1-{1-[2,5-Bis(trifluoromethyl)phenyl]-4-methylpentyl}-2-[4-(trifluoromethyl)phenyl]piperidin-4-one

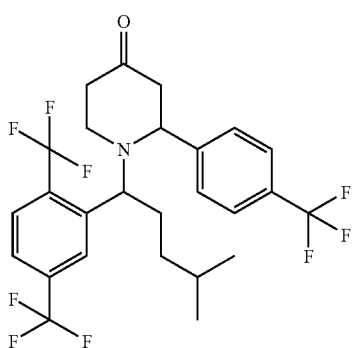

The intermediate was prepared analogously to Example 72 step 4. The reaction gave an approximately 2:1 ratio of diastereoisomers which were separated by column chromatography on silica eluting with 5-10% EtOAc/isoHexane followed by 5% EtOAc/cyclohexane.

The higher diastereoisomer $^1$H NMR (360 MHz, CDCl$_3$): δ 8.21 (1H, s), 7.80 (1H, d, J 8.2), 7.65 (1H, d, J 7.9), 7.49 (2H, t, J 10.9), 7.30 (2H, d, J 8.2), 4.53 (1H, s), 4.13 (1H, s), 3.32 (1H, s), 3.04-2.94 (2H, m), 2.74 (1H, d, J 15.2), 2.62-2.54 (1H, m), 2.28 (1H, d, J 15.0), 2.05 (1H, t, J 12.8), 1.82-1.74 (1H, m), 1.43 (1H, t, J 3.2), 1.16-1.08 (1H, m), 0.83-0.75 (7H, m).

Lower diastereoisomer $^1$H NMR (400 MHz, CDCl$_3$): δ 7.99 (1H, s), 7.80 (1H, d, J 8.3), 7.65-7.55 (3H, m), 7.47 (2H, t, J 12.0), 4.62 (1H, d, J 4.6), 4.46 (1H, t, J 6.4), 3.08-2.88 (3H, m), 2.69-2.55 (2H, m), 2.33-2.27 (1H, m), 1.94-1.86 (1H, m), 1.77-1.69 (1H, m), 1.46-1.36 (2H, m), 1.22-1.10 (1H, m), 0.96-0.88 (1H, m), 0.86-0.78 (5H, m).

Step 4: (±)-{(2S*,4S*)-1-{(1R*)-1-[2,5-Bis(trifluoromethyl)phenyl]-4-methylpentyl}-2-[4-(trifluoromethyl)phenyl]piperidin-4-yl}acetic acid

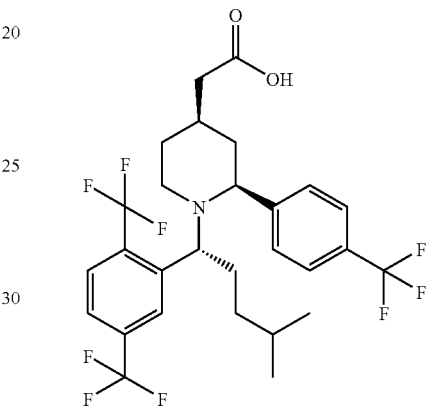

The compound was prepared from the lower running diastereoisomer from step 3, homologating using the procedure from Example 75 step 5, reducing using Example 75 step 6 and hydrolysing analogously to Example 72 step 7 to furnish a white foam. $^1$H NMR (360 MHz, CD$_3$OD): δ 7.79 (1H, d, J 8.2), 7.60 (1H, d, J 8.3), 7.38 (3H, t, J 9.5), 7.25 (2H, d, J 8.2), 4.19 (1H, dd, J 6.2, 8.9), 3.60 (1H, d, J 8.4), 2.76 (1H, t, J 10.7), 2.21-2.13 (2H, m), 2.02-1.94 (1H, m), 1.88-1.66 (4H, m), 1.50-1.35 (2H, m), 1.23 (1H, t, J 5.7), 1.18-0.90 (3H, m), 0.83 (6H, dd, J 2.7, 6.6).

Example 105

(±)-{(2S*,4R*)-1-{(1S*)-1-[2,5-bis(trifluoromethyl)phenyl]-4-methylpentyl}-2-[4-(trifluoromethyl)phenyl]piperidin-4-yl}acetic acid

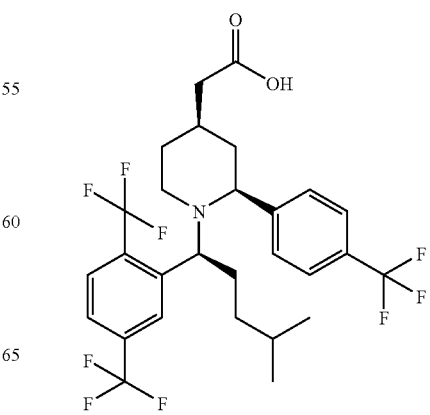

Step 1: (±)-Ethyl(E/Z)-{1-{1-[2,5-bis(trifluoromethyl)phenyl]-4-methylpentyl}-2-[4-(trifluoromethyl)phenyl]piperidin-4-ylidene}ethanoate

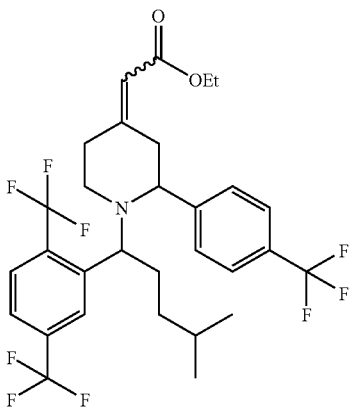

The compound was prepared as a mixture of E and Z isomers, analogously to Example 99 step 4 using the higher running diastereoisomer from Example 104 step 3. $^1$H NMR (400 MHz, CDCl$_3$): δ 8.17 (1H, s), 7.97 (1H, d, J 12.6), 7.77-7.71 (2H, m), 7.60-7.48 (8H, m), 7.35 (2H, t, J 12.0), 5.69 (2H, d, J 16.5), 4.51 (1H, s), 4.35 (1H, t, J 6.5), 4.18-4.10 (4H, m), 3.90-3.84 (3H, m), 3.15-3.07 (2H, m), 3.05-2.77 (6H, m), 2.52-2.44 (2H, m), 2.12-1.92 (3H, m), 1.76-1.70 (2H, m), 1.43-1.39 (2H, m), 1.29-1.25 (7H, m), 1.11-0.97 (2H, m), 0.82-0.74 (13H, m).

Step 2: (±)-Ethyl{(2S*,4R*)-1-{1 [2,5-Bis(trifluoromethyl)phenyl]-4-methylpentyl}-2-[4-(trifluoromethyl)phenyl]piperidin-4-yl}acetate

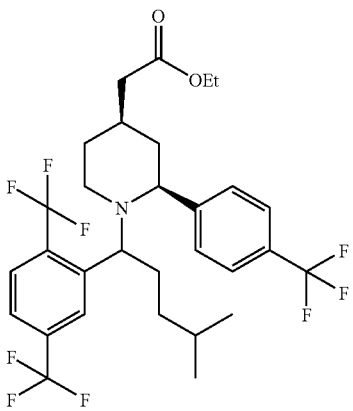

A solution of the alkene (Step 1, 477 mg, 0.78 mmol) in EtOH (20 ml) was hydrogenated over 10% Pd/C (40 mg) under a balloon of H$_2$ for 1.25 hrs. The catalyst was removed by filtration—washing with EtOH. The filtrate was evaporated and the residue was purified by chromatography (silica, 50% PhMe/isohexane) to give the ester (264 mg, 55%, cis across piperidine as an oil). Also obtained was the lower running trans isomer (72 mg, 15%).

Step 3: (±)-{(2S*,4R*)-1-{(1S*)-1-[2,5-bis(trifluoromethyl)phenyl]-4-methylpentyl}-2-[4-(trifluoromethyl)phenyl]piperidin-4-yl}acetic acid The title compound was obtained by hydrolysis of the higher running cis isomer from step 2 using the same method as Example 99 step 6 to give a white solid. $^1$H NMR (360 MHz, CD$_3$OD): δ 8.17 (1H, s), 7.97-7.89 (2H, m), 7.75 (2H, d, J 7.7), 7.66 (2H, d, J 8.0), 4.59 (1H, s), 4.28 (1H, d, J 7.3), 3.49 (1H, s), 2.31 (3H, d, J 6.2), 2.21 (2H, s), 2.07 (2H, s), 1.85 (1H, s), 1.58-1.48 (2H, m), 0.87-0.79 (8H, m), 0.61 (1H, s).

Example 106

(±)-{(2S*,4S*)-1-[(1S*)-1-[2,5-Bis(trifluoromethyl)phenyl]-4-methylpentyl}-2-4-(trifluoromethyl)phenyl]piperidin-4-yl}acetic acid

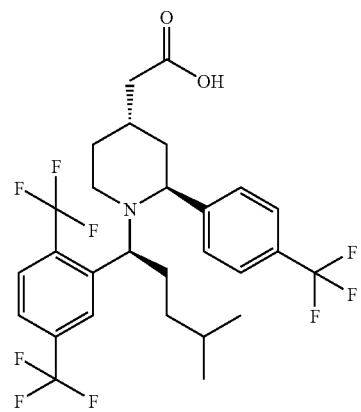

The title compound was obtained by hydrolysis of the lower running trans isomer from Example 105 step 2 using the same method as Example 99 step 6 to give a clear gum. M/Z (ES$^+$) 584 (MH$^+$).

Example 107

(±)-((2S*,4R*)-2-[4-(Trifluoromethyl)phenyl]-1-{(1R*)-1-[4-(trifluoromethyl)phenyl]prop-2-yn-1-yl}piperidin-4-yl)acetic acid

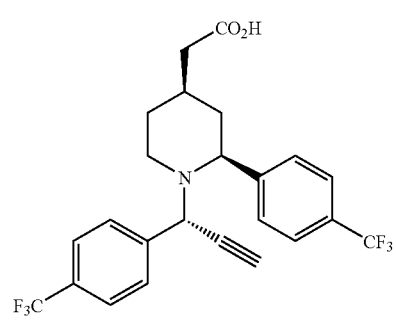

The title compound was made by the procedure in Example 85 using trimethylsilylacetylene instead of 2-methyl-1-buten-3-yne. $^1$H NMR (360 MHz, CD$_3$OD): δ 1.24-1.34 (1H, m), 1.47 (1H, q, J 12.1), 1.74 (1H, m), 1.88-1.96 (2H, m), 2.23 (2H, d, J 7.1), 2.43-2.53 (2H, m), 3.12 (1H, d, J 2.3), 3.74 (1H, dd, J 2.4, 5.5), 4.50 (1H, s), 7.61-7.76 (8H, m).

Example 108

(±)-((2S*,4R*)-2-[4-(Trifluoromethyl)phenyl]-1-{(1R*)-1-[4-(trifluoromethyl)phenyl]propyl}piperidin-4-yl)acetic acid

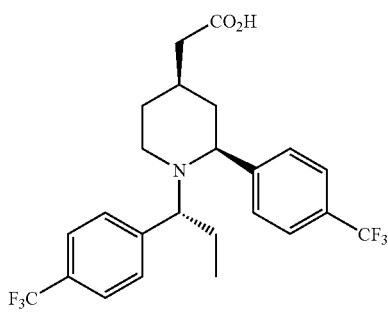

The acetylene from Example 107 (0.539 g, 1.1 mmol) was taken up in EtOAc (30 ml) and hydrogenated under a balloon of hydrogen over 10% Pd/C (120 mg) for 16 hrs. The catalyst was removed by filtration and the filtrate was evaporated. The residue was purified by chromatography (silica, 5-10% MeOH/DCM) to give the acid (0.042 g, 8%). $^1$H NMR (500 MHz, CD$_3$OD): δ 0.61 (3H, t, J 7.3), 0.83-0.93 (1H, m), 1.11-1.19 (1H, m), 1.42 (1H, q, J 12.0), 1.71 (1H, d, J 12.7), 1.85 (1H, dd, J 1.2, 12.9), 1.90-1.97 (2H, m), 2.14-2.22 (2H, m), 2.47 (1H, dt, J 1.8, 11.8), 2.74 (1H, m), 3.41-3.47 (1H, m), 3.85 (1H, dd, J 2.2, 10.9), 7.47 (2H, d, J 8.1), 7.60 (2H, d, J 8.0), 7.69 (4H, m).

Example 109

{(2S,4R)-1-{(1S)-4-Methyl-1-[4-(trifluoromethyl)phenyl]pentyl}-2-[4-(trifluoromethyl)phenyl]piperidin-4-yl}acetic acid

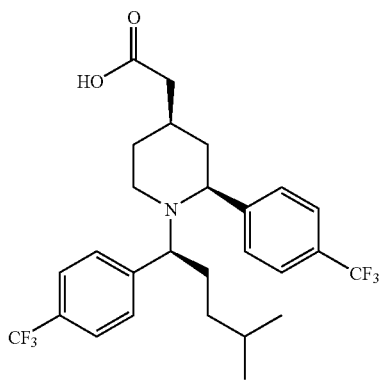

Step 1: Dimethyl allyl{2-oxo-2-[4-(trifluoromethyl)phenyl]ethyl}malonate

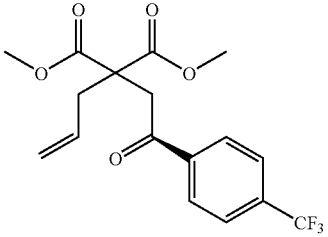

Dimethyl allylmalonate (25 g, 0.145 mol) was dissolved in DMF (200 ml) and sodium hydride (4.17 g) was added portionwise. When all effervescence ceased (4-trifluoromethyl)phenacyl bromide (42 g, 1.1 mol) was added portionwise and the mixture was stirred overnight. Water (1500 ml) was added and the mixture was extracted with EtOAc. The organic layer was separated and was washed with brine, then dried (MgSO$_4$) and concentrated in vacuo to give the product as an oil. This was purified by chromatography on silica using hexane/EtOAc (9:1 to 1:1) as eluant to afford the product (21 g). $^1$H NMR (500 MHz, CDCl$_3$): δ 2.88 (2H, d, J 7.5), 3.68 (2H, s), 3.77 (6H, s), 5.00-5.08 (2H, m), 5.62-5.70 (1H, m), 7.73 (2H, d, J 8.2), 8.06 (2H, d, J 8.1).

Step 2: Dimethyl(2-oxoethyl){2-oxo-2-[4-(trifluoromethyl)phenyl]ethyl}malonate

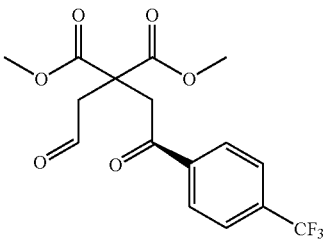

Dimethyl allyl{2-oxo-2-[4-(trifluoromethyl)phenyl]ethyl}malonate (20 g, 0.055 mol) was dissolved in DCM (180 ml) and the solution was cooled to −78° C. Oxygen, containing ozone, was bubbled through the solution until a blue coloration persisted. The mixture was then purged with nitrogen for 10 min in then dimethyl sulfide (20 ml, 0.275 mol) was added and the mixture was stirred overnight at room temperature. Water (500 ml) was added and the mixture was extracted with DCM. The organic layer was separated and was washed with brine, then dried (MgSO$_4$) and concentrated in vacuo to give the product as an oil. This was purified by chromatography on silica using hexane/EtOAc (9:1 to 1:1) as eluant to afford the product (4 g). $^1$H NMR (500 MHz, CDCl$_3$): δ 3.46 (2H, s), 3.77 (7H, s), 3.93 (2H, s), 7.74 (2H, d, J 8.2), 8.06 (2H, d, J 8.1), 9.73 (1H, s).

Step 3: Dimethyl(2R)-1-{(1S)-4-methyl-1-[4-(trifluoromethyl)phenyl]pentyl}-2-[4-(trifluoromethyl)phenyl]piperidine-4,4-dicarboxylate and Dimethyl (2S)-1-{(1S)-4-methyl-1-[4-(trifluoromethyl)phenyl]pentyl}-2-[4-(trifluoromethyl)phenyl]piperidine-4,4-dicarboxylate

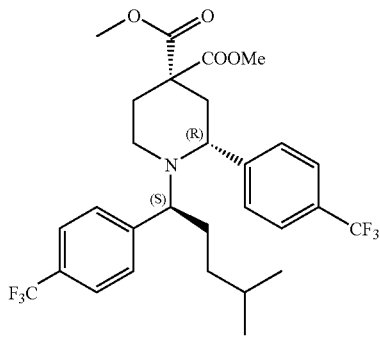

isomer a

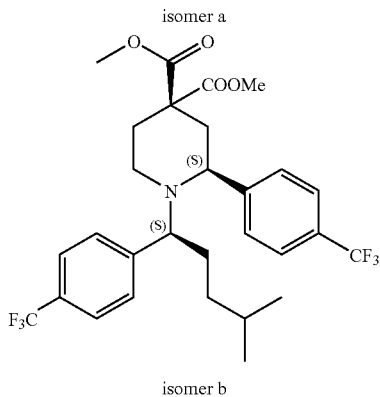

isomer b

Dimethyl(2-oxoethyl){2-oxo-2-[4-(trifluoromethyl)phenyl]ethyl}malonate (4 g, 0.011 mol), (S)-4-methyl-1-[4-(trifluoromethyl)phenyl]pentan-1-amine (T1657PV, Intermediate 8, α$_D$ [c=1, CHCl$_3$]-9°, 2.8 g, 0.011 mol) and triethylamine (9 ml, 6 mmol) were dissolved in DME (50 ml) and the solution was cooled to −78° C. Titanium tetrachloride (2.4 ml, 2 mmol) was added dropwise and the mixture was then allowed to stir for 10 min before coming to room temperature. Sodium cyanoborohydride (4 g, 6 mmol) in MeOH (20 ml) was added to the mixture which was stirred for 1 h. The mixture was then filtered through Celite and the filtrate was concentrated in vacuo. The residue was dispersed between EtOAc and sodium hydrogen carbonate. The organic layer was separated and was washed with brine, then dried (MgSO$_4$) and concentrated in vacuo to give the product, a mixture of 2 diastereomers, as a gelatinous material. This was purified by medium pressure chromatography on silica using toluene as eluant to afford the products:

dimethyl(2R)-1-{(1S)-4-methyl-1-[4-(trifluoromethyl)phenyl]pentyl}-2-[4-(trifluoromethyl)phenyl]piperidine-4,4-dicarboxylate isomer a (2 g) and dimethyl(2S)-1-{(1S)-4-methyl-1-[4-(trifluoromethyl)phenyl]pentyl}-2-[4-(trifluoromethyl)phenyl]piperidine-4,4-dicarboxylate isomer b (0.7 g).

Signals for isomer a are as follows:

$^1$H NMR (400 MHz, CDCl$_3$): δ 0.60-0.68 (1H, m), 0.82 (6H, dd, J 6.6, 9.6), 0.88-0.98 (1H, m), 1.38-1.42 (1H, m), 1.68-1.80 (2H, m), 1.86-1.96 (2H, m), 2.23-2.45 (3H, m), 2.58-2.62 (1H, m), 3.44-3.48 (1H, m), 3.66 (3H, s), 3.83 (3H, s), 3.91 (1H, dd, J 2.8, 11.3), 7.35 (2H, d, J 8.2), 7.53-7.67 (6H, m). MS (ES$^+$) m/z 574 (100%).

Signals for isomer b are as follows:

$^1$H NMR (400 MHz, CDCl$_3$): δ 0.82-0.86 (6H, m), 0.89-1.01 (1H, m), 1.23-1.31 (1H, m), 1.40-1.50 (1H, m), 1.62-1.70 (1H, m), 1.77 (1H, dd, J 11.4, 13.5), 1.85-1.93 (2H, m), 2.04-2.16 (1H, m), 2.28-2.32 (1H, m), 2.39 (1H, dd, J 2.4, 13.3), 3.11-3.15 (1H, m), 3.28 (1H, dd, J 2.8, 11.3), 3.59 (3H, s), 3.64 (4H, t, J 7.7), 6.98 (2H, d, J 8.1), 7.53 (4H, t, J 6.8), 7.67 (2H, d, J 8.2). MS (ES$^+$) m/z 574 (100%).

Step 4: (2S,4R)-1-{(1S)-4-Methyl-1-[4-(trifluoromethyl)phenyl]pentyl}-2-[4-(trifluoromethyl)phenyl]piperidine-4-carboxylic acid hydrochloride

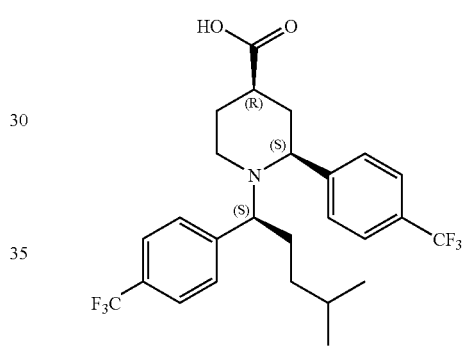

Dimethyl(2S)-1-{(1S)-4-methyl-1-[4-(trifluoromethyl)phenyl]pentyl}-2-[4-(trifluoromethyl)phenyl]piperidine-4,4-dicarboxylate isomer b (0.7 g, 1.29 mmol) was dissolved in DMSO (6 ml) and sodium chloride (226 mg) was added. The mixture was heated at 160° C. for 4 h. The cooled mixture was diluted with brine (100 ml) and extracted with EtOAc. The organic layer was separated and was washed with brine, then dried (MgSO$_4$) and concentrated in vacuo to give the product, a mixture of 2 diastereomers, as an oil. This was purified by medium pressure chromatography on silica using (5% EtOAc in hexane) as eluant to afford the products (450 mg). This mixture was dissolved in MeOH and sodium methoxide (50 mg) was added. This solution was heated under reflux for 2 h, then sodium hydroxide (0.65 ml, 4M) was added and the mixture was stirred for 1 h at 60° C. The cooled mixture was concentrated in vacuo, then neutralized with HCl (1M, 3 ml) and extracted with DCM. The organic layer was separated and was washed with brine, then dried (MgSO$_4$) and concentrated in vacuo to give the product.

$^1$H NMR (400 MHz, CD$_3$OD): δ 0.81-0.83 (7H, m), 1.05-1.18 (1H, m), 1.38-1.48 (1H, m), 1.79-1.91 (2H, m), 2.00-2.12 (4H, m), 2.14-2.20 (1H, m), 2.36-2.43 (1H, m), 3.50-3.67 (1H, m), 3.91-3.99 (1H, m), 7.26 (2H, d, J 7.8), 7.69 (4H, d, J 7.6), 7.81 (2H, d, J 8.1). MS (ES$^+$) m/z 502 (100%).

Step 5: 2-Diazo-1-{(2S,4R)-1-{(1S)-4-methyl-1-[4-trifluoromethyl)phenyl]pentyl}-2-[4-(trifluoromethyl)phenyl]piperidin-4-yl}ethanone

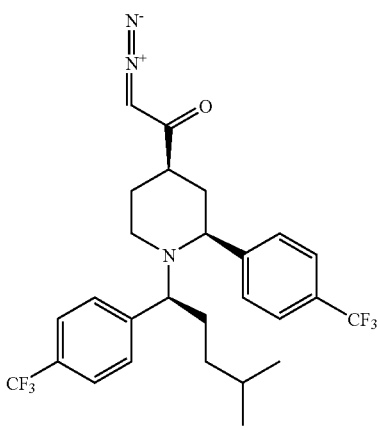

The acid (400 mg, 0.79 mmol) was dissolved in DCM (3 ml) and oxalyl chloride (2 ml) 2M in DCM) was added followed by 1 drop of DMF. The solution was stirred for 30 min. The resulting mixture was concentrated in vacuo and reconstituted in acetonitrile (5 ml, anhydrous) and THF (5 ml, anhydrous). The solution was cooled to 0° C. TMS diazomethane (1.2 ml, 2M in hexane) was added and the mixture was stirred overnight. The mixture was concentrated in vacuo and the residue was purified on silica using 25% ethyl acetate in hexane as eluant to give the product as a pale yellow solid (200 mg). $^1$H NMR (500 MHz, CDCl$_3$): δ 0.83-0.87 (6H, m), 0.91-0.98 (1H, m), 1.24-1.29 (1H, m), 1.42 (1H, qn, J 6.6), 1.61-1.81 (4H, m), 1.86-1.94 (3H, m), 2.08-2.18 (1H, m), 3.11 (1H, dd, J 2.9, 11.0), 3.24-3.28 (1H, m), 3.66 (1H, t, J 7.7), 5.16 (1H, s), 7.03 (2H, d, J 8.0), 7.50-7.56 (4H, m), 7.67 (2H, d, J 8.2). MS (ES$^+$) m/z 526 (100%).

Step 6: {(2S,4R)-1-{(1S)-4-methyl-1-[4-(trifluoromethyl)phenyl]pentyl}-2-[4-(trifluoromethyl)phenyl]piperidin-4-yl}acetic acid

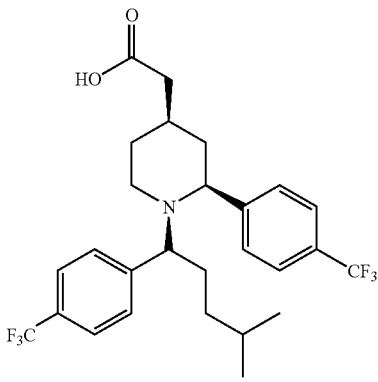

The diazoketone described in Step 5 above (200 mg, 0.38 mmol) was dissolved in dioxane-water (15 ml, 5:1) and silver benzoate (20 mg) was added. The mixture was sonicated for 1 h in the dark. The mixture was acidified with HCl (2N) and the mixture was extracted with ethyl acetate. The organic layer was separated and was washed with brine, then dried (MgSO$_4$) and concentrated in vacuo to give the product. This was purified by chromatography on silica using 1-3% MeOH in DCM as eluant to afford the product as a white solid. $^1$H NMR (500 MHz, CD$_3$OD): δ 0.78-0.87 (6H, m), 0.91-0.99 (1H, m), 1.16-1.28 (2H, m), 1.31-1.46 (2H, m), 1.60-1.65 (1H, m), 1.73 (1H, dd, J 2.7, 13.0), 1.78-1.85 (2H, m), 1.92-2.00 (2H, m), 2.09-2.19 (2H, m), 3.17 (1H, dd, J 2.5, 10.9), 3.26-3.29 (1H, m), 3.67 (1H, t, J 7.6), 7.16 (2H, d, J 8.0), 7.61 (4H, d, 18.0), 7.71 (2H, d, J 8.2). MS (ES$^+$) m/z 516 (100%).

Example 110

(E/Z)-{(2S)-1-{(1R)-4-Methyl-1-[4-(trifluoromethyl)phenyl]pentyl}-2-[4-(trifluoromethyl)phenyl]piperidin-4-ylidene}ethanoic acid

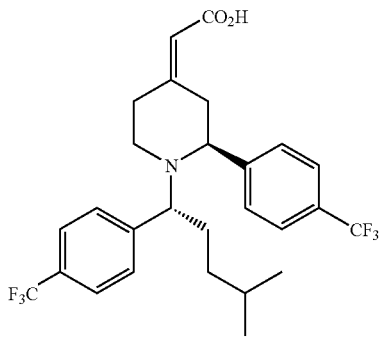

Step 1: (1R)-{4-methyl-1-[4-(trifluoromethyl)phenyl]pentyl}-2-[4-(trifluorophenyl)piperidin-4-one

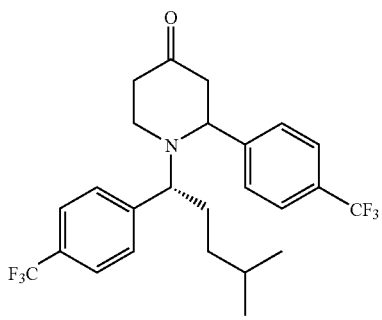

The intermediate was prepared analogously to Example 72 steps 3 and 4 and substituting (1R)-4-methyl-1-[4-(trifluoromethyl)phenyl]pentan-1-amine (T1657PV, Intermediate 8, α$_D$ [c=1, CHCl$_3$]+9°). The reaction gave an approximately 1:1 ratio of diastereoisomers which were separated by column chromatography on silica eluting with 10-25% Et$_2$O/isoHexane followed by 5% Et$_2$O/cHexane. The higher diastereoisomer: $^1$H NMR (400 MHz, CDCl$_3$): δ 7.69 (2H, t, J 10.3), 7.60-7.52 (4H, m), 7.07 (2H, d, J 8.0), 3.75 (1H, t, J 7.6), 3.57 (1H, dd, J 5.0, 9.2), 3.47-3.43 (1H, m), 2.74-2.66 (1H, m), 2.50-2.40 (3H, m), 2.35-2.29 (1H, m), 2.04-1.92 (1H, m), 1.84-1.72 (1H, m), 1.51-1.43 (1H, m), 1.34-1.22 (1H, m), 1.03-0.93 (1H, m), 0.87-0.83 (6H, m).

Lower diastereoisomer: $^1$H NMR (400 MHz, CDCl$_3$): δ 7.68 (2H, d, J 8.2), 7.59 (4H, t, J 8.8), 7.44 (2H, d, J 8.2), 4.10 (1H, dd, J 4.5, 9.0), 3.64 (1H, t, J 6.9), 2.99-2.93 (1H, m), 2.82-2.76 (1H, m), 2.70-2.56 (2H, m), 2.45-2.33 (2H, m), 1.86-1.74 (2H, m), 1.51-1.37 (1H, m), 0.99-0.89 (1H, m), 0.83 (6H, dd, J 4.6, 6.6), 0.75-0.67 (1H, m).

Step 2: (E/Z)-{(2S)-1-{(1R)-4-Methyl-1-[4-(trifluoromethyl)phenyl]pentyl}-2-[4-(trifluoromethyl)phenyl]piperidin-4-ylidene}ethanoic acid

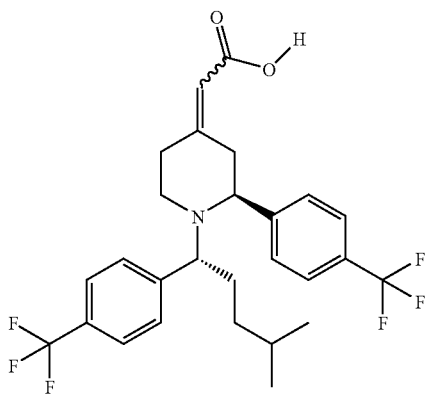

The lower running diastereoisomer from step 1 was subjected to homologation analogous to Example 99 step 4 and hydrolysis analogous to Example 3 step 5 to give an off white solid. M/Z (ES$^+$) 514 (MH$^+$).

Example 111

{(2R,4R)-1-{(1R)-4-methyl-1-[4-(trifluoromethyl)phenyl]pentyl}-2-[4-(trifluoromethyl)phenyl]piperidin-4-yl}acetic acid

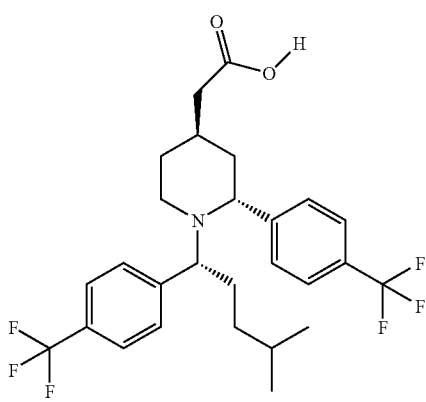

Step 1: Ethyl(2E/Z)-{(2R)-1-{(1R)-4-methyl-1-[4-(trifluoromethyl)phenyl]pentyl}-2-[4-(trifluoromethyl)phenyl]piperidin-4-ylidene}ethanoate

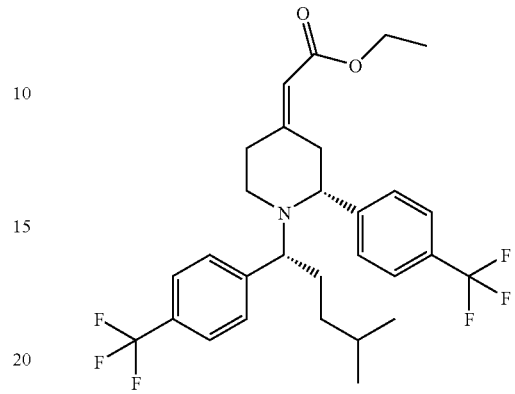

The higher diastereoisomer from Example 110 step 1 was homologated similarly to Example 99 step 4 to give the title compound as a white foam, 1:1 mixture of geometric isomers, after chromatography on silica eluting with 2% EtOAc/iso-Hexane. $^1$H NMR δ (ppm) (CDCl$_3$): 7.70-7.62 (4H, m), 7.55 (8H, t, J 8.9), 7.00 (4H, t, J 9.2), 5.57 (1H, s), 5.49 (1H, s), 4.16-4.02 (4H, m), 3.78 (2H, t, J 12.1), 3.72-3.64 (2H, m), 3.31 (2H, dd, J 3.3, 6.8), 3.24-3.16 (2H, m), 2.50 (1H, d, J 12.4), 2.38-2.28 (3H, m), 2.22-2.08 (2H, m), 2.02-1.92 (3H, m), 1.74 (2H, t, J 12.7), 1.55 (5H, s), 1.51-1.43 (3H, m), 1.31-1.17 (8H, m), 1.00-0.94 (2H, m), 0.87-0.81 (1H, m).

Step 2: {(2R,4R)-1-{(1R)-4-methyl-1-[4-(trifluoromethyl)phenyl]pentyl}-2-[4-(trifluoromethyl)phenyl]piperidin-4-yl}acetic acid

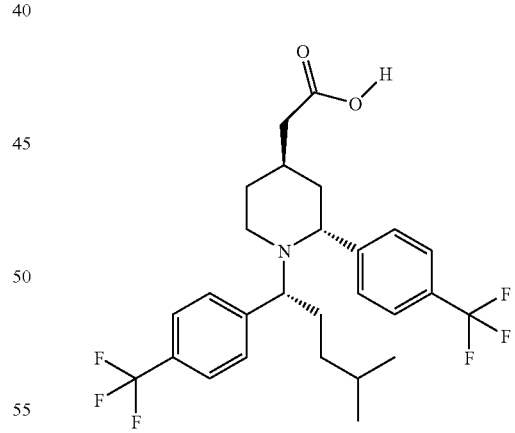

The title compound was prepared by hydrogenation of the alkene from step 1 using the procedure described in Example 105 step 2. Purification of the crude mixture by chromatography on silica eluting with 5% EtOAc/isoHexane gave a lower trans diastereoisomer. $^1$H NMR δ (ppm) (CDCl$_3$): 7.64 (2H, d, J 8.1), 7.53 (4H, dd, J 8.0, 15.9), 7.07 (2H, d, J 8.0), 4.15-4.05 (2H, m), 3.66 (1H, t, J 7.6), 3.38 (1H, dd, J 3.1, 10.5), 2.94-2.88 (1H, m), 2.28 (1H, s), 2.21-2.13 (3H, m), 2.04 (1H, s), 1.93-1.61 (5H, m), 1.48-1.38 (1H, m), 1.27-1.19 (5H, m), 0.92-0.82 (7H, m). The ester was hydrolysed using the procedure described in Example 3 step 5 to give the desired compound as a white solid. M/Z (ES+) 516 (MH+).

Example 112

{(2R,4S)-1-{((R)-4-methyl-1-[4-(trifluoromethyl)phenyl]pentyl}-2-[4-(trifluoromethyl)phenyl]piperidin-4-yl}acetic acid

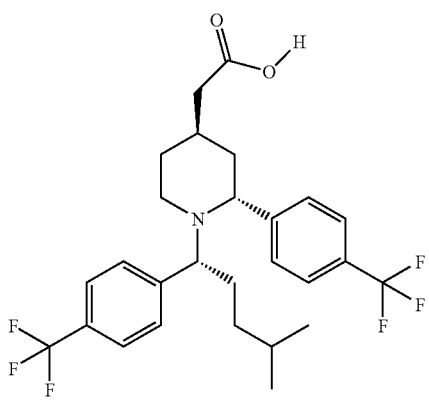

The higher running cis diastereoisomer from Example 111 step 2, ¹H NMR δ (ppm) (CDCl₃): 7.65 (2H, d, J 8.3), 7.58-7.50 (4H, m), 7.02 (2H, t, J 6.8), 4.11-4.01 (2H, m), 3.65 (1H, t, J 7.7), 3.18-3.10 (2H, m), 2.20-2.04 (2H, m), 1.98-1.84 (2H, m), 1.74 (4H, dd, J 15.1, 28.7), 1.43-1.13 (8H, m), 0.96-0.82 (6H, m), was hydrolysed using the using the procedure described in Example 3 step 5 to give the desired compound as a white solid. M/Z (ES+) 516 (MH+).

Example 113

{(2S,4S)-1-{(1R)-4-Methyl-1-[4-(trifluoromethyl)phenyl]pentyl}-2-[4-(trifluoromethyl)phenyl]piperidin-4-yl}acetic acid Hydrochloride

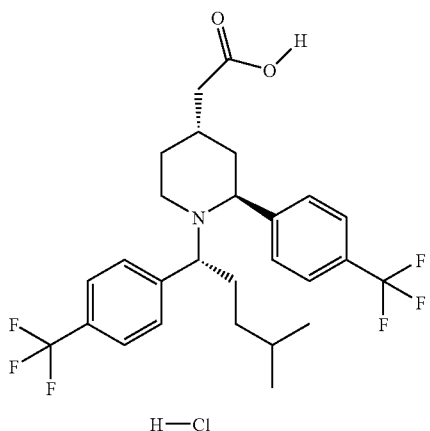

The lower diastereoisomer from Example 110 step 1 was homologated using the procedure described in Example 99 step 4 and hydrogenated using the procedure described in Example 105 step 2 which resulted in the formation of two diastereoisomers which were separated by chromatography on silica eluting with 2% THF/isoHexane Mixed fractions were recolumned eluting with 0-1-2% THF/isoHexane. The lower diastereoisomer [¹H NMR δ (ppm) (CDCl₃): 7.61-7.53 (6H, m), 7.38 (2H, dd, J 0.0, 8.1), 4.17-4.07 (2H, m), 3.85 (1H, dd, J 3.8, 7.9), 3.67 (1H, t, J 5.1), 2.76 (1H, t, J 9.3), 2.59-2.53 (1H, m), 2.42 (2H, d, J 7.6), 2.27-2.17 (2H, m), 1.99-1.91 (1H, m), 1.89-1.67 (3H, m), 1.43 (4H, d, J 5.3), 1.27-1.19 (4H, m), 0.87-0.77 (6H, m)] was hydrolysed using the procedure described in Example 3 step 5 to provide a white solid hydrochloride salt. M/Z (ES+) 516 (MH+).

Example 114

{(2S,4R)-1-{(1R)-4-methyl-1-[4-(trifluoromethyl)phenyl]pentyl}-2-[4-(trifluoromethyl)phenyl]piperidin-4-yl}acetic acid

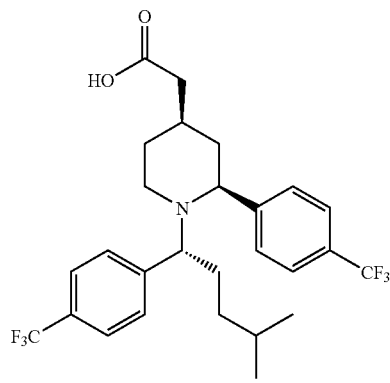

Step 1: (±)-Methyl{(2S,4R)-2-[4-(trifluoromethyl)phenyl]piperidin-4-yl}acetate

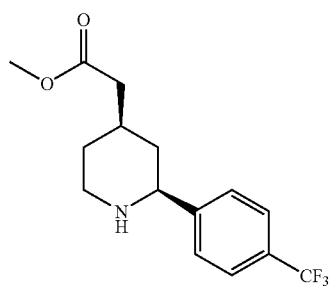

(±)-cis Methyl 4-(trifluoromethyl)phenylpiperidin-4-yl)acetate (Example 3, Step 3 [free base], 32.6 g, 0.108 mol), was dissolved in hot isopropanol (100 ml) and the solution was added to a solution of L-(+)-mandelic acid (9 g, 0.054 mol) in hot isopropanol (170 ml) and the resulting solution was allowed to stand at room temperature overnight. A white crystalline solid was deposited (17.55 g, 36%) and was filtered. The mother liquors were evaporated and the residue was neutralized with sodium carbonate (2M, 100 ml) and extracted with dichloromethane (3×100 ml). The combined extracts were washed with brine, dried (MgSO₄), filtered and evaporated. This extract was dissolved in hot isopropanol (100 ml) and was added to a solution of D-(−)-mandelic acid (9 g, 0.054 mol) in hot isopropanol (170 ml); immediate crystallization occurred and the mixture was allowed to stand for 2 h. The white crystalline solid was isolated by filtration (21 g, 44%) and was recrystallised from isopropyl acetate (250 ml) to give the product (19.8 g, 40%) as a white crystalline material, ee>99.5%. This material was neutralized with sodium carbonate (2M, 100 ml and extracted with dichloromethane (3×100 ml). The combined extracts were washed with brine, dried (MgSO$_4$), filtered and evaporated to give the free base: α$_D$ (c=1, MeOH)+23°; 1H NMR (360 MHz, CDCl$_3$) δ: 1.23 (6H, d, J 6.9), 2.88 (1H, qn, J 6.9), 4.27 (2H, s), 7.15-7.21 (4H, m), 7.71 (2H, d, J 8.2), 8.10 (2H, d, J 8.2).

Step 2: Methyl{(2S,4R)-1-{((R)-4-methyl-1-[4-(trifluoromethyl)phenyl]pentyl}-2-[4-(trifluoromethyl)phenyl]piperidin-4-yl}acetate

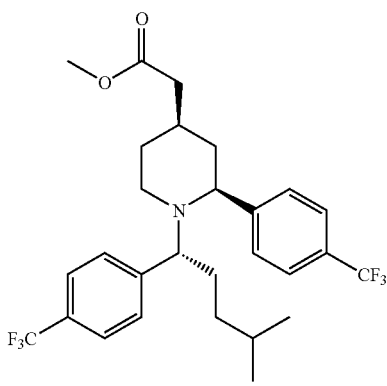

A mixture of (+)-methyl{(2S,4R)-2-[4-(trifluoromethyl)phenyl]piperidin-4-yl}acetate (Step 1, 19.4 g, 64 mmol), 4-(trifluoromethyl)benzaldehyde (11.5 g, 66 mmol) and benzotriazole (7.9 g, 66 mmol) in toluene (320 ml) was stirred and heated at reflux under N$_2$ with a Dean-Stark trap for 18 hrs. After cooling to RT the solvent was removed in vacuo to give a thick oil which was used without further purification. 1-Bomo-3-methylbutane (23 ml, 192 mmol) was added to stirred suspension of activated magnesium (4.7 g, 193 mmol) in dry Et$_2$O (200 ml) under N$_2$ at such a rate as to keep the internal temperature at ~30° C. After 90 mins at RT the reaction was cooled in an ice bath and a solution of zinc chloride in diethyl ether (1.0M, 200 ml) was added such that the internal temperature was <10° C. The cooling bath was removed and the reaction was stirred at RT for 1 hr, then recooled in an ice bath. A solution of the benzotriazole adduct (from above, ~64 mmol) in dry DCM (600 ml) was added via cannula such that the internal temperature <10° C. After 45 min at this temperature, the cooling bath was removed and the mixture was stirred at RT for 18 hrs. The reaction was cooled in an ice bath and quenched with saturated aqueous NH$_4$Cl (400 ml). The mixture was diluted with DCM and H$_2$O, then filtered through Hyflo®. The layers were separated and the aqueous layer was extracted with DCM (×3). The combined extracts were dried (Na$_2$SO$_4$), filtered and evaporated. The residue was purified by chromatography (silica, 3-6% Et$_2$O/isohexane) to give the piperidine (21.5 g, colourless oil, contained ~6% by wt aldehyde). M/Z (ES$^+$) 530 (MH$^+$).

Step 3: {(2S,4R)-1-{(1R)-4-Methyl-1-[4-(trifluoromethyl)phenyl]pentyl}-2-[4-(trifluoromethyl)phenyl]piperidin-4-yl}acetic acid

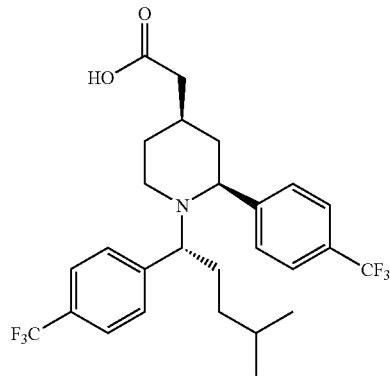

4N aqueous sodium hydroxide (12.6 ml) was added to a stirred solution of methyl {(2S,4R)-1-{(1R)-4-methyl-1-[4-(trifluoromethyl)phenyl]pentyl}-2-[4-(trifluoromethyl)phenyl]piperidin-4-yl}acetate (13.3 g, 25.1 mmol) in MeOH (100 ml) at RT under N2. The mixture was stirred and heated at reflux for 3 hrs. After cooling to RT the MeOH was removed in vacuo. The residue was partitioned between DCM/H$_2$O. The pH of the aqueous layer was adjusted to ~pH7. The aqueous layer was extracted with DCM (×4). The combined extracts were dried (Na$_2$SO$_4$), filtered and evaporated to give the acid (12.3 g) as a colourless foam.

A solution of the acid (12.3 g, 23.9 mmol) in EtOH (140 ml) was added to a stirred solution of maleic acid (2.8 g, 24.1 mmol) in EtOH (100 ml) at reflux. The mixture was stirred at reflux for 30 min, then allowed to cool to RT and stand at this temperature O/N. The solid was isolated by filtration to give the salt (12.7 g) as a colourless solid. This material was recrystallised from EtOH (~40 ml/g), then partitioned between DCM/Na$_2$CO$_3$ (aq) to liberate the free base. M/Z (ES$^+$) 516 (MH$^+$); α$_D$ (c=1, MeOH)+44°.

Example 115

{(2R,4S)-1-{(1S)-4-methyl-1-[4-(trifluoromethyl)phenyl]pentyl}-2-[4-(trifluoromethyl)phenyl]piperidin-4-yl}acetic acid

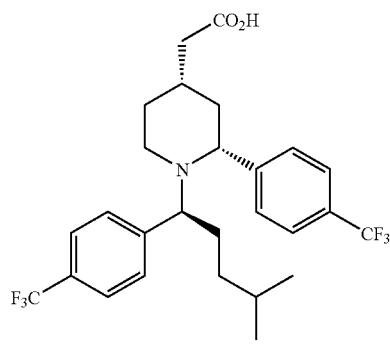

Dimethyl(2R)-1-{(1S)-4-methyl-1-[4-(trifluoromethyl)phenyl]pentyl}-2-[4-(trifluoromethyl)phenyl]piperidine-4,4-dicarboxylate, isomer a from Example 109 Step 3 above, was reacted according to the procedures described in Example 109 Step 4-6 to afford the title compound. $^1$H NMR (500 MHz, CD$_3$OD): δ 0.57-0.64 (1H, m), 0.78-0.85 (6H, m), 0.87-0.97 (1H, m), 1.11-1.19 (1H, m), 1.38-1.48 (2H, m), 1.68-1.74 (1H, m), 1.84-2.00 (4H, m), 2.14-2.22 (2H, m), 2.45-2.51 (1H, m), 2.72-2.79 (1H, m), 3.47-3.55 (1H, m), 3.86 (1H, dd, J 2.3, 10.9), 7.48 (2H, d, J 8.1), 7.60 (2H, d, J 8.1), 7.66-7.72 (4H, m). MS (ES$^+$) m/z 516 (100%). [α$_D$]=−43° C.=1 MeOH.

Example 116

(±)-{(2R*,4S*)-1-[(1R*)-4-Methyl-1-phenylpent-4-en-2-yn-1-yl]-2-[4-(trifluoromethyl)phenyl]piperidin-4-yl}acetic acid

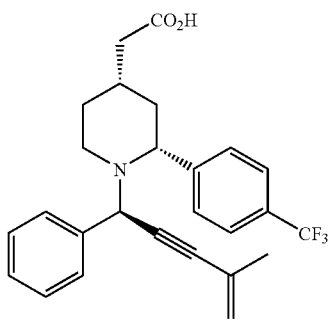

(±)-Methyl{(2R*,4S*)-2-[4-(trifluoromethyl)phenyl]piperidin-4-yl}acetate (Example 3 Step 3, 150 mg, 0.5 mmol), benzaldehyde (159 mg, 1.5 mmol), gold (III) bromide (22 mg, 0.05 mmol) and water (0.5 ml) were combined in a sealed microwave tube. The mixture was de-gassed and placed under an N$_2$-atmosphere before 2-methyl-1-buten-3-yne (99 mg, 1.5 mmol) was added via syringe, followed by heating to 70° C. using microwave irradiation for 20 min. The reaction mixture was diluted with MeOH and loaded onto a SCX cartridge, which was washed with MeOH, then eluted with 2M ammonia in MeOH. The eluant was treated with 6M aq. NaOH (0.25 ml) and heated to reflux for 2 h. The volatiles were removed under vacuum and the residue partitioned between 2M HCl and DCM. The DCM layer was evaporated and the residue purified by preparative reverse phase HPLC to give 21 mg of the title compound as the TFA salt.

| Column | Column Dimensions | Percentage Modifier | Solvent | Mobile Phase | Flow | Detection |
|---|---|---|---|---|---|---|
| Gemini | (100×20) mm | 60-5% | acetonitrile | water | 50 ml/min | MS (ES+) |

Examples 117-148

Examples 117-148 were made by the procedure described in Example 116 using the compound of Example 3, Step 3 (for examples 117-143) or Example 114, Step 1 (for examples 144-8) and the appropriate aldehyde and alkyne as starting materials.

| Example | Structure | Name | ES$^+$m/z [MH]$^+$ |
|---|---|---|---|
| 117 | 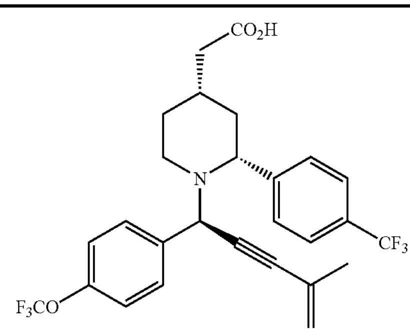 | (±)-(2R*,4S*)-1-[(1R*)-1-(4-(trifluoromethoxy)phenyl)-4-methylpent-4-en-2-yn-1-yl]-2-[4-(trifluoromethyl)phenyl]piperidine-4-yl} acetic acid | 526 |
| 118 | 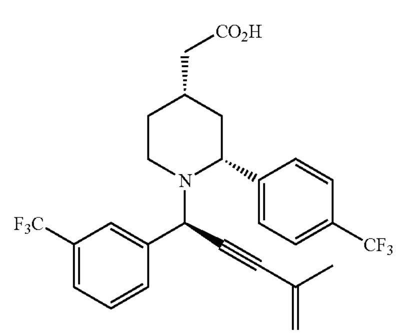 | (±)-{(2R*,4S*)-1-[(1R*)-1-(3-(trifluoromethyl)phenyl)-4-methylpent-4-en-2-yn-1-yl]-2-[4-(trifluoromethyl)phenyl]piperidine-4-yl} acetic acid | 510 |

-continued

| Example | Structure | Name | ES+m/z [MH]+ |
|---|---|---|---|
| 119 | 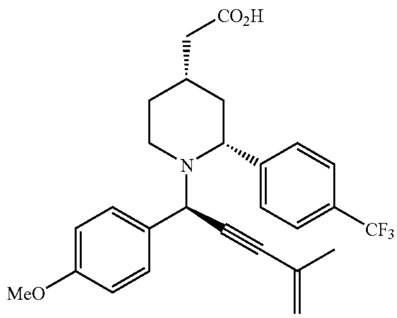 | (±)-{(2R*,4S*)-1-[(1R*)-1-(4-(methoxyphenyl)-4-methylpent-4-en-2-yn-1-yl]-2-[4-(trifluoromethyl)phenyl]piperidine-4-yl} acetic acid | 472 |
| 120 | 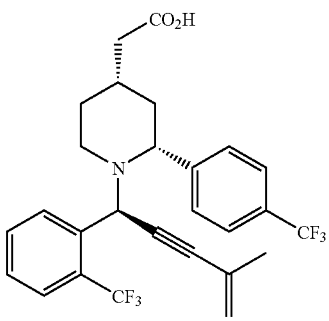 | (±)-{(2R*,4S*)-1-[(1R*)-1-(2-(trifluoromethyl)phenyl)-4-methylpent-4-en-2-yn-1-yl]-2-[4-(trifluoromethyl)phenyl]piperidine-4-yl} acetic acid | 510 |
| 121 | 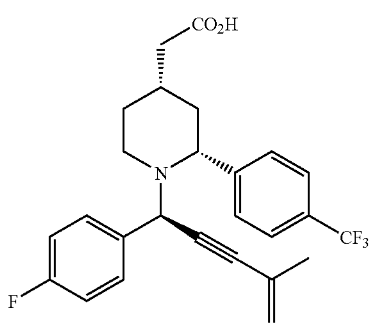 | (±)-{(2R*,4S*)-1-[(1R*)-1-(4-(fluorophenyl)-4-methylpent-4-en-2-yn-1-yl]-2-[4-(trifluoromethyl)phenyl]piperidine-4-yl} acetic acid | 460 |
| 122 | 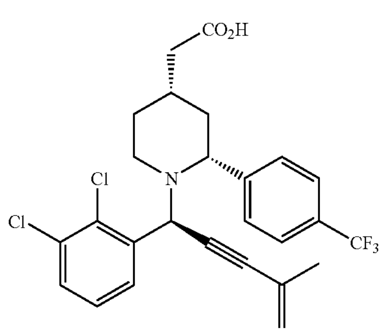 | (±)-{(2R*,4S*)-1-[(1R*)-1-(2,3-dichlorophenyl)-4-methylpent-4-en-2-yn-1-yl]-2-[4-(trifluoromethyl)phenyl]piperidine-4-yl} acetic acid | 511 |

-continued

| Example | Structure | Name | ES⁺m/z [MH]⁺ |
|---|---|---|---|
| 123 | 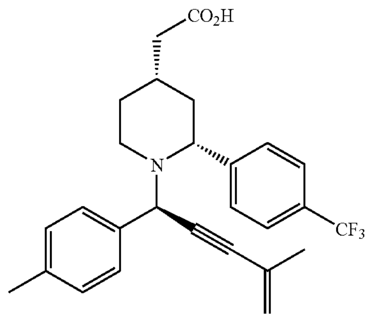 | (±)-{(2R*,4S*)-1-[(1R*)-1-(4-tolyl)-4-methylpent-4-en-2-yn-1-yl]-2-[4-(trifluoromethyl)phenyl]piperidine-4-yl} acetic acid | 456 |
| 124 | 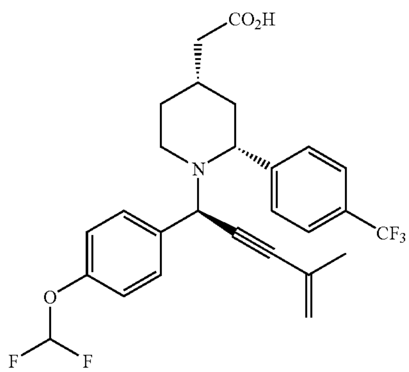 | (±)-{(2R*,4S*)-1-{(1R*)-1-[4-(difluoromethoxy)phenyl]-4-methylpent-4-en-2-yn-1-yl}-2-[4-(trifluoromethyl)phenyl]piperidine-4-yl} acetic acid | 508 |
| 125 | 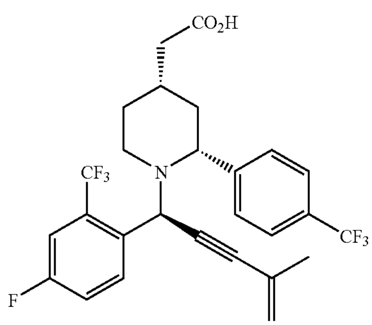 | (±)-{(2R*,4S*)-1-{(1R*)-1-[4-fluoro-2-(trifluoromethyl)phenyl]-4-methylpent-4-en-2-yn-1-yl}-2-[4-(trifluoromethyl)phenyl]piperidine-4-yl} acetic acid | 528 |
| 126 | 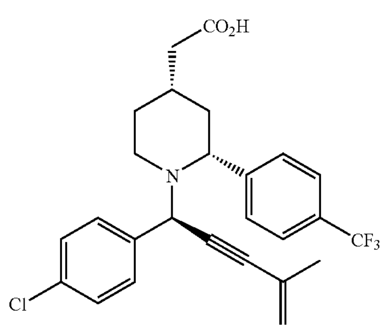 | (±)-{(2R*,4S*)-1-[(1R*)-1-(4-chlorophenyl)-4-methylpent-4-en-2-yn-1-yl]-2-[4-(trifluoromethyl)phenyl]piperidine-4-yl} acetic acid | 476 |

-continued

| Example | Structure | Name | ES+m/z [MH]+ |
|---|---|---|---|
| 127 | 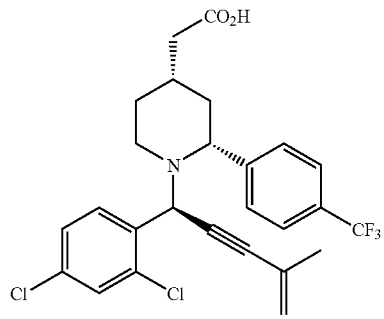 | (±)-{(2R*,4S*)-1-[(1R*)-1-(2-chlorophenyl)-4-methylpent-4-en-2-yn-1-yl]-2-[4-(trifluoromethyl)phenyl]piperidine-4-yl} acetic acid | 477 |
| 128 | 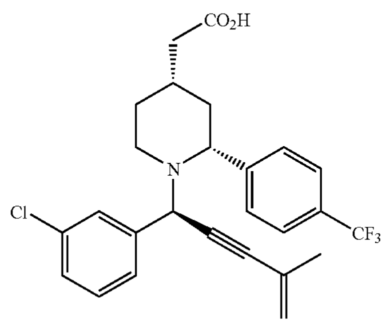 | (±)-{(2R*,4S*)-1-[(1R*)-1-(3-chlorophenyl)-4-methylpent-4-en-2-yn-1-yl]-2-[4-(trifluoromethyl)phenyl]piperidine-4-yl} acetic acid | 477 |
| 129 | 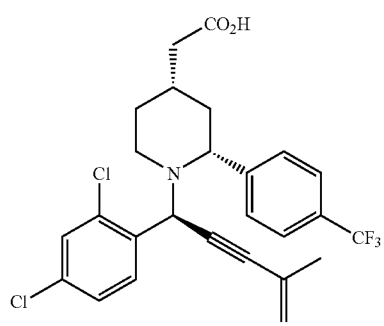 | (±)-{(2R*,4S*)-1-[(1R*)-1-(2,4-dichlorophenyl)-4-methylpent-4-en-2-yn-1-yl]-2-[4-(trifluoromethyl)phenyl]piperidine-4-yl} acetic acid | 511 |
| 130 | 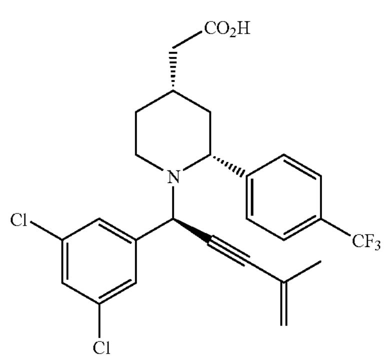 | (±)-{(2R*,4S*)-1-[(1R*)-1-(3,5-dichlorophenyl)-4-methylpent-4-en-2-yn-1-yl]-2-[4-(trifluoromethyl)phenyl]piperidine-4-yl} acetic acid | 511 |

-continued

| Example | Structure | Name | ES+m/z [MH]+ |
|---|---|---|---|
| 131 | 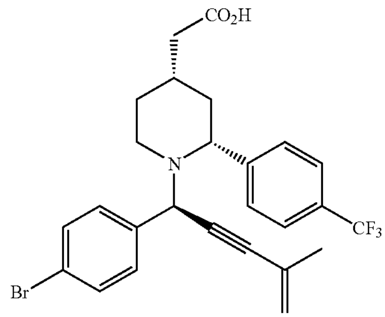 | (±)-{(2R*,4S*)-1-[(1R*)-1-(4-bromophenyl)-4-methylpent-4-en-2-yn-1-yl]-2-[4-(trifluoromethyl)phenyl]piperidine-4-yl} acetic acid | 521 |
| 132 | 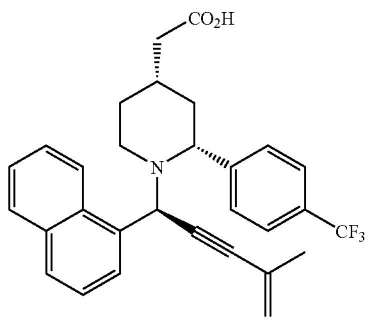 | (±)-{(2R*,4S*)-1-[(1R*)-4-methyl-1-(1-naphthyl)-pent-4-en-2-yn-1-yl]-2-[4-(trifluoromethyl)phenyl]piperidine-4-yl} acetic acid | 492 |
| 133 | 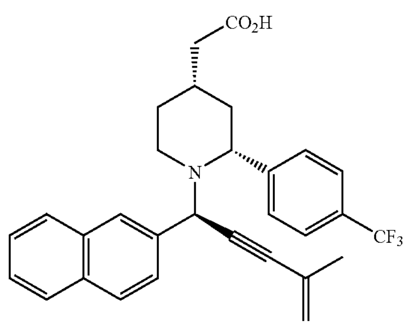 | (±)-{(2R*,4S*)-1-[(1R*)-4-methyl-1-(2-naphthyl)-pent-4-en-2-yn-1-yl]-2-[4-(trifluoromethyl)phenyl]piperidine-4-yl} acetic acid | 492 |
| 134 | 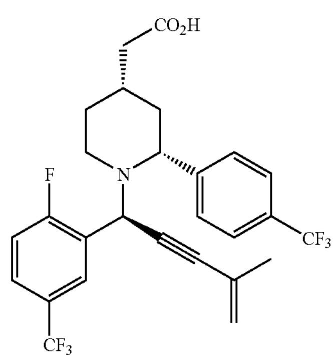 | (±)-{(2R*,4S*)-1-{(1R*)-1-[2-fluoro-5-trifluoromethyl)phenyl]-4-methylpent-4-en-2-yn-1-yl}-2-[4-(trifluoromethyl)phenyl]piperidine-4-yl} acetic acid | 528 |

-continued

| Example | Structure | Name | ES+m/z [MH]+ |
|---|---|---|---|
| 135 | 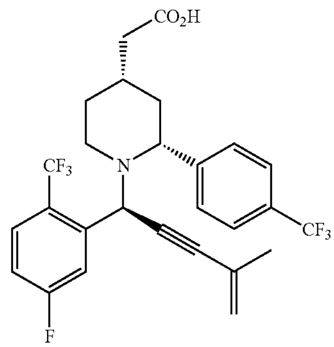 | (±)-{(2R*,4S*)-1-{(1R*)-1-[5-fluoro-2-(trifluoromethyl)phenyl]-4-methylpent-4-en-2-yn-1-yl}-2-[4-(trifluoromethyl)phenyl]piperidine-4-yl} acetic acid | 528 |
| 136 | 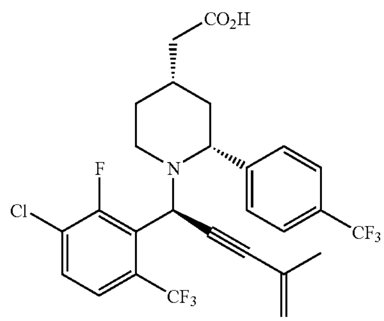 | (±)-{(2R*,4S*)-1-{(1R*)-1-[3-chloro-2-fluoro-6-(trifluoromethyl)phenyl]-4-methylpent-4-en-2-yn-1-yl}-2-[4-(trifluoromethyl)phenyl]piperidine-4-yl} acetic acid | 563 |
| 137 | 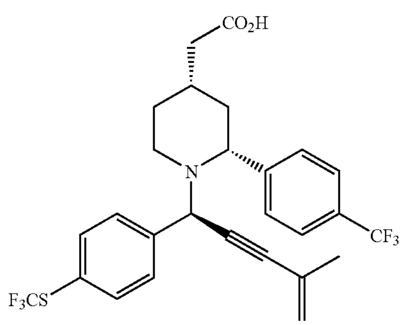 | (±)-{(2R*,4S*)-1-{(1R*)-1-[4-(trifluoromethyl)thio)phenyl]-4-methylpent-4-en-2-yn-1-yl}-2-[4-(trifluoromethyl)phenyl]piperidine-4-yl} acetic acid | 542 |
| 138 | 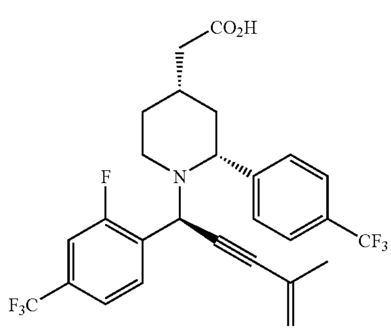 | (±)-{(2R*,4S*)-1-{(1R*)-1-[2-fluoro-4-(trifluoromethyl)phenyl]-4-methylpent-4-en-2-yn-1-yl}-2-[4-(trifluoromethyl)phenyl]piperidine-4-yl} acetic acid | 528 |

-continued

| Example | Structure | Name | ES+m/z [MH]+ |
|---|---|---|---|
| 139 | 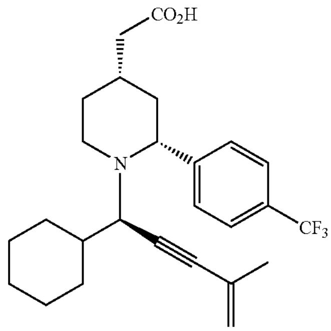 | (±)-{(2R*,4S*)-1-{(1R*)-1-[2-cyclohexyl]-4-methylpent-4-en-2-yn-1-yl}-2-[4-(trifluoromethyl)phenyl] piperidine-4-yl} acetic acid | 448 |
| 140 | 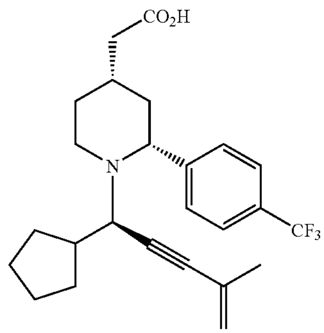 | (±)-{(2R*,4S*)-1-{(1R*)-1-[2-cyclopentyl]-4-methylpent-4-en-2-yn-1-yl}-2-[4-(trifluoromethyl)phenyl] piperidine-4-yl} acetic acid | 434 |
| 141 | 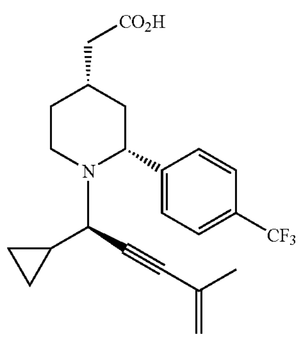 | (±)-{(2R*,4S*)-1-{(1R*)-1-[2-cyclopropyl]-4-methylpent-4-en-2-yn-1-yl}-2-[4-(trifluoromethyl)phenyl] piperidine-4-yl} acetic acid | 406 |
| 142 | 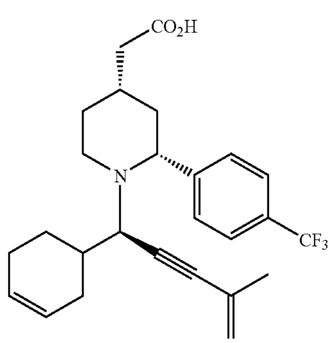 | (±)-{(2R*,4S*)-1-{(1R*)-1-[2-cyclohexen-4-yl]-4-methylpent-4-en-2-yn-1-yl}-2-[4-(trifluoromethyl)phenyl] piperidine-4-yl} acetic acid | 446 |

-continued

| Example | Structure | Name | ES+m/z [MH]+ |
|---|---|---|---|
| 143 | 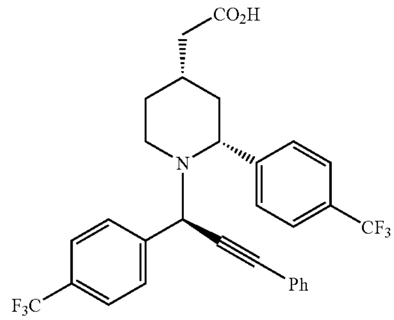 | (±)-{(2R*,4S*)-1-{(1R*)-3-phenyl-1-(4-(trifluoromethyl)phenyl)prop-2-yn-1-yl}-2-[4-(trifluoromethyl)phenyl]piperidine-4-yl} acetic acid | 546 |
| 144 | 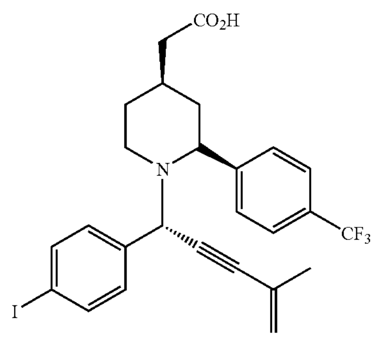 | {(2S,4R)-1-[(1S)-1-(4-iodophenyl)-4-methylpent-4-en-2-yn-1-yl]-2-[4-(trifluoromethyl)phenyl]piperidine-4-yl} acetic acid | 568 |
| 145 | 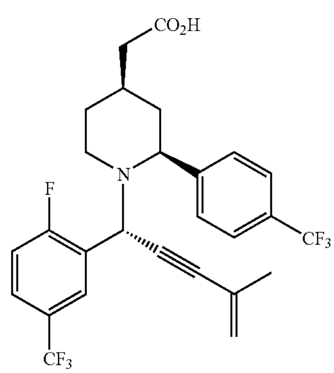 | {(2S,4R)-1-{(1S)-1-[2-fluoro-5-(trifluoromethyl) phenyl]-4-methylpent-4-en-2-yn-1-yl}-2-[4-(trifluoromethyl)phenyl]piperidine-4-yl} acetic acid | 528 |
| 146 | 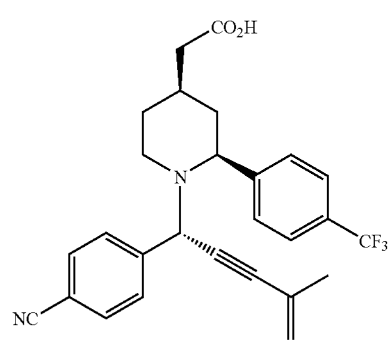 | {(2S,4R)-1-{(1S)-1-[4-cyano phenyl]-4-methylpent-4-en-2-yn-1-yl}-2-[4-(trifluoromethyl)phenyl]piperidine-4-yl} acetic acid | 467 |

| Example | Structure | Name | ES+m/z [MH]+ |
|---|---|---|---|
| 147 | 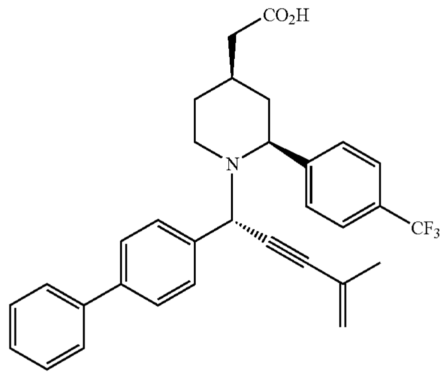 | {(2S,4R)-1-[(1S)-1-(biphenyl-4-yl)-4-methylpent-4-en-2-yn-1-yl]-2-[4-(trifluoromethyl)phenyl]piperidine-4-yl} acetic acid | 518 |
| 148 | 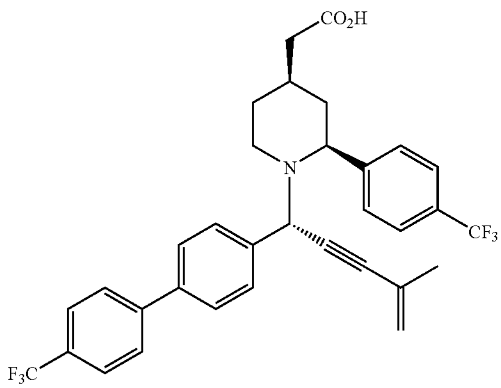 | {(2S,4R)-1-{[(1S)-4-methyl-(4'-(trifluoromethyl)biphen-4-yl)pent-4-en-2-yn-1-yl]-2-(4-(trifluoromethyl)phenyl)piperidine-4-yl} acetic acid | 586 |

Example 149

{(2S,4R)-1-{(1S)-4-Methyl-1-[4-(pentafluoroethyl)phenyl]pent-4-en-2-yn-1-yl}-2-[4-(trifluoromethyl)phenyl]piperidin-4-yl}acetic acid Step 1: 4-(Pentafluoroethyl)benzonitrile

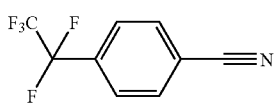

4-Bromobenzonitrile (10 g, 54.9 mmol), sodium pentafluoropropionate (26.5 g, 0.143 mol) and copper (I) iodide (27.1 g, 0.142 mol) were heated to 150° C. in dry DMF (130 ml) for 4 h. The reaction mixture was diluted with water and Et$_2$O and kieselgur filter aid was added. This bi-phasic mixture was stirred for 5 min, filtered and separated. The aqueous phase was extracted with Et$_2$O. The combined organic phases were washed with water and aq. NH$_3$, then dried over MgSO$_4$, filtered and concentrated under reduced pressure to give the crude product as a brown oil. This was purified by flash chromatography (silica gel, 20-30% DCM in iso-hexanes) to give the title compound, 7.5 g (62%). $^1$H NMR (500 MHz, CDCl$_3$): δ 7.75 (2H, d, J 8.3), 7.83 (2H, d, J 8.6), $^{19}$F NMR (470 MHz, CDCl$_3$): δ −84.5, −116.

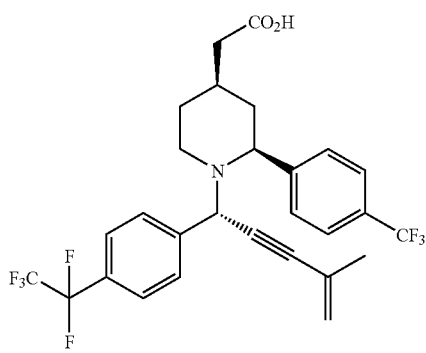

Step 2: 4-(Pentafluoroethyl)benzaldehyde

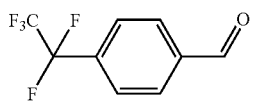

DIBAL (1M in toluene, 9 ml, 9 mmol) was added to a solution of the product from Step 1 in toluene at −30° C. After 20 min at −30° C. the reaction was quenched by the addition of satd. aq. KHSO$_4$. Standard aqueous work-up afforded the crude product, which was purified by flash chromatography (silica gel, 25% toluene in hexane) to give the title compound, 0.88 g (86%). $^1$H NMR (500 MHz, CDCl$_3$): δ 7.79 (2H, d, J 8.2), 8.02 (2H, d, J 8.3), 10.11 (1H, s).

Step 3: {(2S,4R)-1-{(1S)-4-Methyl-1-[4-(pentafluoroethyl)phenyl]pent-4-en-2-yn-1-yl}-2-[4-(trifluoromethyl)phenyl]piperidin-4-yl}acetic acid

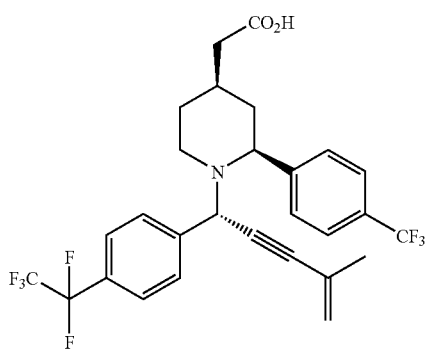

The title compound was prepared from the aldehyde from Step 2, methyl{(2S,4R)-2-[4-(trifluoromethyl)phenyl]piperidin-4-yl}acetate (Example 114, Step 1) and 2-methylbut-1-en-3-yne as described in Example 116. M/Z (ES$^+$) 560 (MH$^+$). $^1$H NMR (400 MHz, CDCl$_3$): δ 1.33 (1H, dq, J 5.2, 13.4), 1.46 (1H, q, J 11.9), 1.75 (1H, d, J 10.6), 1.94 (1H, d, J 13.4), 1.98-2.05 (4H, m), 2.23-2.36 (2H, m), 2.43-2.54 (2H, m), 3.69 (1H, dd, J 2.6, 11.1), 4.60 (1H, s), 5.32 (1H, quintet, J 1.6), 5.4 (1H, s), 7.54 (2H, d, J 8.2), 7.62 (4H, br s), 7.67 (2H, d, J 8.2).

Example 150

{(2S,4R)-1-{(1R)-4-Methyl-1-[4-(pentafluoroethyl)phenyl]pentyl}-2-[4-(trifluoromethyl)phenyl]piperidin-4-yl}acetic acid

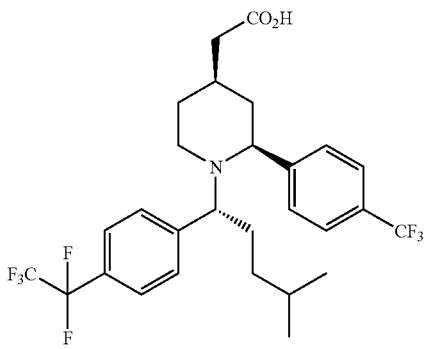

Step 1: Methyl{(2S,4R)-1-{(1R)-4-methyl-1-[4-(pentafluoroethyl)phenyl]pentyl}-2-[4-(trifluoromethyl)phenyl]piperidin-4-yl}acetate Trifluoroacetate

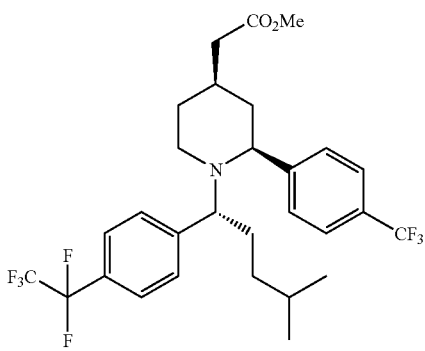

The methyl ester of Example 149 (405 mg, 0.706 mmol) was hydrogenated in a Parr™ apparatus in the presence of Raney-nickel with MeOH as solvent under 50 psi of H$_2$-pressure for 4 d. The reaction mixture was decanted from the catalyst and concentrated under reduced pressure to give the crude product, 92 mg, which was purified by preparative reverse phase HPLC.

| Column | Column Dimensions | % Modifier | Solvent | Mobile Phase | Flow | Detection |
|---|---|---|---|---|---|---|
| Supelcosil ABZ + PLUS | (100 × 21.2) mm | 60-40% | MeCN | 0.1% aq. TFA | 15 ml/min | UV 230 nm |

Step 2: {(2S,4R)-1-{(1R)-4-Methyl-1-[4-(pentafluoroethyl)phenyl]pentyl}-2-[4-(trifluoromethyl)phenyl]piperidin-4-yl}acetic acid

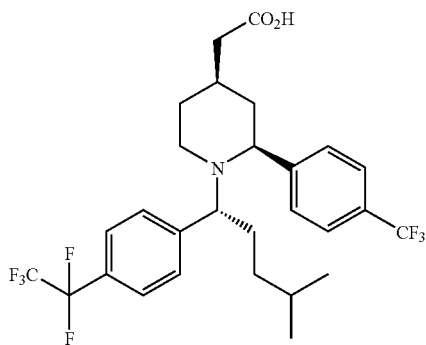

The ester from Step 1 (230 mg, 0.4 mmol) was heated to reflux in MeOH (1 ml) in the presence of 6M aq. NaOH (0.3 ml, 1.6 mmol) for 1 h. The reaction mixture was concentrated under reduced pressure and the residue partitioned between DCM and 2M HCl. The DCM phase was concentrated under reduced pressure to give the title compound as the HCl salt, from which the free base was liberated by column chromatography (silica gel, 5% MeOH in DCM): 150 mg (66%). M/Z (ES$^+$) 566 (MH$^+$). $^1$H NMR (400 MHz, CD$_3$OD+TFA-d): δ 0.62-0.77 (2H, m), 0.82-0.85 (6H, m), 1.49 (1H, septet, J 6.2), 1.60 (1H, q, J 12.9), 1.92 (1H, q, J 12.4), 2.16-2.39 (8H, m), 3.50 (1H, t, J 12.9), 3.69 (1H, d, J 12.4), 4.06 (1H, d, J 11.9), 7.55 (2H, d, J 7.92), 7.77-7.82 (4H, m), 7.96 (2H, d, J 7.7).

Examples 151-155

The following compounds were made by the procedures in Examples 85, using the piperidine from Example 3 Step 3 for Examples 151-153 or from Example 114 Step 1 for Examples 154-155, and the appropriate benzaldehyde, then hydrogenation using either Pd or Raney nickel catalysis, then basic hydrolysis.

| Example | Structure | Name | ES$^+$ m/z [MH]$^+$ |
|---|---|---|---|
| 151 | 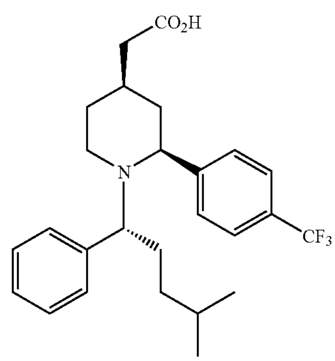 | (±)-{(2S*,4R*)-1-[(1R*)-4-methyl-1-phenylpentyl]-2-[4-(trifluoromethyl)phenyl]piperidin-4-yl}acetic acid | 448 |
| 152 | 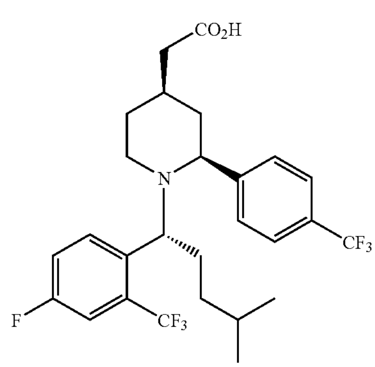 | (±)-{(2S*,4R*)-1-{(1R*)-1-[4-fluoro-2-(trifluoromethyl)phenyl]-4-methylpentyl}-2-[4-(trifluoromethyl)phenyl]piperidin-4-yl} acetic acid | 534 |

-continued

| Example | Structure | Name | ES+ m/z [MH]+ |
|---|---|---|---|
| 153 | 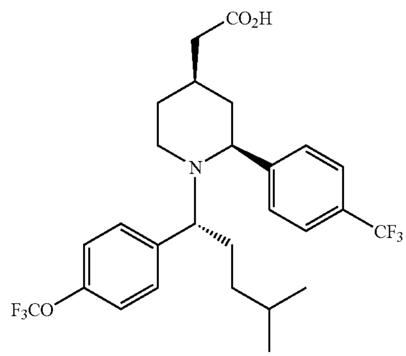 | (±)-{(2S*,4R*)-1-{(1R*)-4-methyl-1-[4-(trifluoromethoxy)phenyl]pentyl}-2-[4-(trifluoromethyl)phenyl]piperidin-4-yl} acetic acid | 532 |
| 154 | 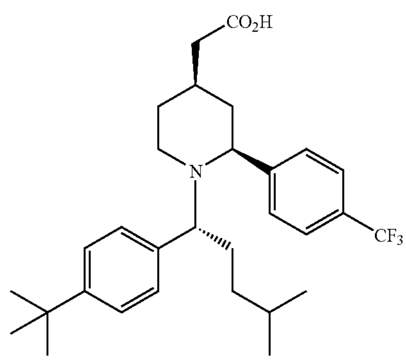 | {(2S,4R)-1-[(1R)-1-(4-tert-butylphenyl)-4-methylpentyl]-2-[4-(trifluoromethyl)phenyl]piperidin-4-yl} acetic acid | 504 |
| 155 | 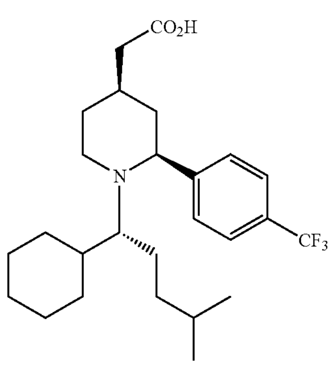 | {(2S,4R)-1-[(1R)-1-cyclohexyl-4-methylpentyl]-2-[4-(trifluoromethyl)phenyl]piperidin-4-yl} acetic acid | 454 |

Example 156

(±)-{(2S*,4R*)-1-{(R*)-Cyclohexyl[4-(trifluoromethyl)phenyl]methyl}-2-[4-(trifluoromethyl)phenyl]piperidin-4-yl}acetic acid

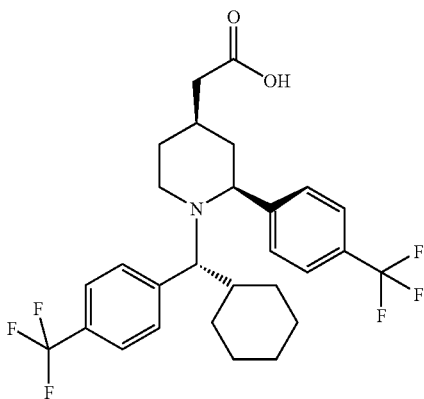

Step 1: (±)-Methyl{(2S*,4R*)-1-{(R*)-cyclohexyl[4-(trifluoromethyl)phenyl]methyl}-2-[4-(trifluoromethyl)phenyl]piperidin-4-yl}acetate

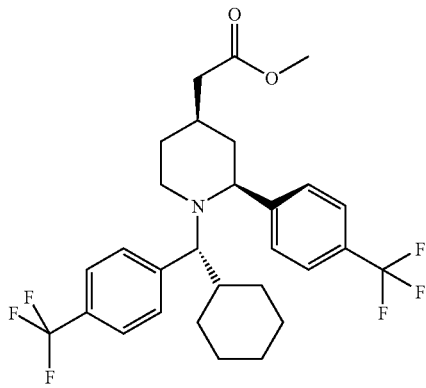

A solution of the piperidine (Example 3 step 3) (3.0 g, 10 mmol), 4-(trifluoromethyl)benzaldehyde (1.37 ml, 10 mmol) and benzotriazole (1.19 g, 10 mmol) in toluene (50 ml) was heated at reflux under Dean & Stark conditions for 3 hours. The cooled reaction was evaporated in vacuo and the residue dissolved in DCM. Cyclohexyl magnesium chloride (2M in $Et_2O$, 0.5 ml, 1.0 mmol) was added to a cold (−78° C.) aliquot of the benzotriazole adduct (1 mmol) in DCM (5 ml) and the mixture was allowed to warm to room temperature overnight. The mixture was diluted with $NH_4Cl$ (half sat) and extracted with DCM. The extracts were dried ($MgSO_4$) and evaporated in vacuo to yellow gum which was purified by flash chromatography (silica gel, 25-50% DCM in isohexane) to give the title compound as a single diastereoisomer. $^1H$ NMR δ (ppm) ($CDCl_3$): 7.59 (2H, d, J 8.1), 7.45 (4H, dd, J 8.0, 25.8), 7.09 (2H, d, J 8.0), 4.02 (1H, d, J 8.3), 3.62 (3H, s), 3.29 (2H, d, J 9.5), 2.86 (1H, t, J 10.6), 2.25-2.11 (3H, m), 2.05-1.91 (2H, m), 1.81-1.67 (4H, m), 1.29-1.13 (4H, m), 1.06 (4H, s), 0.68 (1H, dd, J 6.5, 125.9).

Step 2: (±)-{(2S*,4R*)-1-{(R*)-Cyclohexyl[4-(trifluoromethyl)phenyl]methyl}-2-[4-(trifluoromethyl)phenyl]piperidin-4-yl}acetic acid The title compound was prepared by hydrolysis of the ester from step 1 using the procedure described in Example 3 step 5. $^1H$ NMR δ (ppm) ($CD_3OD$): 7.64 (2H, d, J 8.1), 7.52 (4H, t, J 6.6), 7.20 (2H, d, J 8.1), 4.05 (1H, d, J 8.5), 3.39-3.33 (2H, m), 2.92-2.88 (1H, m), 2.25-2.09 (4H, m), 1.90-1.88 (1H, m), 1.81 (2H, d, J 9.9), 1.70 (1H, dd, J 2.7, 12.8), 1.63 (1H, d, J 11.3), 1.53 (1H, dd, J 11.2, 11.2), 1.40-1.08 (6H, m), 0.90-0.84 (2H, m), 0.54-0.46 (1H, m).

Examples 157-159

The following compounds were made by the procedures in Examples 156 using the appropriate commercial grignard reagent.

| Example | Structure | Name | M/Z ES+ [MH]+ |
|---|---|---|---|
| 157 | (structure) | (±)-((2S*,4R*)-2-[4-(trifluoromethyl)phenyl]-1-{(1R*)-1-[4-(trifluoromethyl)phenyl]butyl}piperidin-4-yl)acetic acid hydrochloride | 488 |

-continued

| Example | Structure | Name | M/Z ES+ [MH]+ |
|---|---|---|---|
| 158 | 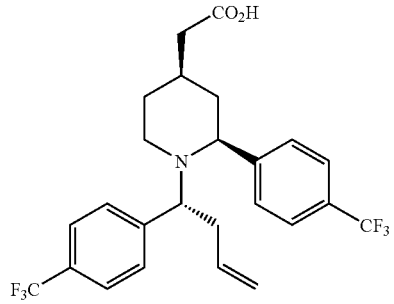 | (±)-((2S*,4R*)-2-[4-(trifluoromethyl)phenyl]-1-{(1R*)-1-[4-(trifluoromethyl)phenyl]hexyl}piperidin-4-yl)acetic acid hydrochloride | 534 |
| 159 | 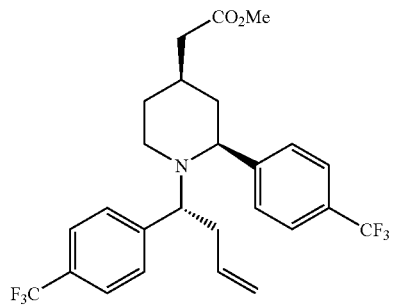 | (±)-((2S*,4R*)-1-{(R*)-cyclopropyl[4-(trifluoromethyl)phenyl]methyl}-2-[4-(trifluoromethyl)phenyl]piperidin-4-yl}acetic acid | 500 |

Example 160
(±)-((2S*,4R*)-2-[4-(Trifluoromethyl)phenyl]-1-{(1R*)-1-[4-(trifluoromethyl)phenyl]but-3-en-1-yl}piperidin-4-yl)acetic acid Step 1: (±)-Methyl((2S*,4R*)-2-[4-(trifluoromethyl)phenyl]-1-{(1R*)-1-[4-(trifluoromethyl)phenyl]but-3-en-1-yl}piperidin-4-yl)acetate Zinc chloride (1M in Et$_2$O, 12 ml, 12 mmol) was added slowly to a cold 0° C. solution of allyl magnesium bromide (1M in Et$_{2O}$, 12 ml, 12 mmol) under a nitrogen atmosphere, maintaining the temperature below 0° C. during the addition. Once the addition was complete the mixture was stirred at room temperature for one hour. The white suspension was cooled to 0° C. and the benzotriazole adduct (Example 156 Step 1. 4.0 mmol) was added slowly as a solution in DCM (20 ml). The cooling was removed and the mixture was stirred at room temperature for 16 hours. The mixture was diluted with NH$_4$Cl (half sat.) and with DCM and the mixture was filtered though a Celite® bed. The phases were separated and the aqueous extracted with DCM. The extracts were dried (MgSO$_4$) and evaporated in vacuo to purple gum which was purified by flash chromatography (silica gel, 50% DCM in isohexane) to give the title compound as a single diastereoisomer (10.8 g, 54%). $^1$H NMR δ (ppm) (CDCl$_3$): 7.63-7.53 (6H, m), 7.45 (2H, d, J 8.3), 5.57-5.45 (1H, m), 4.95-4.89 (2H, m), 3.80-3.76 (1H, m), 3.65 (4H, d, J 17.3), 2.69-2.53 (3H, m), 2.50-2.36 (1H, m), 2.28-2.16 (2H, m), 1.99-1.91 (1H, m), 1.85 (1H, dd, J 2.9, 12.8), 1.68 (1H, s), 1.41-1.33 (1H, m), 1.24-1.14 (1H, m).

Step 2: (±)-((2S*,4R*)-2-[4-(Trifluoromethyl)phenyl]-{(1R*)-1-[4-(trifluoromethyl)phenyl]but-3-en-1-yl}piperidin-4-yl)acetic acid

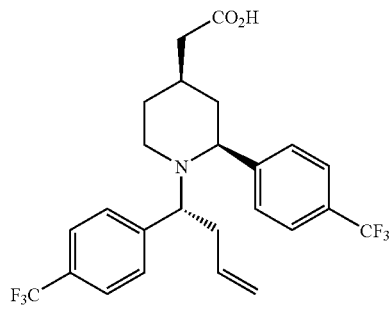

The title compound was prepared by hydrolysis of the ester from step 1 using the procedure described for Example 3 step 5. M/Z (ES+) 486 (M+H).

Examples 161-166

The following compounds were made by the procedures in Examples 160 using the appropriate commercial Grignard reagent, freshly prepared Grignard or commercial zincate.

| Example | Structure | Name | M/Z ES+ [MH]+ |
|---|---|---|---|
| 161† | 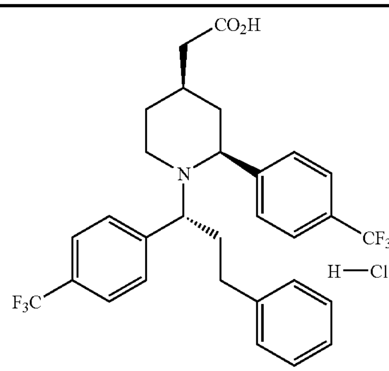 | (±)-((2S*,4R*)-1-{(1R*)-3-phenyl-1-[4-(trifluoromethyl)phenyl]propyl}-2-[4-(trifluoromethyl)phenyl]piperidin-4-yl}acetic acid hydrochloride | 488 |
| 162* | 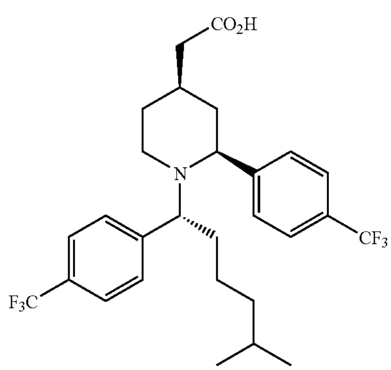 | (±)-((2S*,4R*)-1-{(1R*)-5-methyl-1-[4-(trifluoromethyl)phenyl]hexyl}-2-[4-(trifluoromethyl)phenyl]piperidin-4-yl}acetic acid | |
| 163†† | 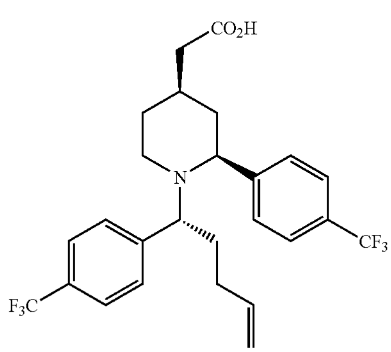 | (±)-((2S*,4R*)-2-[4-(trifluoromethyl)phenyl]-1-{(1R*)-1-[4-(trifluoromethyl)phenyl]pent-4-en-1-yl}piperidin-4-yl)acetic acid | |

-continued

| Example | Structure | Name | M/Z ES⁺ [MH]⁺ |
|---|---|---|---|
| 164* | 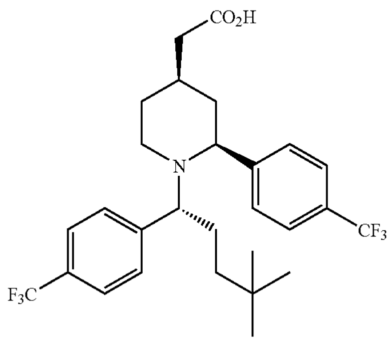 | (±)-((2S*,4R*)-1-{(1R*)-4,4-dimethyl-1-[4-(trifluoromethyl)phenyl]pentyl}-2-[4 (trifluoromethyl)phenyl]piperidin-4-yl}acetic acid | 530 |
| 165†† | 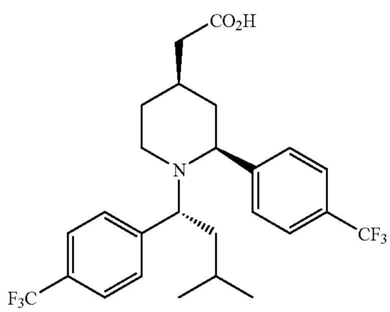 | (±)-((2S*,4R*)-1-{(1R*)-3-methyl-1-[4-(trifluoromethyl)phenyl]butyl}-2-[4-(trifluoromethyl)phenyl]piperidin-4-yl}acetic acid | 502 |
| 166* | 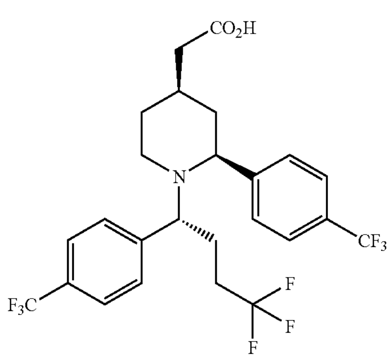 | (±)-((2S*,4R*)-2-[4-(trifluoromethyl)phenyl]-1-{(1R*)-4,4,4-trifluoro-1-[4-(trifluoromethyl)phenyl]butyl}piperidin-4-yl)acetic acid | 542 |

†Commerical Zincate; *Fresh Grignard; ††Commerical Grignard

Example 167

(+L)-((2S*,4R*)-2-[4-(Trifluoromethyl)phenyl]-1-{(1R*)-1-[4-(trifluoromethyl) phenyl]pentyl}piperidin-4-yl)acetic acid

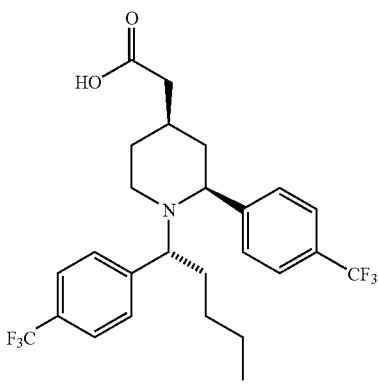

A solution of ((2S*,4R*)-2-[4-(trifluoromethyl)phenyl]-{(1R*)-1-[4-(trifluoromethyl)phenyl]pent-4-en-1-yl}piperidin-4-yl)acetic acid (Example 163, 38 mg, 0.076 mmol) in EtOAc (6 ml) was hydrogenated over 10% Pd/C (5 mg) under a balloon of $H_2$ for 45 min. The catalyst was removed by filtration—washing with EtOAc. The filtrate was evaporated to give the alkane (37 mg) as an off-white foam. $^1$H NMR (400 MHz, $CD_3OD$): δ 0.74-0.82 (4H, m), 0.99-1.25 (4H, m), 1.36-1.44 (1H, m), 1.71 (1H, d, J 12.8), 1.84-1.98 (4H, m), 2.13-2.23 (2H, m), 2.43-2.49 (1H, m), 2.73 (1H, brd, J 11), 3.54 (1H, dd, J 3.4, 10.4), 3.84 (1H, dd, J 2.5, 11.0), 7.49 (2H, d, J 8.2), 7.59 (2H, d, J 8.2), 7.70 (4H, s); M/Z (ES$^+$) 502 (M+H).

Example 168

(±)-{(2R*,4S*)-1-[(1S*)-1-(4-Iodophenyl)-4-methylpentyl]-2-[4-(trifluoromethyl)phenyl]piperidin-4-yl}acetic acid

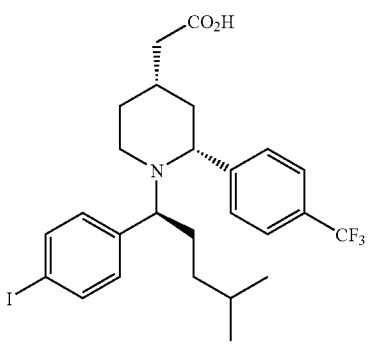

Step 1: (±)-Methyl{(2R*,4S*)-1-[(1S*)-1-(4-iodophenyl)-4-methylpentyl]-2-[4-(trifluoromethyl)phenyl]piperidin-4-yl}acetate

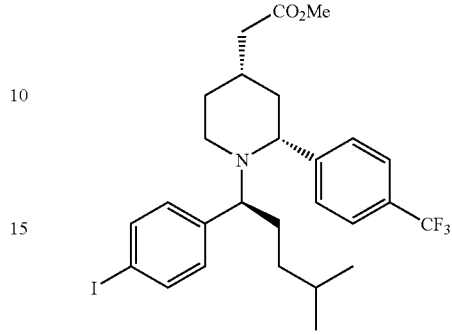

The title compound was prepared from methyl{(2R*,4R*)-2-[4-(trifluoromethyl)phenyl]piperidin-4-yl}acetate, 4-iodobenzaldehyde and 1-bromo-3-methylbutane in an analogous fashion to Example 114, Step 2 in 65% yield. $^1$H NMR (400 MHz, $CDCl_3$) δ (ppm) 0.58-0.69 (1H, m), 0.81-0.83 (6H, m), 0.85-0.96 (1H, m), 1.13 (1H, dq, J 4.5, 12.8), 1.32 (1H, q, J 12.4), 1.42 (1H, septet, J 6.6), 1.63 (1H, br, d, J 13.2), 1.69-1.76 (2H, m), 1.80 (1H, qd, J 2.9, 12.8), 1.87-1.98 (1H, m), 1.13-1.26 (2H, m), 2.33 (1H, dt, J 2.4, 11.9), 2.68 (1H, td, J 3.0, 11.4), 3.35 (1H, dd, J 4.12, 9.6), 3.62 (3H, s), 3.7 (1H, dd, J 2.6, 10.9), 6.99 (2H, d, J 8.3), 7.54 (2H, d, J 7.8), 7.59-7.63 (4H, m); M/Z (ES$^+$) 588 (M+H).

Step 2: (±)-{(2S*,4R*)-1-[(1R*)-1-(4-Iodophenyl)-4-methylpentyl]-2-[4-(trifluoromethyl)phenyl]piperidin-4-yl}acetic acid

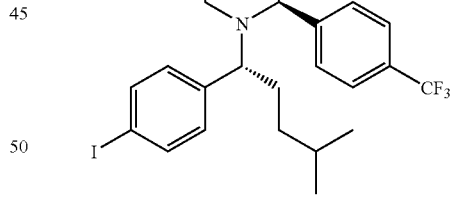

The ester from Step 1 (50 mg, 0.085 mmol) was stirred in MeOH (1 ml) at RT for 3 d. The reaction mixture was concentrated under reduced pressure and the residue partitioned between DCM and 2M HCl. The DCM layer was concentrated under reduced pressure to give the crude product, which was purified by flash chromatography (silica, 3% MeOH in DCM) to give the title compound, 28 mg (57%). $^1$H NMR (500 MHz, $CDCl_3$) δ (ppm) 0.58-0.66 (1H, m), 0.81-0.83 (6H, m), 0.86-0.95 (1H, m), 1.14 (1H, dq, J 3.8, 12.1), 1.34 (1H, q, J 12.1), 1.42 (1H, septet, J 6.5), 1.74-1.76 (3H, m), 1.84 (1H, br, d, J 12.7), 2.16-2.29 (2H, m), 2.33 (1H, dt, J 2.2, 12.1), 2.69 (1H, td, J 3.6, 12.1), 3.35 (1H, dd, J 5.1, 9.9), 3.72 (1H, dd, J 2.5, 10.9), 6.98 (2H, d, J 8.1), 7.54 (2H, br, d, J 7.45), 7.59-7.63 (4H, m); M/Z (ES$^+$) 574 (M+H).

Example 169

(±)-{(2S*,4R*)-1-[(1R*)-4-Methyl-1-(4-vinylphenyl)pentyl]-2-[4-(trifluoromethyl)phenyl]piperidin-4-yl}acetic acid

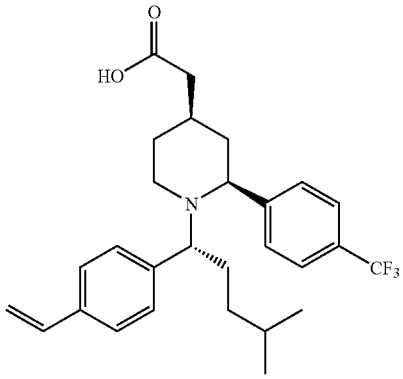

The ester described in Example 168 Step 1 (200 mg, 0.34 mmol) was dissolved in DME and the solution degassed using a Firestone valve. Vinyltributyltin (99.4 μL, 0.34 mmol) and tetrakis(triphenylphosphine)palladium(0) (20 mg) were added and the mixture was heated using microwave irradiation at 160° C. for 15 min. The mixture was diluted with water and was extracted with ethyl acetate. The organic layer was separated and was washed with brine, then dried (MgSO$_4$) and concentrated in vacuo to give the product. This was purified by chromatography on silica using DCM as eluant to afford the product as an oil (69 mg). This was dissolved in MeOH (1 ml) and sodium hydroxide added. The mixture was heated under reflux for 2 h. The cooled mixture was concentrated in vacuo, partitioned between HCl (2M) and DCM. The organic layer was separated and was washed with brine, then dried (MgSO$_4$) and concentrated in vacuo. The residue was purified by reverse phase HPLC with gradient elution (acetonitrile:0.1% TFA). The product fractions were concentrated in vacuo and the residue basified with NaHCO$_3$ (aq.) and extracted with DCM. This was concentrated in vacuo to afford the product as white foam. $^1$H NMR (400 MHz, CD$_3$OD): δ 0.55-0.65 (1H, m), 0.80-0.86 (6H, m), 1.11-1.61 (4H, m), 1.77 (1H, d, J 13.0), 1.84-1.98 (4H, m), 2.12-2.22 (2H, m), 2.62 (1H, t, J 11.2), 2.99 (1H, d, J 11.6), 3.49-3.53 (1H, m), 4.00 (1H, d, J 9.2), 5.21 (1H, d, J 11.5), 5.77 (1H, d, J 17.6), 6.72 (1H, dd, J 11.0, 17.6), 7.22 (2H, d, J 8.2), 7.40 (2H, d, J 8.2), 7.72 (4H, q, J 8.7). MS (ES$^+$) m/z 474 (100%).

Example 170

(±)-{(2S*,4R*)-1-[(1R*)-1-(4-Benzoylphenyl)-4-methylpentyl]-2-[4-(trifluoromethyl)phenyl]piperidin-4-yl}acetic acid

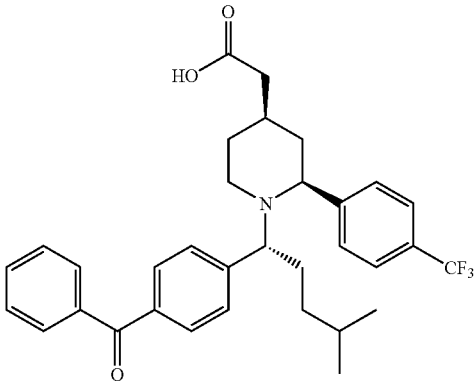

Step 1: (±)-Methyl{(2S*,4R*)-1-[(1R*)-4-methyl-1-(4-{[(triisopropylsilyl)oxy]methyl}phenyl)pentyl]-2-[4-(trifluoromethyl)phenyl]piperidin-4-yl}acetate

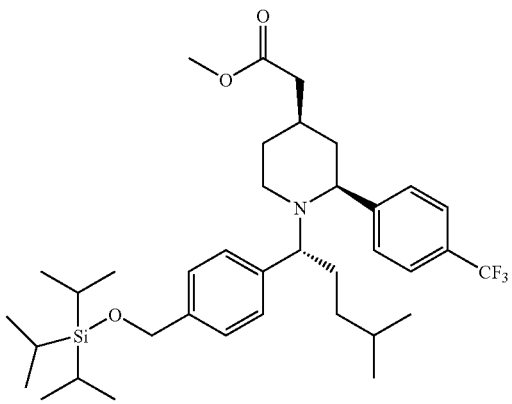

The title compound was prepared in a similar manner to Example 114, Step 2, using (±)-{(2R*,4R*)-2-[4-(trifluoromethyl)phenyl]piperidin-4-yl}acetate and 4-{[(triisopropylsilyl)oxy]methyl}benzaldehyde (J. Med. Chem, 2000, 43, 4084). $^1$H NMR (500 MHz, CDCl$_3$) δ (ppm) 0.58-0.66 (1H, m), 0.82 (6H, t, J 6.7), 0.90-1.0 (1H, m), 1.05-1.24 (22H, m), 1.32 (1H, q, J 11.8), 1.40-1.46 (1H, m), 1.60-1.65 (1H, m), 1.74-1.84 (3H, m), 1.90-1.96 (1H, m), 2.14-2.18 (1H, m), 2.20-2.25 (1H, m), 2.34 (1H, t, J 11.4), 2.62-2.68 (1H, m), 3.40-3.44 (1H, m), 3.62 (3H, s), 3.71 (1H, d, J 8.4), 4.82 (2H, m), 7.20 (2H, d, J 8.1), 7.27 (2H, d, J 8.0), 7.56-7.63 (4H, m);

Step 2: (±)-Methyl{(2S*,4R*)-1-[(1R*)-1-(4-formylphenyl)-4-methylpentyl]-2-[4-(trifluoromethyl)phenyl]piperidin-4-yl}acetate

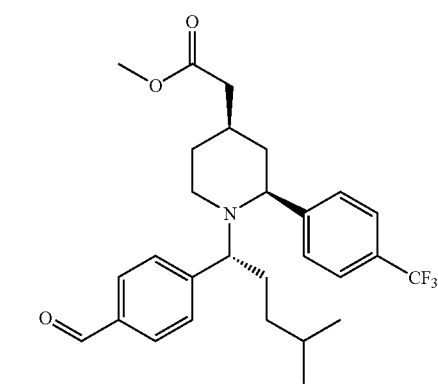

Tetrabutylammonium fluoride (1.0M in THF, 1.1 ml) was added to a stirred solution of the silyl ether (Step 1, 642 mg, 0.99 mmol) in THF (1 ml) at 0° C. After 5 min the cold bath was removed and the reaction was stirred at RT o/n. The reaction was quenched with saturated aqueous NaHCO$_3$ and then extracted with Et$_2$O (×3). The combined extracts were washed with H$_2$O (×1), brine (×1), dried (Na$_2$SO$_4$), filtered and evaporated. The residue was purified by chromatography (silica, 20-40% EtOAc/isohexane) to give the alcohol (463 mg) as a colourless foam.

Manganese (IV) oxide (105 mg, 1.2 mmol) was added to a stirred solution of this alcohol (115 mg, 0.23 mmol) in THF (1 ml) at RT. The mixture was stirred at RT O/N, then diluted with DCM and filtered through Hyflo®—washing with DCM. The filtrate was evaporated and the residue was purified by chromatography (silica, 10-15% EtOAc/isohexane) to give the aldehyde (54 mg) as a colourless oil. M/Z (ES+) 490 (MH+).

Step 3: (±)-Methyl{(2S*,4R*)-1-[(1R*)-1-(4-benzoylphenyl)-4-methylpentyl]-2-[4-(trifluoromethyl)phenyl]piperidin-4-yl}acetate

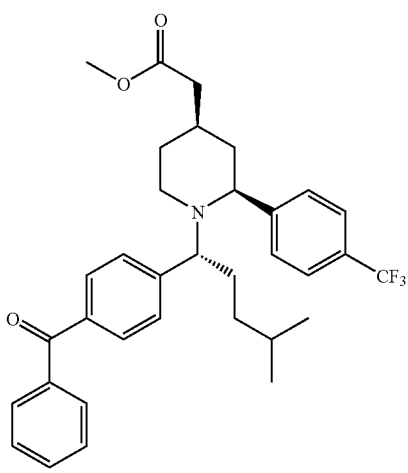

Phenylmagnesium bromide (1.0M in THF, 0.1 ml) was added to a stirred solution of the aldehyde (Step 2, 48 mg, 0.1 mmol) in dry DCM (1 ml) at 0° C. under N₂. After 20 min the reaction was quenched with saturated aqueous NH₄Cl and then partitioned between EtOAc/H₂O. The aqueous layer was extracted with EtOAc (×2). The combined extracts were washed with brine (×1), dried (Na₂SO₄), filtered and evaporated. The residue was purified by chromatography (silica, 15-25% EtOAc/isohexane) to give the benzyl alcohol (53 mg) as a colourless oil.

Tetrapropylammonium perruthenate (~2 mg) was added to a stirred solution/suspension of the alcohol from above (32 mg, 0.056 mmol), N-methyl morpholine N-oxide and 4 Å sieves (~200 mg) in dry DCM (1 ml) at RT. After 20 min, the reaction was diluted with EtOAc and filtered through a silica pad—washing with EtOAc. The filtrate was evaporated and the residue was purified by chromatography (silica, 5-10% EtOAc/isohexane) to give the ketone (25 mg) as a colourless oil. ¹H NMR (500 MHz, CDCl₃) δ (ppm) 0.64-0.72 (1H, m), 0.83 (6H, t, J 6.7), 0.94-1.02 (1H, m), 1.12-1.18 (1H, m), 1.36 (1H, q, J 12.0), 1.46 (1H, sept, J 6.6), 1.65 (1H, brd, J 12.8), 1.79-1.85 (3H, m), 1.90-2.00 (1H, m), 2.17 (1H, dd, J 15.3, 7.5), 2.25 (1H, dd, J 15.3, 6.7), 2.40 (1H, brt, J 10.7), 2.71 (1H, brd, J 10), 3.48 (1H, t, J 6.9), 3.63 (3H, s), 3.75 (1H, dd, J 11, 2.5), 7.37 (2H, d, J 8.2), 7.48 (2H, t, J 7.7), 7.56-7.60 (3H, m), 7.64 (2H, d, J 8.2), 7.74 (2H, d, J 8.2), 7.80 (2H, d, J 8.2).

Step 4: (±)-{(2S*,4R*)-1-[(1R*)-1-(4-Benzoylphenyl)-4-methylpentyl]-2-[4-(trifluoromethyl)phenyl]piperidin-4-yl}acetic acid

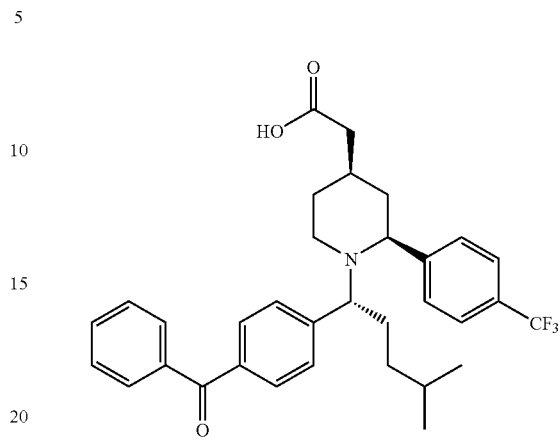

A solution of LiOH (10 mg, 0.42 mmol) in water (0.5 ml) was added to a stirred solution of the ester (Step 3, 42 mg, 0.074 mmol) in THF (1 ml) at RT. The reaction was stirred at RT O/N then quenched with 2N HCl (1 ml). The mixture was partitioned between EtOAc and H₂O. The aqueous layer was extracted with EtOAc (×2). The combined extracts were washed with brine (×1), dried (Na₂SO₄), filtered and evaporated. The residue was purified by chromatography (silica, 2-8% MeOH/DCM) to give the acid (22 mg) as a colourless solid. ¹H NMR (400 MHz, CD₃OD): δ 0.60-0.70 (1H, m), 0.82-1.02 (7H, m), 1.14-1.24 (1H, m), 1.38-1.49 (2H, m), 1.72-1.75 (1H, m), 1.84-1.95 (4H, m), 2.18-2.20 (2H, m), 2.52 (1H, brt, J 11), 2.82 (1H, brd, J 11), 3.53 (1H, dd, J 9.8, 4.0), 3.87 (1H, brd, J 10), 7.45 (2H, d, J 8.2), 7.52 (2H, t, J 7.6), 7.64 (1H, J 7.4), 7.70-7.80 (8H, m); M/Z (ES+) 552 (MH+).

Example 171

(±)-{(2S*,4R*)-1-{(1R*,2Z)-1-[2,5-Bis(trifluoromethyl)phenyl]-4-methylpent-2-en-1-yl}-2-[4-(trifluoromethyl)phenyl]piperidin-4-yl}acetic acid

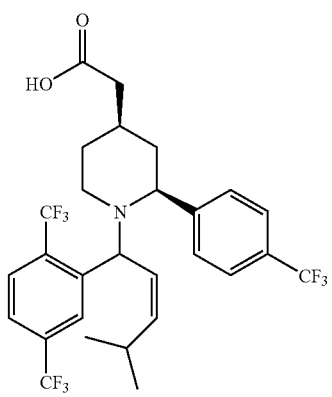

Step 1: (±)-Methyl{(2S*,4R*)-1-{(1R*,2Z)-1-[2,5-Bis(trifluoromethyl)phenyl]-4-methylpent-2-en-1-yl}-2-[4-(trifluoromethyl)phenyl]piperidin-4-yl}acetate

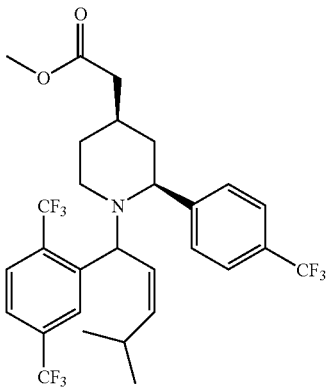

An enyne was prepared as in Example 85 Step 1, using 2,5-bis(trifluoromethyl)benzaldehyde in place of 4-(trifluoromethyl)benzaldehyde. A solution of this enyne (211 mg, 0.36 mmol) in EtOAc (10 ml) was hydrogenated over 10% Pd/C (50 mg) under a balloon of $H_2$ for 30 hrs. The catalyst was removed by filtration—washing with EtOAc. The filtrate was evaporated and the residue was purified by reverse phase preparative HPLC to give the alkene (59 mg) as an oil. M/Z (ES$^+$) 596 (MH$^+$).

Step 2: (±)-{(2S*,4R*)-1-{(1R*,2Z)-1-[2,5-Bis(trifluoromethyl)phenyl]-4-methylpent-2-en-1-yl}-2-[4-(trifluoromethyl)phenyl]piperidin-4-yl}acetic acid

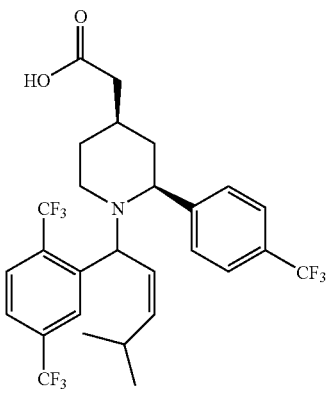

The title compound was prepared as described in Example 170, Step 4. $^1$H NMR (500 MHz, CD$_3$OD): δ 0.49 (3H, d, J 6.6), 0.76 (3H, d, J 6.5), 1.27-1.45 (2H, m), 1.73-1.82 (3H, m), 1.88-1.97 (1H, m), 2.15-2.24 (2H, m), 2.59 (1H, brt, J 11), 2.68 (1H, brd, J 10), 3.68 (1H, d, J 10), 4.91 (1H, d, J 8.9), 5.47 (1H, t, J 10.4), 5.81 (1H, t, J 9.9), 7.48-7.53 (4H, m), 7.70 (1H, d, J 8.2), 7.81 (1H, d, J 8.3), 7.95 (1H, s); M/Z (ES$^+$) 582 (MH$^+$).

Example 172

(±)-{(2S*,4R*)-1-{(1R*,2Z)-4-Methyl-1-[4-(trifluoromethyl)phenyl]pent-2-en-1-yl}-2-[4-(trifluoromethyl)phenyl]piperidin-4-yl}acetic acid

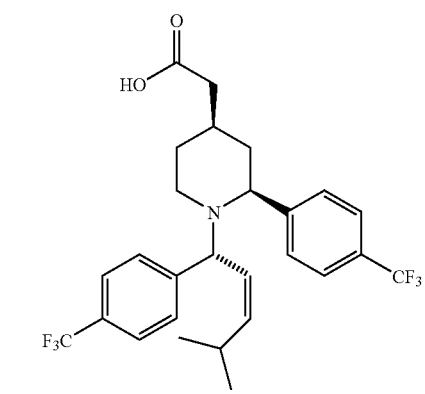

The title compound was prepared in a similar way to Example 171 using the enyne product from Example 85, Step 1. $^1$H NMR (500 MHz, CD$_3$OD): δ 0.59 (3H, d, J 6.7), 0.78 (3H, d, J 6.4), 1.25-1.39 (2H, m), 1.51-1.57 (1H, m), 1.73 (1H, brd, J 12.6), 1.86-1.96 (2H, m), 2.16-2.26 (2H, m), 2.46-2.52 (1H, m), 2.64-2.68 (1H, m), 3.68 (1H, dd, J 11.3, 2.8), 4.61 (1H, m), 5.62-5.70 (2H, m), 7.60-7.66 (8H, m). M/Z (ES$^+$) 514 (MH$^+$).

Example 173

(2S*,4R*)-1-{(1R*)-4-Methyl-1-[4-(trifluoromethyl)phenyl]pentyl}-4-(1H-tetrazol-5-ylmethyl)-2-[4-(trifluoromethyl)phenyl]piperidine

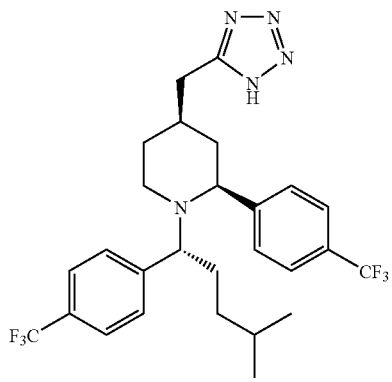

Step 1: {(2S,4R)-1-{(1R)-4-methyl-1-[4-(trifluoromethyl)phenyl]pentyl}-2-[4-(trifluoromethyl)phenyl]piperidin-4-yl}acetonitrile

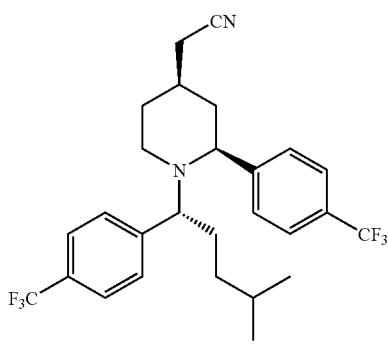

To a suspension of ammonium chloride (107 mg, 2 mmol) in toluene (5 ml) was added a solution of trimethylaluminium in toluene (2M, 1.1 ml) and the mixture stirred for 1.5 h before adding the product of Example 114 Step 2 (268 mg, 0.5 mmol) in toluene (3.5 ml). The mixture was then stirred at reflux for 2.5 h, cooled, and quenched by addition of aqueous ammonium chloride (satd., 15 ml). Solid potassium sodium tartrate was added and the mixture stirred vigorously until all the precipitate had dissolved. After separation of layers, the aqueous was extracted with EtOAc (2×10 ml), the combined organics dried (MgSO$_4$), filtered and evaporated. The residue was purified by chromatography (silica, 15% EtOAc in hexanes) giving the title compound as a colourless gum (88 mg, 35%). $^1$H NMR (500 MHz, CD$_3$OD): δ 0.57-0.65 (1H, m), 0.82 (3H, d, J 11.0), 0.84 (3H, d, J 11.0), 0.89-0.97 (2H, m), 1.22 (1H, dq, J 12.3, 4.0), 1.44 (1H, septet, J 7.0), 1.49 (1H, q, J 11.5), 1.72-1.79 (1H, m), 1.81-1.95 (4H, m), 2.39 (2H, d, J 6.4), 2.45 (1H, dt, J 2.0, 11.5) 2.74-2.76 (1H, m), 3.49 (1H, dd, J 4.0, 9.8), 3.83 (1H, dd, J 2.0, 10.6), 7.46 (2H, d, J 8.1), 7.60 (2H, d, J 8.2), 7.72 (4H, t, J 9.3), M/Z (ES$^+$) 497 (MH$^+$).

Step 2: (2S,4R)-1-{(1R)-4-Methyl-1-[4-(trifluoromethyl)phenyl]pentyl}-4-(1H-tetrazol-5-ylmethyl)-2-[4-(trifluoromethyl)phenyl]piperidine

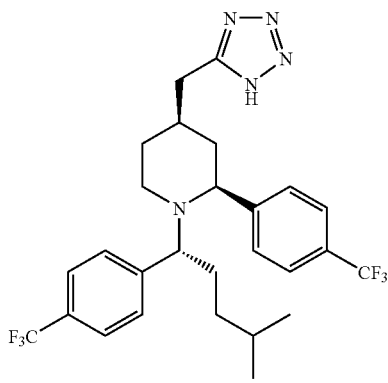

A mixture of the nitrile from the previous step (85 mg, 0.17 mmol), azidotrimethylsilane (0.046 ml, 0.35 mmol), and dibutyltin oxide (5 mg, 0.02 mmol) in toluene (3 ml) was stirred at reflux for 100 h. More azide (0.26 ml, 2 mmol) and butyltin oxide (50 mg, 0.2 mmol) was added and heating at reflux resumed for a further 48 h. On cooling, the solution was evaporated and the residue subjected to chromatography (silica, 5-10% MeOH in dichloromethane) to afford the title compound as a solid (42 mg). $^1$H NMR (500 MHz, CD$_3$OD): δ 0.56-0.63 (1H, m), 0.81-0.91 (7H, m), 1.21 (1H, dq, J 3.2, 11.8), 1.43 (1H, septet, J 6.4), 1.48 (1H, q, J 11.6), 1.64 (1H, d, J 12.7), 1.75-1.82 (1H, m), 1.84-2.04 (3H, m), 2.50 (1H, t, J 11.4), 2.76-2.86 (3H, m), 3.50-3.55 (1H, m), 3.89 (1H, d, J 10.6), 7.45 (2H, d, J 8.1), 7.61 (2H, d, J 8.2), 7.70 (4H, q, J 8.4), M/Z (ES$^+$) 540 (MH$^+$).

Example 174

(±)-{(2S*,4R*)-1-{(1S*,2R* or 2S*)-2-Ethoxy-1-[4-(trifluoromethyl)phenyl]propyl}-2-[4-(trifluoromethyl)phenyl]piperidin-4-yl}acetic acid

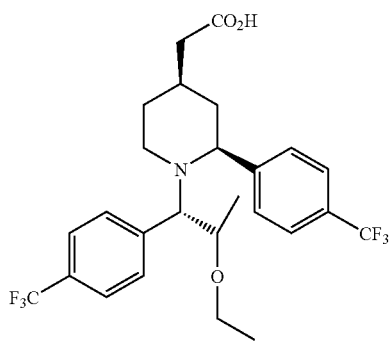

Step 1: (±)-Methyl{(2S*,4R*)-1-{(1S*,2R* or 2S*)-2-ethoxy-1-[4-(trifluoromethyl)phenyl]propyl}-2-[4-(trifluoromethyl)phenyl]piperidin-4-yl}acetate

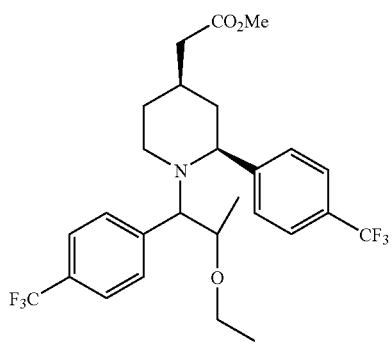

A flask was charged with magnesium turnings (240 mg, 10 mmol) and dried under vacuum with stirring. THF (5 ml) was added followed by 1-bromo-3,3,3-trifluoropropane (1.07 ml, 10 mmol). The addition of a few drops followed by hand warming caused an exothermic reaction to initiate and the remaining bromide was added whilst maintaining the internal temperature at ~40° C. Once the addition was complete the mixture was stirred at room temperature for 30 minutes. The mixture was cooled to 0° C. and zinc chloride (1M in Et$_2$O, 10 ml, 10 mmol) was added slowly maintaining the temperature below 0° C. during the addition. Once the addition was complete the mixture was stirred at room temperature for 90 minutes. The white suspension was cooled to 0° C. and the benzotriazole adduct (Example 156 Step1, 1.0 mmol) was added slowly as a solution in DCM (5 ml). The cooling was removed air was allowed into the flask and the mixture was stirred at room temperature for 16 hours. The mixture was diluted with NH$_4$Cl (half sat.) and with DCM and the mixture was filtered though a Celite® bed. The phases were separated and the aqueous extracted with DCM. The extracts were dried (MgSO$_4$) and evaporated in vacuo to give a yellow gummy solid which was purified by flash chromatography (silica gel, 50% DCM in isohexane) to give the title compound as two diastereoisomers.

Higher running diastereoisomer (48 mg, 9%): $^1$H NMR δ (ppm) (CDCl$_3$): 7.62-7.47 (8H, m), 3.99-3.93 (1H, m), 3.87 (1H, dd, J 2.6, 10.9), 3.61 (4H, m), 3.50 (1H, t, J 6.0), 3.36-3.28 (1H, m), 3.07 (1H, t, J 11.4), 2.78-2.72 (1H, m), 2.25-2.15 (2H, m), 1.96 (1H, s), 1.80 (1H, d, J 9.6), 1.67 (1H, s), 1.37-1.25 (2H, m), 1.17-1.11 (3H, m), 1.00 (3H, d, J 6.4). M/Z (ES$^+$) 532 (M+H).

Lower running diastereoisomer (69 mg, 13%): $^1$H NMR δ (ppm) (CDCl$_3$): 7.62 (2H, d, J 8.2), 7.50 (4H, m), 7.16 (2H, d, J 8.1), 4.40 (1H, t, J 5.7), 4.14 (1H, dd, J 5.9, 9.3), 3.66 (4H, t, J 10.2), 3.50 (1H, t, J 8.4), 3.44-3.38 (1H, m), 3.16 (1H, d, J 11.2), 2.73 (1H, t, J 10.6), 2.24-2.14 (2H, m), 1.95 (1H, s), 1.72 (2H, t, J 12.6), 1.35 (3H, t, J 7.0), 1.27-1.15 (2H, m), 0.78 (3H, d, J 5.9). M/Z (ES$^+$) 532 (M+H).

Step 2: (±)-{(2S*,4R*)-1-{(1S*,2R* or 2S*)-2-Ethoxy-1-[4-(trifluoromethyl)phenyl]propyl}-2-[4-(trifluoromethyl)phenyl]piperidin-4-yl}acetic acid

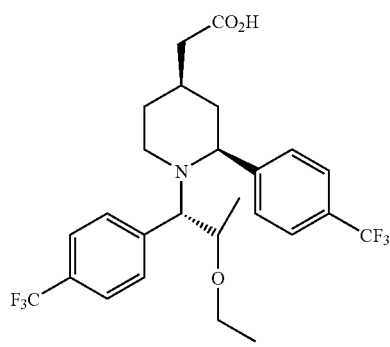

The title compound was prepared by hydrolysis of the ester of the higher running diastereoisomer from step 1 using the procedure described for Example 3 step 5.1 $^1$H NMR δ (ppm) (CD$_3$OD): 7.63-7.47 (8H, m), 4.46 (1H, s), 4.22 (1H, s), 4.07 (1H, s), 3.77-3.67 (2H, m), 3.59-3.53 (1H, m), 2.35 (4H, s), 2.17 (2H, m), 1.88 (2H, m), 1.33 (3H, t, J 6.9), 0.77 (3H, d, J 6.2). M/Z (ES$^+$) 518 (M+H).

Example 175

(±)-{(2S*,4R*)-1-{(1S*,2S* or 2R*)-2-Ethoxy-1-[4-(trifluoromethyl)phenyl]propyl}-2-[4-(trifluoromethyl)phenyl]piperidin-4-yl}acetic acid

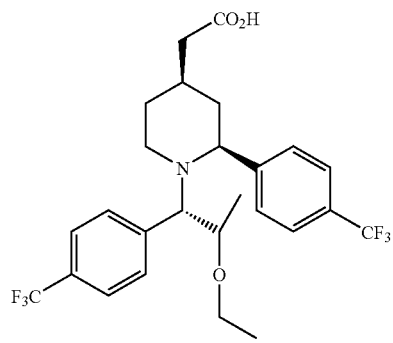

The title compound was prepared by hydrolysis of the ester of the lower running diastereoisomer from Example 174 step 1 using the procedure described for Example 3 step 5.1 $^1$H NMR δ (ppm) (CD$_3$OD): 7.95 (2H, d, J 8.0), 7.77 (4H, dd, J 8.3, 12.7), 7.35 (2H, d, J 7.8), 5.28 (1H, d, J 10.9), 4.60-4.54 (1H, m), 4.11 (2H, d, J 10.5), 3.93-3.85 (1H, m), 3.67-3.61 (2H, m), 2.35 (2H, d, J 5.5), 2.21 (3H, m), 1.93-1.83 (1H, m), 1.72 (1H, t, J 12.4), 1.49 (3H, t, J 7.0), 0.82 (3H, d, J 5.9). M/Z (ES$^+$) 518 (M+H).

Example 176

(±)-{(3S*,5R*)-1-[4-(Trifluoromethyl)benzyl]-5-[4-(trifluoromethyl)phenyl]pyrrolidin-3-yl}acetic acid

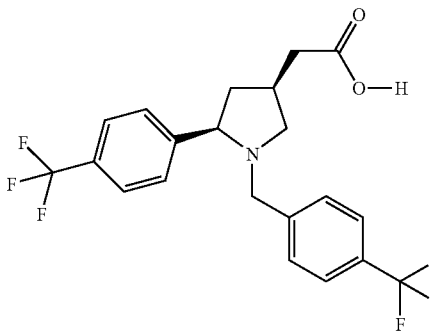

Step 1: 2-Methyl-N-{1-[4-(trifluoromethyl)phenyl]but-3-en-1-yl}propane-2-sulfinamide

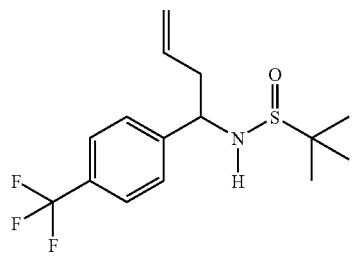

2-Methyl-N-{[4-(trifluoromethyl)phenyl]methylene}propane-2-sulfinamide (prepared according to the procedure described in Example 99 step 1, using 4-(trifluoromethyl)benzaldehyde) (5 g, 0.18 mol) was dissolved in CH$_2$Cl$_2$ and the solution cooled to −50° C. Allylmagnesium bromide (10.8 mL, 2M in THF, 0.22 mol) was added dropwise and the resulting solution was stirred at 0° C. for 30 min. The mixture was quenched with NH$_4$Cl and diluted with water and was extracted with CH$_2$Cl$_2$. The organic layer was separated and was washed with brine, then dried (MgSO$_4$) and concentrated in vacuo to give the product as a 3:2 mixture of diastereoisomers.

MS (ES$^+$) m/z 320 (M+H$^+$).

Step 2: 2-Methyl-N-[4-(trifluoromethyl)benzyl]-N-{1-[4-(trifluoromethyl)phenyl]but-3-en-1-yl}propane-2-sulfinamide

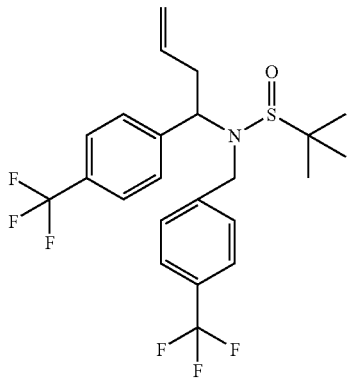

The sulfinamide described in Step 1 (1 g, 3 mmol) was dissolved in DMF (3 mL). Sodium hydride (188 mg, 4.5 mmol) was added and the mixture was stirred for 30 min. 4-(Trifluoromethyl)benzyl bromide (884 mg, 3.6 mmol) was added and the mixture was stirred overnight. The mixture was quenched with water and was extracted into ethyl acetate. The organic extracts were dried (brine, MgSO$_4$) and evaporated. The residue was purified on silica using 10-30% ethyl acetate in iso-hexane to give the product (880 mg).

Step 3: Methyl(2E)-5-{(tert-butylsulfinyl)[4-(trifluoromethyl)benzyl]amino}-5-[4-(trifluoromethyl)phenyl]pent-2-enoate

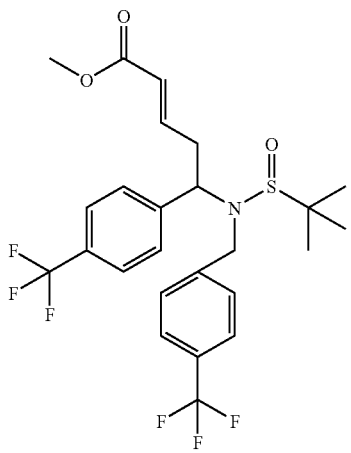

The alkene from Step 2 (800 mg, 1.67 mmol) was dissolved in methyl acrylate (1.5 mL) and Zhan I catalyst (110 mg) was added. This mixture was stirred for 30 min and TLC indicated all starting material had reacted. The mixture was evaporated and purified by chromatography on silica using 10-25% ethyl acetate in iso-hexane to give the product (500 mg) as a mixture of isomers:

Step 4: Methyl(2E)-5-{[4-(trifluoromethyl)benzyl]amino}-5-[4-(trifluoromethyl)phenyl]pent-2-enoate

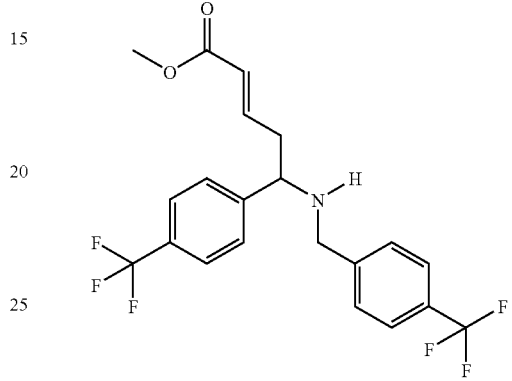

The sulfinamide from Step 3 (450 mg, 0.84 mmol) was dissolved in methanol (3 mL) and the solution was cooled in ice. HCl (4M in dioxane, 0.5 mL) was added and the solution was stirred for 30 min. NaHCO$_3$ was added to neutralize the solution and methanol was removed by evaporation. The residue was extracted into CH$_2$Cl$_2$; this was washed with water, brine, dried (MgSO$_4$) and evaporated and the residue was purified by chromatography on silica using 10-25% ethyl acetate in iso-hexane to give the product (500 mg).

Step 5: Methyl{1-[4-(trifluoromethyl)benzyl]-5-[4-(trifluoromethyl)phenyl]pyrrolidin-3-yl}acetate

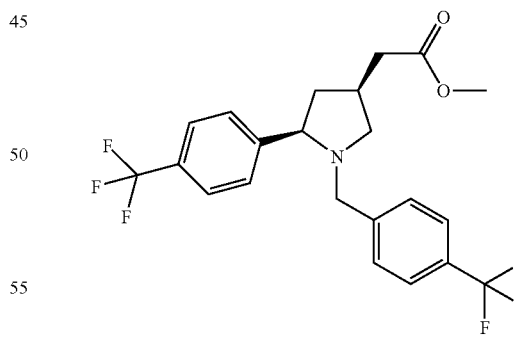

The amine from Step 4 (400 mg, 0.9 mmol) was dissolved in benzene and benzotriazolemethanol (135 mg, 0.9 mmol) was added followed by powdered molecular sieves (470 mg). This was stirred overnight, the molecular sieves removed by filtration through Celite and the filtrate concentrated in vacuo. The residue was dissolved in THF (25 mL) and anhydrous t-butanol (0.17 mL, 0.9 mmol) was added. This solution was added dropwise via cannula onto a solution of samarium diiodide (27 mL, 2.7 mmol, 0.1M in THF) which was precooled to −78° C. The mixture was stirred (−78° C. 0° C.) overnight then quenched with aq. K₂CO₃ and extracted with ethyl acetate. The organic extracts were washed with water, dried (MgSO₄) and evaporated. The residue was purified on silica using 30-50% CH₂Cl₂ in iso-hexane to elute isomer a (245 mg) and isomer b (100 mg).

Isomer a: ¹H NMR (500 MHz, CDCl₃): δ 1.40-1.44 (1H, m), 2.45-2.55 (4H, m), 2.63 (1H, m), 2.84 (1H, dd, J 2.9, 9.8), 3.18 (1H, d, J 13.8), 3.57 (1H, t, J 8.2), 3.63 (3H, s), 3.80 (1H, d, J 13.8), 7.38 (2H, d, J 7.9), 7.53-7.60 (6H, m). MS (ES⁺) m/z (446, MH⁺, 100%)

Step 6: (±)-{(3S*,5R*)-1-[4-(Trifluoromethyl)benzyl]-5-[4-(trifluoromethyl)phenyl]pyrrolidin-3-yl}acetic acid

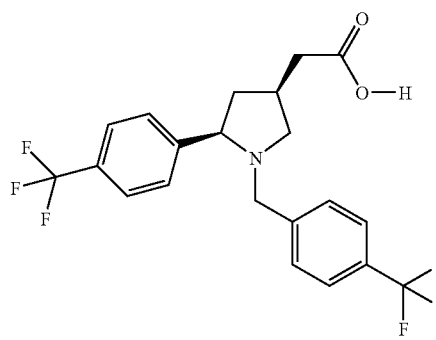

The ester from Step 5 (240 mg, 0.53 mmol) was dissolved in methanol (2 mL) and NaOH (0.67 mL, 2.65 mmol) was added. The mixture was heated at 60° C. for 2 h. then cooled, evaporated, neutralised with HCl (aq.) and extracted into CH₂Cl₂. The organic extracts were pooled, washed with water, brine and dried (MgSO₄) and evaporated. The residue was purified on silica using 10-100% ethyl acetate in iso-hexane as eluant.

¹H NMR (500 MHz, CDCl₃): δ 1.47-1.53 (1H, m), 2.50-2.64 (5H, m), 2.87 (1H, t, J 5.0), 3.18 (1H, d, J 13.6), 3.57 (1H, dd, J 7.4, 9.5), 3.81 (1H, d, J 13.6), 7.36 (2H, d, J 7.9), 7.53-7.61 (6H, m). MS (ES⁺) m/z (432, MH⁺, 100%)

Example 177

(±)-{(3S*,5R*)-1-[2,5-Bis(trifluoromethyl)benzyl]-5-[4-(trifluoromethyl)phenyl]pyrrolidin-3-yl}acetic acid

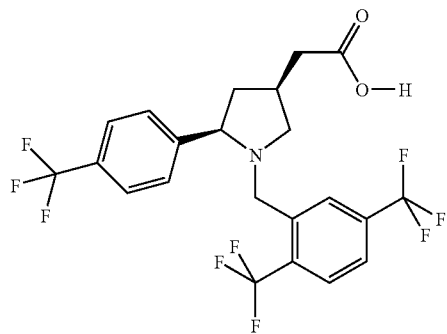

Step 1: (±)-Methyl{(3S*,5R*)-1-benzyl-5-[4-(trifluoromethyl)phenyl]pyrrolidin-3-yl}acetate

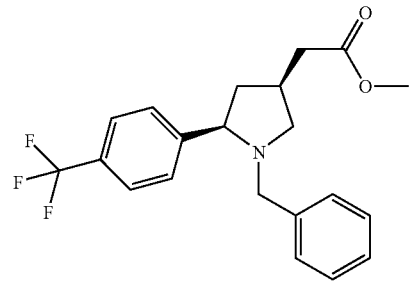

Prepared as in Example 176 Steps 1-5 using benzyl bromide in Step 2.
MS (ES⁺) m/z 378 (MH⁺).

Step 2: (±)-Methyl{(3S*,5R*)-5-[4-(trifluoromethyl)phenyl]pyrrolidin-3-yl}acetate

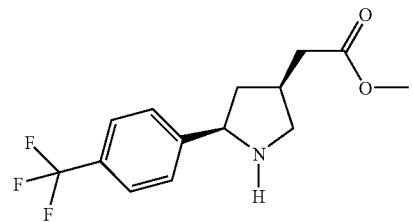

The product from Step 1 (130 mg) was dissolved in methanol and HCl (0.5 mL, 4M in dioxane) and Pd—C (70 mg) was added. This mixture was hydrogenated at 20 psi for 4 hr; the catalyst was removed by filtration and the filtrate was evaporated. The residue was neutralized with sodium bicarbonate (aq.) and extracted into CH₂Cl₂. The organic layer was washed with water, brine, dried (MgSO₄) and evaporated. The residue was purified on silica using 2-5% methanol in CH₂Cl₂ to yield the product.
MS (ES⁺) m/z 288 (MH⁺).

Step 3: (±)-Methyl{(3S*,5R*)-1-[2,5-bis(trifluoromethyl)benzyl]-5-[4-(trifluoromethyl)phenyl]pyrrolidin-3-yl}acetate

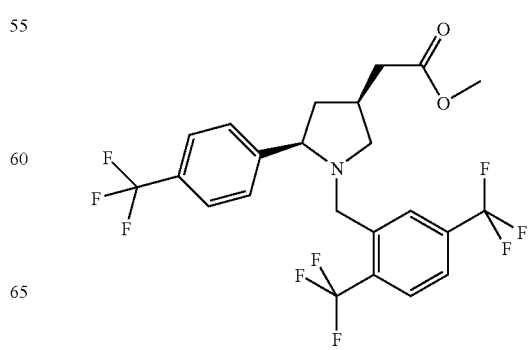

The amine from Step 2 (100 mg, 0.35 mmol) was dissolved in DMF (1 mL). Potassium carbonate (240 mg, 1.74 mmol), sodium iodide (11 mg) and 2,5-bis(trifluoromethyl)benzyl bromide (214 mg, 0.697 mmol) were added and the mixture was stirred for 3 h at 100° C. The mixture was quenched with water and was extracted into ethyl acetate. The organic extracts were dried (brine, MgSO$_4$) and evaporated. The residue was purified on silica using 5% ethyl acetate in iso-hexane to give the product (135 mg).

$^1$H NMR (500 MHz, benzene-d$_6$): δ 1.26-1.32 (1H, m), 2.11-2.31 (3H, m), 2.37-2.47 (2H, m), 2.78 (1H, dd, J 3.0, 9.7), 3.14 (1H, t, J 8.3), 3.43 (3H, s), 3.50 (1H, s), 3.61 (1H, t, J 16.4), 7.11 (1H, d, J 8.0), 7.19 (2H, d, J 8.0), 7.23-7.26 (1H, m), 7.40 (2H, d, J 8.1), 8.18 (1H, s).

Step 4: (±)-{(3S*,5R*)-1-[2,5-Bis(trifluoromethyl)benzyl]-5-[4-(trifluoromethyl)phenyl]pyrrolidin-3-yl}acetic acid The ester described in iv) above (135 mg) was dissolved in dioxane (1 mL) and KOH (105 mg) in water (1 mL) was added. The mixture was heated at 60° C. for 2 h. The cooled mixture was evaporated, then neutralised with HCl (aq.) and extracted into ethyl acetate. The organic extracts were pooled, washed with water, brine and dried (MgSO$_4$) and evaporated to give a white solid (110 mg).

MS (ES$^+$) m/z 500 (MH$^+$).

Example 178

(±)-{4-[2,5-Bis(trifluoromethyl)benzyl]-3-[4-(trifluoromethyl)phenyl]piperazin-1-yl}acetic acid

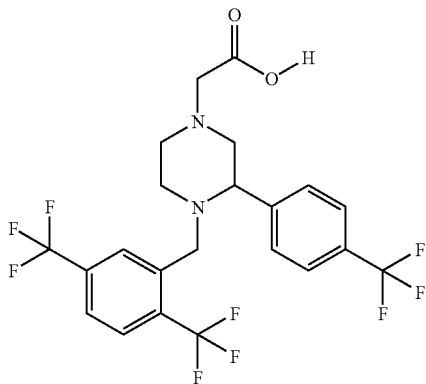

Step 1: 2-[4-(Trifluoromethyl)phenyl]pyrazine

A mixture of chloropyrazine (10, 0.087 mol), 4-(trifluoromethyl)phenylboronic acid (21 g), palladium(diphenylphosphino)ferrocene dichloride (3.5 g, 5 mol %) and sodium carbonate (100 mL, 2M) in dioxane (200 mL) was degassed (×3) via Firestone valve. The mixture was heated under reflux for 1 h., evaporated in vacuo, the residue partitioned between ethyl acetate and water, then the organic phase was washed with brine, dried (MgSO4) and evaporated. The black residue was dry-loaded onto silica and purified by elution with 5-25% ethyl acetate in iso-hexane. This afforded the product as white crystals.

$^1$H NMR (400 MHz, CDCl$_3$): δ 7.78 (2H, d, J 8.2), 8.15 (2H, d, J 8.2), 8.59 (1H, d, J 2.5), 8.68 (1H, t, J 2.0), 9.08 (1H, d, J 1.4).

Step 2: (±)-2-[4-(Trifluoromethyl)phenyl]piperazine

The pyrazine from Step 1 (13 g, 0.058 mol) was dissolved in acetic acid (100 mL) and palladium acetate added. This mixture was hydrogenated at 45 psi for 4 h., then filtered to remove catalyst and the filtrate concentrated in vacuo to give the product as brown solid. $^1$H NMR (500 MHz, CD$_3$OD): δ 1.98 (6H, s), 2.93 (1H, t, J 11.9), 3.03-3.15 (2H, m), 3.26-3.32 (3H, m), 4.09 (1H, dd, J 2.7, 11.2), 7.65 (2H, d, J 8.3), 7.72 (2H, d, J 8.2).

Step 3: (±)-Methyl{3-[4-(trifluoromethyl)phenyl]piperazin-1-yl}acetate

A mixture of the piperazine from Step 2 (2.1 g, 9 mmol), methyl bromoacetate (1 mL, 9 mmol) and potassium carbonate (2.4 g, 18 mmol) in acetonitrile (30 mL) was stirred overnight at room temperature. The mixture was filtered, evaporated and purified on silica using 25-50% ethyl acetate in iso-hexane as eluant.

$^1$H NMR (500 MHz, CDCl$_3$): δ 2.22 (1H, t, J 10.6), 2.37-2.43 (1H, m), 2.93 (2H, t, J 9.4), 3.10-3.17 (2H, m), 3.26 (2H, s), 3.72 (3H, s), 7.52 (2H, d, J 8.1), 7.58 (2H, d, J 8.2).

Step 4: (±)-{4-[2,5-Bis(trifluoromethyl)benzyl]-3-[4-(trifluoromethyl)phenyl]piperazin-1-yl}acetic acid Prepared from the product of Step 3 following the procedure of Example 36.

$^1$H NMR (500 MHz, CD$_3$OD): δ 0.85-0.93 (1H, m), 2.72 (1H, t, J 11.6), 3.03 (1H, d, J 13.1), 3.24 (2H, t, J 10.6), 3.34 (4H, s), 3.53-3.65 (5H, m), 3.76 (1H, d, J 15.5), 3.99 (1H, dd, J 2.8, 11.1), 7.70-7.76 (5H, m), 7.86 (1H, d, J 8.1), 8.18 (1H, s).

Example 179

(±)-{4-{4-Methyl-1-[4-(trifluoromethyl)phenyl]pentyl}-3-[4-(trifluoromethyl)phenyl]piperazin-1-yl}acetic acid

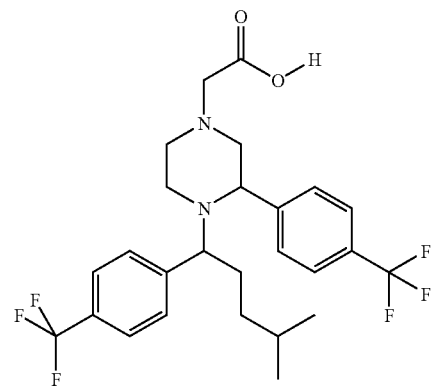

This compound was prepared following the procedure described in Example 86 using the compound of Example 178 Step 3 as the starting material.

$^1$H NMR (500 MHz, CD$_3$OD): δ 0.65-0.72 (1H, m), 0.83 (7H, dd, J 6.6, 9.8), 0.94 (1H, t, J 5.2), 1.30 (1H, t, J 7.3), 1.39-1.47 (1H, m), 1.86-1.98 (2H, m), 2.32 (1H, t, J 10.2), 2.43 (1H, t, J 10.6), 2.64 (1H, d, J 12.0), 2.79 (1H, t, J 10.8), 3.07-3.21 (4H, m), 3.35 (7H, s), 3.54 (1H, dd, J 3.5, 10.2), 4.10 (1H, t, J 5.3), 5.48 (1H, s), 7.46 (2H, d, J 8.1), 7.61 (2H, d, J 8.1), 7.73 (4H, s). MS (ES+) m/z 517 (MH+, 100%).

Example 180

(±)-{(2S*,4R*)-1-[(1R*)-1-(4-allylphenyl)-4-methylpentyl]-2-[4-(trifluoromethyl)phenyl]piperidin-4-yl}acetic acid

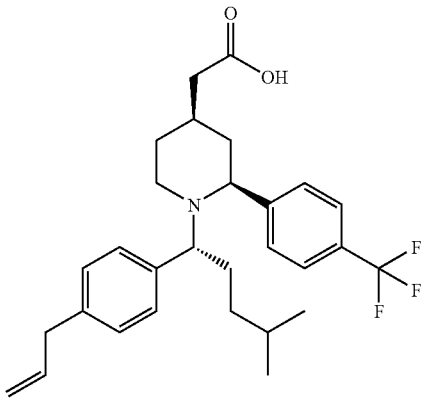

Step 1: (±)-Methyl{(2S*,4R*)-1-[(1R*)-1-(4-allylphenyl)-4-methylpentyl]-2-[4-(trifluoromethyl)phenyl]piperidin-4-yl}acetate The iodide of Example 168 Step 1 (400 mg, 0.68 mmol) was dissolved in DMF (2 mL) and allyltributyl tin (0.27 mL) was added. The mixture was degassed using a Firestone valve and placed under nitrogen. Tetrakis(triphenylphosphine)palladium(0) (100 mg) was added and the mixture was heated at 80° C. overnight. The cooled mixture was diluted with water (20 mL) and extracted with ethyl acetate. The organic extracts were washed with brine, dried (MgSO4) and evaporated. The residue was purified on silica using 20-90% CH2Cl2 in iso-hexane as eluant.

MS (ES+) m/z 502 (MH+, 100%).

Step 2

The ester from Step 1 (100 mg) was dissolved in methanol (1 mL) and sodium hydroxide (0.3 mL, 4N) was added. The mixture was heated at 60° C. overnight, cooled, evaporated and the residue dispersed between CH2Cl2 and HCl (0.1N). The organic extract was separated and washed with brine, dried (MgSO4) and evaporated. The residue was purified on silica using 10-95% ethyl acetate in iso-hexane as eluant.

1H NMR (500 MHz, CD3OD): δ 0.53-0.60 (1H, m), 0.79-0.86 (7H, m), 1.20-1.28 (1H, m), 1.37-1.53 (2H, m), 1.79-2.02 (5H, m), 2.12-2.20 (2H, m), 2.69 (1H, t, J 11.4), 3.07 (1H, d, J 11.7), 3.37 (2H, d, J 6.7), 3.52-3.56 (1H, m), 4.08 (1H, d, J 10.6), 5.02-5.08 (2H, m), 5.91-5.99 (1H, m), 7.17 (4H, s), 7.70 (2H, d, J 7.8), 7.76 (2H, d, J 8.2).

MS (ES+) m/z 488 (MH+, 100%).

Example 181

(±)-{(2S*,4R*)-1-[(1R*)-4-Methyl-1-(4-propylphenyl)pentyl]-2-[4-(trifluoromethyl)phenyl]piperidin-4-yl}acetic acid

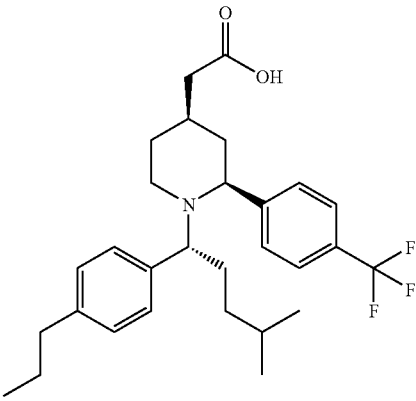

The acid described in Example 180 (40 mg) was hydrogenated at atmospheric pressure for 2 h using palladium on charcoal (10%, 8 mg) as catalyst. The catalyst was removed by filtration and the filtrate was evaporated. The residue was purified on silica using 0-4% methanol in CH2Cl2 as eluant.

1H NMR (500 MHz, CD3OD): δ 0.54-0.61 (1H, m), 0.77-0.85 (7H, m), 0.93 (3H, t, J 7.3), 1.22-1.30 (1H, m), 1.38-1.54 (2H, m), 1.59-1.67 (2H, m), 1.83 (1H, d, J 12.9), 1.91-2.03 (4H, m), 2.12-2.20 (2H, m), 2.57 (2H, t, J 7.6), 2.74 (1H, t, J 11.4), 3.13 (1H, d, J 11.6), 3.57 (1H, dd, J 2.8, 11.3), 4.13 (1H, d, J 10.2), 7.16 (4H, q, J 7.4), 7.71 (2H, d, J 7.8), 7.77 (2H, d, J 8.1).

MS (ES+) m/z 490 (MH+, 100%).

Example 182

(±)-((2S*,4R*)-2-(4-Iodophenyl)-1-{(1R*)-4-methyl-1-[4-(trifluoromethyl)phenyl]pentyl}piperidin-4-yl)acetic acid

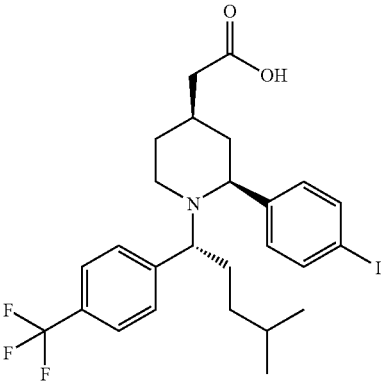

Step 1: (±)-cis-Methyl{2-[4-(trimethylsilyl)phenyl]piperidin-4-yl}acetate

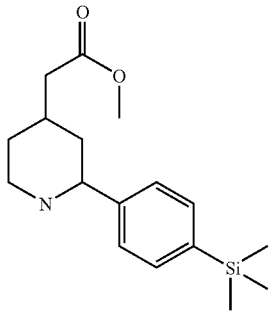

This compound was prepared following the procedure described in Example 3 (Steps 1-3) using 4-(trimethylsilyl)benzeneboronic acid as starting material.
MS (ES+) m/z 306 (MH+, 100%).

Step 2: (±)-Methyl{(2S*,4R*)-1-[(1R*)-4-methyl-1-[4-(trifluoromethyl)phenyl]pentyl]-2-[4-(trimethylsilyl)phenyl]piperidin-4-yl}acetate

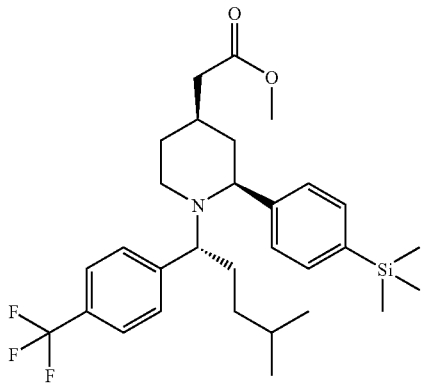

Prepared from the compound described in Step 2 above following the procedures described in Example 114 Step 2.
MS (ES+) m/z 534 (MH+, 100%).

Step 3: (±)-Methyl((2S*,4R*)-2-(4-iodophenyl)-1-{(1R*)-4-methyl-1-[4-(trifluoromethyl)phenyl]pentyl}piperidin-4-yl)acetate

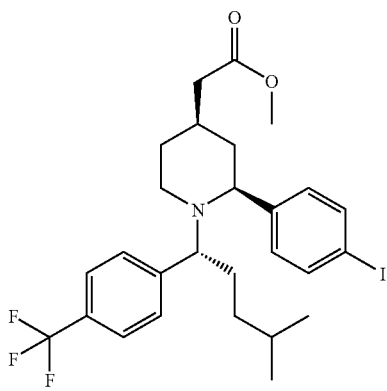

The silane described in Step 2 above (329 mg, 0.6 mmol) was dissolved in dry methanol (3 mL) under N₂ at 0° C. Silver tetrafluoroborate (240 mg, 1.2 mmol) was added followed by iodine (310 mg, 1.2 mmol). This mixture was stirred at room temperature overnight, quenched by addition of sodium thiosulfate and diluted with ethyl acetate and water. The combined organic extracts were washed with brine, dried (MgSO₄) and evaporated. The residue was purified by chromatography on silica using 4-6% ether in iso-hexane as eluant to give the product as a solid (312 mg).
MS (ES+) m/z 588 (MH+, 100%).

Step 4: (±)-((2S*,4R*)-2-(4-Iodophenyl)-1-{(1R*)-4-methyl-1-[4-(trifluoromethyl)phenyl]pentyl}piperidin-4-yl)acetic acid

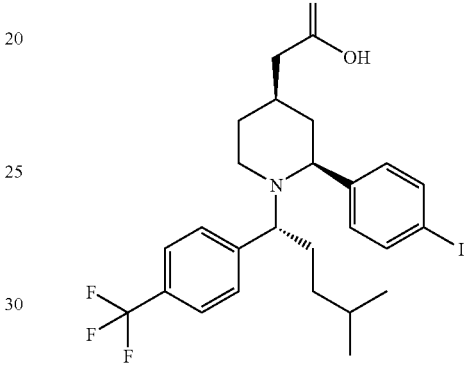

Prepared by hydrolysis of the ester from Step 3 by the procedure of Example 180 Step 2.
¹H NMR (400 MHz, CDCl₃): δ 0.63-0.71 (1H, m), 0.81-0.86 (6H, m), 1.08-1.20 (1H, m), 1.24-1.38 (2H, m), 1.42-1.50 (1H, m), 1.65 (1H, d, J 12.7), 1.73-1.91 (4H, m), 2.15-2.37 (3H, m), 2.63 (1H, d, J 11.4), 3.49 (1H, t, J 6.8), 3.60 (1H, d, J 8.6), 7.19 (2H, d, J 7.7), 7.34 (2H, d, J 8.1), 7.53 (2H, d, J 8.2), 7.70 (2H, d, J 8.2).
MS (ES+) m/z 574 (MH+, 100%).

Example 183

(±)-((2S*,4R*)-2-(4-Allylphenyl)-1-{(1R*)-4-methyl-1-[4-(trifluoromethyl)phenyl]pentyl}piperidin-4-yl)acetic acid

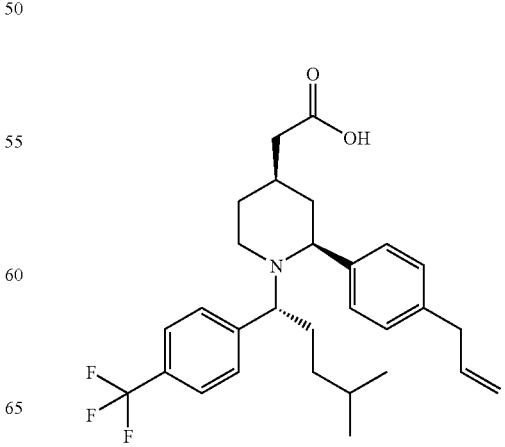

The iodide described in Example 182 (Step 3) was reacted and purified according to the procedure described in Example 180 to afford the title compound.

$^1$H NMR (500 MHz, CD$_3$OD): δ 0.56-0.63 (1H, m), 0.83 (6H, t, J 6.7), 1.16-1.24 (1H, m), 1.40-1.55 (2H, m), 1.77 (1H, d, J 13.0), 1.88-1.98 (5H, m), 2.12-2.19 (2H, m), 2.64 (1H, t, J 11.1), 2.90 (1H, d, J 11.6), 3.42 (2H, d, J 6.6), 3.67 (1H, t, J 7.1), 3.90 (1H, d, J 9.2), 5.05-5.09 (2H, m), 5.96-6.04 (1H, m), 7.27 (2H, d, J 7.9), 7.38-7.47 (4H, m), 7.62 (2H, d, J 8.1). MS (ES$^+$) m/z 488 (MH$^+$, 100%).

Example 184

(±)-((2S*,4R*)-2-(4-Propylphenyl)-1-{(1R*)-4-methyl-1-[4-(trifluoromethyl)phenyl]pentyl}piperidin-4-yl)acetic acid

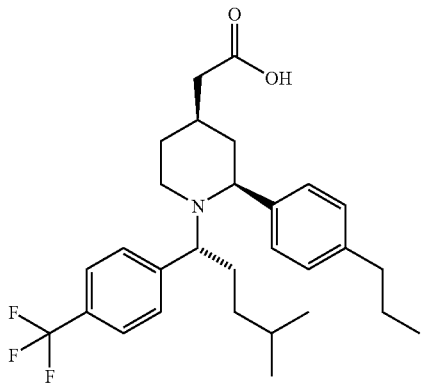

The compound of Example 183 was hydrogenated and purified according to the procedure described in Example 181 to afford the title compound.

$^1$H NMR (500 MHz, CD$_3$OD): δ 0.56-0.64 (1H, m), 0.78.87 (7H, m), 0.94 (3H, t, J 7.3), 1.17-1.29 (1H, m), 1.40-1.56 (2H, m), 1.63-1.71 (2H, m), 1.79 (1H, d, J 13.0), 1.90-2.00 (4H, m), 2.13-2.20 (2H, m), 2.61-2.69 (3H, m), 2.93 (1H, d, J 11.6), 3.69 (1H, t, J 7.1), 3.92 (1H, d, J 9.6), 7.27 (2H, d, J 8.0), 7.39 (2H, d, J 7.3), 7.45 (2H, d, J 8.1), 7.63 (2H, d, J 8.1). MS (ES$^+$) m/z 490 (MH$^+$, 100%).

Example 185

{(2S,4R)-1-{(1R)-4-methoxy-1-[4-(trifluoromethyl)phenyl]butyl}-2-[4-(trifluoromethyl)phenyl]piperidin-4-yl}acetic acid

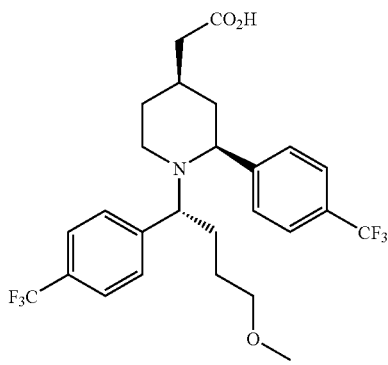

The compound was prepared analogously to Example 160 using the Grignard reagent derived from 1-bromo-3-methoxypropane and starting with the chiral piperidine of Example 114 Step 1. M/Z (ES$^+$) 518 (M+H).

Example 186

{(2S,4R)-1-{bis[4-(trifluoromethyl)phenyl]methyl}-2-[4-(trifluoromethyl)phenyl]piperidin-4-yl}acetic acid

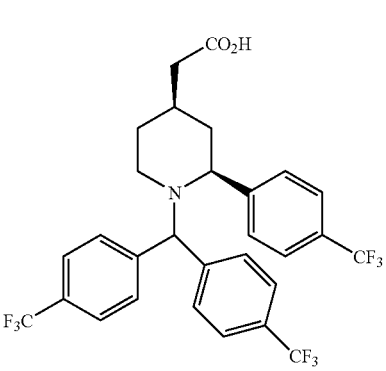

The compound was prepared analogously to Example 160 using the Grignard reagent derived from 4-brombenzotrifluoride and starting with the chiral piperidine of Example 114 Step 1. M/Z (ES$^+$) 590 (M+H).

Example 187

{(2S,4R)-1-[(1R)-1-(4-chlorophenyl)-4-methylpentyl]-2-[4-(trifluoromethyl)phenyl]piperidin-4-yl}acetic acid

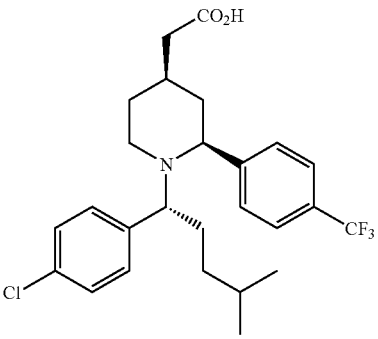

The compound was prepared analogously to Example 160 using the Grignard reagent derived from 1-bromo-3-methylbutane, starting with the chiral piperidine of Example 114 Step 1 and replacing 4-(trifluoromethyl)benzaldehyde with 4-chlorobenzaldehyde. M/Z (ES+) 482 (M+H).

The invention claimed is:

1. A compound of formula II or formula III:

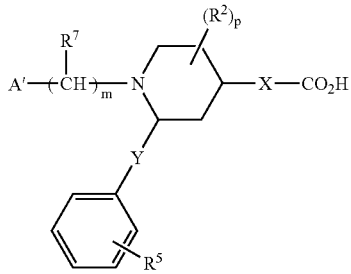

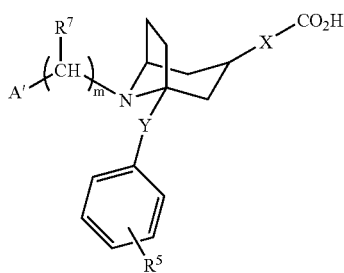

or a pharmaceutically acceptable salt thereof wherein
p is 0 or 1;
X represents a bond or $C(R^1)_2$ or $CH_2C(R^1)_2$;
Y represents a bond or $CH_2$ or $CH_2CH_2$;
m is 0 or 1;
$R^7$ is H or a hydrocarbon group of up to 10 carbon atoms, and A' represents a 3- to 12-membered carbocyclic ring system optionally having one or more acyclic hydrocarbon groups attached thereto, such that the total number of carbon atoms in the moiety A'—$(CHR^7)m$- is in the range of 5 to 25; A' and $R^7$ optionally and independently bearing one or more additional substituents, up to a maximum of 5 in combined total, selected from halogen, CN, $N_3$, $NO_2$, $C_{1-4}$ perfluoroalkyl, $OR^6$, $SR^6$, OH, $CO_2R^6$, $OCOR^6$ and $COR^6$;
each $R^1$ independently represents H or a non-aromatic hydrocarbon group of up to 6 carbon atoms; or the two $R^1$ groups complete a $C_{3-6}$alicyclic group;
$R^2$ represents a non-aromatic hydrocarbon group of up to 6 carbon atoms;
each $R^5$ independently represents halogen, CN, $NO_2$, $R^6$, $OR^6$, $CO_2R^6$, $OCOR^6$ or $COR^6$; and
$R^6$ represents a hydrocarbon group of up to 7 carbon atoms which is optionally substituted with up to 3 halogen atoms.

2. A compound according to claim 1 of Formula II:

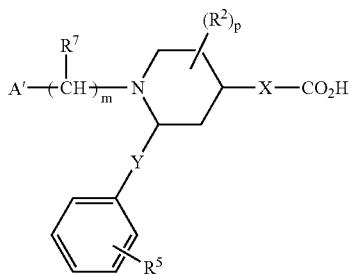

or a pharmaceutically acceptable salt thereof.

3. A compound of claim 1 of formula III:

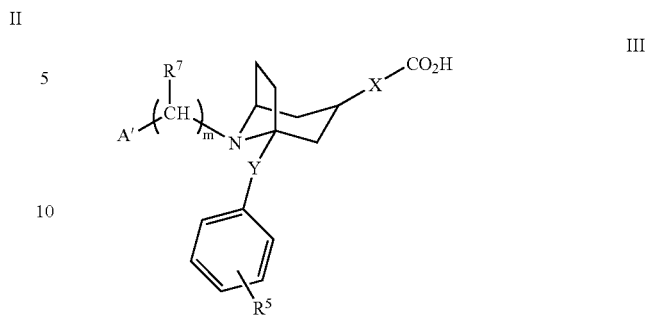

or a pharmaceutically acceptable salt thereof.

4. A compound according to claim 1 of formula IV:

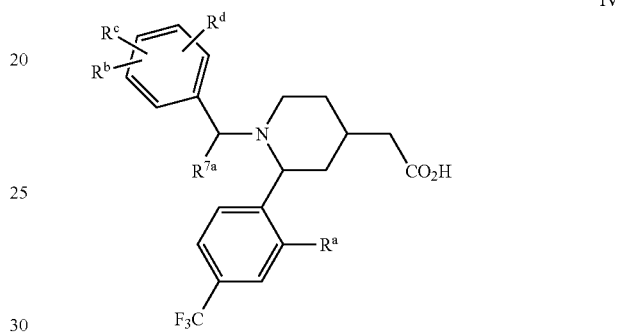

or a pharmaceutically acceptable salt thereof wherein:
$R^a$ represents H, halogen or $CF_3$;
$R^b$, $R^c$ and $R^d$ are independently selected from H, halogen, CN, $N_3$, $C_{1-4}$ perfluoroalkyl, $C_{1-4}$alkoxy, $OCF_3$, $SCF_3$, $C_{1-4}$alkyl, $C_{2-4}$alkenyl, and phenyl which is optionally substituted with halogen or $C_{1-2}$perfluoroalkyl, provided that $R^b$, $R^c$ and $R^d$ together contain not more than 8 carbon atoms; and
$R^{7a}$ represents a hydrocarbon group of up to 10 carbon atoms optionally bearing a $C_{1-4}$perfluoroalkyl substituent or up to 2 halogen substituents.

5. A compound according to claim 4 in which $R^b$, $R^c$ and $R^d$ complete a group selected from phenyl, vinylphenyl, fluorophenyl, chlorophenyl, bromophenyl, iodophenyl, isopropylphenyl, tert-butylphenyl, trifluoromethylphenyl, pentafluoroethylphenyl, cyanophenyl, methoxyphenyl, trifluoromethoxyphenyl, difluoromethoxyphenyl, trifluoromethylthiophenyl, biphenyl, 4'-trifluoromethylbiphenyl, bis(trifluoromethyl)phenyl, dichlorophenyl, dimethylphenyl, 5-fluoro-2-(trifluoromethyl)phenyl, 5-chloro-2-(trifluoromethyl)phenyl, 2-chloro-5-(trifluoromethyl)phenyl, 5-propyl-2-(trifluoromethyl)phenyl and 2-propyl-5-(trifluoromethyl)phenyl.

6. A compound according to claim 4 in which $R^{7a}$ represents a branched alkyl group of up to 6 carbon atoms, or a branched alkenyl group of up to 6 carbon atoms, or a branched alkynyl group of up to 6 carbon atoms.

7. A pharmaceutical composition comprising a compound according to claim 1 and a pharmaceutically acceptable carrier.

8. A compound according to claim 1 wherein $R^5$ is selected from halogen, $R^6$ and $OR^6$, and $R^6$ represents $C_{1-6}$alkyl bearing 0-3 fluorine substituents or $C_{2-6}$alkenyl.

* * * * *